US00RE45364E

(19) United States
(12) Reissued Patent
Hamamoto et al.

(10) Patent Number: US RE45,364 E
(45) **Date of Reissued Patent: *Feb. 3, 2015**

(54) CYCLIC AMINE COMPOUND AND PEST CONTROL AGENT

(71) Applicant: Nippon Soda Co., Ltd., Chiyoda-ku, Tokyo (JP)

(72) Inventors: Isami Hamamoto, Odawara (JP); Jun Takahashi, Odawara (JP); Makio Yano, Odawara (JP); Daisuke Hanai, Aizuwakamatsu (JP); Takao Iwasa, Odawara (JP)

(73) Assignee: Nippon Soda Co., Ltd., Tokyo (JP)

( * ) Notice: This patent is subject to a terminal disclaimer.

(21) Appl. No.: 14/160,305

(22) Filed: Jan. 21, 2014

Related U.S. Patent Documents

Reissue of:
(64) Patent No.: 8,101,768
Issued: Jan. 24, 2012
Appl. No.: 12/142,637
Filed: Jun. 19, 2008

U.S. Applications:
(62) Division of application No. 10/599,388, filed as application No. PCT/JP2005/006887 on Mar. 30, 2005, now Pat. No. 7,485,727.

(30) Foreign Application Priority Data

Mar. 31, 2004 (JP) ..... 2004-106668
Dec. 24, 2004 (JP) ..... 2004-374007

(51) Int. Cl.
*C07D 401/12* (2006.01)
*C07D 221/22* (2006.01)
*C07D 471/08* (2006.01)
*A01N 43/42* (2006.01)
*A01N 43/40* (2006.01)

(52) U.S. Cl.
USPC ..... 546/125; 546/183; 546/194; 546/304; 514/299; 514/304; 514/318

(58) Field of Classification Search
USPC ..... 546/125, 183, 194, 304; 514/299, 304, 514/318
See application file for complete search history.

(56) References Cited

U.S. PATENT DOCUMENTS 4,451,473 A 5/1984 Nador et al.
4,968,704 A * 11/1990 Cross et al. ..... 514/318
4,985,063 A 1/1991 Fischer et al.
5,001,125 A 3/1991 Stokbroekx et al.
5,057,528 A 10/1991 Cross et al.
5,364,865 A * 11/1994 Diana ..... 514/318
5,500,423 A 3/1996 Glamkowski et al.
5,571,815 A 11/1996 Schaper et al.
5,723,450 A 3/1998 Reuschling et al.
5,801,173 A 9/1998 Lohray et al.
5,859,024 A 1/1999 Hotson et al.
5,912,254 A 6/1999 Bishop et al.
5,919,782 A 7/1999 Lohray et al.
5,922,732 A 7/1999 Urch et al.
5,935,953 A 8/1999 Kuhar et al.
5,968,947 A 10/1999 Urch et al.
6,174,894 B1 1/2001 Urch et al.
6,177,442 B1 1/2001 Urch et al.
6,750,228 B1 6/2004 Barta et al.
7,199,147 B2 4/2007 Imazaki et al.
7,262,212 B2 8/2007 Tsubouchi et al.
7,999,102 B2 8/2011 Hamamoto et al.
8,338,607 B2 12/2012 Hamamoto et al.
8,536,340 B2 9/2013 Hamamoto et al.
8,697,867 B2 4/2014 Hamamoto et al.
2004/0147555 A1* 7/2004 Fujimoto et al. ..... 514/317
2006/0094767 A1 5/2006 Tsubouchi et al.
2008/0045569 A1 2/2008 Hamamoto et al.
2009/0099200 A1 4/2009 Li et al.
2009/0118296 A1 5/2009 Black et al.
2009/0143443 A1 6/2009 Hamamoto et al.
2009/0259046 A1 10/2009 Hamamoto et al.

FOREIGN PATENT DOCUMENTS

EP 0605031 7/1994
EP 1 457 490 9/2004

(Continued)

OTHER PUBLICATIONS

Silverman, R.B. The Organic Chemistry of Drug Design and Drug Action 1992, Academic: New York, p. 19.*

(Continued)

*Primary Examiner* — David K O'Dell
(74) *Attorney, Agent, or Firm* — Foley & Lardner LLP

(57) ABSTRACT

A chemical compound represented by the formula [I]:

[1]

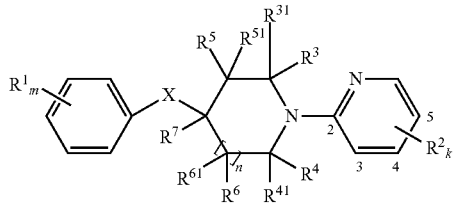

(wherein $R^1$ represents a hydroxyl group or the like, m represents 0 or an integer of 1 to 5, $R^2$ represents a halogen atom or the like, k represents 0 or an integer of 1 to 4, $R^3$, $R^{31}$, $R^4$, $R^{41}$, $R^5$, $R^{51}$, $R^6$, $R^{61}$, and $R^7$ each independently represents a hydrogen atom or the like, X represents an oxygen atom or the like, and n represents 1), a salt, an N-oxide of the chemical compound represented by formula [I], and a pest control agent containing the formula [I] as its active constituent.

15 Claims, No Drawings

(56) References Cited

FOREIGN PATENT DOCUMENTS

| | | | |
|---|---|---|---|
| EP | 1 731 518 | A1 | 12/2006 |
| JP | 58-49383 | A | 3/1983 |
| JP | 02-111773 | A | 4/1990 |
| JP | 6-211839 | A | 8/1994 |
| JP | 7-506347 | A | 7/1995 |
| JP | 9-502446 | A | 3/1997 |
| JP | 2000-514041 | A | 10/2000 |
| JP | 2001-081071 | | 3/2001 |
| JP | 2001-504476 | A | 4/2001 |
| JP | 2001-506989 | A | 5/2001 |
| JP | 02-081448 | A1 | 10/2002 |
| JP | 2003-40773 | A | 2/2003 |
| JP | 2003-137865 | A | 5/2003 |
| TW | 200642591 | | 12/2006 |
| WO | WO 97/28128 | A1 | 8/1997 |
| WO | WO 01/38325 | | 5/2001 |
| WO | WO 02/081448 | | 10/2002 |
| WO | WO 02/089803 | | 11/2002 |
| WO | WO 02/100833 | A1 | 12/2002 |
| WO | WO 03/097604 | A1 | 11/2003 |
| WO | WO 2004/033463 | A1 | 4/2004 |
| WO | WO 2004/099160 | A1 | 11/2004 |
| WO | WO 2005/014578 | A1 | 2/2005 |
| WO | WO 2005/036961 | A2 | 4/2005 |
| WO | WO 2005/095380 | A1 | 10/2005 |
| WO | WO 2006/075004 | A2 | 7/2006 |
| WO | WO 2007/040282 | A1 | 4/2007 |

OTHER PUBLICATIONS

Lohray et al., "Novel Euglycemic and Hypolipidemic Agents. 4. Pyridyl- and Quinolinyl-Containing Thiazolidinediones," Chemical Abstracts, XP002573018, Database Accession No. 1999:384967.
International Search Report and Written Opinion dated Nov. 7, 2006, in PCT/JP2006/320126, issued in related U.S. Appl. No. 12/083,127.
Plimmer et al., "pesticide" in Encyclopedia of Agrochemicals, vols. 1-3, Wiley, Hoboken, 2003, 1199.
Supplementary European Search Report dated Mar. 26, 2010, in EP 05728646.0—1211.
Patent Abstracts of Japan for JP 2001-081071 published Mar. 27, 2001.
Kim et al., "Synthesis and Pharmacology of Site Specific Cocaine Abuse Treatment Agents: 8-Substituted Isotrope (3-Azabicyclo[3.2.1]octane) Dopamine Uptake Inhibitor," Journal of Medicinal Chemistry, Apr. 10, 2003, 46(8):1456-1464.
Garner et al., "Syntheses of Heterocyclic Compounds. Part XXIV. Cyclisation Studies with ortho-Substituted Arylcarbene and Arylnitrene Precursors," J. Chem. Soc., 1971, 3693-3701.
Office Action dated May 12, 2008 in TW 094118838.
Office Action dated Aug. 25, 2009 in TW 095137297.
International Search Report dated Oct. 31, 2006 in PCT/JP2006/320133.
Search Report dated Jul. 22, 2010 in EP 06811460.2.
U.S. Appl. No. 12/083,127, filed Jun. 13, 2008, Hamamoto et al.
U.S. Appl. No. 12/333,227, filed Dec. 11, 2008, Hamamoto et al.
Final Office Action issued Oct. 3, 2011 in U.S. Appl. No. 12/083,127.
Office Action dated Jul. 24, 2011, in IL 178075, 2 pages, with English translation, 1 page.
Office Action dated May 17, 2011 in U.S. Appl. No. 12/083,127.
Lohray et al., "Novel Euglycemic and Hypolipidemic Agents. 4. Pyridyl- and Quinolinyl-Containing Thiazolidinediones," J. Med. Chem., 1999, 42(14):2569-2581.
Supplementary European Search Report dated Aug. 3, 2010 in EP 06811453.7.
Indian Office Action dated Jun. 22, 2010, in IN 2652/KOLNP/2006.
Office Action dated Jul. 19, 2010, in U.S. Appl. No. 12/333,227.
Lohray et al., "Thiazolidinedione Compounds Having Antidiabetic, Hypolipidemic, Antihypertensive Properties, Process for their Preparation and Pharmaceutical Compositions," Chemical Abstracts, XP002573018, Database Accession No. 1999:430613, 1-2.
Lohray et al., "Noval Euglycemic and Hypolipidemic Agents. 4. Pyridyl- and Quinolinyl-Containing Thiazolidinediones," Chemical Abstracts, XP002573019, Database Accession No. 1999:384967.
Supplementary European Search Report dated Mar. 26, 2010, in EP 05728646.1—1211.
International Search Report and Written Opinion dated Nov. 7, 2006, in PCT/JP2006/320126.
Office action dated Feb. 23, 2010, in U.S. Appl. No. 12/333,227.
Varma et al., "A Facile One-Pot Synthesis of 2,5-Disubstituted Oxazoles Using Iodobenzene Diacetate," J. Heterocyclic Chem., Nov.-Dec. 1998, 35:1533-1534.
Cooper et al., "A Chiral Synthesis of D-Homoserine and its Application to the Synthesis of Nocardicin A," Tetrahedron Letters, 1978, 26:2243-2246.
Albert et al., "Design, Synthesis and SAR of Tachykinin Antagonists: Modulation of Balance in NK1/NK2 Receptor Antagonist Activity," Journal of Medicinal Chemistry, 2002, 45(18):3972-3983.
Eichler et al., "1,8-Napthyridines. Part 1. Synthesis of Some Trifluoromethy1-1,8-naphthyridine Derivatives," Journal of Heterocyclic Chemistry, Feb. 1976, 13(1):41-42.
Lowe et al., "Aza-Tricyclic Substance P Antagonists," Journal of Medicinal Chemistry, Sep. 2, 1994, 37(18):2831-2840.
Ek et al., "Aromatic Allylation via Diazotization: Metal-Free C-C Bond Formation," Journal of Organic Chemistry, 2002, 67:6376-6381.
Kim et al., "Synthesis and Pharmacology of Site Specific Cocaine Abuse Treatment Agents: 8-Substituted Isotrope (3-Azabicyclo[3.2.1]octane) Dopamine Uptake," Journal of Medicinal Chemistry, Apr. 10, 2003, 46(8):1456-1464.
Ferguson et al., "Efficient New Syntheses of (+)- and (−)-Anatoxin-a. Revised Configuration of Resolved 9-Methyl-9-azabicyclo[4.2.1]nonan-2-one," Tetrahedron Letters, 1995, 36(48):8867-8870.
Comins et al., "Reduction of N-Acyl-2,3-dihydro-4-pyridones to N-Acyl-4-piperidones Using Zinc/Acetic Acid," Journal of Organic Chemistry, 2001, 66:2181-2182.
Montska et al,. "2,2,2-Trichloroethyl Chloroformate: A General Reagent for Demethylation of Tertiary Methylamines," Tetrahedron Letters, 1974, 14:1325-1327.
Comins et al., "Addition of Grignard Reagents to 1-Acyl-4-Methoxypyridinium Salts. An Approach to the Synthesis of Quinolizidinones," Tetrahedron Letters, 1986, 27(38):4549-4552/.
Taylor et al., "A Convenient Synthesis of 1-Aryl-4-Piperidones," International Journal of Methods in Synthetic Organic Chemistry, 1981, 8:606-608.
Boswell et al., Synthesis of Some N-Carboxylic Acid Derivatives of 3-Phenoxypyrrolidines, 4-Phenoxypiperidines, and 3-Phenoxynortropanes with Muscle Relaxant and Anticonvulsant Activities, Journal of Medicinal Chemistry, 1974, 17(9):1000-1008.
Idoux et al., "Aromatic Fluoroalkoxylation via Direct Aromatic Nucleophilic Substitution," Journal of Organic Chemistry, Oct. 21, 1983, 48(21):3771-3773.
Gupton et al., "Regioselective Fluoroalkoxylation and Polyfluoroalkoxylation of Activated Polyhalobenzenes," Synthetic Communications, 1984, 14(7):621-629.
Gonzalez et al., "Chapter 6: Synthesis of Phenols," The Chemistry of Phenols, 2003, Part 1, 395-489.
McCarthy et al., "Stereospecific Syntheses of the Four Diasteromeric 2-Amino-5-phenoxycyclopentanols," Journal of Organic Chemistry, Aug. 23, 1985, 50(17):3095-3103.
Garner et al., "Synthesis of Heterocyclic Compounds. Part XXIV. Cyclisation Studies with ortho-Substituted Arylcarbene and Arylnitrene Precursors," J. Chem. Soc., 1971, 3693-3701.
Magee, Thomas A., "Insecticidal Substituted 2-Butanone O-(Methylaminocarbonyl1)oximes," Journal of Agriculture and Food Chemistry, 1977, 25:1376-1382.
Kurtz et al., "Novel Insecticidal Oxathiolane and Oxathiane Oxime Carbamates," Journal of Agricultural and Food Chemistry, 1987, 35:106-114.
Henrick et al., "Ovicidal Activity and its Relation to Chemistry Structure for the Two-spotted Spider Mite (*Tetranychus urticae* Koch) in a New Class of Miticides Containing the Cyclopropyl Group," Journal of Agricultural and Food Chemistry, 1976, 24:1023-1029.

(56) References Cited

OTHER PUBLICATIONS

Dekeyser et al,. "Synthesis and Miticidal and Insecticidal Activities of 4-(2-Fluoroethyl)-5,6-dihydro-4H-1,3,4-oxadiazines," Journal of Agricultural and Food Chemistry, 1993, 41:1329-1331.
Plimmer et al., "pesticide" in Encoclopedia of Agrochemicals, vols. 1-3, Wiley, Hoboken, 2003, 1199.
Office Action dated Jun. 6, 2011, in U.S. Appl. No. 12/142,637.
Office Action dated Feb. 25, 2010, in U.S. Appl. No. 12/142,637.
Final Office Action dated Aug. 2, 2010, in U.S. Appl. No. 12/142,637.
Notice of Allowance dated Nov. 8, 2011, in U.S. Appl. No. 12/142,637.
Patent Abstracts of Japan for JP 2001-081070 published Mar. 27, 2001.
U.S. Appl. No. 12/333,227, filed Dec. 11, 2008 to Hamamoto et al.
Office Action dated Jun. 9, 2011, in EP 05728646.0, 5 pages.
Office Action dated Jul. 12, 2011, in JP 2007-538803, 2 pages, with English translation, 2 pages.
Bardone-Gaudemar, Francoise, "Allenic and acetylenic mono- and diketones," Ann. Chim., Paris, 1958, 3:52-107, 3 page Abstract only.

* cited by examiner

CYCLIC AMINE COMPOUND AND PEST CONTROL AGENT

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

The present application *is a Reissue Application of U.S. Ser. No. 12/142,637, filed Jun. 19, 2008, now U.S. Pat. No. 8,101,768 granted Jan. 24, 2012, which* is a divisional application of U.S. patent application Ser. No. 10/599,388, filed Sep. 27, 2006. The latter application is a national phase of International Application No. PCT/JP2005/006887, filed Mar. 30, 2005, which claims priority of Japanese Patent Application No. 2004-106668 filed on Mar. 31, 2004 and Japanese Patent Application No. 2004-374007 filed on Dec. 24, 2004, the contents of all of which are incorporated herein by reference.

SEQUENCE LISTING

Not Applicable.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

This invention relates to novel cyclic amine compounds and pest control agents containing the compounds as active ingredients.

2. Description of Related Art Including Information Disclosed

Under 37 CFR 1.97 and 1.98

Although many insecticides and acaricides have been conventionally used, it has been difficult to view them as satisfactory control agents in view of their inadequate effects, resistance problems limiting their use, possibilities of causing chemical injuries or pollution on plants, or high toxicity on humans, beasts, fishes, and the like, which are considerable. Therefore, it is required to develop agents having few such problems and being safely useable.

Although a chemical compound having a backbone similar to that of the compound of the present invention is described as an antivirus agent in European Patent Application No. 0605031, its insecticidal and acaricidal activities are not described, and synthesis and biological activity of the compounds of the present invention have not yet been reported.

BRIEF SUMMARY OF THE INVENTION

The present invention has as an object to provide novel compounds which can serve as pest control agents which can be commercially and profitably synthesized and can be safely used with certain effects.

That is, the present invention provides a chemical compound represented by the formula [I]:

[I]

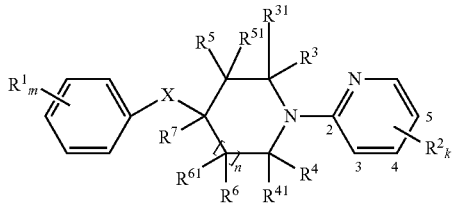

wherein $R^1$ represents a hydroxyl group, a halogen atom, a cyano group, a nitro group, a formyl group, a $C_{1-6}$ alkyl group which may be substituted by $G^1$, a $C_{2-6}$ alkenyl group, a $C_{2-6}$ alkynyl group, a $C_{1-6}$ haloalkyl group, a $C_{1-6}$ haloalkenyl group, a $C_{1-6}$ alkylcarbonyl group, a $C_{1-6}$ alkoxy group which may be substituted by $G^2$, a $C_{1-6}$ haloalkoxy group, a $C_{2-6}$ alkenyloxy group, a $C_{2-6}$ haloalkenyloxy group, a $C_{2-6}$ alkynyloxy group, a $C_{1-6}$ alkylcarbonyloxy group, a $C_{1-6}$ alkoxycarbonyloxy group, a $C_{1-6}$ alkylthiocarbonyloxy group, an amino group which may be substituted by $G^3$, a $C_{1-6}$ alkylthio group, a $C_{1-6}$ haloalkylthio group, $C_{1-6}$ alkylsulfonyl group, a $C_{1-6}$ haloalkylsulfinyl group, a $C_{1-6}$ alkylsulfonyl group, a $C_{1-6}$ haloalkylsulfonyl group, a $C_{1-6}$ alkylsulfonyloxy group, a $C_{1-6}$ haloalkylsulfonyloxy group, a heterocyclic group (a five or six membered heterocyclic group having at least one hetero atom selected from an oxygen atom, a nitrogen atom, and a sulfur atom), which may be substituted by $G^4$, or any one of substituents represented by the following formula:

$$—OP(O)(OR^8)SR^9$$

$$—Y^1C(=Y^2)—Y^3R^8$$

$$—O\text{-}A$$

$$—CO_2—R^{10}$$

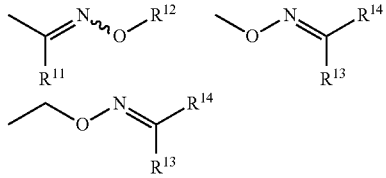

wherein $R^8$ and $R^9$ each independently represents a $C_{1-6}$ alkyl group, $Y^1$, $Y^2$, and $Y^3$ each independently represents an oxygen atom or a sulfur atom, A represents a heterocyclic group (a five or six membered heterocyclic group having at least one hetero atom selected from an oxygen atom and a nitrogen atom), which may be substituted by $G^4$, $R^{10}$ represents a $C_{1-6}$ alkyl group, a $C_{2-6}$ alkenyl group, a $C_{2-6}$ alkynyl group, a $C_{1-6}$ alkyl $C_{1-6}$ alkoxy group, a $C_{1-6}$ haloalkyl group, or a heterocyclic group (a five or six membered heterocyclic group having at least one hetero atom selected from an oxygen atom, a nitrogen atom, and a sulfur atom), which may be substituted by $G^4$, $R^{11}$ and $R^{12}$ each independently represents a hydrogen atom, a $C_{1-6}$ alkyl group, a $C_{2-6}$ alkenyl group, or a $C_{2-6}$ alkynyl group, $R^{13}$ and $R^{14}$ each independently represents a $C_{1-6}$ alkyl group, and $R^{13}$ and $R^{14}$ may be bound together to form a ring, m represents 0 or an integer of 1 to 5, $R^2$ represents a halogen atom, a nitro group, a $C_{1-6}$ alkyl group, a $C_{1-6}$ alkoxy group, a $C_{1-6}$ haloalkyl group, a heterocyclic cyclic group (a five or six membered heterocyclic group having at least one hetero atom selected from an oxygen atom, a nitrogen atom, and a sulfur atom), which may be substituted by $G^4$, or a $C_{1-6}$ haloalkoxy group, k represents 0 or an integer of 1 to 4, $R^3$, $R^{31}$, $R^4$,$R^{41}$, $R^5$, $R^{51}$, $R^6$, $R^{61}$, and $R^7$ each independently represents a hydrogen atom, a $C_{1-6}$ alkyl group, a $C_{1-6}$ alkoxycarbonyl group, or a $C_{1-6}$ alkoxy group, and both $R^3$ and $R^4$, or both $R^5$ and $R^6$, may be bound together to form a saturated ring, X represents an oxygen atom, a sulfur atom, a sulfinyl group, or a sulfonyl group, $G^1$ represents a hydroxyl group, a $C_{1-6}$ alkoxycarbonyl group, a $C_{1-6}$ alkoxy group, a $C_{1-6}$ alkoxy $C_{1-6}$ alkoxy group, a heterocyclic group (a five or six membered heterocyclic group having at least one hetero atom selected from an oxygen atom, a nitrogen atom, and a sulfur atom) which may be substituted by $G^4$, or a $C_{3-6}$ cycloalkyl group, $G^2$ represents a hydroxyl group, a cyano group, an amino group which may be substituted by $G^4$, a $C_{1-6}$ alkoxycarbonyl group, a $C_{1-6}$ alkylthio group, a $C_{1-6}$ alkylsulfonyl group, a $C_{1-6}$ alkoxy group, a $C_{1-6}$ alkoxy $C_{1-6}$ alkoxy group, a $C_{3-6}$ cycloalkyl group, or a $C_{6-10}$ aryl group which may be substituted by a halogen atom or a $C_{1-6}$ alkyl group, $G^3$ represents a $C_{1-6}$ alkyl group, a $C_{1-6}$ alkylcarbonyl group, or a $C_{1-06}$ alkylsulfonyl group, $G^4$ represents a $C_{1-6}$ alkyl group, or a $C_{1-6}$ alkoxy group, n represents 0 or 1, a salt or an N-oxide of the chemical compound represented by formula [I], and a pest control agent containing it as an active constituent.

BRIEF DESCRIPTION OF THE SEVERAL VIEWS OF THE DRAWING(S)

Not Applicable.

DETAILED DESCRIPTION OF THE INVENTION

In the present invention, examples of the halogen atom in formula [I] may include fluorine, chlorine, bromine, iodine, and the like.

Examples of the $C_{1-6}$ alkyl group may include methyl, ethyl, propyl, isopropyl, cyclopropyl, n-butyl, sec-butyl, isobutyl, t-Butyl, pentyl and isomers thereof, hexyl and isomers thereof, and the like.

Examples of the $C_{2-6}$ alkenyl group may include ethenyl, 1-propenyl, 2-propenyl, 1-butenyl, 2-butenyl, 3-butenyl, 1-methyl-2-propenyl, 2-methyl-2-propenyl, 1-pentenyl, 2-pentenyl, 3-pentenyl, 4-pentenyl, 1-methyl-2-butenyl, 2-methyl-2-butenyl, 1-hexenyl, 2-hexenyl, 3-hexenyl, 4-hexenyl, 5-hexenyl, and the like.

Examples of the $C_{2-6}$ alkynyl group may include ethynyl, 1-propynyl, 2-propynyl, 1-butynyl, 2-butynyl, 3-butynyl, 1-methyl-2-propynyl, 2-methyl-3-butynyl, 1-pentynyl, 2-pentynyl, 3-pentynyl, 4-pentynyl, 1-methyl-2-butynyl, 2-methyl-3-pentynyl, 1-hexynyl, 1,1-dimethyl-2-butynyl, and the like.

Examples of the $C_{1-6}$ haloalkyl group may include chloromethyl, fluoromethyl, bromomethyl, dichloromethyl, difluoromethyl, dibromomethyl, trichloromethyl, trifluoromethyl, monobromo difluoromethyl, trifluoroethyl, 1-chloroethyl, 2-chloroethyl, 1-bromoethyl, 2-bromoethyl pentafluoroethyl, 1-floropropyl, 2-floropropyl, and the like.

Examples of the $C_{1-6}$ haloalkenyl group may include 3-chloro-2-propenyl, 3, 3-dichloro-2-propenyl, 4-chloro-2-butenyl, 4,4-dichloro-3-butenyloxy, 4,4-difluoro-3-butenyloxy, and the like.

Examples of the $C_{1-6}$ alkylcarbonyl group may include methylcarbonyl, ethylcarbonyl, propylcarbonyl, butylcarbonyl, and the like.

Examples of the $C_{1-6}$ alkoxy group may include methoxy, ethoxy, propoxy, isopropoxy, butoxy, sec-butoxy, isobutoxy, t-butoxy, and the like.

Examples of the $C_{1-6}$ haloalkoxy group may include chloromethoxy, dichloromethoxy, trichloromethoxy, trifluoromethoxy, bromodifluoromethoxy, 1-fluoroethoxy, 2-fluoroethoxy, 2-chloroethoxy, 2-bromoethoxy, 1,1-difluoroethoxy, fluoroethoxy, 1,1-difluoroethoxy, 3-chloropropoxy, and the like.

Examples of the $C_{2-6}$ alkenyloxy group may include vinyloxy, aryloxy, arenyloxy, butenyloxy, 3-methyl-2-butyleneoxy, and the like.

Examples of the $C_{2-6}$ haloalkenyloxy group may include 3-chloro-2-propenyloxy, 3,3-dichloro-2-propenyloxy, 4-chloro-2-butenyloxy, 4,4-dichloro-3-butenyloxy, 4,4-difluoro-3-butenyloxy, and the like.

Examples of the $C_{2-6}$ alkynyloxy group may include ethynyloxy, propargyloxy, 2-propynyloxy, 2-butynyloxy, 1-methyl-2-propynyloxy, and the like.

Examples of the $C_{1-6}$ alkylcarbonyloxy group may include acetyloxy, propionyloxy, butyryloxy, and the like.

Examples of the $C_{1-6}$ alkoxycarbonyloxy group may include methoxycarbonyloxy, ethoxycarbonyloxy, and the like.

Examples of the $C_{1-6}$ alkylthiocarbonyloxy group may include methylthiocarbonyloxy, ethylthiocarbonyloxy, and the like.

Examples of the $C_{1-6}$ alkylthio group may include methylthio, ethylthio, propylthio, and the like.

Examples of the $C_{1-6}$ haloalkylthio group may include monofluoromethylthio, difluoromethylthio, trifluoromethylthio, and the like.

Examples of the $C_{1-6}$ alkylsulfinyl group may include methylsulfinyl, ethylsulfinyl, propylsulfinyl, and the like.

Examples of the $C_{1-6}$ haloalkylsulfinyl group may include trifluoromethyl methylsulfinyl, pentafluoroethylsulfinyl, and the like.

Examples of the $C_{1-6}$ alkylsulfonyl group may include methylsulfonyl, ethanesulfonyl, and the like.

Examples of the $C_{1-6}$ haloalkylsulfonyl group may include trifluoromethylsulfonyl, pentafluoroethylsulfonyl, and the like.

Examples of the $C_{1-6}$ alkylsulfonyloxy group may include methylsulfonyloxy, ethanesulfonyloxy, and the like.

Examples of the $C_{1-6}$ haloalkylsulfonyloxy group may include trifluoromethyl sulfonyloxy, pentafluoroethyl sulfonyloxy, and the like.

Examples of the $C_{1-6}$ alkoxyalkoxy group may include methoxymethoxy, methoxyethoxy, ethoxymethoxy, and the like.

Examples of the $C_{3-6}$ cycloalkyl group may include cyclopropyl, 1-methylcyclopropyl, 2,2,3,3-tetramethylcyclopropyl, cyclobutyl, cyclopentyl, 1-methylcyclopentyl, cyclohexyl, 1-methylcyclohexyl, 4-methylcyclohexyl, and the like.

Examples of the $C_{6-10}$ aryl group may include phenyl, naphthyl, and the like.

Examples of the five or six membered heterocyclic group having at least one hetero atom selected from an oxygen atom, a nitrogen atom, and a sulfur atom may include tetrahydrofuryl, dioxolanyl, 1,2,3-oxadiazoryl, oxazoryl, 1,3-dioxolanyl, thienyl, pyridyl, 4,5-dihydrofuryl, furyl, and the like.

m represents 0 or an integer of 1 to 5. When $R^1$ plurally exists, each of them may be same or different.

In formula [1], both $R^3$ and $R^4$ or both $R^5$ and $R^6$ may together form a saturated ring. Both $R^3$ and $R^4$ or both $R^5$ and $R^6$ may together form a saturated ring for forming, on the whole, a cross-linking ring such as, for example, 8-azabicyclo[3.2.1]octanoic ring (hereinafter referred to as tropane ring), 3-azabicyclo[3.2.1]octanoic ring (hereinafter referred to as isotropane ring), 3-azabicyclo[3.3.]nonane, and the like.

Moreover, chemical compounds produced by oxidization of nitrogen atoms of the pyridine rings, or nitrogen atoms of cyclic amine portions of the piperidine rings, tropane rings, isotropane rings, or the like, of the present chemical compounds [I] exist, and all of these N-oxides are also included within the scope of this invention.

When both $R^3$ and $R^4$ or both $R^5$ and $R^6$ of the chemical compound [I] of the present invention are together to form a saturated ring, two kinds of isomers, such as shown in the following examples, respectively exist. These isomers are without exception intended to be within the scope of the present invention.

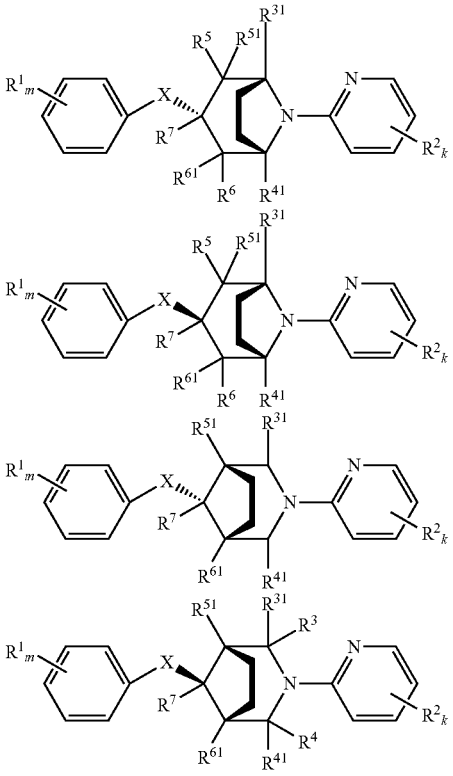

-continued

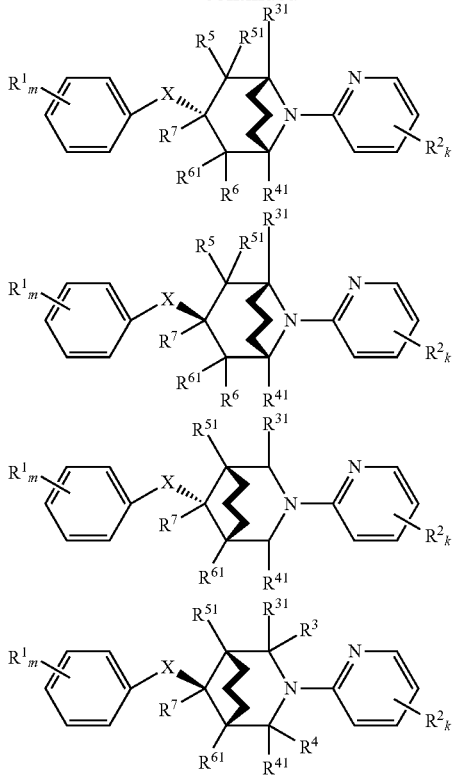

Next, methods of producing the chemical compounds of the present invention will be explained. In the first place, a method of producing an intermediate (3) will be explained.

(III)

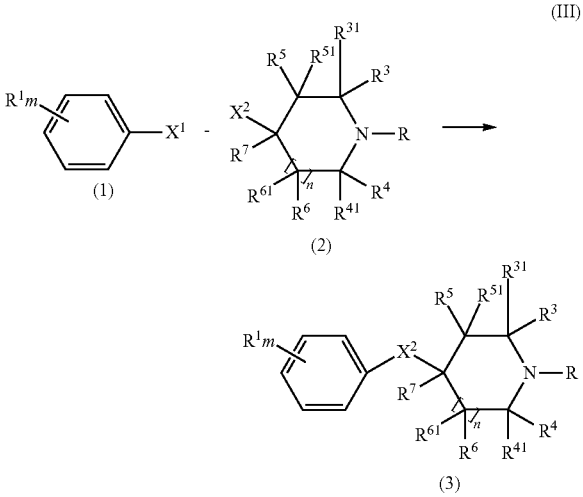

(IV)

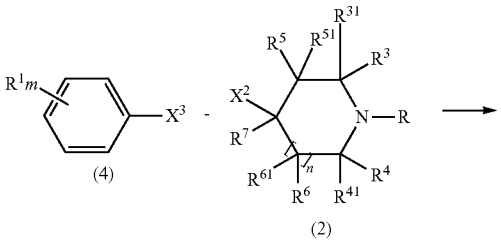

-continued

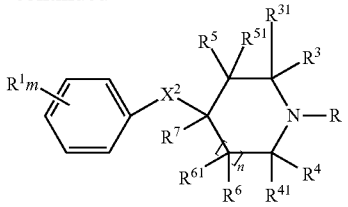

(3)

wherein $R^1$ to $R^7$, $R^{31}$, $R^{41}$, $R^{51}$, $R^{61}$, m and n represent the same meanings as those in the formula [I], $X^1$ and $X^2$ each independently represents a hydroxyl group or a thiol, $X^3$ represents an eliminated group such as a halogen atom or the like, $X^4$ represents an oxygen atom or a sulfur atom, and R represents any one of a 2-pyridyl group, a methyl group, and a benzyl group, which are substituted by $R^2_k$.

As shown in the reaction formula (III), the intermediate (3) can be produced by a conventional dehydration reaction, such as, for example, Mitsunobu reaction (which is described in, for example, Tetrahedron Lett., 1978, 2243, J. Org. Chem., 50, 3095, 1985, or the like), between the chemical compound (1) and the chemical compound (2). The chemical compound (1) can be produced according to a known method (which is described in, for example, "The Chemistry of Phenols," Eds. Z. Rappoport, J. Wiley (2003), Part 1, pp 395, or the like).

Alternatively, the intermediate (3) can also be produced by coupling between an arylhalide (4) and the chemical compound (2), as shown in the reaction formula (IV). Specifically, it can be produced according to a known method (which is described in, for example, Synth. Commun., 1984, 14, 621; J. Org. Chem., 48, 3771 (1983); J. Med. Chem., 17, 1000 (1974), or the like).

Examples of bases which can be used in this case may include alkali metal hydroxides such as sodium hydroxide, potassium hydroxide, and the like, carbonates such as sodium carbonate, potassium carbonate, and the like, metal alkoxides such as sodium methoxide, potassium t-butoxide, magnesium ethoxide, and the like, organic metals such as n-butyllithium, LDA, and the like, metal hydrides such as sodium hydride, potassium hydride, and the like, organic bases such as triethylamine, diisopropylamine, pyridine, and the like. This reaction can be carried out in the presence of solvents or in the absence of solvents. The solvents which can be used are not particularly limited, provided that they are chemically stable solvents, and examples thereof may include hydrocarbon base solvents such as pentane, hexane, heptane, benzene, toluene, xylene, and the like, halogen base solvents such as dichloromethane, 1,2-dichloroethane, chloroform, carbon tetrachloride, and the like, nitrile base solvents such as acetonitrile, propionitrile, and the like, ether base solvents such as diethylether, dioxane, tetrahydrofuran, and the like, aprotic polar solvents such as N,N-dimethylformamide (DMF), dimethylsulfoxide (DMSO), and the like, and mixed solvents containing two or more kinds of these solvents. The reaction can be carried out at an optional temperature within a range from −78° C. to the boiling point of the used solvent.

When R of the chemical compound (2) is a 2-pyridyl group substituted by $R_2$ (chemical compound (7)), the chemical compound [I] can be directly produced according to the reaction formula (III) or the reaction formula (IV).

As shown in the reaction formula (V), the chemical compound (7) can be synthesized by coupling between amine (5) and 2-halopyridine (6). Specifically, it can be produced according to a known method (which is described in, for example, Synthesis, 1981, 606; J. Chem. Soc., C, 3693 (1971), or the like).

(V)

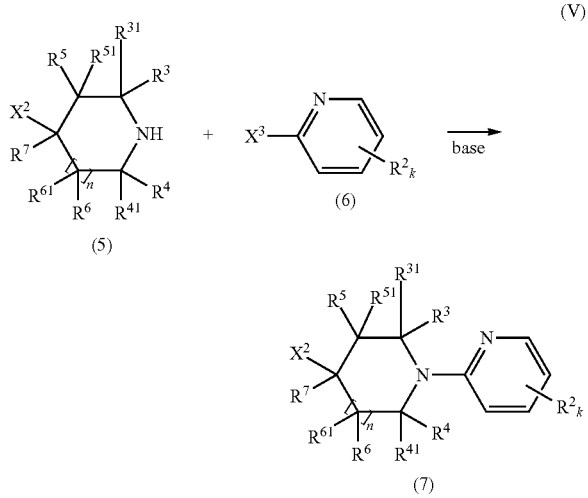

wherein $R^2$ to $R^7$, $R^{31}$, $R^{41}$, R|, $R^{61}$, n, $X^2$, and $X^3$ represents the same meanings as those described above.

By way of contrast, when R of the chemical compound (2) is a methyl group or a benzyl group, the intermediate (3) produced by the reaction formula (III) or the reaction formula (IV) should be demethylated or debenzylated. The demethylation can be carried out according to a known method (which is described in, for example, Tetrahedron Lett., 1974, 1325; ibid., 1977, 1565; ibid., 1995, 8867, or the like). Moreover, the debenzylation may be carried out by using a known hydrogenation. As shown in the reaction formula (VI), the chemical compound [I'] of the present invention can be produced by producing an intermediate (8) from the intermediate (3), followed by coupling it with 2-halopyridine (6). The specific method of this coupling is the same as that of the reaction formula (V).

(VI)

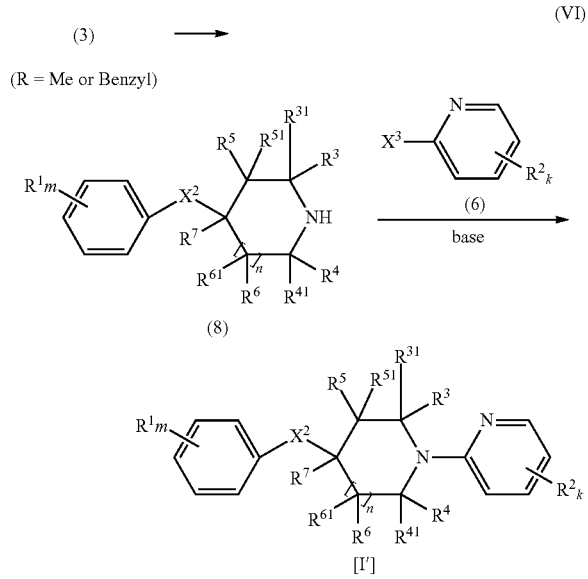

As the chemical compound (2) (in which R is a methyl group or a benzyl group), commercial products may be directly used. The intermediate (8) may exist alone as an amine, or may form a salt together with hydrochloric acid, acetic acid, or the like.

After an end of the abovementioned condensation reaction, purification of the obtained product may be carried out, if needed, according to a known conventional method such as distillation, recrystallization, column chromatography, or the like.

The chemical compounds of the present invention (the chemical compounds represented by the formula [I], the salts, or the N-oxides thereof) may be used for controlling agricultural pests, sanitary pest insects, stored grain pest insects, cloth pest insects, house pest insects and the like, and have activities of killing adults, nymphs, larvae and eggs. Their representative examples are shown in the following.

Examples of Lepidopterous pest insects include cotton leafworm, cabbage armyworm, black cutworm, common cabbageworm, cabbage looper, diamond-back moth, smaller tea tortrix, tea leaf roller, peach fruit moth, oriental fruit moth, citrus leaf miner, tea leaf roller, apple leaf miner, gypsy moth, tea tussock moth, rice stem borer, grass leaf roller, European corn borer, fall webworm, almond moth, Heliothis sp., Helicoverpa sp., Agrotis sp., casemaking clothes moth, codling moth and cotton bollworm.

Examples of Hemipterous pest insects include green peach aphid, cotton aphid, turnip aphid, grain aphid, bean bug, common green stink bug, arrowhead scale, mulberry mealy scale, greenhouse whitefly, tobacco whitefly, silverleaf whitefly, pear psylla, Japanese pear lace bug, brown planthopper, small brown planthopper, white-backed planthopper and green rice leafhopper.

Examples of Coleopterous pest insects include striped flea beetle, cucurbit leaf beetle, Colorado potato beetle, rice water weevil, rice weevil, adzuki bean weevil, Japanese beetle, soybean beetle, Diabrotica sp., cigarette beetle, powder post beetle, pine sawyer, white-spotted longicom beetle, Agriotis sp., Twenty eight-spotted lady beetle, rust-red flour beetle and cotton boll weevil.

Examples of Dipterous pest insects include housefly, Calliphora lata, Boettcherisca peregrina, cucurbit fruit fly, citrus fruit fly, seed maggot, rice leaf miner, yellow drosophila, Stomoxys calcitrans, Culex tritaeniarhynchus, Aedes aegypti and Anopheles hyrcanus.

Examples of Thysanopterous pest insects include Thrips palmi and tea thrips.

Examples of Hymenopterous pest insects include Monomorium pharaonis, yellow hamet and cabbage sawfly.

Examples of Orhtopterous pest insects include grasshopper, German cockroach, American cockroach and Japanese cockroach.

Examples of Isopterous pest insects include Formosan subterranean termite and Reticulitermes speratus Kolbe.

Examples of Aphanipterous pest insects include human flea.

Examples of Anoplurous pest insects include human louse.

Examples of mites include two-spotted spider mite, carmine spider mite, Kanzawa spider mite, citrus red mite, European red mite, citrus rust mite, apple rust mite, Tarsonemus sp., Brevipalpus sp., Eotetranychus sp., Robin bulb mite, common grain mite, Desmatophagoides farinae, Boophilus microplus and Haemaphysallis bispinosa.

Examples of plant-parasitic nematodes include southern root-knot nematode, root lesion nematode, soybean cyst nematode, rice white-tip nematode, and pine wood nematode.

Among the pest insects as recited above, Lepidopterous pest insects, Hemipterous pest insects, mites, Thysanopterous pest insects, and Coleopterous pest insects are preferable targets for the compounds of the present invention, and particularly, mites are the most preferable targets.

In the recent time, various pest insects, such as diamond-back moths, planthoppers, leafhoppers, aphids, and the like, have developed resistance against organophosphorous insecticides, carbamate insecticides, acaricides, or the like. Therefore, the foresaid insecticides and acaricides have lost their efficacies against the pest insects and mites those which have developed resistance against them. Accordingly, there has been a desire for chemicals effective on pest insects and mites of the resistance strains. The compounds of the present invention are chemicals having excellent insecticidal and acaricidal effects on pest insects resistant to organophosphorous pesticides, carbamate insecticides or pyrethroid pesticides and mites resistant to acaricides, as well as those of sensitive strains.

The compounds of the present invention induce very slight phytotoxicity on plants, have low toxicity on fishes and warm-blood animals, and are highly safe.

Further, the compounds of the present invention can be used also as an anti-fouling agent that prevents aqueous adhesive organisms from adhering to structures placed in water such as the outer bottom of a vessel and fishing nets.

The chemical compounds of the present invention may have germicidal activities, weeding activities, or plant controlling effects. Moreover, the intermediate chemical compounds of the chemical compounds of the present invention may have activities of killing insects or mites.

Insecticides and acaricides of the present invention include at least one kind of the chemical compounds of the present invention as their active ingredients. Although the chemical compounds of the present invention may be directly used without adding other constituents, they are generally used by mixing them with solid carriers, liquid carriers, or gaseous carriers, or by immersing them in substrates such as porous-ceramic plates, nonwoven fabrics, or the like, followed by adding surfactants or other adjuvants, if needed, to formulate them, for using as agrichemicals, in forms of conventional agrichemicals, that is, water dispersible powders, granules, dusting powders, emulsions, water soluble powders, suspensions, granular water dispersible powders, floables, aerosols, aerosols, heat-transpiration agents, fumigants, poison baits, microcapsules, or the like.

When the chemical compounds are used as solid agents, vegetable powders such as soy bean grains, wheats, or the like, mineral impalpable powders such as diatomites, apatites, gypsums, talcs, bentonites, pyrophyllites, clays, or the like, organic or inorganic chemical compounds such as benzoates of soda, ureas, mirabilites, or the like, can be used as the additives or the carriers. When the chemical compounds are used as liquid agents, petroleum fractions such as kerosenes, xylenes, and solvent naphthas, or the like, cyclohexanes, cyclohexanons, dimethylformamides, dimethylsulfoxides, alcohols, acetones, methyl isobutylketons, mineral oils, vegetable oils, water, or the like, can be used as solvents. As the gaseous carriers used for propellants, butane gases, LPG, dimethyl ethers, or carbonic acid gases can be use.

As substrates for the poison baits, bait constituents such as, for example, cereal powders, vegetable oils, sugars, crystalline celluloses, or the like, antioxidants such as dibutylhydroxytoluene, nordihydroguairetic acid, or the like, preservatives such as dehydroacetic acid, or the like, agents for preventing children or pets from eating them by mistake, such as powdered capsicums or the like, or flavors for attracting pest insects, such as cheese flavors, onion flavors, or the like, can be used.

If needed, surfactants may be added to these formulations so as to form their uniform and stable conformations. Although there is no limitations on the surfactants, their examples include nonionic surfactants such as alkyl ethers added with polyoxyethylenes, higher fatty acid esters added with polyoxyethylenes, sorbitan higher fatty acid esters added with polyoxyethylenes, tristyrylphenyl ethers added with polyoxyethylenes, and the like, sulfuric ester salts of alkylphenylethers added with polyoxyethylenes, alkylnaphthalene sulfonates, polycarboxylates, lignin sulfonates, formaldehyde condensates of alkylnaphthalene sulfonates, copolymers of isobutylene-maleic anhydrides, and the like.

When the chemical compounds of the present invention are used on pest control agents for farming, the amounts of their active ingredients are from 0.01 to 90% by weight, preferably from 0.05 to 85% by weight, and, they may be used as solutions, suspensions, or emulsions, in which their water dispersible powders, emulsions, suspensions, floable agents, water soluble powders, or granular water dispersible powders are diluted with water to their determined concentrations, they may be used by directly sparging them onto plants or soils, in case that they are dusting powders or granules.

When the chemical compounds of the present invention are used as pest control agents for preventing epidemics, they may be used by diluting them with water to their determined concentrations, in case that they are emulsions, water dispersible powders, floable agents, or the like, or, they may be directly used, in case that they are oil solutions, aerosols, aerosols, poison baits, anti-mite sheets, or the like.

When the chemical compounds of the present invention are used as pest control agents for preventing animal external parasites from breeding on, and exterminating them from, domestic animals such as cattles, pigs, or the like, or pets such as dogs, cats, or the like, formulations of the chemical compounds of the present invention are generally used according to a method known in a veterinary art. Examples of the method include a method of administering them for systemic control by tablets, capsules, immersion liquids, mixtures with feeds, suppositories, injections (intramuscular, subcutaneous, intravenous, intraperitoneal, or the like), or the like, a method of administering them for non-systemic control by spraying, pouring on, or spotting on oily or aqueous liquid formulations, and a method of wearing materials produced by molding resin formulations into suitable forms such as collars, ear tags, or the like. In this case, the chemical compounds of the present invention are generally used at a rate of 0.01 to 1000 mg per 1 kg of a host animal.

It goes without saying that the chemical compounds of the present invention can be used alone for exerting their sufficient effects, they can also be mixed with, or used with at least one kind of other pest control agents, fungicides, insecticides, acaricides, pesticides, plant growth regulators, synergists, fertilizers, soil conditioners, animal feeds, or the like.

Typical examples of active ingredients of the fungicides, the insecticides, the acaricides, the plant growth regulators, or the like, which may be mixed with, or used with the chemical compounds of the present invention, are shown hereinafter.

Fungicide:

captan, folpet, thiuram, ziram, zineb, maneb, mancozeb, propineb, polycarbamate, chlorothalonil, quintozene, captafol, iprodione, procymidone, vinclozolin, fluoroimide, cymoxanil, mepronil, flutolanil, pencycuron, oxycarboxin, fosetyl-aluminum, propamocarb, triadimefon, triadimenol, propiconazole, dichlobutorazol, bitertanol, hexaconazol, microbutanil, flusilazole, etaconazole, fluotrirnazole, flutriafen, penconazole, diniconazole, cyproconazole, fenarimol, triflumizole, prochloraz, imazalil, pefurazoate, tridemorph, fenpropimorph, triforine, buthiobate, pyrifenox, anilazine, polyoxin, metalaxyl, oxadixyl, furalaxyl, isoprothiolane, probenazole, pyrrolnitrin, blasticidin S, kasugamycin, balidamycin, dihydrostreptomycin sulfate, benomyl, carbendazim, thiophanate methyl, hymexazol, basic copper chloride, basic copper sulfate, fentin acetate, triphenyltin hydroxide, diethofencarb, methasulfocarb, qinomethionate, binapacryl, lecithin, sodium hydrogencarbonate, dithianon, dinocap, fenaminosulf, diclomezine, guazatine, dodine, IBP, edifenphos, mepanipyrim, ferimzone, trichlamide, methasulfocarb, fluazinam, ethoqinolac, dimethomorph, pyroquilon, tecloftalam, fthalide, phenazine oxide, thiabendazole, tricyclazole, vinclozolin, cymoxanil, cyclobutanil, guazatine, propamocarb hydrochloride, oxolinic acid, and the like.

Organic Phosphorus and Carbamate Base Insecticides:

fenthion, fenitrothion, diazinon, chlorpyrifos, ESP, vamidothion, phenthoate, dimethoate, formothion, malathion, trichlorfon, thiometon, phosmet, dichlorvos, acephate, EPBP, methyl parathion, oxydemetone methyl, ethion, salithion, cyanophos, isoxathion, pyridafenthion, phosalone, methidathion, sulprofos, chlorfenvinphos, tetrachlorovinphos, dimethylvinphos, propaphos, isofenphos, ethyl thiometon, profenofos, pyraclofos, monocrotophos, azinphos methyl, aldicarb, methomyl, thiodicarb, carbofuran, carbosulphan, benfuracarb, furathiocarb, propoxur, BPMC, MTMC, MIPC, carbaryl, pirimicarb, ethiophencarb, phenoxycarb, cartap, thiocyclam, bensultap, and the like.

Pyrethroid Base Insecticides:

permethrin, cypermethrin, deltamethrin, fenvalerate, fenpropathrin, pyrethrin, allethrin, tetramethrin, resmethrin, dimethrin, propathrin, phenothrin, prothrin, fluvalinate, cyfluthrin, cyhalothrin, flucythrinate, etofenprox, cycloprothrin, tralomethrin, silafluofen, acrinathrin, and the like.

Benzoylurea Base and Other Insecticides:

diflubenzuron, chlorfluazuron, hexaflumuron, triflumuron, tetra benzuron, flufenoxuron, flucycloxuron, buprofezin, pyriproxyfen, methoprene, benzoepin, diafenthiuron, imidacloprid, acetamiprid, fipronil, nicotine sulfate, rotenone, metaldehyde, machine oil, BT and microbial agrichemicals such as insect pathogenic viruses, and the like.

Nematocide:

phenamiphos, fosthiazate, and the like.

Acaricide:

Chlorobenzilate, phenisobromolate, dicofol, amitraz, BPPS, benzomate, hexathiazox, fenbutatin oxide, polynactins, quinomethionate, CPCBS, tetradifon, avermectin, milbemectin, clofentezine, cyhexatin, pyridaben, fenpyroxymate, tebufenpyrad, pyrimidifen, fenothiocarb, dienochlor, and the like.

Plant Growth Regulator:

gibberellins (for example, gibberellin A3, gibberellin A4, gibberellin A7) IAA, NAA.

EXAMPLES

In the following, the present invention will be explained in more detail with examples, but the present invention should not be interpreted to be limited to these examples.

Preparation Example 1

Preparation of 4-[4-nitro-3-(trifluoromethyl)phenoxy]-1-[5-(trifluoromethyl)-2-pyridyl]-piperidine (Chemical Compound No. 1-39)

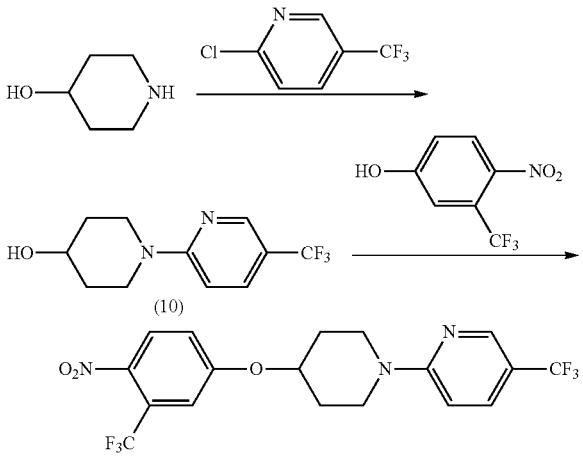

Triethylamine (4.5 g) was added into the ethanol solution (25 ml) of 4-hydroxypiperidine (3.0 g) and 2-chloro-5-trifluoromethylpyridine (5.4 g), and the mixture was then refluxed with heating over night. The mixture was poured into water, and was then subjected to extraction with chloroform. Its organic layer was washed with water, and was then dried with anhydrous magnesium sulfate. The solvent was evaporated under reduced pressure to obtain the chemical compound (10) (5.98 g), which was used for the following reaction.

The THF (30 ml) solution of azodicarboxylic acid diisopropyl ester (4.3 g) was dropped, with chilling on ice, into the THF (30 ml) solution of the chemical compound (10) (4.9 g), 5-hydroxy-2-nitrobenzotrifluoride (3.2 g), and triphenylphosphine (5.6 g). After the mixture was warmed to room temperature, and was then stirred for 3 hours, it was concentrated under reduced pressure. Its residue was purified by column chromatography to obtain the chemical compound mentioned in the above title (5.98 g).

Viscous Oil $^1$HNMR ($CDCl_3$) δ 1.86-1.97 (m, 2H), 2.04-2.14 (m, 2H), 3.64-3.72 (m, 2H), 3.90-3.99 (m, 2H), 4.71-4.77 (m, 1H), 6.70 (d, 1H), 7.13 (d, 1H), 7.32 (d, 1H), 7.65 (d, 1H), 8.02 (d, 1H), 8.41 (s, 1H)

Preparation Example 2

Preparation of 4-[4-amino-3-(trifluoromethyl)phenoxy]-1-[5-(trifluoromethyl)-2-pyridyl]-piperidine (Chemical Compound No. 1-68)

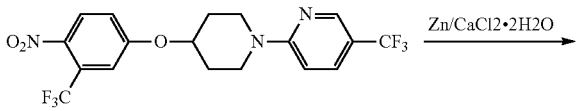

-continued

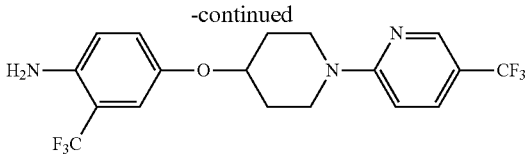

Zinc powders (18.8 g) and calcium chloride dihydrate (1.9 g) were added into the ethanol (300 ml) solution of the piperidine produced in Preparation Example 1 (Chemical compound No. 1-39, 5.7 g), and the mixture was then refluxed with heating over night. After the mixture was cooled to room temperature, it was filtered through a pad of CELITE, and its filtrate was concentrated under reduced pressure. Its residue was diluted with chloroform, was washed, and was then dried with anhydrous magnesium sulfate. Its solvent was evaporated under reduced pressure to produce the chemical compound mentioned in the above title (5.4 g).

$n_D^{21.6}$ 1.5259

$^1$H NMR ($CDCl_3$) δ 1.77-1.88 (m, 2H), 1.94-2.04 (m, 2H), 3.53-3.61 (m, 2H), 3.90-3.99 (m, 3-4H), 4.38-4.45 (m, 1H), 6.69 (t, 2H), 7.00 (d, 1H), 7.04 (d, 1H), 7.62 (d, 1H), 8.39 (s, 1H)

Preparation Example 3

Preparation of 4-[4-chloro-3-(trifluoromethyl)phenoxy]-1-[5-(trifluoromethyl)-2-pyridyl]-piperidine (Chemical compound No. 1-15)

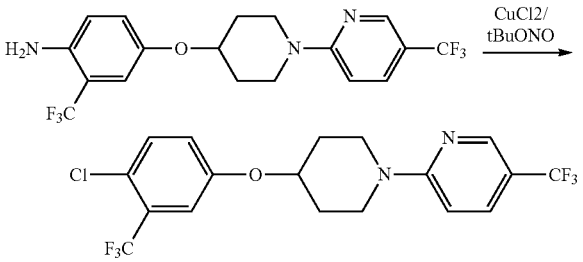

t-Butyl nitrite (0.13 g) was dropped into the acetonitrile suspension (5 ml) of copper chloride (II) (0.14 g) with chilling on ice. After the mixture was stirred for 10 minutes, the acetonitrile (3 ml) solution of the piperidine (Chemical compound No. 1-168, 0.35 g) produced in Preparation Example 2 was added into it with chilling on ice. The mixture was warmed to room temperature, and was then stirred for 1 more hour. The mixture was poured into ice-water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (0.2 g).

$n_D^{21.9}$ 1.5275

$^1$H NMR ($CDCl_3$) δ 1.82-1.92 (m, 2H), 1.99-2.08 (m, 2H), 3.60-3.68 (m, 2H), 3.89-3.97 (m, 2H), 4.56-4.63 (m, 1H), 6.69 (d, 1H), 7.01 (d, 1H), 7.24 (d, 1H), 7.40 (d, 1H), 7.63 (d, 1H), 8.40 (s, 1H)

Preparation Example 4

Preparation of 4-[4-bromo-3-(trifluoromethyl)phenoxy]-1-[5-(trifluoromethyl)-2-pyridyl]-piperidine (Chemical Compound No. 1-23)

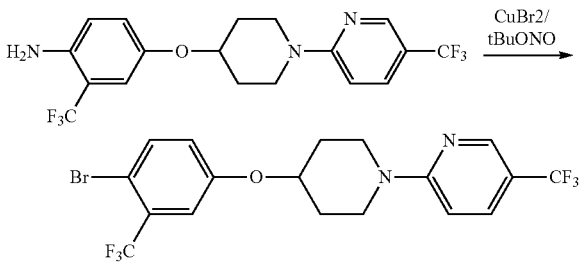

t-Butyl nitrite (0.12 g) was dropped into the acetonitrile (5 ml) suspension of copper bromide (II) (0.22 g) with chilling on ice. After the mixture was stirred for 10 minutes, the acetonitrile (2 ml) solution of the piperidine (Chemical compound No. 1-168, 0.32 g) produced in Preparation Example 2 was added into it with chilling on ice. The mixture was warmed to room temperature, and was then stirred for 2.5 more hours. The mixture was poured into ice-water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (0.21 g).

$n_D^{21.9}$1.5365

$^1$H NMR ($CDCl_3$) δ 1.81-1.92 (m, 2H), 1.99-2.08 (m, 2H), 3.60-3.68 (m, 2H), 3.88-3.96 (m, 2H), 4.57-4.63 (m, 1H), 6.68 (d, 1H), 6.94 (d, 1H), 7.24 (s, 1H), 7.58 (s, 1H), 7.63 (d, 1H), 8.40 (s, 1H)

Preparation Example 5

Preparation of 4-[4-bis(methylsulfonyl)amino-3-(trifluoromethyl)phenoxy]-1-[5-trifluoromethyl-2-pyridyl]piperidine (Chemical Compound No. 1-78)

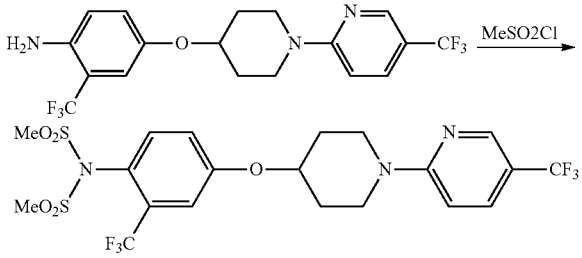

Methane sulfonyl chloride (0.09 g) and triethylamine (0.08 g) were added, with chilling on ice, into the THF (5 ml) solution of the piperidine (Chemical compound No. 1-168, 0.32 g) produced in Preparation Example 2. After the mixture was warmed to room temperature, and was then stirred for 4 hours, it was refluxed with heating for 3.5 more hours. After the mixture was cooled to room temperature, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (0.20 g).

Amorphous $^1$H NMR ($CDCl_3$) δ 1.87-1.96 (m, 2H), 2.01-2.10 (m, 2H), 3.47 (s, 6H), 3.64-3.73 (m, 2H), 3.88-3.96 (m, 2H), 4.64-4.69 (m, 1H), 6.70 (d, 1H), 7.13 (dd, 1H), 7.32 (d, 1H), 7.37 (d, 1H), 7.64 (d, 1H), 8.41 (s, 1H)

Preparation Example 6

Preparation of 4-[2-methoxymethoxy-4-(trifluoromethyl)-phenoxy]-1-[5-(trifluoromethyl)-2-pyridyl] piperidine (Chemical Compound No. 1-105)

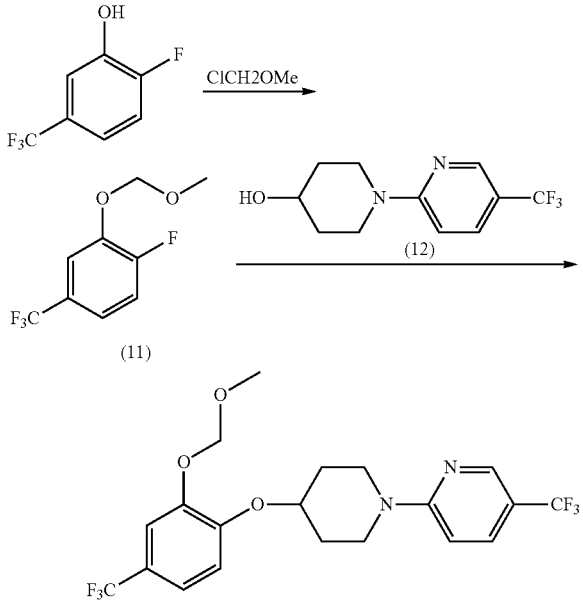

After 60% sodium hydride (88 mg) was added into the DMF (5 ml) solution of 4-fluoro-3-hydroxybenzotrifluoride (0.36 g), onto which chloromethyl methyl ether (0.24 g) was dropped with chilling on ice, the mixture was warmed to room temperature, and was then stirred for 5 hours. The mixture was poured into water, and was then subjected to extraction with ethyl acetate. Its organic layer was washed with brine, and was then dried with anhydrous magnesium sulfate. Its solvent was evaporated under reduced pressure to produce a crude chemical compound (11) (0.45 g), which was used for the next reaction.

60% sodium hydride (90 mg) was added into the DMF (5 ml) solution of piperidinol (12) (0.49 g) at room temperature. After the mixture was stirred for 10 minutes, the DMF (5 ml) solution of benzotrifluoride (11) was added into it, which was then heated to about 100° C., followed by stirring over night. After the mixture was cooled to room temperature, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (0.56 g).

$n_D^{23.9}$1.4969

$^1$H NMR ($CDCl_3$) δ 1.87-1.96 (m, 2H), 2.00-2.08 (m, 2H), 3.53 (s, 3H), 3.56-3.65 (m, 2H), 3.95-4.03 (m, 2H), 4.61-4.65 (m, 1H), 5.21 (s, 2H), 6.69 (d, 1H), 7.02 (d, 1H), 7.25 (d, 1H), 7.38 (s, 1H), 7.63 (d, 1H), 8.40 (s, 1H)

Preparation Example 7

Preparation of 4-[2-hydroxy-4-(trifluoromethyl)phenoxy]-1-[5-(trifluoromethyl)-2-pyridyl]piperidine (Chemical Compound No. 1-4)

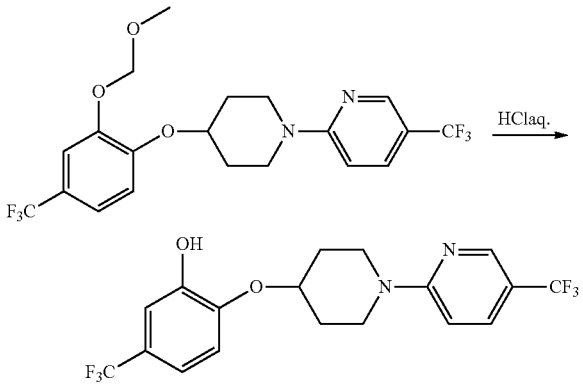

10% hydrochloric acid solution (5 ml) was added into the THF (5 ml) solution of the piperidine (chemical compound No. 1-105, 0.38 g) produced in Preparation Example 6 at room temperature. After its mixture was stirred for 2 hours, 10% hydrochloric acid solution (5 ml) was added into it, and was then stirred over night. The mixture was poured into water, and was then subjected to extraction with ethyl acetate. Its organic layer was washed with a saturated bicarbonate solution and brine, and was then dried with anhydrous magnesium sulfate. Its solvent was evaporated under reduced pressure to produce the chemical compound mentioned in the above title (0.31 g).

Viscous Oil $^1$H NMR ($CDCl_3$) δ 1.85-1.94 (m, 2H), 2.11-2.17 (m, 2H), 3.48-3.57 (m, 2H), 4.02-4.10 (m, 2H), 4.66-4.70 (m, 1H), 5.72 (s, 1H), 6.70 (d, 1H), 6.95 (d, 1H), 7.13 (d, 1H), 7.20 (s, 1H), 7.65 (d, 1H), 8.41 (s, 1H)

Preparation Example 8

Preparation of 4-[2-acetoxy-4-(trifluoromethyl)phenoxy]-1-[5-(trifluoromethyl)-2-pyridyl]piperidine (Chemical Compound No. 1-167)

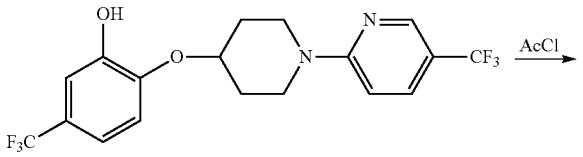

-continued

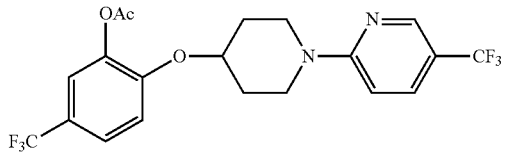

Acetyl chloride (36 mg) was added, with chilling on ice, into the acetonitrile (5 ml) solution of the piperidine (Chemical compound No. 1-4, 0.17 g) produced in Preparation Example 7 and triethylamine (50 mg). After its mixture was warmed to room temperature, and was then stirred for 3 hours, it was poured into water, and was then subjected to extraction with ethyl acetate. Its organic layer was washed with brine, and was then dried with anhydrous magnesium sulfate. Its solvent was evaporated under reduced pressure to produce the chemical compound mentioned in the above title (0.22 g).

mp. 85-95° C.

$^1$H NMR ($CDCl_3$) δ 1.88-2.05 (m, 4H), 2.30 (s, 3H), 3.70-3.84 (m, 4H), 4.68-4.70 (m, 1H), 6.68 (d, 1H), 7.05 (d, 1H), 7.33 (s, 1H), 7.47 (d, 1H), 7.63 (d, 1H), 8.39 (s, 1H)

Preparation Example 9

Preparation of 3-[4-(trifluoromethyl)phenoxy]-1-[5-(trifluoromethyl)-2-pyridy]pyrrolidine (Chemical compound No. 8-63)

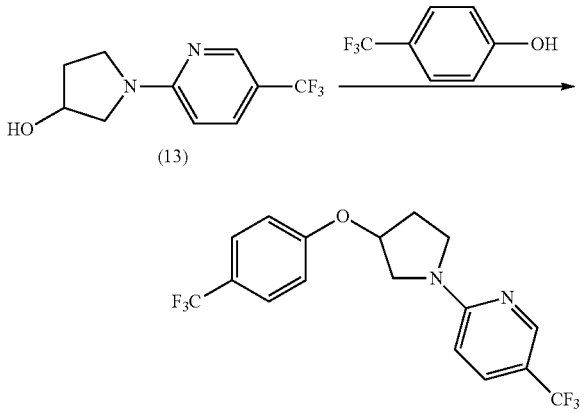

The chemical compound mentioned in the above title (0.32 g) was produced by using pyrrolidinol (13) (0.35 g) and 4-trifluoromethylphenol (0.16 g) in a manner similar to that of Example 1. The chemical compound (13) was produced in a manner similar to that of the chemical compound (10) in Preparation Example 1.

mp. 109-112° C.

$^1$H NMR ($CDCl_3$) δ 2.26-2.46 (m, 2H), 3.62-3.75 (m, 2H), 3.85 (s, 2H), 5.10-5.15 (m, 1H), 6.42 (d, 1H), 6.96 (d, 2H), 7.56 (d, 2H), 7.62 (d, 1H), 8.39 (s, 1H)

Preparation Example 10

Preparation of 2-methyl-4-[2-propoxy-4-(trifluoromethyl)phenoxy]-1-[5-(trifluoromethyl)-2-pyridyl] piperidine (Chemical compound No. 1-93)

Step 1

Preparation of 1-benzyloxycarbonyl-2-methyl-4-piperidinol (14)

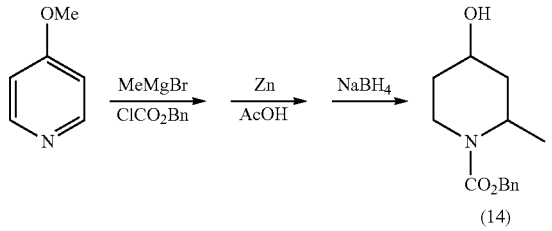

The following reaction was carried out according to a method described in Tetrahedron Lett. 1986, 27, 4549.

Methyl magnesium bromide (3.0 M, ether solution, 7.6 ml) was dropped into the THF (25 ml) solution of 4-methoxypyridine (2.50 g) with maintaining a temperature between −30° C. and −20° C. After its mixture was stirred for 10 minutes, benzyl chloroformate (3.90 g) was dropped into it with maintaining a temperature between −30° C. and −20° C. After the mixture was stirred for 30 minutes, it was warmed to room temperature. The mixture was poured into 10% hydrochloric acid, and was then subjected to extraction with ethyl acetate. Its organic layer was washed with a brine, and was then dried with magnesium sulfate. Its solvent was evaporated under reduced pressure to produce an oily matter (5.34 g), which was directly used for the next reaction.

The following reaction was carried out according to a method described in J. Org. Chem., 2001, 66, 2181.

This oily matter was dissolved in acetic acid (150 ml), into which zinc (21.4 g) was added at room temperature. Its suspension was refluxed with heating for 6 hours. After the mixture was cooled, it was filtered through a pad of CELITE, and its filtrate was evaporated under reduced pressure. Water was added into its residue, which was then neutralized with sodium hydroxide, and was then subjected to extraction with ethyl acetate. Its organic layer was washed with brine, and was then dried with magnesium sulfate. Its solvent was evaporated under reduced pressure to produce an oily matter (5.01 g). Into the ethanol (25 ml) solution of this oily matter (2.47 g), sodium borohydride (0.38 g) was added at room temperature, and its mixture was then stirred for 1 hour. The mixture was concentrated under reduced pressure, into which water was then added, and was then subjected to extraction with ethyl acetate. Its organic layer was washed with brine, and was then dried with magnesium sulfate. Its solvent was evaporated under reduced pressure to produce a crude chemical compound (14) (2.39 g).

$^1$H NMR ($CDCl_3$) δ 1.16-1.93 (m, 7H), 2.95-3.37 (m, 1H), 3.88-4.70 (m, 3H), 5.13 (m, 2H), 7.35 (m, 5H)

Step 2

Preparation of 1-benzyloxycarbonyl-2-methyl-4-[2-propoxy-4-(trifluoromethyl) phenoxy]piperidine

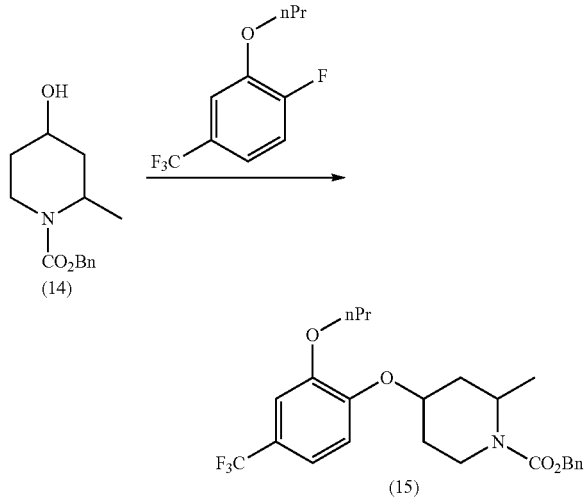

60% sodium hydride (0.42 g) was added to the DMF (25 ml) solution of the chemical compound (14) at room temperature. After its mixture was stirred for 30 minutes, 4-fluoro-3-propoxy benzotrifluoride (2.13 g) was added to it, and was then heated at 100° C. over night. After the mixture was cooled to room temperature, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce a chemical compound (15) (1.02 g).

$^1$H NMR ($CDCl_3$) δ 1.05 (t, 3H), 1.26 (m, 3H), 1.50-2.04 (m, 6H), 3.00-3.40 (m, 1H), 3.92-4.16 (m, 3H), 4.50-4.73 (m, 2H), 5.15 (m, 2H), 6.93 (m, 1H), 7.10 (m. 2H), 7.33 (m, 5H)

Step 3

Preparation of 2-methyl-4-[2-propoxy-4-(trifluoromethyl)phenoxy-1-[5-(trifluoromethyl)-2-pyridyl]piperidine

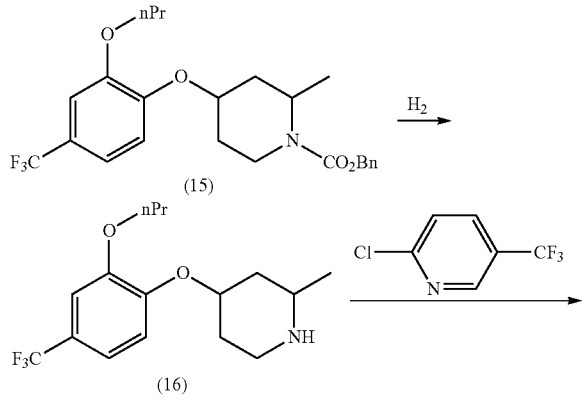

-continued

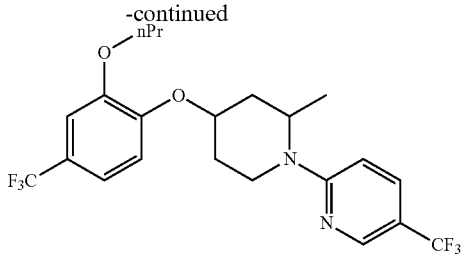

5% palladium-carbon (0.20 g) was added to the ethanol (25 ml) solution of the chemical compound (15). This suspension was heated at 80° C. for 8 hours in a hydrogen atmosphere. After its mixture was cooled, it was filtered through a pad of CELITE. Its filtrate was evaporated under reduced pressure to produce a crude chemical compound (16) (0.70 g).

2-chloro-5-(trifluoromethyl)pyridine (4.0 g) and potassium carbonate (1.53 g) were added to the acetonitrile (15 ml) solution of this piperidine, and its mixture was then refluxed with heating for 3 days. After the mixture was cooled, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (30 mg).

Viscous Oil $^1$HNMR ($CDCl_3$) δ 1.04 (t, 3H), 1.23 (d, 3H), 1.71-1.97 (m, 4H), 2.10-2.26 (m, 2H), 3.05 (m, 1H), 3.98 (t, 2H), 4.43 (m, 1H), 4.63 (m, 1H), 4.88 (m, 1H), 6.61 (d, 1H), 7.00-7.26 (m, 3H), 7.62 (d, 1H), 8.39 (s, 1H)

Preparation Example 11

Preparation of 3α-[2-methoxy-4-(trifluoromethyl) phenoxy]-8-[5-(trifluoromethyl)-2-pyridyl]-8-azabicyclo[3.2.1]octane (Chemical compound No. 2-77).

Step 1

Preparation of 3α-hydroxy-8-azabocyclo[3.2.1]octane acetic acid (18)

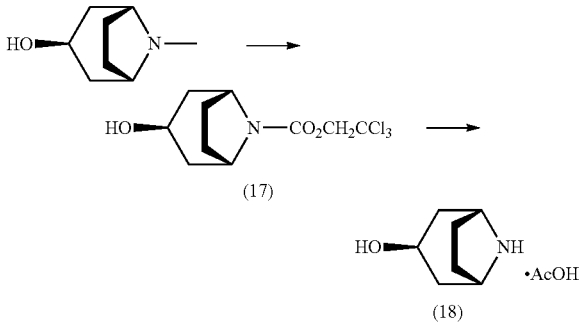

2,2,2-trichloroethyl chloroformate ester (23.3 g) was added to the benzene (150 ml) suspension of tropine (14.1 g) and potassium carbonate (1.4 g) at room temperature, and its mixture was refluxed with heating for 3.5 hours. After the mixture was cooled to room temperature, it was poured into water, and was then subjected to extraction with ethyl acetate. Its organic layer was washed with brine, and was then dried with anhydrous magnesium sulfate. Its solvent was evaporated under reduced pressure to produce an oily carbonate (17) (30.08 g), which was directly used for the next reaction. Into the acetic acid (250 ml) solution of this carbonate (17), zinc powders (65 g) was added. After this mixture was stirred for 5 minutes, it was heated at 80° C. for 1 hour. After the mixture was cooled to room temperature, it was filtered through a pad of CELITE. Its filtrate was evaporated under reduced pressure to produce a crude chemical compound (18) (15.5 g).

Step 2

Preparation of 3α-hydroxy-8-[5-(trifluoromethyl)-2-pyridyl]-8-azabicyclo[3.2.1]octane (19)

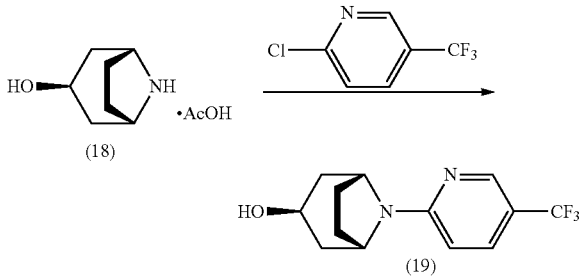

The acetonitrile (150 ml) suspension of the crude chemical compound (18) (5.64 g), potassium carbonate (41.5 g), and 2-chloro-5-trifluoromethylpyridine (8.2 g) was refluxed with heating for 3.5 hours. After its mixture was cooled to room temperature, it was poured into water, and was then subjected to extraction with ethyl acetate. Its organic layer was washed with brine, and was then dried with anhydrous magnesium sulfate. Its solvent was evaporated under reduced pressure to produce a chemical compound (19) (3.5 g) as a crystal form.

$^1$H NMR ($CDCl_3$) δ 1.42 (d, 1H), 1.77 (d, 2H), 2.05-2.20 (m, 4H), 2.32-2.39 (m, 2H), 4.09 (brs, 1H), 4.53 (brs, 2H), 6.52 (d, 1H), 7.58 (dd, 1H), 8.38 (d, 1H)

Step 3

Preparation of 3α-[2-methoxy-4-(trifluoromethyl) phenoxy]-8-[5-(trifluoromethyl)-2-pyridyl]-8-azabicyclo[3.2.1]octane compound (19)

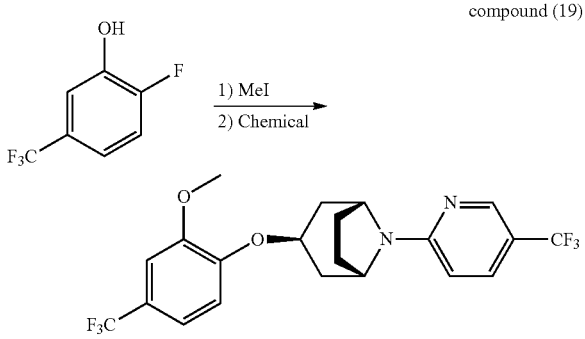

60% sodium hydride (35 mg) was added into the DMF (3 ml) solution of 4-fluoro 3-hydroxybenzotrifluoride (0.17 g)

with chilling on ice. After its mixture was stirred for 20 minutes, iodomethane (0.11 g) was added into it, and was then heated at 60° C. with stirring for 40 minutes. After the mixture was cooled to room temperature, the chemical compound (19) (0.22 g) and 60% sodium hydride (35 mg) were added to it at room temperature, followed by heating at 100° C. over night. After the mixture was cooled to room temperature, it was poured into ice-water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (0.18 g).

Viscous Oil.

$^1$H NMR ($CDCl_3$) δ 2.00-2.22 (m, 6H), 2.38-2.44 (m, 2H), 3.90 (s, 3H), 4.56-4.61 (m, 3H), 6.56 (d, 1H), 6.77 (d, 1H), 7.10 (s, 1H), 7.16 (d, 1H), 7.60 (dd, 1H), 8.40 (brd, 1H)

Preparation Example 12

Preparation of 3α-[2-propoxy-4-(trifluoromethyl) phenoxy]-8-[5-(trifluoromethyl)-2-pyridyl]-8-azabicyclo[3.2.1]octane (Chemical compound No. 2-82)

Step 1

Preparation of 8-methyl-3α-[4-propoxy-4-(trifluoromethyl)phenoxy]-8-azabicyclo[3.2.1]octane (20)

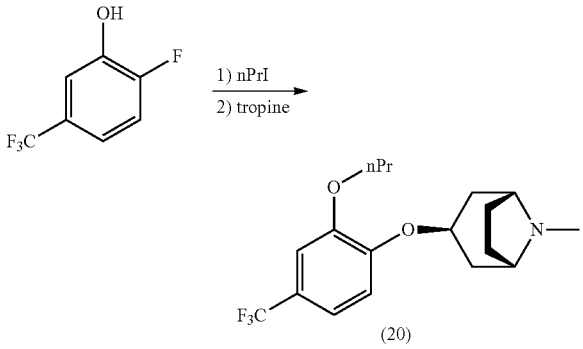

60% sodium hydride (0.44 g) was added into the DMF (15 ml) solution of 4-fluoro-3-hydroxybenzotrifluoride (1.8 g) with chilling on ice. After its mixture was stirred for 20 minutes, the DMF (3 ml) solution of 1-iodopropane (1.7 g) was added to it, and was then stirred for 4 more hours. To the mixture, tropine (1.42 g) and 60% sodium hydride (0.43 g) were added at room temperature, and were then heated at 100° C. with stirring over night. After the mixture was cooled to room temperature, it was poured into ice-water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce an oily chemical compound (20) (1.1 g).

$^1$HNMR ($CDCl_3$) δ 1.08 (t, 3H), 1.83 (q, 2H), 1.90-2.20 (m, 8H), 2.30 (s, 3H), 3.10-3.11 (m, 2H), 3.95 (t, 2H), 4.58 (t, 1H), 6.79 (d, 1H), 7.05 (s, 1H), 7.13 (d, 1H)

Step 2

Preparation of 3α-[2-propoxy-4-(trifluoromethyl) phenoxy]-8-azabicyclo[3.2.1]octane hydrochloride (22)

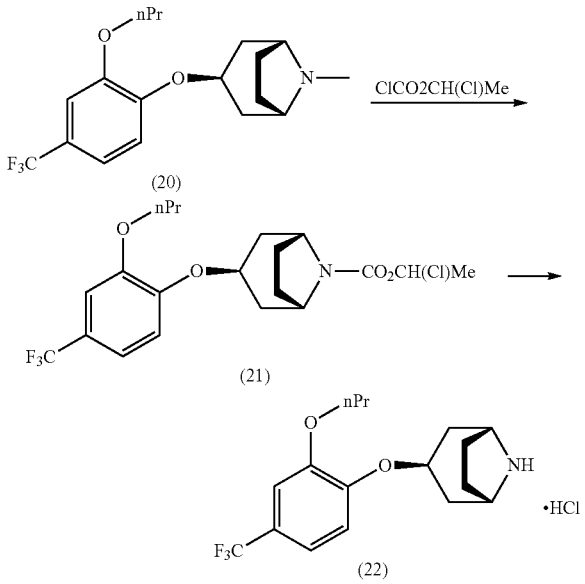

The methylene chloride (4 ml) solution of 1-chloroethyl chloroformate (0.83 g) was added to the methylene chloride (6 ml) solution of the chemical compound (20) (1.0 g) at room temperature, and the mixture was then refluxed with heating over night. The mixture was diluted with methylene chloride, was then washed with a saturated bicarbonate solution and a brine, and was then dried with anhydrous magnesium sulfate. Its solvent was evaporated under reduced pressure to produce a crude carbonate (21), which was directly used for the next reaction.

Methanol (6 ml) was added to the chemical compound (21), and was then refluxed with heating for 2.5 hours. Its mixture was concentrated under reduced pressure to produce a crude (22), which was directly used for the next reaction.

$^1$HNMR of the salt-free (22) ($CDCl_3$) δ 1.10 (t, 3H), 1.61 (brs, 1H), 1.70-1.92 (m, 4H), 2.01-2.09 (m, 4H), 2.20-2.31 (m, 2H), 3.52 (brs, 2H), 3.95 (t, 2H), 4.63-4.65 (m, 1H), 6.78 (d, 1H), 7.06 (s, 1H), 7.15 (d, 1H)

Step 3

Preparation of 3α-[2-propoxy-4-(trifluoromethyl) phenoxy]-8-[5-(trifluoromethyl)-2-pyridyl]-8-azabicyclo[3.2.1]octane

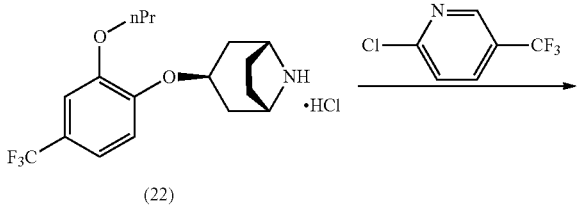

-continued

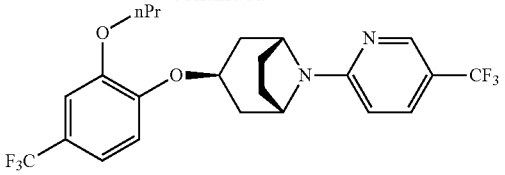

(23)

The ethanol (10 ml) solution of the crude (22), triethylamine (1.18 g), and 2-chloro-5-trifluoromethylpyridine (0.53 g) was refluxed with heating over night. Into its mixture, triethylamine (3 g), 2-chloro-5-trifluoromethylpyridine (1.6 g), and ethanol (10 ml) were added, and were then further refluxed with heating over night. After the mixture was cooled to room temperature, it was poured into ice-water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (0.31 g).

mp. 90-92° C.

$^1$H NMR ($CDCl_3$) δ 1.09 (t, 3H), 1.82-1.93 (m, 2H), 2.01-2.23 (m, 6H), 2.43-2.50 (m, 2H), 3.97 (t, 2H), 4.56-4.62 (m, 3H), 6.55 (d, 1H), 6.77 (d, 1H), 7.08 (s, 1H), 7.15 (d, 1H), 7.60 (dd, 1H), 8.40 (s, 1H)

Preparation Example 13

Preparation of 8β-[2-propoxy-4-(trifluoromethyl) phenoxy]-3-[5-(trifluoromethyl)-2-pyridyl]-3-azabicyclo[3.2.1]octane (Chemical compound No. 5-97)

Step 1

Preparation of N-benzyl-8β-[2-propoxy-4-(trifluoromethyl)phenoxy]-3-azabicyclo[3.2.1]octane (25)

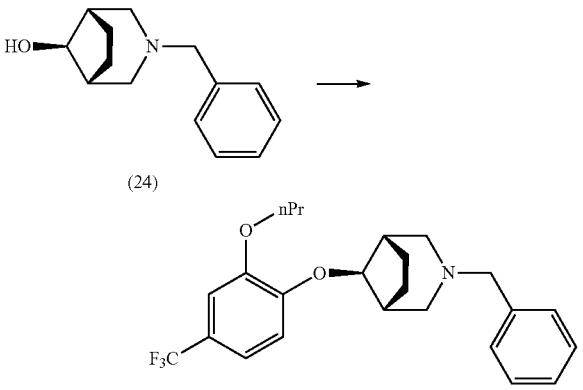

(24)

(25)

N-benzyl-3-azabicyclo[3.2.1]octane-8β-ol (24) was synthesized according to a method described in J. Med. Chem. 2003, 46, 1456-1464.

60% sodium hydride (0.12 g) was added into the DMF (4 ml) solution of 4-fluoro-3-hydroxybenzotrifluoride (0.50 g) with chilling on ice. After the mixture was stirred for 30 minutes at room temperature, 1-iodopropane (0.51 g) was added to it. The mixture was heated to 90° C., and was then stirred for 30 minutes. After the DMF (4 ml) solution of (24) (0.41 g) and 60% sodium hydride (0.09 g) were added to the mixture at room temperature, and were then stirred for 15 minutes, they were heated to 100° C., and were then stirred for 2 hours. After the mixture was cooled to room temperature, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce an oily matter (25) (0.75 g).

$^1$H NMR ($CDCl_3$) δ 1.05 (t, 3H), 1.75-1.91 (m, 6H), 2.19 (d, 2H), 2.34 (brs, 2H), 2.74 (d, 2H), 3.51 (s, 2H), 3.96 (t, 2H), 4.33 (s, 1H), 6.94 (d, 1H), 7.07 (s, 1H), 7.13 (d, 1H), 7.20-7.34 (m, 5H)

Step 2

Preparation of 8β-[2-propoxy-4-(trifluoromethyl) phenoxy]-3-[5-(trifluoromethyl)-2-pyridyl]-3-azabicyclo[3.2.1]octane

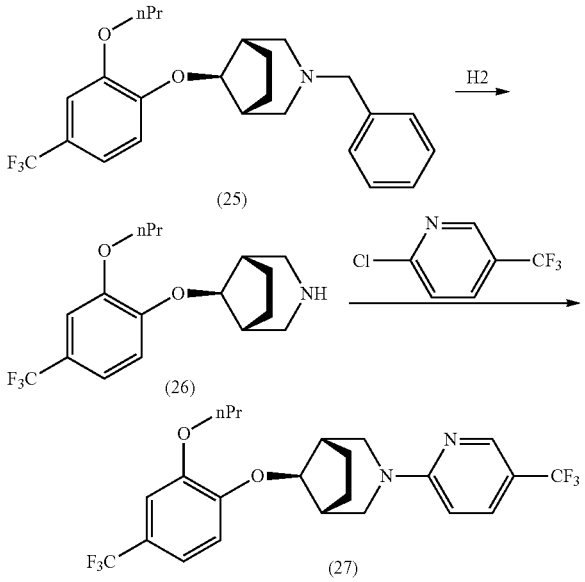

(25)

(26)

(27)

10% palladium-carbon (0.13 g) was added into the ethanol (20 ml) solution of the chemical compound (25) (0.66 g). This suspension was stirred over night at room temperature in a hydrogen atmosphere. After its mixture was filtered through a pad of CELITE, its filtrate was evaporated under reduced pressure to produce a crude chemical compound (26) (0.55 g).

After 2-chloro-5-(trifluoromethyl)pyridine (0.57 g) and potassium carbonate (0.66 g) were added into the acetonitrile (12 ml) solution of the crude chemical compound (26) (0.55 g), the mixture was refluxed with heating for 22 hours. After the mixture was cooled, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (0.26 g).

mp. 48-50° C.

$^1$H NMR ($CDCl_3$) δ 1.06 (t, 3H), 1.57-1.63 (m, 2H), 1.85 (sext, 2H), 2.03-2.06 (m, 2H), 2.57 (brs, 2H), 3.08 (d, 2H), 3.98 (t, 2H), 4.15 (d, 2H), 4.63 (s, 1H), 6.60 (d, 1H), 7.01 (d, 1H), 7.11 (s, 1H), 7.18 (d, 1H), 7.62 (d, 1H), 8.39 (s, 1H)

Preparation Example 14

Preparation of 3α-[2-nitro-4-(trifluoromethyl)phenoxy]-8-[5-(trifluoromethyl)-2-pyridyl]-8-azabicyclo[3.2.1]octane (Chemical Compound No. 2-35)

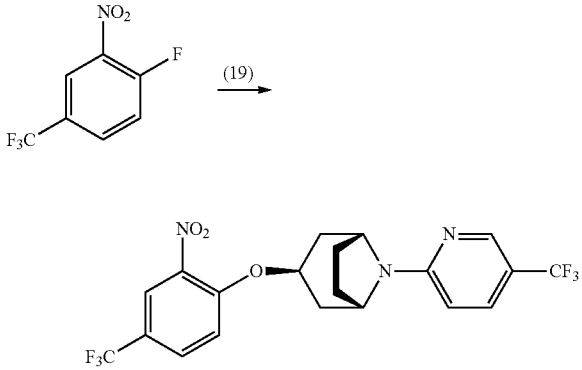

60% sodium hydride (0.81 g) was added, with chilling on ice, into the DMF (50 ml) solution of the chemical compound (19) (5 g) produced at Step 2 in Preparation Example 11. After its mixture was stirred for 30 minutes at room temperature, 4-fluoro 3-nitrobenzotrifluoride (3.84 g) was added to it. After the mixture was stirred for 1 hour at room temperature, it was heated to 100° C., and was then stirred over night. After the mixture was cooled to room temperature, it was poured into ice water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (4.95 g).

Viscous Oil $^1$H NMR ($CDCl_3$) δ 2.01-2.36 (m, 8H), 4.59 (brs, 2H), 4.75 (t, 1H), 6.58 (d, 1H), 7.01 (d, 1H), 7.63 (d, 1H), 7.76 (d, 1H), 8, 12 (s, 1H), 8.40 (s, 1H)

Example 15

Preparation of 3α-[2-amino-4-(trifluoromethyl)phenoxy]-8-[5-(trifluoromethyl)-2-pyridyl]-8-azabicyclo[3.2.1]octane (Chemical Compound No. 2-158)

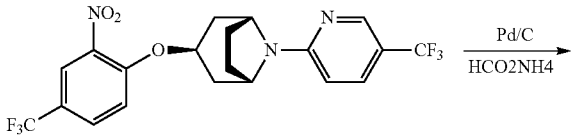

-continued

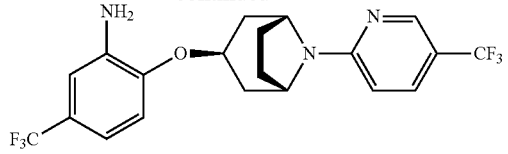

10% palladium-carbon (0.21 g) and ammonium formate (1.43 g) were added into the methanol (24 ml) solution of the chemical compound No. 2-35 (2.14 g) produced in Example 14. Its mixture was stirred for 1 hour at room temperature. After the mixture was filtered through a pad of CELITE, its filtrate was concentrated under reduced pressure. Its residue was purified by column chromatography to produce the chemical compound mentioned in the above title (1.86 g).

mp. 87-89° C.

$^1$HNMR ($CDCl_3$) δ 2.03-2.30 (m, 8H), 3.95 (s, 2H), 4.59-4.64 (m, 3H), 6.56 (d, 1H), 6.62 (d, 1H), 6.94 (s, 1H), 6.96 (s, 1H), 7.62 (d, 1H), 8.41 (s, 1H)

Preparation Example 16

Preparation of 3α-[2-allyl-4-(trifluoromethyl)phenoxy]-8-[5-(trifluoromethyl)-2-pyridyl]-azabicyclo[3.2.1]octane (Chemical compound No. 2-62)

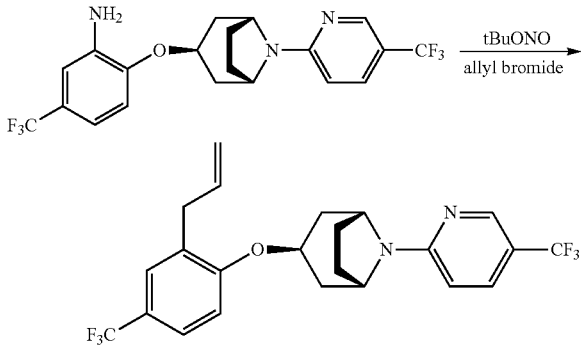

The following reaction was carried out according to a method described in J. Org. Chem., 2002, 67, 6376-6381.

The chemical compound No. 2-158 (0.5 g) produced in Example 15 was gradually added into the acetonitrile (7.5 ml) solution of t-butyl nitrite (0.18 g) and allyl bromide (2.1 g) at room temperature in a nitrogen atmosphere. After the mixture was stirred for 3 hours at room temperature, it was poured into water, and was then subjected to extraction with ethyl acetate. After its organic layer was washed with water, and was then dried with anhydrous magnesium sulfate, it was filtered, and was then concentrated under reduced was purified by column chromatography to produce the chemical compound mentioned in the above title (76 mg).

Viscous Oil $^1$H NMR ($CDCl_3$) δ 1.99-2.33 (m, 8H), 3.46 (d, 2H), 4.58 (brs, 3H), 5.08-5.15 (m, 2H), 5.94-6.07 (m, 1H), 6.57 (d, 1H), 6.69 (d, 1H), 7.42 (brs, 2H), 7.62 (d, 1H), 8.41 (s, 1H)

Example 17

Preparation of 9β-[2-methoxymethoxy-4-(trifluoromethyl)phenoxy]-3-[5-(trifluoromethyl)-2-pyridyl]-3-azabicyclo[3.3.1]nonane (Chemical compound No. 7-100)

Step 1

Preparation of N-benzyl-3-azabicyclo[3.3.1]nonane-9-ol (29)

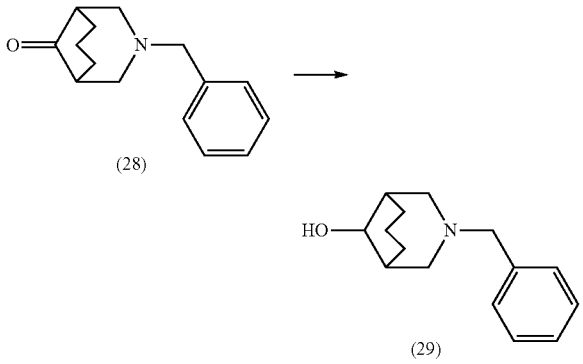

N-benzyl-3-azabicyclo[3.3.1]nonane-9-one (28) was synthesized according to a method described in J. Med. Chem. 1994, 37, 2831-2840. Sodium borohydride (1.49 g) was added into the MeOH (80 ml) solution of (28) (6.75 g) with chilling on ice. After its mixture was stirred for 1 hour with chilling on ice, its solvent was evaporated under reduced pressure. Water was added to its residue, which was then subjected to extraction with methylene chloride, followed by drying its organic layer with anhydrous magnesium sulfate. Its solvent was evaporated under reduced pressure to produce a crude compound (29) (6.52 g).

Step 2

Preparation of 9-[2-methoxymethoxy-4-(trifluoromethyl)phenoxy]-3-benzyl-3-azabicyclo[3.3.1]nonane (30), (31)

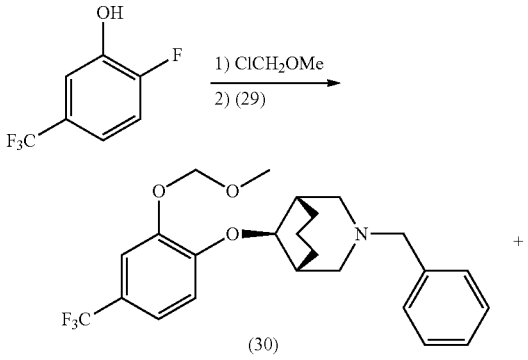

-continued

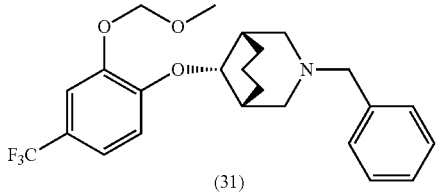

60% sodium hydride (1.77 g) was added to the DMF (75 ml) solution of 4-fluoro-3-hydroxybenzotrifluoride (7.49 g) with chilling on ice. After its mixture was stirred for 30 minutes at room temperature, chloromethyl methyl ether (3.57 g) was dropped into it with chilling on ice. After the mixture was warmed to room temperature, and was then stirred for 30 minutes, it was further heated to 80° C., and was then stirred for 30 minutes. The chemical compound (29) (6.4 g) and 60% sodium hydride (1.33 g) were added to the mixture at room temperature, and were then stirred for 30 minutes, they were heated to 100° C., and were then stirred for 3 hours. After the mixture was cooled to room temperature, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce a chemical compound (30) (6.3 g) and a chemical compound (31) (4.25 g). (0.56 g) was obtained.

Chemical Compound (30): Viscous Oil $^1$HNMR ($CDCl_3$) δ 1.43-1.60 (m, 3H), 2.01-2.08 (m, 4H), 2.36 (d, 2H), 2.65-2.80 (m, 1H), 3.02 (d, 2H), 3.42 (s, 2H), 3.53 (s, 3H), 4.35 (brs, 1H), 5.23 (s, 2H), 6.93 (d, 1H), 7.21-7.33 (m, 8H)

Chemical Compound (31): Viscous Oil $^1$HNMR ($CDCl_3$) δ 1.46-1.55 (m, 1H), 1.68-1.80 (m, 2H), 1.91-1.97 (m, 2H), 2.09 (brd, 3H), 2.68-2.82 (s plus m, 5H), 3.41 (s, 2H), 3.54 (s, 3H), 4.31 (t, 1H), 5.22 (s, 2H), 6.92 (d, 1H), 7.20-7.33 (m, 8H)

Step 3

Preparation of 9'-[2-methoxymethoxy-4-(trifluoromethyl)phenoxy]-3-[5-(trifluoromethyl)-2-pyridyl]-3-azabicyclo[3.3.1]nonane (Chemical compound No. 7-100)

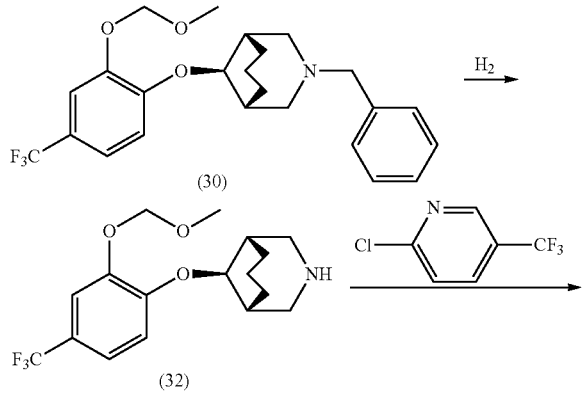

-continued

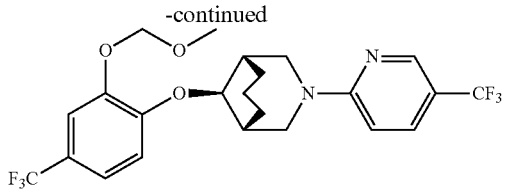

10% palladium-carbon (1.22 g) was added to the ethanol (180 ml) solution of the chemical compound (30) (6.11 g). After this suspension was stirred for 1 hour at room temperature in a hydrogen atmosphere, it was further heated to 80° C., and was then stirred for 7 hours. After the mixture was cooled to room temperature, it was filtered through a pad of CELITE, and its filtrate was evaporated under reduced pressure to produce a crude (32) (4.54 g).

2-chloro-5-(trifluoromethyl)pyridine (11.92 g) and potassium carbonate (10.9 g) were added to the acetonitrile (180 ml) solution of the crude chemical compound (32) (4.54 g), which were then refluxed with heating over night. After the mixture was cooled, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (2.61 g).

Viscous Oil.

$^1$H NMR ($CDCl_3$) δ 1.44-1.69 (m, 3H), 1.74-1.91 (m, 1H), 2.08-2.21 (m, 2H), 2.32 (brs, 2H), 3.28 (d, 2H), 3.54 (s, 3H), 4.47 (d, 2H), 4.62 (t, 1H), 5.25 (s, 2H), 6.66 (d, 1H), 7.02 (d, 1H), 7.25 (d, 1H), 7.37 (s, 1H), 7.63 (dd, 1H), 8.42 (s, 1H)

Example 18

Preparation of 90-[2-hydroxy-4-(trifluoromethyl) phenoxy]-3-[5-(trifluoromethyl)-2-pyridyl]-3-azabicyclo[3.3.1]nonane (Chemical Compound No. 7-4)

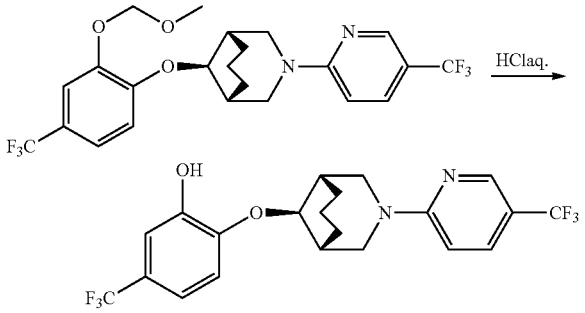

The chemical compound mentioned in the above title (2.12 g) was produced in a manner similar to that of Example 7 by using the chemical compound No. 7-100 (2.54 g) produced in Preparation Example 17.

mp. 108-110° C.

$^1$HNMR ($CDCl_3$) δ 1.46-1.54 (m, 1H), 1.71-1.78 (m, 2H), 1.82-1.93 (m, 1H), 1.98-2.07 (m, 2H), 2.37 (brs, 2H), 3.31 (d, 2H), 4.51 (d, 2H), 4.70 (t, 1H), 5.81 (s, 1H), 6.68 (d, 1H), 6.94 (d, 1H), 7.12 (d, 1H), 7.15-7.29 (m, 1H), 7.65 (dd, 1H), 8.43 (s, 1H)

Preparation Example 19

Preparation of 90-[2-propoxy-4-(trifluoromethyl) phenoxy]-3-[5-(trifluoromethyl)-2-pyridyl]-3-azabicyclo[3.3.1]nonane (Chemical compound No. 7-82)

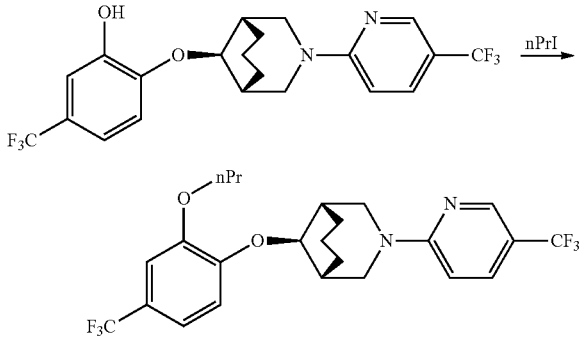

60% sodium hydride (0.03 g) was added, with chilling on ice, to the DMF (15 ml) solution of the chemical compound No. 7-4 (0.3 g) produced in Example 18. After the mixture was stirred for 30 minutes at room temperature, 1-iodopropane (0.13 g) was added to it with chilling on ice, and was then stirred for 30 minutes at room temperature. The mixture was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (0.27 g).

Viscous Oil.

$^1$H NMR ($CDCl_3$) δ 1.09 (t, 3H), 1.45-1.49 (m, 3H), 1.55-1.93 (m, 3H), 2.16-2.30 (m, 4H), 3.25 (d, 2H), 4.00 (t, 2H), 4.45 (d, 2H), 4.61 (s, 1H), 6.65 (d, 1H), 7.01 (d, 1H), 7.12-7.24 (m, 2H), 7.63 (dd, 1H), 8.42 (s, 1H)

Example 20

Preparation of 3α-[2-propoxy-4-(trifluoromethyl) phenoxy]-8-oxy-8-[5-(trifluoromethyl)-2-pyridyl]-8-azabicyclo[3.2.1]octane (Chemical Compound No. 2-84)

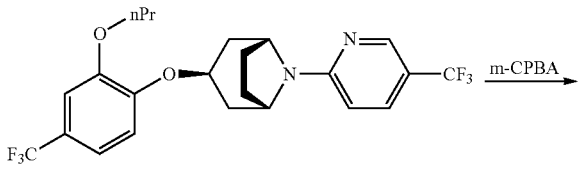

-continued

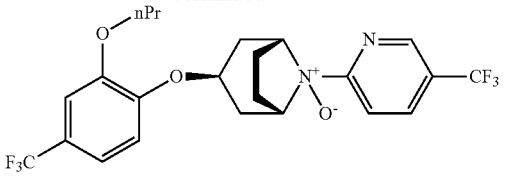

m-Chloroperbenzoic acid (purity 65%, 0.28 g) was added to the methylene chloride (5 ml) solution of (the chemical compound No. 2-82) (0.48 g) produced in Example 12. After refluxing with heating for 2 hours, the mixture was diluted with methylene chloride, and was then washed with one by one of a saturated sodium sulfite solution, a potassium carbonate solution, and a saturated brine. After it was dried with anhydrous magnesium sulfate, it was filtered, and was then concentrated under reduced pressure. Its residue was purified by column chromatography to produce the chemical compound mentioned in the above title (0.28 g).

mp. 129-130° C.

$^1$H NMR ($CDCl_3$) δ 1.09 (t, 3H), 1.82-1.94 (m, 2H), 2.20-2.41 (m, 8H), 3.77 (brs, 2H), 3.97 (t, 2H), 4.54 (t, 1H), 6.81 (d, 1H), 7.08 (s, 1H), 7.15 (d, 1H), 7.36 (d, 1H), 7.86 (dd, 1H), 8.48 (s, 1H)

Example 21

Preparation of 3α-[2-propoxy-4-(trifluoromethyl) phenoxy]-8-[5-(trifluoromethyl)-2-pyridyl-1-oxy]-8-azabicyclo[3.2.1]octane (Chemical Compound No. 2-83)

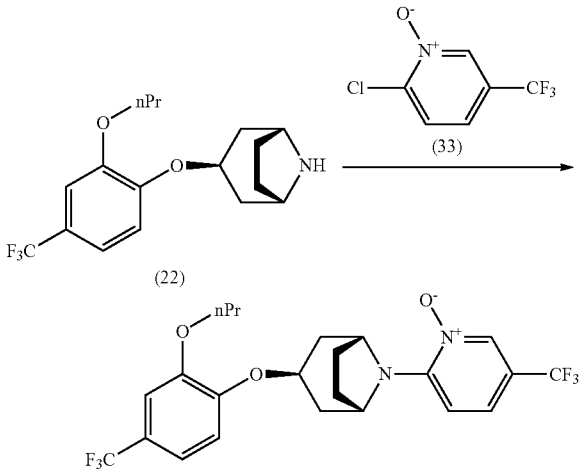

Pyridine N-oxide (33) was synthesized according to a method described in J. Heterocycl. Chem. 1976, 13, 41-42. The pyridine N-oxide (33) (0.395 g) and potassium carbonate (0.82 g) were added to the acetonitrile (6 ml) suspension of (22) (0.65 g) produced in Example 13, and the mixture was then refluxed with heating for 8 hours. After the mixture was cooled, it was poured into water, and was then subjected to extraction with ethyl acetate. After its organic layer was washed with water, and was then dried with anhydrous magnesium sulfate, it was filtered, and was then concentrated under reduced pressure to produce the chemical compound mentioned in the above title (0.88 g).

mp. 143-145° C.

$^1$H NMR ($CDCl_3$) δ 1.08 (t, 3H), 1.83-1.90 (m, 2H), 2.04-2.15 (m, 4H), 2.25-2.31 (m, 2H), 2.44-2.48 (m, 2H), 3.97 (t, 2H), 4.68 (brs, 1H), 5.02 (brs, 2H), 6.79-6.84 (m, 2H), 7.08 (s, 1H), 7.15 (d, 1H), 7.23-7.33 (m, 1H), 8.39 (s, 1H)

Example 22

Preparation of cis-3-methyl-4-[2-propoxy-4-(triphloromethyl)phenoxy]-1-[5-(trifluoromethyl)-2-pyridyl] piperidine (Chemical compound No. 1-97)

Step 1

Preparation of cis-3-methyl-1-[5-(trifluoromethyl)-2-pyridyl]-4-piperidinol (37) and trans-3-methyl-1-[5-(trifluoromethyl)-2-pyridyl]-4-piperidinol (38)

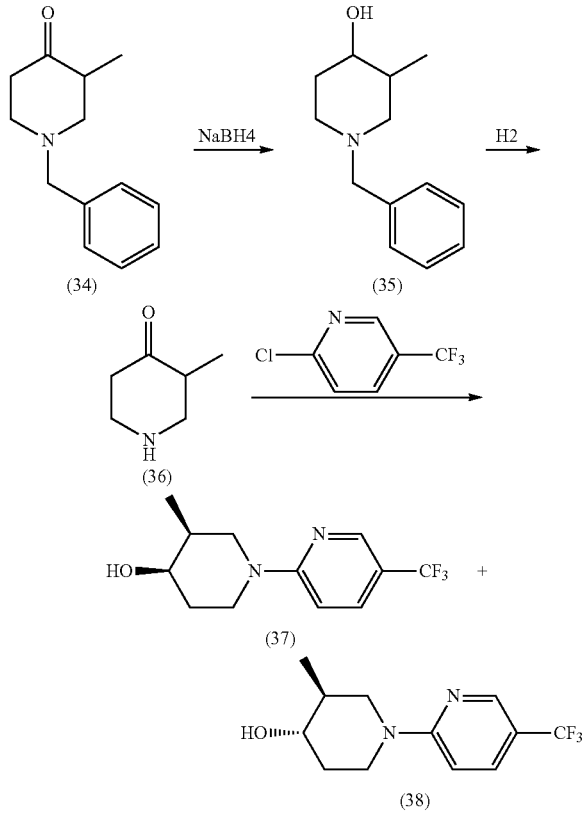

N-benzyl-3-methyl-4-piperidinon (34) is a known chemical compound described in a literature (CAS. no. [34737-89-8]) and can be available from commercial products. Sodium borohydride (0.47 g) was added, with chilling on ice, to the EtOH (40 ml) solution of the chemical compound (34) (2.53 g). After the mixture was stirred for 2 hours at room temperature, it was neutralized by 10% hydrochloric acid with chilling on ice. After the mixture was subjected to extraction with methylene chloride, its organic layer was dried with anhydrous magnesium sulfate. Its solvent was evaporated under reduced pressure to produce a crude (35) (2.27 g), which was used for the next reaction.

20% palladium-carbon hydroxide (0.2 g) was added to the methanol (30 ml) solution of the crude (35) (1.82 g). This suspension was heated to 70° C. in a hydrogen atmosphere, and was then stirred all day and night. After its mixture was cooled to room temperature, it was filtered through a pad of CELITE. Into its filtrate, 20% palladium carbon hydroxide (0.9 g) was added, which was then heated to 70° C., followed by stirring over night. After the mixture was cooled to room temperature, it was filtered through a pad of CELITE. Its filtrate was evaporated under reduced pressure to produce a crude (36) (1.22 g), which was used for the next reaction.

2-chloro-5-(trifluoromethyl)pyridine (2.3 g) and potassium carbonate (4.4 g) were added to the acetonitrile (50 ml) solution of the crude chemical compound (36) (1.22 g), which were then refluxed with heating over night. After its mixture was cooled, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compounds mentioned in the above titles (37) (0.15 g) and (38) (0.55 g).

(37): an Yellow Oily Matter $^1$HNMR ($CDCl_3$) δ 1.01 (d, 3H), 1.59 (brs, 1H), 1.77-1.94 (m, 3H), 3.21 (t, 1H), 3.44-3.53 (m, 1H), 3.85-3.98 (m, 3H), 6.65 (d, 1H), 7.58 (dd, 1H), 8.37 (s, 1H)

(38): an Yellow Oily Matter $^1$HNMR ($CDCl_3$) δ 1.07 (d, 3H), 1.46-1.63 (m, 3H), 2.00-2.07 (m, 1H), 2.65 (t, 1H), 3.02 (t, 1H), 3.40-3.47 (m, 1H), 4.26-4.40 (m, 2H), 6.66 (d, 1H), 7.60 (dd, 1H), 8.37 (s, 1H)

Step 2

Preparation of cis-3-methyl-4-[2-propoxy-4-(trifluoromethyl)phenoxy]-1-[5(trifluoromethyl)-2-pyridyl] piperidine (Chemical compound No. 1-97)

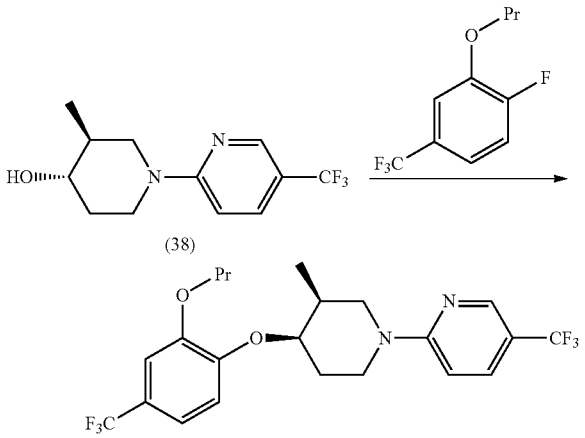

60% sodium hydride (0.023 g) was added to the DMF (4 ml) solution of the chemical compound (38) (0.15 g) at room temperature. After its mixture was heated to 70° C., 4-fluoro-3-propoxybenzotrifluoride (0.14 g) was added to it, and was then heated at 100° C. over night. After the mixture was cooled to room temperature, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (0.18 g).

$n_D^{22.8}$1.5000

$^1$HNMR ($CDCl_3$) δ 1.05 (t, 3H), 1.12 (d, 3H), 1.71-1.92 (m, 4H), 2.02-2.08 (m, 2H), 3.40 (t-like, 1H), 3.51 (t-like, 1H), 3.95-4.05 (m, 3H), 4.55 (brs-like, 1H), 6.67 (d, 1H), 7.00 (d, 1H), 7.08 (d, 1H), 7.16 (d, 1H), 7.61 (dd, 1H), 8.39 (s, 1H)

Preparation Example 23

Preparation of 3α-[2-butyl-4-(trifluoromethyl)phenoxy]-8-[5-(trifluoromethyl)-2-pyridyl]-8-azabicyclo[3.2.1]octane (Chemical compound No. 2-187)

Step 1

Preparation of 3α-{2-([1,3]dioxolane-yl)-4-(trifluoromethyl)phenoxy}-8-[5-(trifluoromethyl)-2-pyridyl]-8-azabicyclo[3.2.1]octane (Chemical compound No. 2-169)

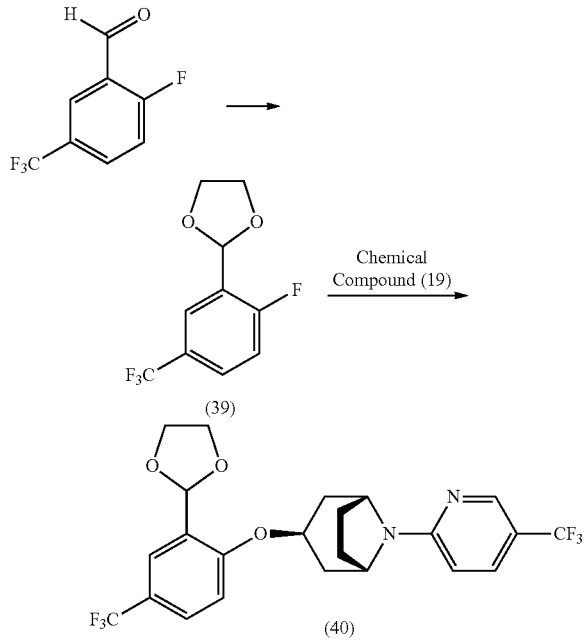

The benzene (50 ml) solution of 2-fluoro-5-(trifluoromethyl)benzaldehyde (5.00 g), ethylene glycol (1.78 g), and p-toluene sulfonate monohydrate (0.49 g) were refluxed with heating over night. After the mixture was cooled to room temperature, it was poured into water, and was then subjected to extraction with ethyl acetate. After its organic layer was washed with brine, and was then dried with anhydrous magnesium sulfate, it was filtered, and its solvent was then evaporated to produce a crude chemical compound (39) (5.81 g).

60% sodium hydride (0.50 g) was added at 80° C. to the DMF (20 ml) solution of the crude (39) (2.00 g) and the chemical compound (19) (2.30 g) by dividing it into 5 times. The mixture was directly stirred for 1 hour at 80° C. After it was cooled to room temperature, it was poured into ice water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (3.24 g).

mp. 148-151° C.

$^1$H NMR ($CDCl_3$) δ 2.01-2.14 (m, 4H), 2.24-2.37 (m, 4H), 4.04-4.20 (m, 4H), 4.58 (brs, 2H), 4.63 (t, 1H), 6.17 (s, 1H), 6.57 (d, 1H), 6.75 (d, 1H), 7.55 (dd, 1H), 7.62 (dd, 1H), 7.84 (d, 1H), 8.41 (s, 1H)

Step 2

Preparation of 3α-[2-formyl-4-(trifluoromethyl)phenoxy]-8-[5-(trifluoromethyl)-2-pyridyl]-8-azabicyclo[3.2.1]octane (41)

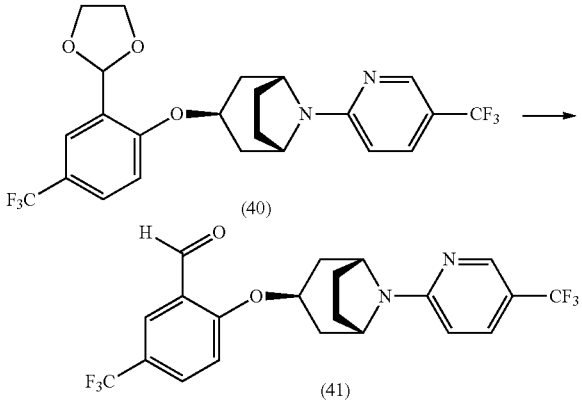

6 normal hydrochloric acid (100 ml) was added, with chilling on ice, to the THF (100 ml) solution of the chemical compound (40) (3.24 g). Its mixture was warmed to room temperature, and was then stirred for 2 hours. The mixture was poured into water, and was then subjected to extraction with ethyl acetate. After its organic layer was washed with 10% sodium carbonate aqueous solution and brine, and was then dried with anhydrous magnesium sulfate, it was filtered, and was then concentrated under reduced pressure. Its residue was purified by column chromatography to produce the chemical compound mentioned in the above title (2.95 g).

$^1$H NMR ($CDCl_3$) δ 2.04-2.39 (m, 8H), 4.64 (brs, 2H), 4.78 (t, 1H), 6.60 (d, 1H), 6.92 (d, 1H), 7.65 (dd, 1H), 7.77 (dd, 1H), 8.15 (s, 1H), 8.42 (s, 1H), 10.53 (s, 1H)

Step 3

Preparation of 3α-[2-(1-hydroxybutyl)-4-(trifluoromethyl)phenoxy]-8-[5-(trifluoromethyl)-2-pyridyl]-8-azabicyclo[3.2.1]octane (42)

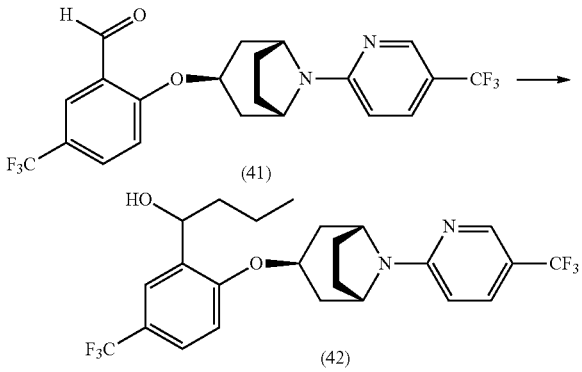

After the THF solution (1.02 mol/l) (6.06 ml) of n-propyl magnesium bromide was dropped, in a nitrogen atmosphere at 0° C., into the THF solution of the chemical compound (41) (1.83 g), it was warmed to room temperature, and was then stirred for 2 hours. The mixture was poured into a saturated ammonium chloride aqueous solution, and was then subjected to extraction with ethyl acetate. After its organic layer was washed with brine, and was then dried with anhydrous magnesium sulfate, it was concentrated under reduced pressure. Its residue was purified by column chromatography to produce the chemical compound mentioned in the above title (42) (0.96 g).

mp. 141-145° C.

$^1$H NMR ($CDCl_3$) δ 0.98 (t, 3H), 1.41-1.60 (m, 2H), 1.71-1.81 (m, 2H), 1.98-2.04 (m, 3H), 2.16-2.37 (m, 5H), 4.59-4.62 (m, 3H), 5.09-5.14 (m, 1H), 6.57 (d, 1H), 6.70 (d, 1H), 7.46 (dd, 1H), 7.63 (dd, 1H), 7.74 (s, 1H), 8.41 (s, 1H)

Step 4

Preparation of 3α-[2-(buten-1-yl)-4-(trifluoromethyl)phenoxy]-8-[5-(trifluoromethyl)-2-pyridyl]-8-azabicyclo[3.2.1]octane (43)

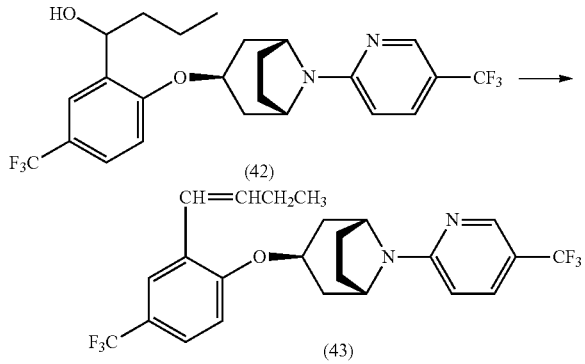

The toluene (4 ml) solution of the chemical compound (42) (0.40 g) and p-toluene sulfonate monohydrate (0.14 g) was refluxed with heating over night. After the mixture was cooled to room temperature, it was poured into water, and was then subjected to extraction with ethyl acetate. After its organic layer was washed with brine, and was then dried with anhydrous magnesium sulfate, it was concentrated under reduced pressure. Its residue was purified by column chromatography to produce the chemical compound mentioned in the above title (43) (0.37 g).

mp. 94-98° C.

$^1$H NMR ($CDCl_3$) δ 1.14 (t, 3H), 2.00-2.32 (m, 10H), 4.58-4.63 (m, 3H), 6.26-6.35 (m, 1H), 6.57 (d, 1H), 6.69-6.77 (m, 2H), 7.40 (d, 1H), 7.62 (dd, 1H), 7.69 (s, 1H), 8.41 (s, 1H)

Step 5

Preparation of 3α-[2-butyl-4-(trifluoromethyl)phenoxy]-8-[5-(trifluoromethyl)-2-pyridyl]-8-azabicyclo[3.2.1]octane

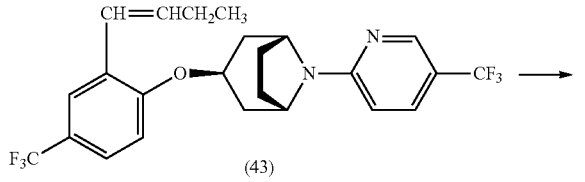

-continued

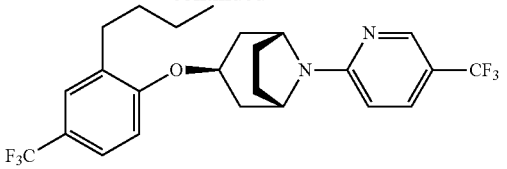

5% palladium-carbon (0.04 g) was added to the ethanol (6 ml) solution of the chemical compound (43) (0.22 g). This suspension was stirred over night at room temperature in a hydrogen atmosphere. Its mixture was filtered through a pad of CELITE, and its filtrate was evaporated under reduced pressure. Its residue was purified by column chromatography to produce the chemical compound mentioned in the above title (0.18 g).

mp. 86-88° C.

$^1$H NMR ($CDCl_3$) δ 0.96 (t, 3H), 1.35-1.47 (m, 2H), 1.54-1.66 (m, 2H), 1.97-2.03 (m, 2H), 2.10-2.14 (m, 2H), 2.21-2.32 (m, 4H), 2.64 (t, 2H), 4.54-4.56 (m, 3H), 6.51 (d, 1H), 6.60 (d, 1H), 7.33 (d, 1H), 7.34 (s, 1H), 7.56 (dd, 1H), 8.31 (s, 1H)

Preparation Example 24

Preparation of 4-[2-propoxy-4-(trifluoromethyl)phenylsulfanyl]-1-[5-(trifluoromethyl)-2-pyridyl]piperidine (Chemical compound No. 9-94)

Step 1

Preparation of 1-benzyloxy-2-propoxy-4-(trifluoromethyl)benzene (44)

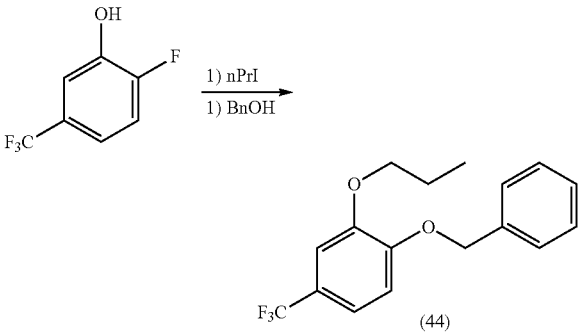

After 60% sodium hydride (0.44 g) was added, with chilling on ice, to the DMF (20 ml) solution of 4-fluoro-3-hydroxybenzotrifluoride (1.80 g), and the obtained mixture was then warmed to room temperature, followed by stirring for 30 minute, the DMF (5 ml) solution of 1-iodopropane (1.87 g) was added to it. The mixture was heated to 80° C., and was then stirred for 30 minutes. After the mixture was cooled to room temperature, benzyl alcohol (2.16 g) and 60% sodium hydride were added to it, which was then heated to 80° C., followed by stirring for 30 minutes. After the mixture was cooled to room temperature, it was poured into ice-water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (44) (2.95 g).

$^1$HNMR ($CDCl_3$) δ 1.07 (t, 3H), 1.82-1.94 (m, 2H), 4.00 (t, 2H), 5.18 (s, 2H), 6.92 (d, 1H), 7.09-7.14 (m, 2H), 7.28-7.44 (m, 5H)

Step 2

Preparation of 2-propoxy-4-(trifluoromethyl)benzenethiol (46)

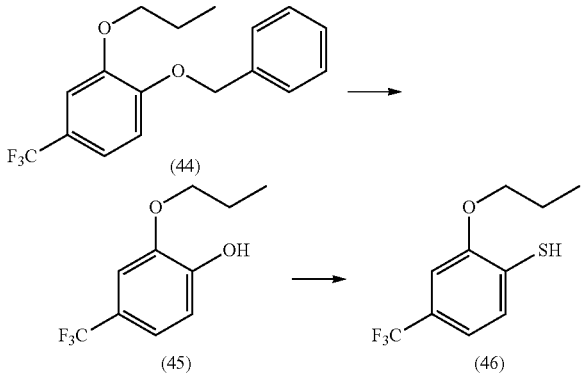

After 10% palladium-carbon (0.59 g) was added to the ethanol solution of the chemical compound (44) (2.95 g), the suspension was stirred over night at room temperature in a hydrogen atmosphere. After the mixture was filtered through a pad of CELITE, its filtrate was evaporated under reduced pressure to produce a crude chemical compound (45) (2.01 g).

The chemical compound mentioned in the above title (46) (1.82 g) was produced from the crude chemical compound (45) (2.01 g) according to a method described in J. Med. Chem. 2002, 45, 3972-3983.

$^1$H NMR ($CDCl_3$) δ 1.10 (t, 3H), 1.84-1.96 (m, 2H), 4.07 (t, 2H), 7.01 (s, 1H), 7.09 (d, 1H), 7.32 (d, 1H)

Step 3

Preparation of 4-bromo-1-[5-(trifluoromethyl)-2-pyridyl]piperidine (48)

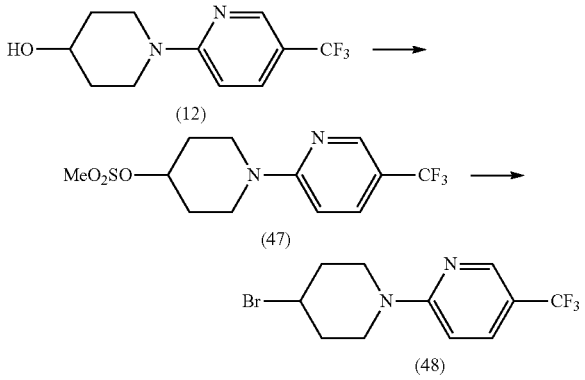

Triethylamine (0.45 g) and methane sulfonyl chloride (0.51 g) were added, with chilling on ice, to the acetonitrile (10 ml) solution of the chemical compound (12) (1.00 g), and the mixture was warmed to room temperature. After it was stirred for 30 minutes, it was poured into water, and was then subjected to extraction with ethyl acetate. After its organic layer was washed with brine, and was then dried with anhydrous magnesium sulfate, it was filtered, and was then concentrated under reduced pressure to produce a crude (47) (1.32 g).

Lithium bromide (1.06 g) was added to the DMF (13 ml) solution of the crude chemical compound (47) (1.32 g), and the mixture was stirred at 80° C. for 1 hour. After the mixture was cooled, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (48) (0.74 g).

$^1$HNMR ($CDCl_3$) δ 1.99-2.10 (m, 2H), 2.16-2.25 (m, 2H), 3.55-3.62 (m, 2H), 3.91-4.00 (m, 2H), 4.42-4.49 (m, 1H), 6.66 (d, 1H), 7.63 (dd, 1H), 8.39 (s, 1H)

Step 4

Preparation of 4-[2-propoxy-4-(trifluoromethyl)phenylsulfanyl]-1-[5-(trifluoromethyl)-2-pyridyl]piperidine

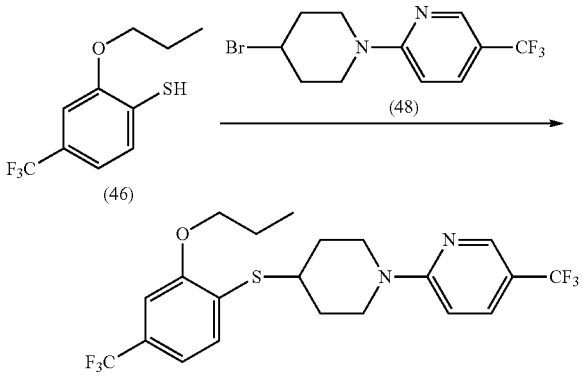

After 60% sodium hydride was added, with chilling on ice, to the DMF (7 ml) solution of the chemical compound (46) (0.62 g), it was warmed to room temperature, and was then stirred for 30 minutes. After the chemical compound (48) (0.74 g) was added to the mixture, it was heated to 100° C., and was then stirred for 1 hour. After the mixture was cooled, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (0.90 g).

Viscous Oil $^1$HNMR ($CDCl_3$) δ 1.09 (t, 3H), 1.63-1.75 (m, 2H), 1.84-1.95 (m, 2H), 2.04-2.10 (m, 2H), 3.19-3.28 (m, 2H), 3.54-3.62 (m, 1H), 4.03 (t, 2H), 4.21-4.28 (m, 2H), 6.64 (d, 1H), 7.04 (s, 1H), 7.16 (d, 1H), 7.40 (d, 1H), 7.61 (dd, 1H), 8.38 (s, 1H)

Preparation Example 25

Preparation of 3α-[2-propoxy-4-(trifluoromethyl) phenylsulfany]-8-[5-(trifluoromethyl)-2-pyridyl]-8-azabicyclo[3.2.1]octane Step 1

Preparation of 3β-acetoxy-8-[5-(trifluoromethyl)-2-pyridyl]-8-azabicyclo[3.2.1]octane (50)

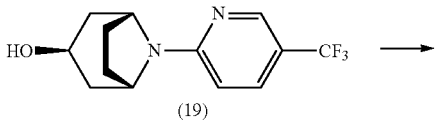

-continued

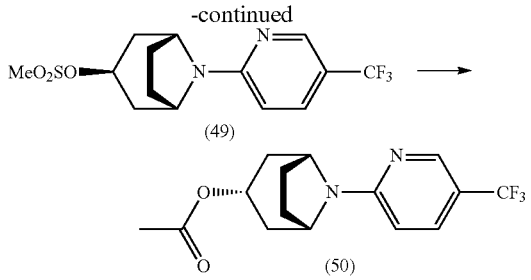

Triethylamine (1.12 g) and methane sulfonylchloride (1.26 g) were added, with chilling on ice, to the methylene chloride (20 ml) solution of the chemical compound (19) (2.00 g), and were then stirred for 30 minutes. The mixture was poured into water, and was then subjected to extraction with ethyl acetate. Its organic layer was washed with a saturated brine, and was then dried with anhydrous magnesium sulfate. Its solvent was evaporated under reduced pressure to produce a crude chemical compound (49) (2.29 g).

Cesium acetate (1.88 g) was added to the DMF (35 ml) solution of the crude chemical compound (49) (2.29 g), and was then heated to 100° C., followed by stirring over night. After the mixture was cooled to room temperature, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (50) (1.15 g).

$^1$HNMR ($CDCl_3$) δ 1.66-1.75 (m, 2H), 1.87-2.18 (m, 9H), 4.61 (brs, 2H), 5.25-5.36 (m, 1H), 6.57 (d, 1H), 7.62 (dd, 1H), 8.41 (s, 1H)

Step 2

Preparation of 3α-[2-propoxy-4-(trifluoromethyl) phenoxysulfanyl]-8-[5-(trifluoromethyl)-2-pyridyl]-8-azabicyclo[3.2.1]octane

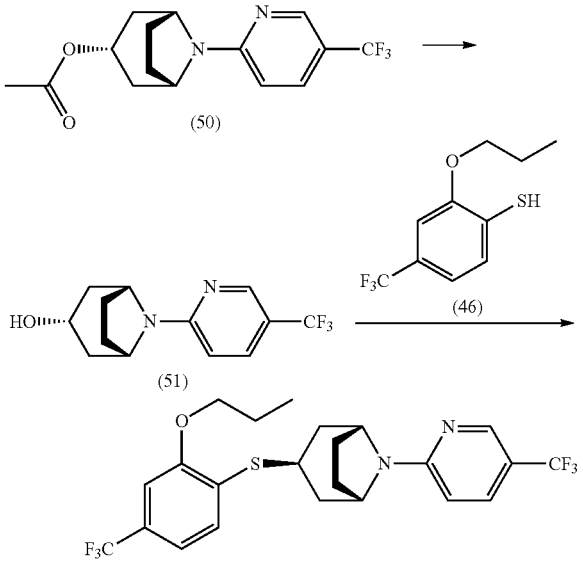

The methanol solution (0.07 g) of 28% sodium methoxide was added to the methanol (25 ml) solution of the chemical compound (50) (1.15 g), and the mixture was then stirred with refluxing for 2 hours. After cooling it. methanol was evaporated under reduced pressure, into which water was poured, followed by subjecting to extraction with ethyl acetate. Its organic layer was washed with brine, and was then dried with anhydrous magnesium sulfate. Its solvent was evaporated under reduced pressure to produce a crude chemical compound (51) (1.00 g).

Triphenylphosphine (1.93 g) and diisopropyl azodicarboxylate (1.49 g) were added to the toluene (10 ml) solution of the crude chemical compound (51) (1.00 g) and the chemical compound (46) (0.87 g), and were then stirred over night at room temperature. The mixture was poured into water, and was then subjected to extraction with ethyl acetate. After its organic layer was washed with brine, and was then dried with anhydrous magnesium sulfate, it was filtered, and was then concentrated under reduced pressure. Its residue was purified by column chromatography to produce the chemical compound mentioned in the above title (0.39 g).

mp. 72-74° C.

$^1$HNMR ($CDCl_3$) δ 1.07 (t, 3H), 1.83-1.92 (m, 4H), 2.13-2.17 (m, 2H), 2.35-2.55 (m, 4H), 3.69 (t. 1H), 4.01 (t, 2H), 4.57 (brs, 2H), 6.51 (d, 1H), 7.02 (s, 1H), 7.15 (d, 1H), 7.26 (d, 1H), 7.60 (d, 1H), 8.38 (d, 1H)

Preparation Example 26

Preparation of 3α-[2-isopropylideneaminoxy-4-(trifluoromethyl)phenoxy]-8-[5-(trifluoromethyl)-2-pyridyl]-8-azabicyclo[3.2.1]octane (Chemical compound No. 2-212)

Step 1

Preparation of 3α-[2-methoxymethoxy-4-(trifluoromethyl)phenoxy]-8-[5-(trifluoromethyl)-2-pyridyl]-8-azabicyclo[3.2.1]octane (52)

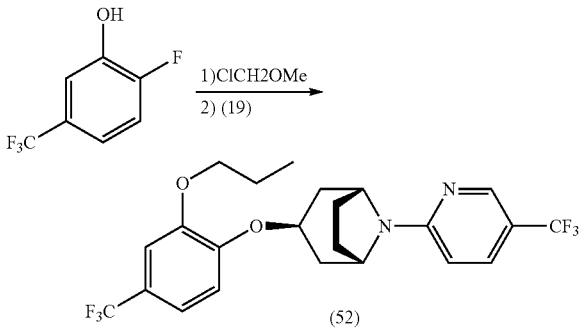

60% sodium hydride (0.59 g) was added, with chilling on ice, to the DMF (30 ml) solution of 4-fluoro-3-hydroxybenzotrifluoride (2.48 g). After the mixture was stirred for 30 minutes at room temperature, chloromethyl methyl ether (1.18 g) was dropped into it with chilling on ice. After the mixture was warmed to room temperature, and was then stirred for 30 minutes, it was further heated to 80° C., and was then stirred for 30 minutes. After the chemical compound (19) (2.50 g) and 60% sodium hydride (0.55 g) were added to the mixture at room temperature, and were then stirred for 30 minutes, they were heated to 100° C., and were then stirred for 2 hours. After the mixture was cooled to room temperature, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (52) (3.98 g).

mp. 69-73° C.

$^1$H NMR ($CDCl_3$) δ 2.01-2.25 (m, 6H), 2.37-2.44 (m, 2H), 3.54 (s, 3H), 4.57-4.63 (m, 3H), 5.23 (s, 2H), 6.56 (d, 1H), 6.79 (d, 1H), 7.23 (d, 1H), 7.35 (s, 1H), 7.61 (dd, 1H), 8.41 (s, 1H)

Step 2

Preparation of 3α-[2-hydroxy-4-(trifluoromethyl)phenoxy]-8-[5-(trifluoromethyl)-2-pyridyl]-8-azabicyclo[3.2.1]octane (53)

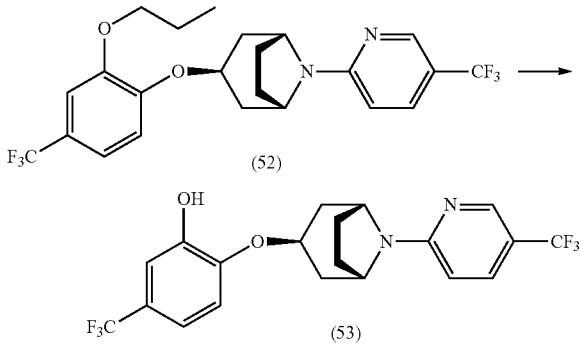

The chemical compound mentioned in the above title (53) (3.61 g) was produced by using a chemical compound (52) (3.98 g) according to a method similar to that of Example 7.

mp. 90-94° C.

$^1$H NMR ($CDCl_3$) δ 2.03-2.34 (m, 8H), 4.61 (brs, 2H), 4.67 (t, 1H), 5.88 (s, 1H), 6.58 (d, 1H), 6.73 (d, 1H), 7.11 (d, 1H), 7.21 (s, 1H), 7.63 (dd, 1H), 8.41 (s, 1H)

Step 3

Preparation of 3α-[2-isopropylideneaminoxy-4-(trifluoromethyl)phenoxy]-8-[5-(trifluoromethyl)-2-pyridyl]-8-azabicyclo[3.2.1]octane

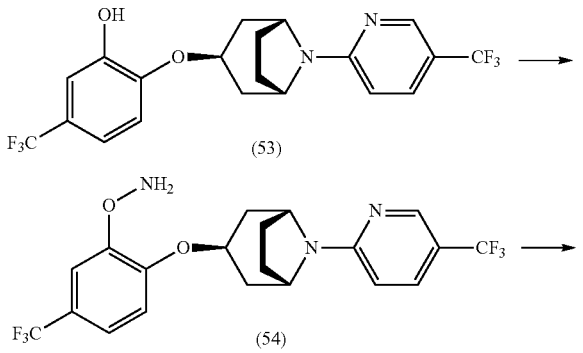

-continued

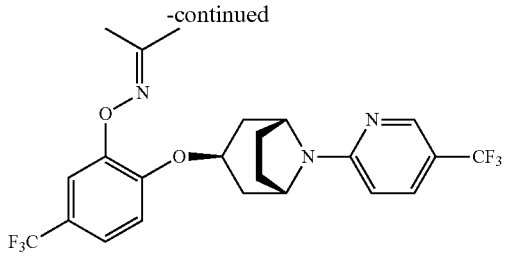

The chemical compound (54) (0.54 g) was synthesized by using the chemical compound (53) (1.00 g) according to a method described in Japanese Unexamined Patent Application No. 2001-81071.

Acetone (1 ml) and concentrated hydrochloric acid (0.03 g) were added to the ethanol (2 ml) solution of the chemical compound (54) (0.25 g), and were then stirred for 1 hour at room temperature. The mixture was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (0.20 g).

mp. 107-109° C.

$^1$H NMR ($CDCl_3$) δ 2.01-2.28 (m, 12H), 2.40-2.48 (m, 2H), 4.56 (brs, 2H), 4.64 (t, 1H), 6.55 (d, 1H), 6.78 (d, 1H), 7.19 (dd, 1H), 7.61 (dd, 1H), 7.70 (d, 1H), 8.40 (s, 1H)

Preparation Example 27

Preparation of 3α-[2-(2-methylpropenyloxy)-4-(trifluoromethyl)phenoxy]-8-[5-(trifluoromethyl)-2-pyridyl]-8-azabicyclo[3.2.1]octane (Chemical Compound No. 2-245) Step 1

Preparation of 3α-[2-(2-methylallyloxy)-4-(trifluoromethyl)phenoxy]-8-[5-(trifluoromethyl)-2-pyridyl]-8-azabicyclo[3.2.1]octane (55)

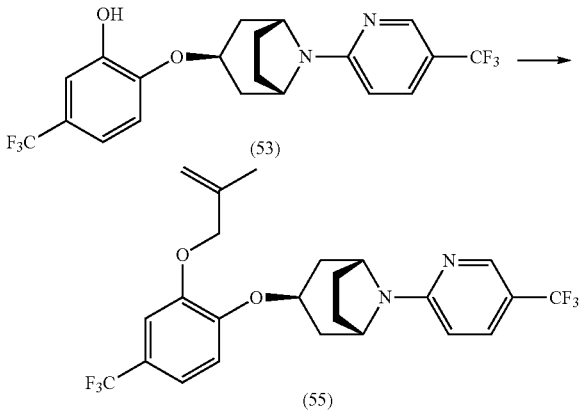

60% sodium hydride (0.05 g) was added, with chilling on ice, to the DMF (5 ml) solution of the chemical compound (53) (0.50 g). After the mixture was stirred for 30 minutes at room temperature, methallyl chloride (0.14 g) and sodium iodide (0.23 g) were added to it with chilling on ice, and the mixture was warmed to room temperature followed by stirring for 30 minutes, and was then further heated to 80° C. followed by stirring for 1 hour. After the mixture was cooled to room temperature, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (55) (0.48 g).

mp. 96-98° C.

$^1$H NMR ($CDCl_3$) δ 1.87 (s, 3H), 2.01-2.24 (m, 6H), 2.41-2.47 (m, 2H), 4.47 (s, 2H), 4.56 (brs, 2H), 4.61 (t, 1H), 5.03 (s, 1H), 5.16 (s, 1H), 6.56 (d, 1H), 6.78 (d, 1H), 7.10 (s, 1H), 7.16 (d, 1H), 7.60 (dd, 1H), 8.40 (s, 1H)

Step 2

Preparation of 3α-[2-(2-methylpropenyloxy)-4-(trifluoromethyl)phenoxy]-8-[5-(trifluoromethyl)-2-pyridyl]-8-azabicyclo[3.2.1]octane

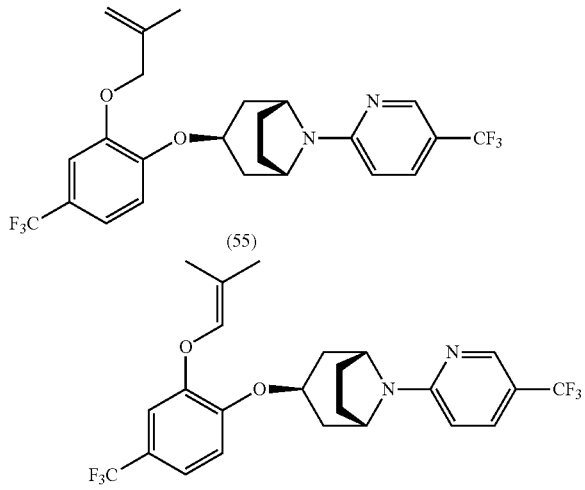

t-Butoxypotassium (0.11 g) was added to the DMSO solution of the chemical compound (55) (0.42 g), and was then stirred for 5 hours at 100° C. After the mixture was cooled to room temperature, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (0.19 g).

mp. 90-92° C.

$^1$H NMR ($CDCl_3$) δ 1.73 (d, 6H), 2.01-2.24 (m, 6H), 2.41-2.48 (m, 2H), 4.56 (brs, 2H), 4.63 (t, 1H), 6.20 (s, 1H), 6.56 (d, 1H), 6.80 (d, 1H), 7.17-7.22 (m, 2H), 7.61 (dd, 1H), 8.40 (s, 1H)

Preparation Example 28

Preparation of 5-trifluoromethyl-2-{3α-[5-(trifluoromethyl)pyridyl]-8-azabicyclo[3.2.1]octa-3-yloxy}benzoic acid furan-2-yl ester (Chemical compound No. 2-244)

Step 1

Preparation of 3α-[2-cyano-4-(trifluoromethyl)phenoxy]-8-[5-(trifluoromethyl)-2-pyridyl]-8-azabicyclo[3.2.1]octane (56)

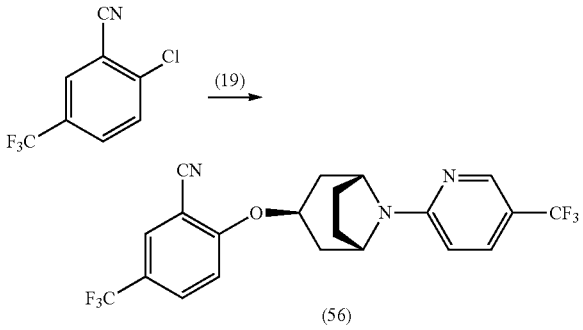

60% sodium hydride (0.71 g) was added, with chilling on ice, to the DMF (30 ml) solution of the chemical compound (19) (3.69 g). After the mixture was stirred at room temperature for 30 minutes, 4-chloro-3-cyanobenzotrifluoride (2.78 g) was added to it. After the mixture was stirred for 30 minutes at room temperature, it was further heated to 100° C., and was then stirred for 4 hours. After the mixture was cooled to room temperature, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (56) (4.24 g).

mp. 110-113° C.

$^1$HNMR ($CDCl_3$) δ 2.01-2.45 (m, 8H), 4.60 (brs, 2H), 4.74 (t, 1H), 6.59 (d, 1H), 6.91 (d, 1H), 7.63 (dd, 1H), 7.77 (dd, 1H), 7.86 (s, 1H), 8.41 (s, 1H)

Step 2

Preparation of 5-trifluoromethyl-2-{3α-[5-(trifluoromethyl)pyridyl]-8-azabicyclo[3.2.1]octa-3-yloxy}benzoic acid furan 2-yl ester

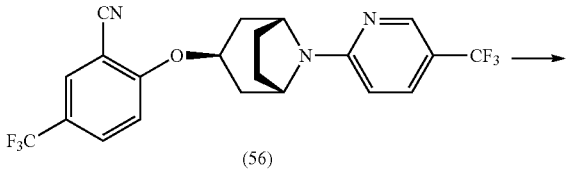

-continued

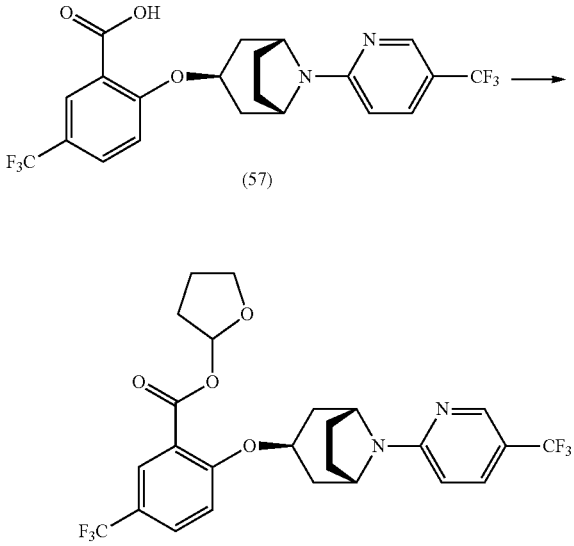

Potassium hydroxide (5.38 g) was added to the ethanol (100 ml) solution of the chemical compound (56) (4.24 g), and was then stirred with refluxing over night. After the mixture was cooled to room temperature, it was poured into water, and was then neutralized by using hydrochloric acid, followed by extraction with acetic acid ester. After its organic layer was washed with brine, and was then dried with anhydrous magnesium sulfate, it was filtered, and was then concentrated under reduced pressure. The produced crystal was dissolved in acetic acid (22 ml), into which sodium nitrite (0.99 g) and concentrated sulfuric acid (3.59 g) were added bit by bit with chilling on ice. The mixture was warmed to room temperature, and was then stirred for 5 hours. The mixture was poured into ice-water, and was then subjected to extraction with ethyl acetate. After its organic layer was washed with brine, and was then dried with anhydrous magnesium sulfate, it was filtered, and was then concentrated under reduced pressure to produce a crude chemical compound (57) (4.17 g).

A solution, which was produced by dropping sulfuryl chloride (0.17 g) into THF (2 ml) at 30° C. or below, followed by stirring for 10 minutes at room temperature, was dropped, with chilling on ice, into the THF (4 ml) solution of the chemical compound (57) (0.20 g), into which triethylamine (0.22 g) was further added. This mixture was warmed to room temperature, and was then stirred for 30 minutes. The mixture was poured into water, and was then subjected to extraction with ethyl acetate. After its organic layer was washed with brine, and was then dried with anhydrous magnesium sulfate, it was filtered, and was then concentrated under reduced pressure. Its residue was purified by column chromatography to produce the chemical compound mentioned in the above title (72 mg).

mp. 85-88° C.

$^1$H NMR ($CDCl_3$) δ 2.01-2.23 (m, 10H), 2.35-2.47 (m, 2H), 4.56 (brs, 2H), 4.66 (t, 1H), 6.54-6.59 (m, 2H), 6.84 (d, 1H), 7.60-7.68 (m, 2H), 7.96 (s, 1H), 8.41 (s, 1H)

Preparation Example 29

Preparation of 3α-[2(2-methyloxazole-5-yl)-4(trifluoromethyl)phenoxy]-8-[5 (trifluoromethyl)-2-pyridyl]-8-azabicyclo[3.2.1]octane (Chemical compound No. 2-214)

Step 1

Preparation of 3α-[2-(2-methyl[1,3]dioxalane-2-yl)-4-(trifluoromethyl)phenoxy]-8-[5-(trifluoromethyl)-2-pyridyl]-8-azabicyclo[3.2.1]octane (61)

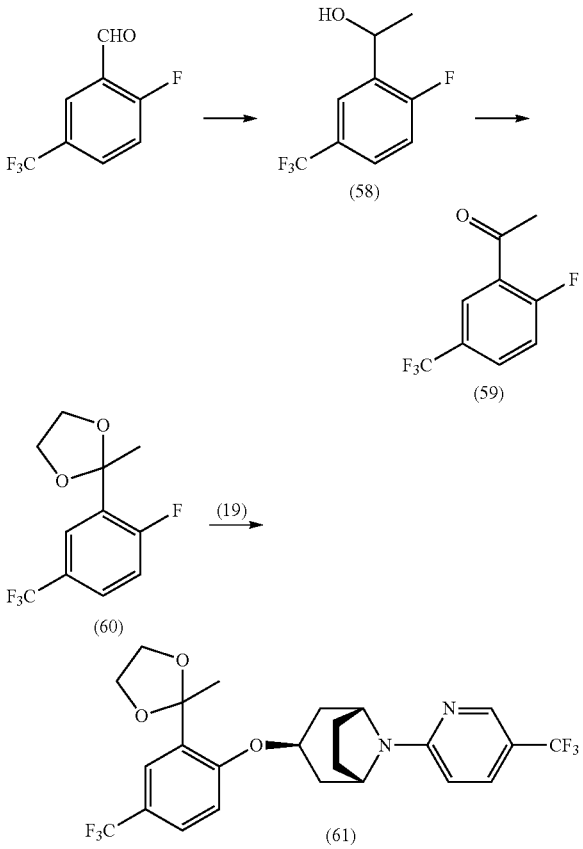

3.0 M methylmagnesiumbromide (7.8 ml) was dropped, in a nitrogen atmosphere at 0° C., into the THF (30 ml) solution of 2-fluoro-5-trifluoromethyl benzaldehyde (3.0 g). After the mixture was warmed to room temperature, and was then stirred for 30 minutes, it was poured into a saturated ammonium chloride aqueous solution, and was then subjected to extraction with ethyl acetate. After its organic layer was washed with brine, and was then dried with anhydrous magnesium sulfate, it was filtered, and was then concentrated under reduced pressure to produce a crude chemical compound (58) (3.42 g).

After manganese dioxide (6.78 g) was added to the chloroform solution of the crude chemical compound (58) (3.42 g), this suspension was stirred for 2 hours while refluxing with heating. After the suspension was cooled to room temperature, it was filtered through a pad of CELITE. Its filtrate was concentrated under reduced pressure to produce a crude chemical compound (59).

Ethylene glycol (0.66 g) and p-toluene sulfonic acid monohydrate (0.09 g) were added to the benzene (10 ml) solution of the crude chemical compound (59) (1.00 g), and were then stirred for 5 hours while refluxing with heating. After the mixture was cooled to room temperature, it was poured into water, and was then subjected to extraction with ethyl acetate. After its organic layer was washed with brine, and was then dried with anhydrous magnesium sulfate, it was filtered, and was then concentrated under reduced pressure to produce a crude chemical compound (60) (1.13 g).

60% sodium hydride (0.18 g) was added, with chilling on ice, to the DMF (10 ml) solution of the chemical compound (19) (1.02 g). After the mixture was stirred for 30 minutes at room temperature, the crude chemical compound (60) (1.13 g) was added to it. The mixture was stirred for 30 minutes at room temperature, further heated to 100° C., and then stirred for 8 hours. After the mixture was cooled to room temperature, it was poured into water, and was then subjected to extraction with ethyl acetate. After its organic layer was washed with water, and was then dried with anhydrous magnesium sulfate, it was filtered, and was then concentrated under reduced pressure. Its residue was purified by column chromatography to produce the chemical compound mentioned in the above title (61) (0.55 g).

$^1$H NMR ($CDCl_3$) δ 1.81 (s, 3H), 2.01-2.12 (m, 4H), 2.25-2.33 (m, 2H), 2.46-2.53 (m, 2H), 3.77-3.88 (m, 2H), 4.01-4.13 (m, 2H), 4.57-4.58 (m, 3H), 6.57 (d, 1H), 6.73 (d, 1H), 7.50 (dd, 1H), 7.62 (dd, 1H), 7.81 (s, 1H), 8.42 (s, 1H)

Step 2

Preparation of 3α-[2-(2-methyloxazol-5-yl)-4-(trifluoromethyl)phenoxy]-8-[5-(trifluoromethyl)-2-pyridyl]-8-azabicyclo[3.2.1]octane

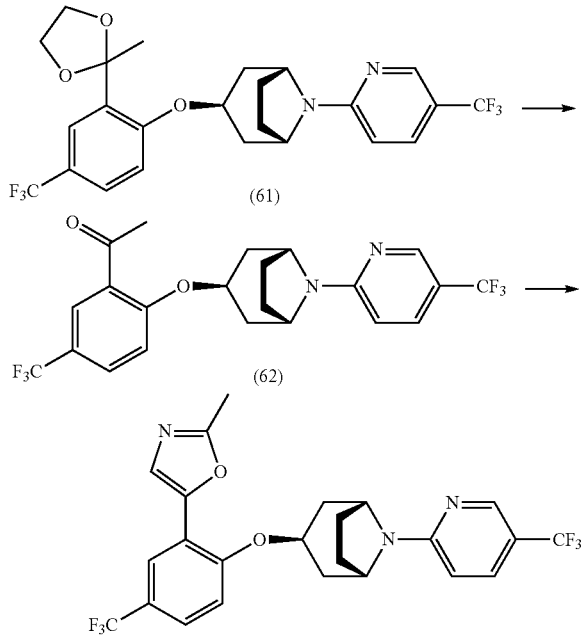

6N Hydrochloric acid (21 ml) was added to the THF (21 ml) solution of the chemical compound (61) (0.55 g), and was then stirred for 2 hours at room temperature. After the mixture was poured into water, and was then neutralized with 10% sodium hydroxide aqueous solution, it was subjected to extraction with ethyl acetate. After its organic layer was washed with brine, and was then dried with anhydrous magnesium sulfate, it was filtered, and was then concentrated under reduced pressure to produce a crude chemical compound (62) (0.46 g).

The chemical compound mentioned in the above title (0.20 g) was produced by using the crude chemical compound (62) (0.30 g) according to a method described in J. Heterocyclic Chem., 1998, 35, 1533-1534.

mp. 121-123° C.

$^1$H NMR ($CDCl_3$) δ 2.04-2.28 (m, 6H), 2.34-2.42 (m, 2H), 2.39 (s, 3H), 4.59 (brs, 2H), 4.71 (t, 1H), 6.58 (d, 1H) 6.83 (d, 1H), 7.50 (dd, 1H), 7.52 (s, 1H), 7.63 (dd, 1H), 7.96 (s, 1H), 8.42 (s, 1H)

Specific examples of the present invention, including the aforementioned examples, are shown in Tables 1 to 14. The scope of the present invention is not limited to these examples.

Abbreviations used in the tables have the following meanings.

Vis: Viscous matter

Amor: Amorphous

Me: Methyl, Et: Ethyl, Pr: Propyl, Bu: Butyl, Hex: Hexyl, Pen: Pentyl, i: iso, n: normal, t: tertiary, c: cyclo Ac: Acetyl

TABLE 1

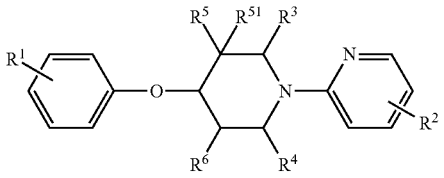

| Compound NO. | R1 | R2 | R3 | R4 | R5 | R51 | R6 | Physical constant [ ]: melting point ° C. | Note |
|---|---|---|---|---|---|---|---|---|---|
| 1-1 | 4-OH | 5-CF3 | H | H | H | H | H | nD22.2-1.5499 | |
| 1-2 | 3-OH | 5-CF3 | H | H | H | H | H | | |
| 1-3 | 2-OH | 5-CF3 | H | H | H | H | H | | |
| 1-4 | 2-OH-4-CF3 | 5-CF3 | H | H | H | H | H | vis | |
| 1-5 | 4-F | 5-CF3 | H | H | H | H | H | | |
| 1-6 | 3-F | 5-CF3 | H | H | H | H | H | | |
| 1-7 | 2-F | 5-CF3 | H | H | H | H | H | | |
| 1-8 | 2-F-4-CF3 | 5-CF3 | H | H | H | H | H | [72-74] | |
| 1-9 | 3-CF3-4-F | 5-CF3 | H | H | H | H | H | nD23.1-1.5071 | |
| 1-10 | 4-Cl | 5-CF3 | H | H | H | H | H | [90-92] | |
| 1-11 | 3-Cl | 5-CF3 | H | H | H | H | H | | |
| 1-12 | 2-Cl | 5-CF3 | H | H | H | H | H | | |
| 1-13 | 2-Cl-4-CF3 | 5-CF3 | H | H | H | H | H | nD21.8-1.5210 | |
| 1-14 | 3-Cl-4-CF3 | 5-CF3 | H | H | H | H | H | | |
| 1-15 | 3-CF3-4-Cl | 5-CF3 | H | H | H | H | H | nD21.9-1.5275 | |
| 1-16 | 2,6-Cl2-4-CF3 | 5-CF3 | H | H | H | H | H | [65-66] | |
| 1-17 | 2-Br-4-CF3-6-Cl | 5-CF3 | H | H | H | H | H | [71-73] | |
| 1-18 | 2-Cl-6-O$^n$Pr-4-CF3 | 5-CF3 | H | H | H | H | H | [70-72] | |
| 1-19 | 4-Br | 5-CF3 | H | H | H | H | H | [87-90] | |
| 1-20 | 3-Br | 5-CF3 | H | H | H | H | H | | |
| 1-21 | 2-Br | 5-CF3 | H | H | H | H | H | | |
| 1-22 | 2-Br-4-CF3 | 5-CF3 | H | H | H | H | H | nD21.8-1.5320 | |
| 1-23 | 3-CF3-4-Br | 5-CF3 | H | H | H | H | H | nD21.9-1.5365 | |
| 1-24 | 4-I | 5-CF3 | H | H | H | H | H | | |
| 1-25 | 3-I | 5-CF3 | H | H | H | H | H | | |
| 1-26 | 2-I | 5-CF3 | H | H | H | H | H | | |
| 1-27 | 2-I-4-CF3 | 5-CF3 | H | H | H | H | H | vis | |
| 1-28 | 2-CF3-4-I | 5-CF3 | H | H | H | H | H | | |
| 1-29 | 4-CN | 5-CF3 | H | H | H | H | H | [157-161] | |
| 1-30 | 3-CN | 5-CF3 | H | H | H | H | H | | |
| 1-31 | 2-CN | 5-CF3 | H | H | H | H | H | | |
| 1-32 | 2-CN-4-CF3 | 5-CF3 | H | H | H | H | H | [101-102] | |
| 1-33 | 2-CF3-4-CN | 5-CF3 | H | H | H | H | H | | |
| 1-34 | 4-NO2 | 5-CF3 | H | H | H | H | H | [140-144] | |
| 1-35 | 3-NO2 | 5-CF3 | H | H | H | H | H | | |
| 1-36 | 2-NO2 | 5-CF3 | H | H | H | H | H | | |
| 1-37 | 2-Cl-4-CF3-6-NO2 | 5-CF3 | H | H | H | H | H | [69-70] | |
| 1-38 | 2-NO2-4-CF3 | 5-CF3 | H | H | H | H | H | [96-97] | |
| 1-39 | 3-CF3-4-NO2 | 5-CF3 | H | H | H | H | H | vis | |
| 1-40 | 2-CHO-4-CF3 | 5-CF3 | H | H | H | H | H | [85-90] | |
| 1-41 | 4-Me | 5-CF3 | H | H | H | H | H | | |
| 1-42 | 3-Me | 5-CF3 | H | H | H | H | H | | |
| 1-43 | 2-Me | 5-CF3 | H | H | H | H | H | | |
| 1-44 | 2,4-Me2 | 5-CF3 | H | H | H | H | H | nD22.3-1.5410 | |
| 1-45 | 2-Me-4-CF3 | 5-CF3 | H | H | H | H | H | | |
| 1-46 | 2-Me-4-OCF3 | 5-CF3 | H | H | H | H | H | nD24.4-1.5089 | |
| 1-47 | 2,4,6-Me3 | 5-CF3 | H | H | H | H | H | nD22.2-1.5339 | |
| 1-48 | 2-Me-4-F | 5-CF3 | H | H | H | H | H | nD24.3-1.5373 | |

TABLE 1-continued

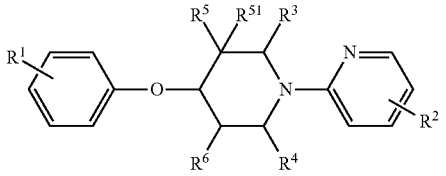

| Compound NO. | $R^1$ | $R^2$ | $R^3$ | $R^4$ | $R^5$ | $R^{51}$ | $R^6$ | Physical constant [ ]: melting point ° C. | Note |
|---|---|---|---|---|---|---|---|---|---|
| 1-49 | 2-Me-4-Cl | 5-CF3 | H | H | H | H | H | nD22.9-1.5505 | |
| 1-50 | 2-Me-4-Br | 5-CF3 | H | H | H | H | H | | |
| 1-51 | 2-Et-4-CF3 | 5-CF3 | H | H | H | H | H | | |
| 1-52 | 2-Me-4-Cl | 5-CF3 | H | H | H | H | H | | |
| 1-53 | 2-Me-4-Br | 5-CF3 | H | H | H | H | H | | |
| 1-54 | 2-Et-4-Cl | 5-CF3 | H | H | H | H | H | nD24.6-1.5445 | |
| 1-55 | 2-Et-4-CF3 | 5-CF3 | H | H | H | H | H | | |
| 1-56 | 2-Et-4-OCF3 | 5-CF3 | H | H | H | H | H | | |
| 1-57 | 2-$^n$Pr-4-Cl | 5-CF3 | H | H | H | H | H | nD24.9-1.5394 | |
| 1-58 | 2-$^n$Pr-4-Br | 5-CF3 | H | H | H | H | H | | |
| 1-59 | 2-$^n$Pr-4-CF3 | 5-CF3 | H | H | H | H | H | nD22.5-1.5141 | |
| 1-60 | 2-$^i$Pr-4-CF3 | 5-CF3 | H | H | H | H | H | | |
| 1-61 | 2-$^i$Pr-4-Cl | 5-CF3 | H | H | H | H | H | | |
| 1-62 | 2-$^i$Pr-4-Br | 5-CF3 | H | H | H | H | H | | |
| 1-63 | 2-CH2OMe-4-CF3 | 5-CF3 | H | H | H | H | H | nD2.62-1.5110 | |
| 1-64 | 2-CH2OMe-4-Cl | 5-CF3 | H | H | H | H | H | | |
| 1-65 | 2-CH2OMe-4-Br | 5-CF3 | H | H | H | H | H | | |
| 1-66 | 2-CH2OEt-4-CF3 | 5-CF3 | H | H | H | H | H | nD23.3-1.5090 | |
| 1-67 | 2-CH(OH)Et-4-CF3 | 5-CF3 | H | H | H | H | H | vis | |
| 1-68 | 2-CH2OH-4-CF3 | 5-CF3 | H | H | H | H | H | vis | |
| 1-69 | 2-CH2OCH2OMe-4-CF3 | 5-CF3 | H | H | H | H | H | vis | |
| 1-70 | 3-CH2OCH2OMe-4-CF3 | 5-CF3 | H | H | H | H | H | | |
| 1-71 | 2-CH2OCH2OEt-4-CF3 | 5-CF3 | H | H | H | H | H | nD22.5-1.5069 | |
| 1-72 | 2-CH2OCH(Me)OMe-4-CF3 | 5-CF3 | H | H | H | H | H | nD2.26-1.5018 | |
| 1-73 | 2-CH═CHMe-4-CF3 | 5-CF3 | H | H | H | H | H | [68-71] | |
| 1-74 | 2-allyl-4-CF3 | 5-CF3 | H | H | H | H | H | vis | |
| 1-75 | 4-CF3 | 5-CF3 | H | H | H | H | H | [48-50] | |
| 1-76 | 3-CF3 | 5-CF3 | H | H | H | H | H | nD23.1-1.5151 | |
| 1-77 | 2-CF3 | 5-CF3 | H | H | H | H | H | | |
| 1-78 | 3,4-(CF3)2 | 5-CF3 | H | H | H | H | H | | |
| 1-79 | 3,5-(CF3)2 | 5-CF3 | H | H | H | H | H | nD21.6-1.4889 | |
| 1-80 | 2,4-(CF3)2 | 5-CF3 | H | H | H | H | H | vis | |
| 1-81 | 2-CH2Cl-4-CF3 | 5-CF3 | H | H | H | H | H | vis | |
| 1-82 | 2-CH(Cl)Et-4-CF3 | 5-CF3 | H | H | H | H | H | vis | |
| 1-83 | 4-CF3 | 3-Cl-5-CF3 | H | H | H | H | H | nD23.0-1.5150 | |
| 1-84 | 4-CF3 | 4-Me-6-CF3 | H | H | H | H | H | nD23.2-1.5089 | |
| 1-85 | 4-OMe | 5-CF3 | H | H | H | H | H | [86-88] | |
| 1-86 | 3-OMe | 5-CF3 | H | H | H | H | H | | |
| 1-87 | 2-OMe | 5-CF3 | H | H | H | H | H | | |
| 1-88 | 2-OMe-4-CF3 | 5-CF3 | H | H | H | H | H | nD22.8-1.5150 | |
| 1-89 | 2-OEt-4-CF3 | 5-CF3 | H | H | H | H | H | [50-53] | |
| 1-90 | 2-OEt-4-CF3 | 5-Cl | H | H | H | H | H | vis | |
| 1-91 | 2-OEt-4-CF3 | 5-Br | H | H | H | H | H | [39-41] | |
| 1-92 | 2-O$^n$Pr-4-CF3 | 5-CF3 | H | H | H | H | H | [55-65] | |
| 1-93 | 2-O$^n$Pr-4-CF3 | 5-CF3 | Me | H | H | H | H | vis | |
| 1-94 | 2-O$^n$Pr-4-CF3 | 5-Me | H | H | H | H | H | nD21.4-1.5295 | |
| 1-95 | 2-O$^n$Pr-4-CF3 | 5-CF3 | H | H | Me | CO2Et | H | vis | |
| 1-96 | 2-O$^n$Pr-4-CF3 | 5-CF3 | H | H | H | H | H | nD22.2-1.4834 | N-oxide (Note 1) |
| 1-97 | 2-O$^n$Pr-4-CF3 | 5-CF3 | H | H | Me | H | H | nD22.8-1.5000 | cis |
| 1-98 | 2-O$^n$Pr-4-CF3 | 5-CF3 | H | H | Me | H | H | vis | trans |
| 1-99 | 2-O$^n$Pr-5-CF3 | 5-CF3 | H | H | H | H | H | nD22.4-1.5088 | |
| 1-100 | 2-O$^i$Pr-4-CF3 | 5-CF3 | H | H | H | H | H | nD25.3-1.5060 | |
| 1-101 | 2-O$^n$Bu-4-CF3 | 5-CF3 | H | H | H | H | H | [70-74] | |
| 1-102 | 2-O$^t$Bu-4-CF3 | 5-CF3 | H | H | H | H | H | [103-104] | |
| 1-103 | 2-O$^n$Hex-4-CF3 | 5-CF3 | H | H | H | H | H | [68-73] | |
| 1-104 | 2-O$^n$Pen-4-CF3 | 5-CF3 | H | H | H | H | H | | |
| 1-105 | 2-OCH2OMe-4-CF3 | 5-CF3 | H | H | H | H | H | nD23.9-1.4969 | |
| 1-106 | 2-OCH2OEt-4-CF3 | 5-CF3 | H | H | H | H | H | | |
| 1-107 | 2-OCH2O$^n$Pr-4-CF3 | 5-CF3 | H | H | H | H | H | | |
| 1-108 | 2-OCH2$^c$Pr-4-CF3 | 5-CF3 | H | H | H | H | H | [49-51] | |
| 1-109 | 2-OCH2$^c$Pr-4-CF3 | 5-CO2Me | H | H | H | H | H | | |
| 1-110 | 2-OCH2$^c$Pr-4-CHF2 | 5-CF3 | H | H | H | H | H | | |
| 1-111 | 2-OCH2$^c$Pr-4-CHO | 5-CF3 | H | H | H | H | H | | |
| 1-112 | 2-OCH2$^c$Pr-4-CF3 | 5-CN | H | H | H | H | H | | |
| 1-113 | 2-OCH2$^c$Pr-4-CN | 5-CF3 | H | H | H | H | H | | |

TABLE 1-continued

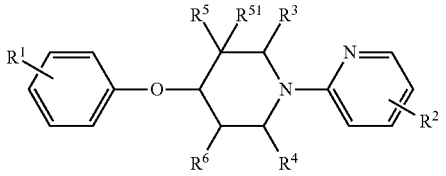

| Compound NO. | $R^1$ | $R^2$ | $R^3$ | $R^4$ | $R^5$ | $R^{51}$ | $R^6$ | Physical constant [ ]: melting point ° C. | Note |
|---|---|---|---|---|---|---|---|---|---|
| 1-114 | 2-OCH2tBu-4-CF3 | 5-CF3 | H | H | H | H | H | vis | |
| 1-115 | 2-O(CH2)2OMe-4-CF3 | 5-CF3 | H | H | H | H | H | [51-54] | |
| 1-116 | 2-O(CH2)2OMe-4-CF3 | 5-CN | H | H | H | H | H | | |
| 1-117 | 2-O(CH2)2OCH2OMe-4-CF3 | 5-CF3 | H | H | H | H | H | vis | |
| 1-118 | 2-O(CH2)2OH-4-CF3 | 5-CF3 | H | H | H | H | H | nD22.2-1.5121 | |
| 1-119 | 2-OCH2Ac-4-CF3 | 5-CF3 | H | H | H | H | H | | |
| 1-120 | 2-OCH2CH(OH)Me-4-CF3 | 5-CF3 | H | H | H | H | H | | |
| 1-121 | 2-OCH2CH(OMe)Me-4-CF3 | 5-CF3 | H | H | H | H | H | | |
| 1-122 | 2-OCH2C(OH)Me2-4-CF3 | 5-CF3 | H | H | H | H | H | | |
| 1-123 | 2-OCH2C(OMe)Me2-4-CF3 | 5-CF3 | H | H | H | H | H | | |
| 1-124 | 2-OCH2C(Me2)CO2Me-4-CF3 | 5-CF3 | H | H | H | H | H | | |
| 1-125 | 2-OCH2C(O)OMe-4-CF3 | 5-CF3 | H | H | H | H | H | | |
| 1-126 | 2-OCH2C(O)OEt-4-CF3 | 5-CF3 | H | H | H | H | H | | |
| 1-127 | 2-O(CH2)2OAc-4-CF3 | 5-CF3 | H | H | H | H | H | | |
| 1-128 | 2-O(CH2)2NH2-4-CF3 | 5-CF3 | H | H | H | H | H | | |
| 1-129 | 2-O(CH2)2NHAc-4-CF3 | 5-CF3 | H | H | H | H | H | | |
| 1-130 | 2-O(CH2)2NMe2-4-CF3 | 5-CF3 | H | H | H | H | H | | |
| 1-131 | 2-OCH2CH(COMe-4-CF3 | 5-CF3 | H | H | H | H | H | | |
| 1-132 | 2-OCH2CH═CMe2-4-CF3 | 5-CF3 | H | H | H | H | H | | |
| 1-133 | 4-OCF3 | 5-CF3 | H | H | H | H | H | [30-32] | |
| 1-134 | 3-OCF3 | 5-CF3 | H | H | H | H | H | | |
| 1-135 | 2-OCF3 | 5-CF3 | H | H | H | H | H | | |
| 1-136 | 4-OCF2Br | 5-CF3 | H | H | H | H | H | vis | |
| 1-137 | 3-OCF2Br | 5-CF3 | H | H | H | H | H | | |
| 1-138 | 2-OCF2Br | 5-CF3 | H | H | H | H | H | | |
| 1-139 | 2-O(CH2)2Br-4-CF3 | 5-CF3 | H | H | H | H | H | [82-84] | |
| 1-140 | 2-O(CH2)2Cl-4-CF3 | 5-CF3 | H | H | H | H | H | vis | |
| 1-141 | 2-O(CH2)2F-4-CF3 | 5-CF3 | H | H | H | H | H | | |
| 1-142 | 2-Oallyl-4-CF3 | 5-CF3 | H | H | H | H | H | [75-77] | |
| 1-143 | 2-Oallenyl-4-CF3 | 5-CF3 | H | H | H | H | H | vis | |
| 1-144 | 4-CO2Me | 5-CF3 | H | H | H | H | H | [124-126] | |
| 1-145 | 3-CO2Me | 5-CF3 | H | H | H | H | H | | |
| 1-146 | 2-CO2Me | 5-CF3 | H | H | H | H | H | | |
| 1-147 | 4-SCF3 | 5-CF3 | H | H | H | H | H | [81-82] | |
| 1-148 | 3-SCF3 | 5-CF3 | H | H | H | H | H | | |
| 1-149 | 2-SCF3 | 5-CF3 | H | H | H | H | H | | |
| 1-150 | 4-S(O)CF3 | 5-CF3 | H | H | H | H | H | [83-86] | |
| 1-151 | 3-S(O)CF3 | 5-CF3 | H | H | H | H | H | | |
| 1-152 | 2-S(O)CF3 | 5-CF3 | H | H | H | H | H | | |
| 1-153 | 4-OSO2CF3 | 5-CF3 | H | H | H | H | H | [52-54] | |
| 1-154 | 3-OSO2CF3 | 5-CF3 | H | H | H | H | H | | |
| 1-155 | 2-OSO2CF3 | 5-CF3 | H | H | H | H | H | | |
| 1-156 | 4-OC(O)Ph | 5-CF3 | H | H | H | H | H | [154-156] | |
| 1-157 | 3-OC(O)Ph | 5-CF3 | H | H | H | H | H | | |
| 1-158 | 2-OC(O)Ph | 5-CF3 | H | H | H | H | H | | |
| 1-159 | 4-OCH2Ph | 5-CF3 | H | H | H | H | H | [109-110] | |
| 1-160 | 3-OCH2Ph | 5-CF3 | H | H | H | H | H | | |
| 1-161 | 2-OCH2Ph | 5-CF3 | H | H | H | H | H | | |
| 1-162 | 4-OCH2(Naph-1-yl) | 5-CF3 | H | H | H | H | H | [123-124] | |
| 1-163 | 2-Opropargyl-4-CF3 | 5-CF3 | H | H | H | H | H | vis | |
| 1-164 | 2-(OCH2CH═CCl2)-4-CF3 | 5-CF3 | H | H | H | H | H | [93-95] | |
| 1-165 | 2,3,6-Cl3-4-OCH2CH═CCl2) | 3-Cl-5-CF3 | H | H | H | H | H | [58-60] | |
| 1-166 | 2,3,6-Cl3-4-OCH2CH═CCl2) | 5-CF3 | H | H | H | H | H | vis | |
| 1-167 | 2-OAc-4-CF3 | 5-CF3 | H | H | H | H | H | [85-95] | |
| 1-168 | 3-CF3-4-NH2 | 5-CF3 | H | H | H | H | H | nD21.6-1.5259 | |
| 1-169 | 2-NH2-4-CF3 | 5-CF3 | H | H | H | H | H | vis | |
| 1-170 | 2-NH2-4-CF3-6-Cl | 5-CF3 | H | H | H | H | H | vis | |
| 1-171 | 2-NHMe-4-CF3 | 5-CF3 | H | H | H | H | H | | |
| 1-172 | 2-NHEt-4-CF3 | 5-CF3 | H | H | H | H | H | vis | |
| 1-173 | 1-NH″Pr-4-CF3 | 5-CF3 | H | H | H | H | H | vis | |
| 1-174 | 2-N(″Pr)2-4-CF3 | 5-CF3 | H | H | H | H | H | nD22.0-1.5121 | |
| 1-175 | 2-N(Ac)″Pr-4-CF3 | 5-CF3 | H | H | H | H | H | [110-114] | |
| 1-176 | 2-OC(O)OMe-4-CF3 | 5-CF3 | H | H | H | H | H | nD23.9-1.5000 | |
| 1-177 | 2-OC(O)SMe-4-CF3 | 5-CF3 | H | H | H | H | H | [77-79] | |
| 1-178 | 3-CF3-4-N(SO2Me)2 | 5-CF3 | H | H | H | H | H | amer | |
| 1-179 | 2-C(O)Et-4-CF3 | 5-CF3 | H | H | H | H | H | vis | |

TABLE 1-continued

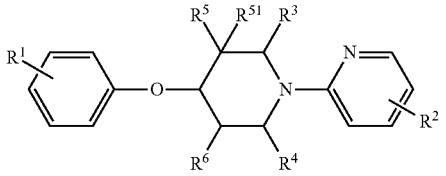

| Compound NO. | $R^1$ | $R^2$ | $R^3$ | $R^4$ | $R^5$ | $R^{51}$ | $R^6$ | Physical constant [ ]: melting point ° C. | Note |
|---|---|---|---|---|---|---|---|---|---|
| 1-180 | 2-CH2O-tetrahydrofuran-2-yl-4-CF3 | 5-CF3 | H | H | H | H | H | nD22.7-1.5105 | |
| 1-181 | 2-(1,3-dioxolanyl)-4-CF3 | 5-CF3 | H | H | H | H | H | nD23.2-1.5155 | |
| 1-182 | 2-CH2OnPr-4-CF3 | 5-CF3 | H | H | H | H | H | [67-70] | |
| 1-183 | 2-CH2OCH2OMe-4-CF3 | 5-CF3 | H | H | Me | H | H | nD22.2-1.5062 | cis:trans = 1:1 |
| 1-184 | 2-CH(Me)OCH2OMe-4-CF3 | 5-CF3 | H | H | H | H | H | nD23.7-1.4995 | |
| 1-185 | 2-CH2OCH(Me)Et-4-CF3 | 5-CF3 | H | H | H | H | H | Nd24.1-1.5015 | |
| 1-186 | 2-OnPr-4-CF3 | 5-CF3 | H | H | Et | H | H | vis | cis |
| 1-187 | 2-OnPr-4-CF3 | 5-CF3 | H | H | Et | H | H | vis | trans |
| 1-188 | 2-CH2OCH(Me)OMe-4-CF3 | 5-CF3 | H | H | Me | H | H | nD23.2-1.5035 | trans |
| 1-189 | 2-CH2OCH(Me)OMe-4-CF3 | 5-CF3 | H | H | Me | H | H | nD24.6-1.5039 | cis |
| 1-190 | 2-(3-Me-1,2,4-oxidazol-5-yl)-4-CF3 | 5-CF3 | H | H | H | H | H | vis | |
| 1-191 | 2-OnPr-4-CF3 | 5-CF3 | H | H | nPr | H | H | nD22.3-1.5055 | cis |
| 1-192 | 2-OnPr-4-CF3 | 5-CF3 | H | H | nPr | H | H | vis | trans |

Note 1)

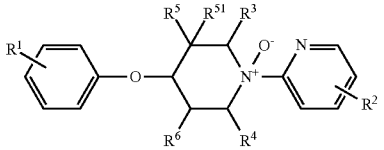

TABLE 2

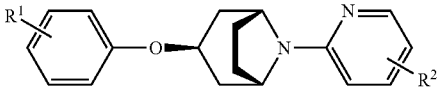

| Compound NO. | $R^1$ | $R^2$ | Physical constant [ ]: melting point ° C. | Note |
|---|---|---|---|---|
| 2-1 | 4-OH | 5-CF3 | | |
| 2-2 | 3-OH | 5-CF3 | | |
| 2-3 | 2-OH | 5-CF3 | | |
| 2-4 | 2-OH-4-CF3 | 5-CF3 | [90-94] | |
| 2-5 | 4-F | 5-CF3 | | |
| 2-6 | 3F | 5-CF3 | | |
| 2-7 | 2F | 5-CF3 | | |
| 2-8 | 2-F-4-CF3 | 5-CF3 | | |
| 2-9 | 3-CF3-4-F | 5-CF3 | | |
| 2-10 | 4-Cl | 5-CF3 | | |
| 2-11 | 3-Cl | 5-CF3 | | |
| 2-12 | 2-Cl | 5-CF3 | | |
| 2-13 | 2-Cl-4-CF3 | 5-CF3 | vis | |
| 2-14 | 3-CF3-4-Cl | 5-CF3 | | |
| 2-15 | 2,6-Cl2-4-CF3 | 5-CF3 | | |
| 2-16 | 2-Br-4-CF3-6-Cl | 5-CF3 | | |
| 2-17 | 2-Cl-6-O$^n$Pr-4-CF3 | 5-CF3 | | |
| 2-18 | 4-Br | 5-CF3 | | |
| 2-19 | 3-Br | 5-CF3 | | |
| 2-20 | 2-Br | 5-CF3 | | |
| 2-21 | 2-Br-4-CF3 | 5-CF3 | [112-115] | |
| 2-22 | 3-CF3-4-Br | 5-CF3 | | |
| 2-23 | 4-I | 5-CF3 | | |
| 2-24 | 3-I | 5-CF3 | | |
| 2-25 | 2-I | 5-CF3 | | |
| 2-26 | 2-I-4-CF3 | 5-CF3 | | |
| 2-27 | 4-CN | 5-CF3 | | |
| 2-28 | 3-CN | 5-CF3 | | |

TABLE 2-continued

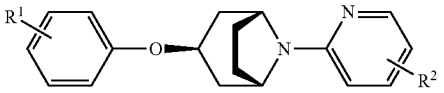

| Compound NO. | $R^1$ | $R^2$ | Physical constant [ ]: melting point ° C. | Note |
|---|---|---|---|---|
| 2-29 | 2-CN | 5-CF3 | | |
| 2-30 | 2-CN-4-CF3 | 5-CF3 | [110-113] | |
| 2-31 | 4-NO2 | 5-CF3 | | |
| 2-32 | 3-NO2 | 5-CF3 | | |
| 2-33 | 2-NO2 | 5-CF3 | | |
| 2-34 | 2-Cl-4-O2 | 5-CF3 | | |
| 2-35 | 2-NO2-4-CF3 | 5-CF3 | vis | |
| 2-36 | 3-CF3-4-NO2 | 5-CF3 | | |
| 2-37 | 2-CHO-4-CF3 | 5-CF3 | | |
| 2-38 | 4-Me | 5-CF3 | | |
| 2-39 | 3-Me | 5-CF3 | | |
| 2-40 | 2-Me | 5-CF3 | | |
| 2-41 | 2,4-Me2 | 5-CF3 | | |
| 2-42 | 2-Me-3-CF3 | 5-CF3 | [121-123] | |
| 2-43 | 2-Me-4-CF3 | 5-CF3 | | |
| 2-44 | 2-Me-4-OCF3 | 5-CF3 | [88-91] | |
| 2-45 | 2-Et-4-CF3 | 5-CF3 | | |
| 2-46 | 2,4,6-Me3 | 5-CF3 | | |
| 2-47 | 2-Me-4-F | 5-CF3 | [98-100] | |
| 2-48 | 2-Me-4-Cl | 5-CF3 | | |
| 2-49 | 2-Et-4-Cl | 5-CF3 | | |
| 2-50 | 2-$^n$Pr-4-Cl | 5-CF3 | | |
| 2-51 | 2-$^n$Pr-4-CF3 | 5-CF3 | vis | |
| 2-52 | 2-$^i$Pr-4-CF3 | 5-CF3 | | |
| 2-53 | 2-CH2OMe-4-CF3 | 5-CF3 | | |
| 2-54 | 2-CH2OEt-4-CF3 | 5-CF3 | [91-93] | |
| 2-55 | 2-CH(OH)Et-4-CF3 | 5-CF3 | | |
| 2-56 | 2-CH2OH-4-CF3 | 5-CF3 | | |
| 2-57 | 2-CH2OCH2OMe-4-CF3 | 5-CF3 | vis | |
| 2-58 | 2-CH2OCH2OEt-4-CF3 | 5-CF3 | vis | |
| 2-59 | 2-CH2OCH(Me)OMe-4-CF3 | 5-CF3 | [89-91] | |
| 2-60 | 2-CH2OCH(Me)OMe-4-CF3 | 5-CF3 | [95-98] | N-oxide (Note 2-1) |
| 2-61 | 2-CH═CHMe-4-CF3 | 5-CF3 | | |
| 2-62 | 2-allyl-4-CF3 | 5-CF3 | vis | |
| 2-63 | 4-CF3 | 5-CF3 | | |
| 2-64 | 3-CF3 | 5-CF3 | | |
| 2-65 | 2-CF3 | 5-CF3 | | |
| 2-66 | 3,4-(CF3)2 | 5-CF3 | | |
| 2-67 | 3,5-(CF3)2 | 5-CF3 | vis | |
| 2-68 | 2,4-(CF3)2 | 5-CF3 | | |
| 2-69 | 2-CH2Cl-4-CF3 | 5-CF3 | | |
| 2-70 | 2-CH(Cl)Et-4-CF3 | 5-CF3 | | |
| 2-71 | 4-CF3 | 3-Cl-5-CF3 | | |
| 2-72 | 4-CF3 | 4-Me-5-CF3 | | |
| 2-73 | 4-OMe | 5-CF3 | | |
| 2-74 | 3-OMe | 5-CF3 | | |
| 2-75 | 2-OMe | 5-CF3 | | |
| 2-76 | 2-OMe-4-CN | 5-CF3 | [85-90] | |
| 2-77 | 2-OMe-4-CF3 | 5-CF3 | vis | |
| 2-78 | 2-OEt-4-CF3 | 5-CF3 | vis | |
| 2-79 | 2-OEt-4-CF3 | 5-Cl | | |
| 2-80 | 2-OEt-4-CF3 | 5-Br | | |
| 2-81 | 2-O$^n$Pr-4-CN | 5-CF3 | vis | |
| 2-82 | 2-O$^n$Pr-4-CF3 | 5-CF3 | [90-92] | |
| 2-83 | 2-O$^n$Pr-4-CF3 | 5-CF3 | [143-145] | N-oxide (Note 2-2) |
| 2-84 | 2-O$^n$Pr-4-CF3 | 5-CF3 | [129-130] | N-oxide (Note 2-3) |
| 2-85 | 2-O$^n$Pr-4-CF3 | 5-Cl | [92-97] | |
| 2-86 | 2-O$^n$Pr-4-CF3 | 5-Br | [50-52] | |
| 2-87 | 2-O$^n$Pr-4-CF3 | 5-NO2 | [159-160] | |
| 2-88 | 2-O$^n$Pr-4-CF3 | 5-NH2 | amor | |
| 2-89 | 2-O$^n$Pr-4-CF3 | 5-Me | [97-98] | |
| 2-90 | 2-O$^n$Pr-4-CF3 | 5-NHSO2Me | amor | |
| 2-91 | 2-O$^n$Pr-5-CF3 | 5-CF3 | | |
| 2-92 | 2-O$^n$Pr-4-CF3 | 6-CF3 | nD22.5-1.5090 | |
| 2-93 | 2-O$^n$Pr-4-CF3 | 5-CN | [124-125] | |
| 2-94 | 2-O$^n$Pr-4-CF3 | 5-CF3-6-CN | [132-134] | |
| 2-95 | 2-Cl-6-O$^n$Pr-4-CF3 | 5-CF3 | vis | |
| 2-96 | 2-O$^i$Pr-4-CF3 | 5-CF3 | [113-115] | |
| 2-97 | 2-O$^n$Bu-4-CF3 | 5-CF3 | [53-55] | |
| 2-98 | 2-O$^i$Bu-4-CF3 | 5-CF3 | [126-129] | |

TABLE 2-continued

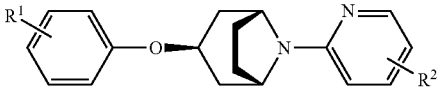

| Compound NO. | $R^1$ | $R^2$ | Physical constant [ ]: melting point ° C. | Note |
|---|---|---|---|---|
| 2-99 | 2-O″Hex-4-CF3 | 5-CF3 | | |
| 2-100 | 2-O″Pen-4-CF3 | 5-CF3 | vis | |
| 2-101 | 2-OCH2CN-4-CF3 | 5-CF3 | vis | |
| 2-102 | 2-OCH2OMe-4-CF3 | 5-CF3 | [69-73] | |
| 2-103 | 2-OCH2OEt-4-CF3 | 5-CF3 | | |
| 2-104 | 2-OCH2O″Pr-4-CF3 | 5-CF3 | | |
| 2-105 | 2-OCH2ᶜPr-4-CF3 | 5-CF3 | [114-116] | |
| 2-106 | 2-OCH2ᶜPr-4-CF3 | 5-CO2Me | | |
| 2-107 | 2-OCH2ᶜPr-4-CHF2 | 5-CF3 | | |
| 2-108 | 2-OCH2ᶜPr-4-CHO | 5-CF3 | | |
| 2-109 | 2-OCH2ᶜPr-4-CF3 | 5-CN | | |
| 2-110 | 2-OCH2ᶜPr-4-CN | 5-CF3 | | |
| 2-111 | 2-OCH2ᶜBu-4-CF3 | 5-CF3 | [148-150] | |
| 2-112 | 2-O(CH2)2OMe-4-CF3 | 5-CF3 | vis | |
| 2-113 | 2-O(CH2)2OMe-4-CF3 | 5-CN | | |
| 2-114 | 2-O(CH2)2OCH2OMe-4-CF3 | 5-CF3 | | |
| 2-115 | 2-O(CH2)2OH-4-CF3 | 5-CF3 | vis | |
| 2-116 | 2-OCH2Ac-4-CF3 | 5-CF3 | | |
| 2-117 | 2-OCH2CH(OH)Me-4-CF3 | 5-CF3 | | |
| 2-118 | 2-OCH2CH(OMe)Me-4-CF3 | 5-CF3 | | |
| 2-119 | 2-OCH2C(OH)Me-4-CF3 | 5-CF3 | | |
| 2-120 | 2-OCH2C(OMe)Me-4-CF3 | 5-CF3 | | |
| 2-121 | 2-OCH2C(Me2)CO2Me-4-CF3 | 5-CF3 | | |
| 2-122 | 2-OCH2C(O)OMe-4-CF3 | 5-CF3 | | |
| 2-123 | 2-OCH2C(O)OEt-4-CF3 | 5-CF3 | | |
| 2-124 | 2-O(CH2)2OAc-4-CF3 | 5-CF3 | | |
| 2-125 | 2-O(CH2)2NH2-4-CF3 | 5-CF3 | | |
| 2-126 | 2-O(CH2)2NHAc-4-CF3 | 5-CF3 | | |
| 2-127 | 2-O(CH2)2NMe2-4-CF3 | 5-CF3 | | |
| 2-128 | 2-OCH2CH(COMe-4-CF3 | 5-CF3 | | |
| 2-129 | 2-OCH2CH═CMe2-4-CF3 | 5-CF3 | | |
| 2-130 | 2-OCH2CH(Me)OMe-4-CF3 | 5-CF3 | vis | |
| 2-131 | 4-OCF3 | 5-CF3 | | |
| 2-132 | 3-OCF3 | 5-CF3 | | |
| 2-133 | 2-OCF3 | 5-CF3 | | |
| 2-134 | 4-OCF2Br | 5-CF3 | | |
| 2-135 | 3-OCF2Br | 5-CF3 | | |
| 2-136 | 2-OCF2Br | 5-CF3 | | |
| 2-137 | 2-O(CH2)2Br-4-CF3 | 5-CF3 | | |
| 2-138 | 2-O(CH2)2Cl-4-CF3 | 5-CF3 | vis | |
| 2-139 | 2-O(CH2)2F-4-CF3 | 5-CF3 | | |
| 2-140 | 2-OCH2(Ph-4-Cl)-4-CF3 | 5-CF3 | [115-118] | |
| 2-141 | 2-Oallyl-4-CF3 | 5-CF3 | vis | |
| 2-142 | 2-Oallenyl-4-CF3 | 5-CF3 | | |
| 2-143 | 2-Opropargyl-4-CF3 | 5-CF3 | vis | |
| 2-144 | 2-O(CH2)2CH═CH2-4-CF3 | 5-CF3 | vis | |
| 2-145 | 2-OCH2CH═CHMe-4-CF3 | 5-CF3 | [65-67] | mixture of cis and trans |
| 2-146 | 2-OCH2CH═CMe2-4-CF3 | 5-CF3 | [54-57] | |
| 2-147 | 2-OCH2C(Me)═CH2-4-CF3 | 5-CF3 | [96-98] | |
| 2-148 | 2-OCH2CH═CHCl-4-CF3 | 5-CF3 | vis | mixture of cis and trans |
| 2-149 | 2-OAc-4-CF3 | 5-CF3 | [93-97] | |
| 2-150 | 2-OC(O)ᵗBu-4-CF3 | 5-CF3 | [112-115] | |
| 2-151 | 2-OSO2Me-4-CF3 | 5-CF3 | [107-110] | |
| 2-152 | 2-OSO2Et-4-CF3 | 5-CF3 | [121-124] | |
| 2-153 | 2-SO2″Pr-4-CF3 | 5-CF3 | amor | |
| 2-154 | 2-OSO2″Bu-4-CF3 | 5-CF3 | [133-136] | |
| 2-155 | 2-OSO2NMe2-4-CF3 | 5-CF3 | [140-143] | |
| 2-156 | 2-OC(S)NMe2-4-CF3 | 5-CF3 | [150-153] | |
| 2-157 | 2-SC(O)NMe2-4-CF3 | 5-CF3 | [165-168] | |
| 2-158 | 2-NH2-4-CF3 | 5-CF3 | [87-89] | |
| 2-159 | 2-N(″Pr)2-4-CF3 | 5-CF3 | amor | |
| 2-160 | 2-NH″Pr-4-CF3 | 5-CF3 | [94-96] | |
| 2-161 | 2-N(Me)″Pr-4-CF3 | 5-CF3 | vis | |
| 2-162 | 2-NHSO2Me-4-CF3 | 5-CF3 | [165-168] | |
| 2-163 | 2-NHSO2Et-4-CF3 | 5-CF3 | [171-174] | |
| 2-164 | 2-N(SO2″Bu)2-4-CF3 | 5-CF3 | [181-183] | |
| 2-165 | 2-S″Pr-4-CF3 | 5-CF3 | [87-90] | |
| 2-166 | 2-SCHᶜPr-4-CF3 | 5-CF3 | [110-112] | |
| 2-167 | 2-OP(O)(OEt)S″Pr-4-CF3 | 5-CF3 | vis | |

TABLE 2-continued

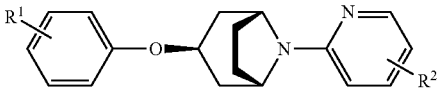

| Compound NO. | $R^1$ | $R^2$ | Physical constant [ ]: melting point ° C. | Note |
|---|---|---|---|---|
| 2-168 | 2-O$^n$Pr-4-CF3 | 1,3-Me2-pyrazolyl-5-yl | [132-134] | |
| 2-169 | 2-(1,3-dioxolanyl)-4-CF3 | 5-CF3 | [148-151] | |
| 2-170 | 2-CH(Me)OCH2OMe-4-CF3 | 5-CF3 | nD23.7-1.5045 | |
| 2-171 | 2-CH2OnPr-4-CF3 | 5-CF3 | nD23.7-1.5137 | |
| 2-172 | 2-CH2OAc-4-CF3 | 5-CF3 | Nd24.1-1.5263 | |
| 2-173 | 2-OCH2CH(OH)Me-4-CF3 | 5-CF3 | amor | |
| 2-174 | 2-OCH2CH(OMe)Me-4-CF3 | 5-CF3 | [105-108] | N-oxide (Note 2-4) |
| 2-175 | 2-OCH2CH(OEt)Me-4-CF3 | 5-CF3 | Nd22.8-1.5138 | |
| 2-176 | 2-OCH2CH(OSO2Me)Me-4-CF3 | 5-CF3 | Nd22.9-1.5092 | |
| 2-177 | 2-OCH(Me)Et-4-CF3 | 5-CF3 | [89-91] | |
| 2-178 | 2-OCH(Me)CH2OMe-4-CF3 | 5-CF3 | [56-58] | |
| 2-179 | 2-(O-tetrahydrofuranyl-3-yl)-4-CF3 | 5-CF3 | [91-93] | |
| 2-180 | 2-CH2OH-4-CF3 | 5-CF3 | [115-118] | |
| 2-181 | 2-OCH2CH(F)Me-4-CF3 | 5-CF3 | [99-102] | |
| 2-182 | 2-OCH2SMe-4-CF3 | 5-CF3 | [76-80] | |
| 2-183 | 2-OCH2C(═CH2)Cl-4-CF3 | 5-CF3 | [83-85] | |
| 2-184 | 2-CH(OH)nPr-4-CF3 | 5-CF3 | [141-145] | |
| 2-185 | 2-CH(OMe)nPr-4-CF3 | 5-CF3 | Nd24.9-1.5070 | |
| 2-186 | 2-CH═CHEt-4-CF3 | 5-CF3 | [94-98] | mixture of cis and trans |
| 2-187 | 2-nBu-4-CF3 | 5-CF3 | [86-88] | |
| 2-188 | 2-CH═CHCO2Et-4-CF3 | 5-CF3 | [107-110] | mixture of cis and trans |
| 2-189 | 2-CH2CH2CH2OH-4-CF3 | 5-CF3 | amor | |
| 2-190 | 2-CH2CH2CH2OMe-4-CF3 | 5-CF3 | Nd22.5-1.5249 | |
| 2-191 | 2-CH2CH2CHO-4-CF3 | 5-CF3 | Nd22.6-1.5335 | |
| 2-192 | 2-CH2CH2CH(OMe)Me-4-CF3 | 5-CF3 | Nd22.6-1.5110 | |
| 2-193 | 2-CO2Et-4-CF3 | 5-CF3 | [94-98] | |
| 2-194 | 2-CH(OH)sBu-4-CF3 | 5-CF3 | [121-124] | |
| 2-195 | 2-OCH2CH(Br)Me-4-CF3 | 5-CF3 | [114-119] | |
| 2-196 | 2-CO2iPr-4-CF3 | 5-CF3 | [95-97] | |
| 2-197 | 2-CH(OH)CH2tBu-4-CF3 | 5-CF3 | [179-181] | |
| 2-198 | 2-CO2tBu-4-CF3 | 5-CF3 | [118-120] | |
| 2-199 | 2-(4-Me-oxazolizinyl-2-yl)-4-CF3 | 5-CF3 | [102-106] | |
| 2-200 | 2-(3-Me-1,2,4-oxadiazol-5-yl)-4-CF3 | 5-CF3 | [148-151] | |
| 2-201 | 2-(5-Me-oxazolizinyl-2-yl)-4-CF3 | 5-CF3 | [105-107] | |
| 2-202 | 2-(5-Me-1,2,4-oxadiazol-2-yl)-4-CF3 | 5-CF3 | [177-179] | |
| 2-203 | 2-CH═NOEt-4-CF3 | 5-CF3 | amor | (E) |
| 2-204 | 2-CO2CH2CCH-4-CF3 | 5-CF3 | [95-97] | |
| 2-205 | 2-(5-Me-oxazolyl-2-yl)-4-CF3 | 5-CF3 | [120-122] | |
| 2-206 | 2-CO2CH(Me)CCH-4-CF3 | 5-CF3 | [111-113] | |
| 2-207 | 2-O$^n$Pr-4-CF3 | 3-Cl-5-CF3 | [24-25] | |
| 2-208 | 2-CO2sBu-4-CF3 | 5-CF3 | [92-94] | |
| 2-209 | 2-(4-Me-oxazolyl-2-yl)-4-CF3 | 5-CF3 | [100-103] | |
| 2-210 | 2-(4,4-Me2-oxazolizinyl-2-yl)-4-CF3 | 5-CF3 | [122-124] | |
| 2-211 | 2-CH═NOMe-4-CF3 | 5-CF3 | [92-94] | |
| 2-212 | 2-ON═C(Me)2-4-CF3 | 5-CF3 | [107-109] | |
| 2-213 | 2-ON═CHMe-4-CF3 | 5-CF3 | [64-66] | mixture of E and Z |
| 2-214 | 2-(2-Me-oxazolyl-5-yl)-4-CF3 | 5-CF3 | [121-123] | |
| 2-215 | 2-CH═NO$^i$Pr-4-CF3 | 5-CF3 | [110-112] | |
| 2-216 | 2-(5-Me-1,2,4-oxazolizinyl-2-yl)-4-CF3 | 5-CF3 | [174-177] | |
| 2-217 | 2-(5-OMe-oxazolyl-2-yl)-4-CF3 | 5-CF3 | [143-146] | |
| 2-218 | 2-C(Me)═NOEt-4-CF3 | 5-CF3 | [91-94] | (E) |
| 2-219 | 2-C(Me)═NOEt-4-CF3 | 5-CF3 | [92-96] | (Z) |
| 2-220 | 2-(4-Et-oxazolizinyl-2-yl)-4-CF3 | 5-CF3 | [95-99] | |
| 2-221 | 2-CH═NOCH2CCH-4-CF3 | 5-CF3 | [96-98] | |
| 2-222 | 2-N═C(Me)OMe-4-CF3 | 5-CF3 | [81-83] | (E) |
| 2-223 | 2-CO2cPen-4-CF3 | 5-CF3 | [66-68] | |
| 2-224 | 2-N═C(Me)OEt-4-CF3 | 5-CF3 | vis | (E) |
| 2-225 | 2-CO2-(tetrahydrofuranyl-3-yl)-4-CF3 | 5-CF3 | [94-96] | |
| 2-226 | 2-ON═C(Me)Et-4-CF3 | 5-CF3 | [77-80] | mixture of E and Z |
| 2-227 | 2-ON-(cyclopentylidenyl)-4-CF3 | 5-CF3 | [96-98] | |
| 2-228 | 2-ON═CHEt-4-CF3 | 5-CF3 | Nd.22.2-1.5170 | mixture of E and Z |
| 2-229 | 2-ON-(cyclopentylidenyl)-4-CF3 | 5-CF3 | [99-103] | |
| 2-230 | 2-CO2CH2CH2OMe-4-CF3 | 5-CF3 | Nd.22.5-1.5159 | |
| 2-231 | 2-CO2cHex-4-CF3 | 5-CF3 | Nd.22.4-1.5042 | |
| 2-232 | 2-CO2CH(Me)iPr-4-CF3 | 5-CF3 | Nd.22.4-1.5083 | |
| 2-233 | 2-CO2CH(Me)CH2Cl-4-CF3 | 5-CF3 | Nd.22.4-1.5105 | |
| 2-234 | 2-CO2CH(Me)CH2OMe-4-CF3 | 5-CF3 | Nd.22.4-1.5065 | |
| 2-235 | 2-CO2CH(Mc)CH2═CH2-4-CF3 | 5-CF3 | [77-81] | |

TABLE 2-continued

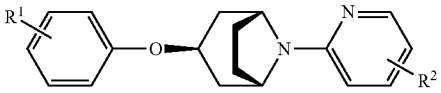

| Compound NO. | $R^1$ | $R^2$ | Physical constant [ ]: melting point ° C. | Note |
|---|---|---|---|---|
| 2-236 | 2-CO2CH(Me)CH2Br-4-CF3 | 5-CF3 | [94-98] | |
| 2-237 | 2-CO2CH2cPr-4-CF3 | 5-CF3 | [90-94] | |
| 2-238 | 2-CO2cPr-4-CF3 | 5-CF3 | [143-145] | |
| 2-239 | 2-CO2CH(Me)cPr-4-CF3 | 5-CF3 | [123-125] | |
| 2-240 | 2-CO2CH2CF3-4-CF3 | 5-CF3 | [83-86] | |
| 2-241 | 2-OC(O)OiPr-4-CF3 | 5-CF3 | [38-42] | |
| 2-242 | 2-CH2CN═C(Me)2-4-CF3 | 5-CF3 | [110-112] | |
| 2-243 | 2-NHCO2iPr-4-CF3 | 5-CF3 | [140-143] | |
| 2-244 | 2-CO2-(tetrahydrofuran-2-yl-4-CF3 | 5-CF3 | [85-88] | |
| 2-245 | 2-OCH═C(Me)2-4-CF3 | 5-CF3 | [90-92] | |
| 2-246 | 2-OCH2CHF2-4-CF3 | 5-CF3 | [85-87] | |
| 2-247 | 2-CO2CH(Me)CH═CH2-4-CF3 | 5-CF3 | [119-121] | N-oxide (Note 2-5) |
| 2-248 | 2-CN═C(Me)CH2OMe-4-CF3 | 5-CF3 | [105-108] | (Z) |
| 2-249 | 2-CN═C(Me)CH2OMe-4-CF3 | 5-CF3 | [58-62] | (E) |
| 2-250 | 2-CN═C(Me)OMe-4-CF3 | 5-CF3 | [120-122] | (E) |

(Note 2-1)

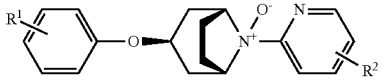

(Note 2-2)

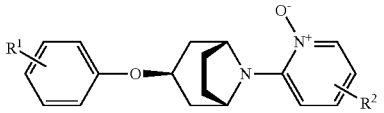

(Note 2-3)

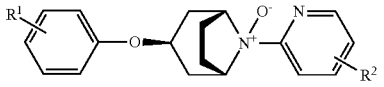

(Note 2-4)

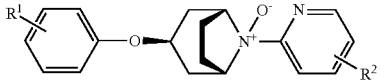

(Note 2-5)

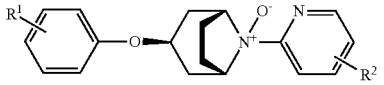

TABLE 3

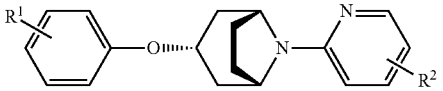

| Compound NO. | $R^1$ | $R^2$ | Physical constant [ ]: melting point ° C. | Note |
|---|---|---|---|---|
| 3-1 | 4-OH | 5-CF3 | | |
| 3-2 | 3-OH | 5-CF3 | | |
| 3-3 | 2-OH | 5-CF3 | | |
| 3-4 | 2-OH-4-CF3 | 5-CF3 | | |
| 3-5 | 4-F | 5-CF3 | | |
| 3-6 | 3-F | 5-CF3 | | |
| 3-7 | 2-F | 5-CF3 | | |
| 3-8 | 2-F-4-CF3 | 5-CF3 | | |
| 3-9 | 3-CF3-4-F | 5-CF3 | | |
| 3-10 | 4-Cl | 5-CF3 | | |
| 3-11 | 3-Cl | 5-CF3 | | |
| 3-12 | 2-Cl | 5-CF3 | | |

TABLE 3-continued

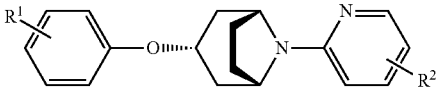

| Compound NO. | $R^1$ | $R^2$ | Physical constant [ ]: melting point ° C. | Note |
|---|---|---|---|---|
| 3-13 | 2-Cl-4-CF3 | 5-CF3 | | |
| 3-14 | 3-CF3-4-Cl | 5-CF3 | | |
| 3-15 | 2,6-Cl2-4-CF3 | 5-CF3 | | |
| 3-16 | 2-Br-4-CF3-6-Cl | 5-CF3 | | |
| 3-17 | 2-Cl-6-O″Pr-4-CF3 | 5-CF3 | | |
| 3-18 | 4-Br | 5-CF3 | | |
| 3-19 | 3-Br | 5-CF3 | | |
| 3-20 | 2-Br | 5-CF3 | | |
| 3-21 | 2-Br-4-CF3 | 5-CF3 | | |
| 3-22 | 3-CF3-4-Br | 5-CF3 | | |
| 3-23 | 4-I | 5-CF3 | | |
| 3-24 | 3-I | 5-CF3 | | |

TABLE 3-continued

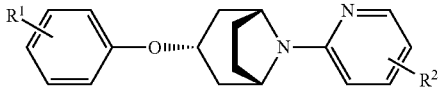

| Compound NO. | $R^1$ | $R^2$ | Physical constant [ ]: melting point ° C. | Note |
|---|---|---|---|---|
| 3-25 | 2-I | 5-CF3 | | |
| 3-26 | 2-I-4-CF3 | 5-CF3 | | |
| 3-27 | 4-CN | 5-CF3 | | |
| 3-28 | 3-CN | 5-CF3 | | |
| 3-29 | 2-CN | 5-CF3 | | |
| 3-30 | 2-CN-4-CF3 | 5-CF3 | | |
| 3-31 | 4-NO2 | 5-CF3 | | |
| 3-32 | 3-NO2 | 5-CF3 | | |
| 3-33 | 2-NO2 | 5-CF3 | | |
| 3-34 | 2-Cl-4-CF3-6-NO2 | 5-CF3 | | |
| 3-35 | 2-NO2-4-CF3 | 5-CF3 | | |
| 3-36 | 3-CF3-4-NO2 | 5-CF3 | | |
| 3-37 | 2-CHO-4-CF3 | 5-CF3 | | |
| 3-38 | 4-Me | 5-CF3 | | |
| 3-39 | 3-Me | 5-CF3 | | |
| 3-40 | 2-Me | 5-CF3 | | |
| 3-41 | 2,4-Me2 | 5-CF3 | | |
| 3-42 | 2-Me-3-CF3 | 5-CF3 | | |
| 3-43 | 2-Me-4-CF3 | 5-CF3 | | |
| 3-44 | 2-Me-4-OCF3 | 5-CF3 | | |
| 3-45 | 2-Et-4-CF3 | 5-CF3 | | |
| 3-46 | 2,4,6-Me3 | 5-CF3 | | |
| 3-47 | 2-Me-4-F | 5-CF3 | | |
| 3-48 | 2-Me-4-Cl | 5-CF3 | | |
| 3-49 | 2-Et-4-Cl | 5-CF3 | | |
| 3-50 | 2-$^{n}$Pr-4-Cl | 5-CF3 | | |
| 3-51 | 2-$^{n}$Pr-4-CF3 | 5-CF3 | | |
| 3-52 | 2-$^{i}$Pr-4-CF3 | 5-CF3 | | |
| 3-53 | 2-CH2OMe-4-CF3 | 5-CF3 | | |
| 3-54 | 2-CH2OEt-4-CF3 | 5-CF3 | | |
| 3-55 | 2-CH(OH)Et-4-CF3 | 5-CF3 | | |
| 3-56 | 2-CH2OH-4-CF3 | 5-CF3 | | |
| 3-57 | 2-CH2OCH2OMe-4-CF3 | 5-CF3 | | |
| 3-58 | 2-CH2OCH2OEt-4-CF3 | 5-CF3 | | |
| 3-59 | 2-CH2OCH(Me)OMe-4-CF3 | 5-CF3 | | |
| 3-60 | 2-CH2OCH(Me)OMe-4-CF3 | 5-CF3 | | |
| 3-61 | 2-CH═2CHMe-4-CF3 | 5-CF3 | | |
| 3-62 | 2-allyl-4-CF3 | 5-CF3 | vis | |
| 3-63 | 4-CF3 | 5-CF3 | [56-58] | |
| 3-64 | 3-CF3 | 5-CF3 | | |
| 3-65 | 2-CF3 | 5-CF3 | | |
| 3-66 | 3,4-(CF3)2 | 5-CF3 | | |
| 3-67 | 3,5-(CF3)2 | 5-CF3 | | |
| 3-68 | 2,4-(CF3)2 | 5-CF3 | | |
| 3-69 | 2-CH2Cl-4-CF3 | 5-CF3 | | |
| 3-70 | 2-CH(Cl)Et-4-CF3 | 5-CF3 | | |
| 3-71 | 4-CF3 | 3-Cl-5-CF3 | | |
| 3-72 | 4-CF3 | 4-Me-6-CF3 | | |
| 3-73 | 4-OMe | 5-CF3 | | |
| 3-74 | 3-OMe | 5-CF3 | | |
| 3-75 | 2-OMe | 5-CF3 | | |
| 3-76 | 2-OMe-4-CN | 5-CF3 | | |
| 3-77 | 2-OMe-4-CF3 | 5-CF3 | | |
| 3-78 | 2-OEt-4-CF3 | 5-CF3 | | |
| 3-79 | 2-OEt-4-CF3 | 5-Cl | | |
| 3-80 | 2-OEt-4-CF3 | 5-Br | | |
| 3-81 | 2-O$^{n}$Pr-4-CN | 5-CF3 | | |
| 3-82 | 2-O$^{n}$Pr-4-CF3 | 5-CF3 | [56-58] | |
| 3-83 | 2-O$^{n}$Pr-4-CF3 | 5-CF3 | | |
| 3-84 | 2-O$^{n}$Pr-4-CF3 | 5-CF3 | | |
| 3-85 | 2-O$^{n}$Pr-4-CF3 | 5-Cl | | |
| 3-86 | 2-O$^{n}$Pr-4-CF3 | 5-Br | | |
| 3-87 | 2-O$^{n}$Pr-4-CF3 | 5-NO2 | | |
| 3-88 | 2-O$^{n}$Pr-4-CF3 | 5-NH2 | | |
| 3-89 | 2-O$^{n}$Pr-4-CF3 | 5-Me | | |
| 3-90 | 2-O$^{n}$Pr-4-CF3 | 5-NHSO2Me | | |
| 3-91 | 2-O$^{n}$Pr-5-CF3 | 5-CF3 | | |
| 3-92 | 2-O$^{n}$Pr-4-CF3 | 6-CF3 | | |

TABLE 3-continued

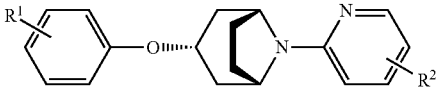

| Compound NO. | $R^1$ | $R^2$ | Physical constant [ ]: melting point ° C. | Note |
|---|---|---|---|---|
| 3-93 | 2-O$^{n}$Pr-4-CF3 | 5-CN | | |
| 3-94 | 2-O$^{n}$Pr-4-CF3 | 5-CF3-6-CN | | |
| 3-95 | 2-Cl-6-O$^{n}$Pr-4-CF3 | 5-CF3 | | |
| 3-96 | 2-O$^{i}$Pr-4-CF3 | 5-CF3 | | |
| 3-97 | 2-O$^{n}$Bu-4-CF3 | 5-CF3 | | |
| 3-98 | 2-O$^{i}$Bu-4-CF3 | 5-CF3 | | |
| 3-99 | 2-O$^{n}$Hex-4-CF3 | 5-CF3 | | |
| 3-100 | 2-O$^{n}$Pen-4-CF3 | 5-CF3 | | |
| 3-101 | 2-OCH2CN-4-CF3 | 5-CF3 | | |
| 3-102 | 2-OCH2OMe-4-CF3 | 5-CF3 | | |
| 3-103 | 2-OCH2OEt-4-CF3 | 5-CF3 | | |
| 3-104 | 2-OCH2O$^{n}$Pr-4-CF3 | 5-CF3 | | |
| 3-105 | 2-OCH2$^{c}$Pr-4-CF3 | 5-CF3 | | |
| 3-106 | 2-OCH2$^{c}$Pr-4-CF3 | 5-CO2Me | | |
| 3-107 | 2-OCH2$^{c}$Pr-4-CHF2 | 5-CF3 | | |
| 3-108 | 2-OCH2$^{c}$Pr-4-CHO | 5-CF3 | | |
| 3-109 | 2-OCH2$^{c}$Pr-4-CF3 | 5-CN | | |
| 3-110 | 2-OCH2$^{c}$Pr-4-CN | 5-CF3 | | |
| 3-111 | 2-OCH2$^{t}$Bu-4-CF3 | 5-CF3 | | |
| 3-112 | 2-O(CH2)2OMe-4-CF3 | 5-CF3 | | |
| 3-113 | 2-O(CH2)2OMe-4-CF3 | 5-CN | | |
| 3-114 | 2-O(CH2)2OCH2OMe-4-CF3 | 5-CF3 | | |
| 3-115 | 2-O(CH2)2OH-4-CF3 | 5-CF3 | | |
| 3-116 | 2-OCH2Ac-4-CF3 | 5-CF3 | | |
| 3-117 | 2-OCH2CH(OH)Me-4-CF3 | 5-CF3 | | |
| 3-118 | 2-OCH2CH(OMe)Me-4-CF3 | 5-CF3 | | |
| 3-119 | 2-OCH2C(OH)Me-4-CF3 | 5-CF3 | | |
| 3-120 | 2-OCH2C(OMe)Me-4-CF3 | 5-CF3 | | |
| 3-121 | 2-OCH2C(Me2)CO2Me-4-CF3 | 5-CF3 | | |
| 3-122 | 2-OCH2C(O)OMe-4-CF3 | 5-CF3 | | |
| 3-123 | 2-OCH2C(O)OEt-4-CF3 | 5-CF3 | | |
| 3-124 | 2-O(CH2)2OAc-4-CF3 | 5-CF3 | | |
| 3-125 | 2-O(CH2)2NH2-4-CF3 | 5-CF3 | | |
| 3-126 | 2-O(CH2)2NHAc-4-CF3 | 5-CF3 | | |
| 3-127 | 2-O(CH2)2NMe2-4-CF3 | 5-CF3 | | |
| 3-128 | 2-OCH2CH(Cl)Me-4-CF3 | 5-CF3 | | |
| 3-129 | 2-OCH2CH═CMe2-4-CF3 | 5-CF3 | | |
| 3-130 | 2-OCH2CH(Me)OMe-4-CF3 | 5-CF3 | | |
| 3-131 | 4-OCF3 | 5-CF3 | | [92-93] |
| 3-132 | 3-OCF3 | 5-CF3 | | |
| 3-133 | 2-OCF3 | 5-CF3 | | |
| 3-134 | 4-OCF2Br | 5-CF3 | | |
| 3-135 | 3-OCF2Br | 5-CF3 | | |
| 3-136 | 2-OCF2Br | 5-CF3 | | |
| 3-137 | 2-O(CH2)2Br-4-CF3 | 5-CF3 | | |
| 3-138 | 2-O(CH2)2Cl-4-CF3 | 5-CF3 | | |
| 3-139 | 2-O(CH2)2F-4-CF3 | 5-CF3 | | |
| 3-140 | 2-OCH2(Ph-4-Cl)-4-CF3 | 5-CF3 | | |
| 3-141 | 2-Oallyl-4-CF3 | 5-CF3 | | |
| 3-142 | 2-Oallenyl-4-CF3 | 5-CF3 | | |
| 3-143 | 2-Opropargyl-4-CF3 | 5-CF3 | | |
| 3-144 | 2-O(CH2)2CH═CH2-4-CF3 | 5-CF3 | | |
| 3-145 | 2-OCH2CH═CHMe-4-CF3 | 5-CF3 | | |
| 3-146 | 2-OCH2CH═CMe2-4-CF3 | 5-CF3 | | |
| 3-147 | 2-OCH2C(Me)═CH2-4-CF3 | 5-CF3 | | |
| 3-148 | 2-OCH2CH═CHCl-4-CF3 | 5-CF3 | | |
| 3-149 | 2-OAc-4-CF3 | 5-CF3 | | |
| 3-150 | 2-OC(O)$^{t}$Bu-4-CF3 | 5-CF3 | | |
| 3-151 | 2-OSO2Me-4-CF3 | 5-CF3 | | |
| 3-152 | 2-OSO2Et-4-CF3 | 5-CF3 | | |
| 3-153 | 2-SO2$^{n}$Pr-4-CF3 | 5-CF3 | | |
| 3-154 | 2-OSO2$^{n}$Bu-4-CF3 | 5-CF3 | | |
| 3-155 | 2-OSO2NMe2-4-CF3 | 5-CF3 | | |
| 3-156 | 2-OC(S)NMe2-4-CF3 | 5-CF3 | | |
| 3-157 | 2-SC(O)NMe2-4-CF3 | 5-CF3 | | |
| 3-158 | 2-NH2-4-CF3 | 5-CF3 | | |
| 3-159 | 2-N($^{n}$Pr)2-4-CF3 | 5-CF3 | | |
| 3-160 | 2-NH$^{n}$Pr-4-CF3 | 5-CF3 | | |

TABLE 3-continued

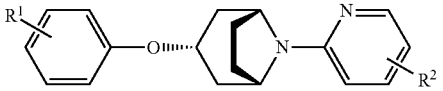

| Compound NO. | $R^1$ | $R^2$ | Physical constant [ ]: melting point ° C. | Note |
|---|---|---|---|---|
| 3-161 | 2-N(Me)"Pr-4-CF3 | 5-CF3 | | |
| 3-162 | 2-NHSO2Me-4-CF3 | 5-CF3 | | |
| 3-163 | 2-NHSO2Et-4-CF3 | 5-CF3 | | |
| 3-164 | 2-N(SO2"Bu)2-4-CF3 | 5-CF3 | | |
| 3-165 | 2-S"Pr-4-CF3 | 5-CF3 | | |
| 3-166 | 2-SCH2cPr-4-CF3 | 5-CF3 | | |
| 3-167 | 2-OP(O)(OEt)S"Pr-4-CF3 | 5-CF3 | | |

TABLE 4

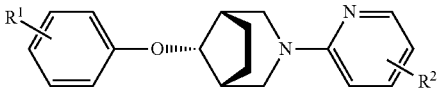

| Compound NO. | $R^1$ | $R^2$ | Physical constant [ ]: melting point ° C. | Note |
|---|---|---|---|---|
| 4-1 | 4-OH | 5-CF3 | | |
| 4-2 | 3-OH | 5-CF3 | | |
| 4-3 | 2-OH | 5-CF3 | | |
| 4-4 | 2-OH-4-CF3 | 5-CF3 | | |
| 4-5 | 4-F | 5-CF3 | | |
| 4-6 | 3-F | 5-CF3 | | |
| 4-7 | 2-F | 5-CF3 | | |
| 4-8 | 2-F-4-CF3 | 5-CF3 | | |
| 4-9 | 3-CF3-4-F | 5-CF3 | | |
| 4-10 | 4-Cl | 5-CF3 | | |
| 4-11 | 3-Cl | 5-CF3 | | |
| 4-12 | 2-Cl | 5-CF3 | | |
| 4-13 | 2-Cl-4-CF3 | 5-CF3 | | |
| 4-14 | 3-CF3-4-Cl | 5-CF3 | | |
| 4-15 | 2,6-Cl2-4-CF3 | 5-CF3 | | |
| 4-16 | 2-Br-4-CF3-6-Cl | 5-CF3 | | |
| 4-17 | 2-Cl-6-O"Pr-4-CF3 | 5-CF3 | | |
| 4-18 | 4-Br | 5-CF3 | | |
| 4-19 | 3-Br | 5-CF3 | | |
| 4-20 | 2-Br | 5-CF3 | | |
| 4-21 | 2-Br-4-CF3 | 5-CF3 | | |
| 4-22 | 3-CF3-4-Br | 5-CF3 | | |
| 4-23 | 4-I | 5-CF3 | | |
| 4-24 | 3-I | 5-CF3 | | |
| 4-25 | 2-I | 5-CF3 | | |
| 4-26 | 2-I-4-CF3 | 5-CF3 | | |
| 4-27 | 4-CN | 5-CF3 | | |
| 4-28 | 3-CN | 5-CF3 | | |
| 4-29 | 2-CN | 5-CF3 | | |
| 4-30 | 2-CN-4-CF3 | 5-CF3 | | |
| 4-31 | 4-NO2 | 5-CF3 | | |
| 4-32 | 3-NO2 | 5-CF3 | | |
| 4-33 | 2-NO2 | 5-CF3 | | |
| 4-34 | 2-Cl-4-CF3-6-NO2 | 5-CF3 | | |
| 4-35 | 2-NO2-4-CF3 | 5-CF3 | | |
| 4-36 | 3-CF3-4-NO2 | 5-CF3 | | |
| 4-37 | 2-CHO-4-CF3 | 5-CF3 | | |
| 4-38 | 4-Me | 5-CF3 | | |
| 4-39 | 3-Me | 5-CF3 | | |
| 4-40 | 2-Me | 5-CF3 | | |
| 4-41 | 2,4-Me2 | 5-CF3 | | |
| 4-42 | 2-Me-3-CF3 | 5-CF3 | | |
| 4-43 | 2-Me-4-CF3 | 5-CF3 | | |
| 4-44 | 2-Me-4-OCF3 | 5-CF3 | | |
| 4-45 | 2-Et-4-CF3 | 5-CF3 | | |

TABLE 4-continued

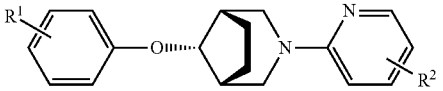

| Compound NO. | $R^1$ | $R^2$ | Physical constant [ ]: melting point ° C. | Note |
|---|---|---|---|---|
| 4-46 | 2,4,6-Me3 | 5-CF3 | | |
| 4-47 | 2-Me-4-F | 5-CF3 | | |
| 4-48 | 2-Me-4-Cl | 5-CF3 | | |
| 4-49 | 2-Et-4-Cl | 5-CF3 | | |
| 4-50 | 2-"Pr-4-Cl | 5-CF3 | | |
| 4-51 | 2-"Pr-4-CF3 | 5-CF3 | | |
| 4-52 | 2-"Pr-4-CF3 | 5-CF3 | | |
| 4-53 | 2-CH2OMe-4-CF3 | 5-CF3 | | |
| 4-54 | 2-CH2OEt-4-CF3 | 5-CF3 | | |
| 4-55 | 2-CH(OH)Et-4-CF3 | 5-CF3 | | |
| 4-56 | 2-CH2OH-4-CF3 | 5-CF3 | | |
| 4-57 | 2-CH2OCH2OMe-4-CF3 | 5-CF3 | | |
| 4-58 | 2-CH2OCH2OEt-4-CF3 | 5-CF3 | | |
| 4-59 | 2-CH2OCH(Me)OMe-4-CF3 | 5-CF3 | | |
| 4-60 | 2-CH2OCH(Me)OMe-4-CF3 | 5-CF3 | | |
| 4-61 | 2-CH═CHMe-4-CF3 | 5-CF3 | | |
| 4-62 | 2-allyl-4-CF3 | 5-CF3 | | |
| 4-63 | 4-CF3 | 5-CF3 | | |
| 4-64 | 3-CF3 | 5-CF3 | | |
| 4-65 | 2-CF3 | 5-CF3 | | |
| 4-66 | 3,4-(CF3)2 | 5-CF3 | | |
| 4-67 | 3,5-(CF3)2 | 5-CF3 | | |
| 4-68 | 2,4-(CF3)2 | 5-CF3 | | |
| 4-69 | 2-CH2Cl-4-CF3 | 5-CF3 | | |
| 4-70 | 2-CH(Cl)Et-4-CF3 | 5-CF3 | | |
| 4-71 | 4-CF3 | 3-Cl-5-CF3 | | |
| 4-72 | 4-CF3 | 4-Me-6-CF3 | | |
| 4-73 | 4-OMe | 5-CF3 | | |
| 4-74 | 3-OMe | 5-CF3 | | |
| 4-75 | 2-OMe | 5-CF3 | | |
| 4-76 | 2-OMe-4-CN | 5-CF3 | | |
| 4-77 | 2-OMe-4-CF3 | 5-CF3 | | |
| 4-78 | 2-OEt-4-CF3 | 5-CF3 | | |
| 4-79 | 2-OEt-4-CF3 | 5-Cl | | |
| 4-80 | 2-OEt-4-CF3 | 5-Br | | |
| 4-81 | 2-O"Pr-4-CN | 5-CF3 | | |
| 4-82 | 2-O"Pr-4-CF3 | 5-CF3 | [55-57] | |
| 4-83 | 2-O"Pr-4-CF3 | 5-CF3 | | |
| 4-84 | 2-O"Pr-4-CF3 | 5-CF3 | | |
| 4-85 | 2-O"Pr-4-CF3 | 5-Cl | | |
| 4-86 | 2-O"Pr-4-CF3 | 5-Br | | |
| 4-87 | 2-O"Pr-4-CF3 | 5-NO2 | | |
| 4-88 | 2-O"Pr-4-CF3 | 5-NH2 | | |
| 4-89 | 2-O"Pr-4-CF3 | 5-Me | | |
| 4-90 | 2-O"Pr-4-CF3 | 5-NHSO2Me | | |
| 4-91 | 2-O"Pr-5-CF3 | 5-CF3 | | |
| 4-92 | 2-O"Pr-4-CF3 | 6-CF3 | | |
| 4-93 | 2-O"Pr-4-CF3 | 5-CN | | |
| 4-94 | 2-O"Pr-4-CF3 | 5-CF3-6-CN | | |
| 4-95 | 2-Cl-6-O"Pr-4-CF3 | 5-CF3 | | |
| 4-96 | 2-O$^i$Pr-4-CF3 | 5-CF3 | | |
| 4-97 | 2-O"Bu-4-CF3 | 5-CF3 | | |
| 4-98 | 2-O$^i$Bu-4-CF3 | 5-CF3 | | |
| 4-99 | 2-O"Hex-4-CF3 | 5-CF3 | | |
| 4-100 | 2-O"Pen-4-CF3 | 5-CF3 | | |
| 4-101 | 2-OCH2CN-4-CF3 | 5-CF3 | | |
| 4-102 | 2-OCH2OMe-4-CF3 | 5-CF3 | | |
| 4-103 | 2-OCH2OEt-4-CF3 | 5-CF3 | | |
| 4-104 | 2-OCH2O"Pr-4-CF3 | 5-CF3 | | |
| 4-105 | 2-OCH2cPr-4-CF3 | 5-CF3 | | |
| 4-106 | 2-OCH2cPr-4-CF3 | 5-CO2Me | | |
| 4-107 | 2-OCH2cPr-4-CHF2 | 5-CF3 | | |
| 4-108 | 2-OCH2cPr-4-CHO | 5-CF3 | | |
| 4-109 | 2-OCH2cPr-4-CF3 | 5-CN | | |
| 4-110 | 2-OCH2cPr-4-CN | 5-CF3 | | |
| 4-111 | 2-OCH2tBu-4-CF3 | 5-CF3 | | |
| 4-112 | 2-O(CH2)2OMe-4-CF3 | 5-CF3 | | |
| 4-113 | 2-O(CH2)2OMe-4-CF3 | 5-CN | | |

TABLE 4-continued

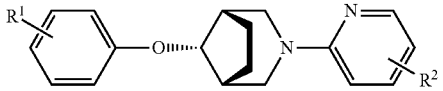

| Compound NO. | $R^1$ | $R^2$ | Physical constant [ ]: melting point ° C. | Note |
|---|---|---|---|---|
| 4-114 | 2-O(CH2)2OCH2OMe-4-CF3 | 5-CF3 | | |
| 4-115 | 2-O(CH2)2OH-4-CF3 | 5-CF3 | | |
| 4-116 | 2-OCH2Ac-4-CF3 | 5-CF3 | | |
| 4-117 | 2-OCH2CH(OH)Me-4-CF3 | 5-CF3 | | |
| 4-118 | 2-OCH2CH(OMe)Me-4-CF3 | 5-CF3 | | |
| 4-119 | 2-OCH2C(OH)Me2-4-CF3 | 5-CF3 | | |
| 4-120 | 2-OCH2C(OMe)Me2-4-CF3 | 5-CF3 | | |
| 4-121 | 2-OCH2C(Me2)CO2Me-4-CF3 | 5-CF3 | | |
| 4-122 | 2-OCH2C(O)OMe-4-CF3 | 5-CF3 | | |
| 4-123 | 2-OCH2C(O)OEt-4-CF3 | 5-CF3 | | |
| 4-124 | 2-O(CH2)2OAc-4-CF3 | 5-CF3 | | |
| 4-125 | 2-O(CH2)2NH2-4-CF3 | 5-CF3 | | |
| 4-126 | 2-O(CH2)2NHAc-4-CF3 | 5-CF3 | | |
| 4-127 | 2-O(CH2)2NMe2-4-CF3 | 5-CF3 | | |
| 4-128 | 2-OCH2CH(Cl)Me-4-CF3 | 5-CF3 | | |
| 4-129 | 2-OCH2CH═CMe2-4-CF3 | 5-CF3 | | |
| 4-130 | 2-OCH2CH(Me)OMe-4-CF3 | 5-CF3 | | |
| 4-131 | 4-OCF3 | 5-CF3 | | |
| 4-132 | 3-OCF3 | 5-CF3 | | |
| 4-133 | 2-OCF3 | 5-CF3 | | |
| 4-134 | 4-OCF2Br | 5-CF3 | | |
| 4-135 | 3-OCF2Br | 5-CF3 | | |
| 4-136 | 2-OCF2Br | 5-CF3 | | |
| 4-137 | 2-O(CH2)2Br-4-CF3 | 5-CF3 | | |
| 4-138 | 2-O(CH2)2Cl-4-CF3 | 5-CF3 | | |
| 4-139 | 2-O(CH2)2F-4-CF3 | 5-CF3 | | |
| 4-140 | 2-OCH2(Ph-4-Cl)-4-CF3 | 5-CF3 | | |
| 4-141 | 2-Oallyl-4-CF3 | 5-CF3 | | |

TABLE 4-continued

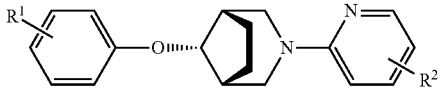

| Compound NO. | $R^1$ | $R^2$ | Physical constant [ ]: melting point ° C. | Note |
|---|---|---|---|---|
| 4-142 | 2-Oallenyl-4-CF3 | 5-CF3 | | |
| 4-143 | 2-Opropargyl-4-CF3 | 5-CF3 | | |
| 4-144 | 2-O(CH2)2CH═CH2-4-CF3 | 5-CF3 | | |
| 4-145 | 2-OCH2CH═CHMe-4-CF3 | 5-CF3 | | |
| 4-146 | 2-OCH2CH═CMe2-4-CF3 | 5-CF3 | | |
| 4-147 | 2-OCH2C(Me)═CH2-4-CF3 | 5-CF3 | | |
| 4-148 | 2-OCH2CH═CHCl-4-CF3 | 5-CF3 | | |
| 4-149 | 2-OAc-4-CF3 | 5-CF3 | | |
| 4-150 | 2-OC(O)$^t$Bu-4-CF3 | 5-CF3 | | |
| 4-151 | 2-OSO2Me-4-CF3 | 5-CF3 | | |
| 4-152 | 2-OSO2Et-4-CF3 | 5-CF3 | | |
| 4-153 | 2-SO2″Pr-4-CF3 | 5-CF3 | | |
| 4-154 | 2-OSO2″Bu-4-CF3 | 5-CF3 | | |
| 4-155 | 2-OSO2NMe2-4-CF3 | 5-CF3 | | |
| 4-156 | 2-OC(S)NMe2-4-CF3 | 5-CF3 | | |
| 4-157 | 2-SC(O)NMe2-4-CF3 | 5-CF3 | | |
| 4-158 | 2-NH2-4-CF3 | 5-CF3 | | |
| 4-159 | 2-N(″Pr)2-4-CF3 | 5-CF3 | | |
| 4-160 | 2-NH″Pr-4-CF3 | 5-CF3 | | |
| 4-161 | 2-N(Me)″Pr-4-CF3 | 5-CF3 | | |
| 4-162 | 2-NHSO2Me-4-CF3 | 5-CF3 | | |
| 4-163 | 2-NHSO2Et-4-CF3 | 5-CF3 | | |
| 4-164 | 2-N(SO2″Bu)2-4-CF3 | 5-CF3 | | |
| 4-165 | 2-S″Pr-4-CF3 | 5-CF3 | | |
| 4-166 | 2-SCH$^c$Pr-4-CF3 | 5-CF3 | | |
| 4-167 | 2-OP(O)(OEt)S″Pr-4-CF3 | 5-CF3 | | |

TABLE 5

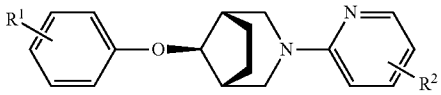

| Compound NO. | $R^1$ | $R^2$ | Physical constant [ ]: melting point ° C. | Note |
|---|---|---|---|---|
| 5-1 | 4-OH | 5-CF3 | | |
| 5-2 | 3-OH | 5-CF3 | | |
| 5-3 | 2-OH | 5-CF3 | | |
| 5-4 | 2-OH-4-CF3 | 5-CF3 | amor | |
| 5-5 | 4-F | 5-CF3 | | |
| 5-6 | 3-F | 5-CF3 | | |
| 5-7 | 2-F | 5-CF3 | | |
| 5-8 | 2-F-4-CF3 | 5-CF3 | | |
| 5-9 | 3-CF3-4-F | 5-CF3 | | |
| 5-10 | 4-Cl | 5-CF3 | | |
| 5-11 | 3-Cl | 5-CF3 | | |
| 5-12 | 2-Cl | 5-CF3 | | |
| 5-13 | 2-Cl-4-CF3 | 5-CF3 | | |
| 5-14 | 2-Cl-4-CF3 | 5-CF3 | | |
| 5-15 | 3-CF3-4-Cl | 5-CF3 | | |
| 5-16 | 2,6-Cl2-4-CF3 | 5-CF3 | | |
| 5-17 | 2-Br-4-CF3-6-Cl | 5-CF3 | | |
| 5-18 | 2-Cl-6-O″Pr-4-CF3 | 5-CF3 | | |
| 5-19 | 4-Br | 5-CF3 | | |
| 5-20 | 3-Br | 5-CF3 | | |
| 5-21 | 2-Br | 5-CF3 | | |
| 5-22 | 2-Br-4-CF3 | 5-CF3 | [85-87] | |
| 5-23 | 3-CF3-4-Br | 5-CF3 | | |
| 5-24 | 4-I | 5-CF3 | | |
| 5-25 | 3-I | 5-CF3 | | |

TABLE 5-continued

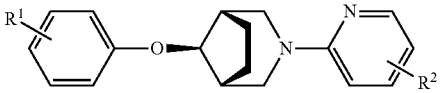

| Compound NO. | $R^1$ | $R^2$ | Physical constant [ ]: melting point ° C. | Note |
|---|---|---|---|---|
| 5-26 | 2-I | 5-CF3 | | |
| 5-27 | 2-I-4-CF3 | 5-CF3 | | |
| 5-28 | 2-CF3-4-Br | 5-CF3 | | |
| 5-29 | 4-CN | 5-CF3 | | |
| 5-30 | 3-CN | 5-CF3 | | |
| 5-31 | 2-CN | 5-CF3 | | |
| 5-32 | 2-CN-4-CF3 | 5-CF3 | [125-126] | |
| 5-33 | 2-CF3-4-CN | 5-CF3 | | |
| 5-34 | 4-NO2 | 5-CF3 | | |
| 5-35 | 3-NO2 | 5-CF3 | | |
| 5-36 | 2-NO2 | 5-CF3 | | |
| 5-37 | 2-Cl-4-CF3-6-NO2 | 5-CF3 | | |
| 5-38 | 2-NO2-4-CF3 | 5-CF3 | [107-109] | |
| 5-39 | 3-CF3-4-NO2 | 5-CF3 | | |
| 5-40 | 2-CHO-4-CF3 | 5-CF3 | | |
| 5-41 | 4-Me | 5-CF3 | | |
| 5-42 | 3-Me | 5-CF3 | | |
| 5-43 | 2-Me | 5-CF3 | | |
| 5-44 | 2,4-Me2 | 5-CF3 | | |
| 5-45 | 2-Me-4-CF3 | 5-CF3 | | |
| 5-46 | 2-Me-4-OCF3 | 5-CF3 | | |
| 5-47 | 2,4,6-Me3 | 5-CF3 | | |
| 5-48 | 2-Me-4-F | 5-CF3 | | |
| 5-49 | 2-Me-4-Cl | 5-CF3 | | |
| 5-50 | 2-Me-4-Br | 5-CF3 | | |
| 5-51 | 2-Et-4-CF3 | 5-CF3 | | |
| 5-52 | 2-Me-4-Cl | 5-CF3 | | |
| 5-53 | 2-Me-4-Br | 5-CF3 | | |
| 5-54 | 2-Et-4-Cl | 5-CF3 | | |
| 5-55 | 2-Et-4-CF3 | 5-CF3 | | |
| 5-56 | 2-Et-4-OCF3 | 5-CF3 | | |
| 5-57 | 2-″Pr-4-Cl | 5-CF3 | | |
| 5-58 | 2-″Pr-4-Br | 5-CF3 | | |
| 5-59 | 2-″Pr-4-CF3 | 5-CF3 | | |
| 5-60 | 2-″Pr-4-CF3 | 5-CF3 | | |
| 5-61 | 2-″Pr-4-Cl | 5-CF3 | | |
| 5-62 | 2-″Pr-4-Br | 5-CF3 | | |
| 5-63 | 2-CH2OMe-4-CF3 | 5-CF3 | | |
| 5-64 | 2-CH2OMe-4-Cl | 5-CF3 | | |
| 5-65 | 2-CH2OMe-4-Br | 5-CF3 | | |
| 5-66 | 2-CH2OEt-4-CF3 | 5-CF3 | | |
| 5-67 | 2-CH(OH)Et-4-CF3 | 5-CF3 | | |
| 5-68 | 2-CH2OH-4-CF3 | 5-CF3 | | |
| 5-69 | 2-CH2OCH2OMe-4-CF3 | 5-CF3 | vis | |
| 5-70 | 3-CH2OCH2OMe-4-CF3 | 5-CF3 | nD22.5-1.5110 | |
| 5-71 | 2-CH2OCH2OEt-4-CF3 | 5-CF3 | | |
| 5-72 | 2-CH2OCH(Me)OMe-4-CF3 | 5-CF3 | [56-57] | |
| 5-73 | 2-CH(Me)OCH2OMe-4-CF3 | 5-CF3 | vis | |
| 5-74 | 2CH═CHMe-4-CF3 | 5-CF3 | | |
| 5-75 | 2-allyl-4-CF3 | 5-CF3 | amor | |
| 5-76 | 4-CF3 | 5-CF3 | | |
| 5-77 | 3-CF3 | 5-CF3 | | |
| 5-78 | 2-CF3 | 5-CF3 | | |
| 5-79 | 3,4-(CF3)2 | 5-CF3 | | |
| 5-80 | 3,5-(CF3)2 | 5-CF3 | | |
| 5-81 | 2,4-(CF3)2 | 5-CF3 | | |
| 5-82 | 2-CH2Cl-4-CF3 | 5-CF3 | | |
| 5-83 | 2-CH(Cl)Et-4-CF3 | 5-CF3 | | |
| 5-84 | 4-CF3 | 3-Cl-5-CF3 | | |
| 5-85 | 4-CF3 | 4-Me-6-CF3 | | |
| 5-86 | 4-OMe | 5-CF3 | | |
| 5-87 | 3-OMe | 5-CF3 | | |
| 5-88 | 2-OMe | 5-CF3 | | |
| 5-89 | 2-OMe-4-CF3 | 5-CF3 | vis | |
| 5-90 | 2-OEt-4-CF3 | 5-CF3 | vis | |
| 5-91 | 2-OEt-4-CF3 | 5-Cl | | |
| 5-92 | 2-OEt-4-CF3 | 5-Br | | |
| 5-93 | 2-O″Pr-4-CF3 | 5-CH2F | vis | |

TABLE 5-continued

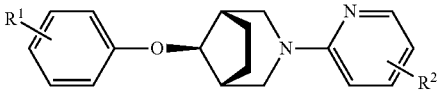

| Compound NO. | $R^1$ | $R^2$ | Physical constant [ ]: melting point ° C. | Note |
|---|---|---|---|---|
| 5-94 | 2-O$^n$Pr-4-CF3 | 5-Me | | |
| 5-95 | 2-O$^n$Pr-4-CF3 | 4-CF3 | | |
| 5-96 | 2-O$^n$Pr-4-CF3 | 5-CN | [95-97] | |
| 5-97 | 2-O$^n$Pr-4-CF3 | 5-CF3 | [48-50] | |
| 5-98 | 2-O$^n$Pr-4-CF3 | 5-CF3 | vis | N-oxide (Note 4) |
| 5-99 | 2-O$^n$Pr-4-CF3 | 5-CHF2 | vis | |
| 5-100 | 2-O$^n$Pr-4-CF3 | 5-CHO | [98-100] | |
| 5-101 | 2-O$^n$Pr-4-CF3 | 5-CH2OH | vis | |
| 5-102 | 2-O$^n$Pr-4-CN | 5-CF3 | [97-101] | |
| 5-103 | 3-O$^n$Pr-5-CF3 | 5-CF3 | vis | |
| 5-104 | 2-(O$^c$Pr-2,2Cl2)-4-CF3 | 5-CF3 | vis | |
| 5-105 | 2-O$^i$Bu-4-CF3 | 5-CF3 | [74-77] | |
| 5-106 | 2-OBn-4-CF3 | 5-CF3 | nD22.3-1.5441 | |
| 5-107 | 2-O$^i$Bu-4-CF3 | 5-CF3 | | |
| 5-108 | 2-O$^n$Hex-4-CF3 | 5-CF3 | | |
| 5-109 | 2-O$^n$Pen-4-CF3 | 5-CF3 | | |
| 5-110 | 2-OCH2OMe-4-CF3 | 5-CF3 | [86-88] | |
| 5-111 | 2-OCH2OMe-4-CF3 | 5-CN | [117-119] | |
| 5-112 | 2-OCH2OEt-4-CF3 | 5-CF3 | | |
| 5-113 | 2-OCH2O$^n$Pr-4-CF3 | 5-CF3 | | |
| 5-114 | 2-OCH2CH(Me)OAc-4-CF3 | 5-CF3 | vis | |
| 5-115 | 2-OCH2C(Me2)OAc-4-CF3 | 5-CF3 | vis | |
| 5-116 | 2-OCH2$^c$Pr-4-CF3 | 5-CF3 | [51-53] | |
| 5-117 | 2-OCH2$^c$Pr-4-CF3 | 5-CO2Me | [136-138] | |
| 5-118 | 2-OCH2$^c$Pr-4-CHF2 | 5-CF3 | vis | |
| 5-119 | 2-OCH2$^c$Pr-4-CHO | 5-CF3 | [106-109] | |
| 5-120 | 2-OCH2$^c$Pr-4-CF3 | 5-CN | [87-89] | |
| 5-121 | 2-OCH2$^c$Pr-4-CN | 5-CF3 | [109-112] | |
| 5-122 | 2-OCH2$^t$Bu-4-CF3 | 5-CF3 | | |
| 5-123 | 2-O(CH2)2OH-4-CF3 | 5-CF3 | vis | |
| 5-124 | 2-O(CH2)2OMe-4-CF3 | 5-CF3 | vis | |
| 5-125 | 2-O(CH2)2OMe-4-CF3 | 5-CN | [90-92] | |
| 5-126 | 2-OCH2Ac-4-CF3 | 5-CF3 | vis | |
| 5-127 | 2-OCH2CH(OH)Me-4-CF3 | 5-CF3 | vis | |
| 5-128 | 2-OCH2CH(OMe)Me-4-CF3 | 5-CF3 | vis | |
| 5-129 | 2-OCH2C(OH)Me2-4-CF3 | 5-CF3 | vis | |
| 5-130 | 2-OCH2C(OMe)Me2-4-CF3 | 5-CF3 | vis | |
| 5-131 | 2-OCH2C(Me2)CO2Me-4-CF3 | 5-CF3 | vis | |
| 5-132 | 2-OCH2C(O)OMe-4-CF3 | 5-CF3 | vis | |
| 5-133 | 2-OCH2C-O(O)OEt-4-CF3 | 5-CF3 | vis | |
| 5-134 | 2-O(CH2)2OAc-4-CF3 | 5-CF3 | vis | |
| 5-135 | 2-O(CH2)2NH2-4-CF3 | 5-CF3 | [61-62] | |
| 5-136 | 2-O(CH2)2NHAc-4-CF3 | 5-CF3 | vis | |
| 5-137 | 2-O(CH2)2NMe2-4-CF3 | 5-CF3 | vis | |
| 5-138 | 2-OCH2CH(Cl)Me-4-CF3 | 5-CF3 | vis | |
| 5-139 | 2-OCH2CH═CMe2-4-CF3 | 5-CF3 | vis | |
| 5-140 | 4-OCF3 | 5-CF3 | | |
| 5-141 | 3-OCF3 | 5-CF3 | | |
| 5-142 | 2-OCF3 | 5-CF3 | | |
| 5-143 | 4-OCF2Br | 5-CF3 | | |
| 5-144 | 3-OCF2Br | 5-CF3 | | |
| 5-145 | 2-OCF2Br | 5-CF3 | | |
| 5-146 | 2-O(CH2)2Br-4-CF3 | 5-CF3 | | |
| 5-147 | 2-O(CH2)2Cl-4-CF3 | 5-CF3 | vis | |
| 5-148 | 2-O(CH2)2F-4-CF3 | 5-CF3 | | |
| 5-149 | 2-Oallyl-4-CF3 | 5-CF3 | [47-51] | |
| 5-150 | 2-Oallenyl-4-CF3 | 5-CF3 | | |
| 5-151 | 4-CO2Me | 5-CF3 | | |
| 5-152 | 3-CO2Me | 5-CF3 | | |
| 5-153 | 2-CO2Me | 5-CF3 | | |
| 5-154 | 4-SCF3 | 5-CF3 | | |
| 5-155 | 3-SCF3 | 5-CF3 | | |
| 5-156 | 2-SCF3 | 5-CF3 | | |
| 5-157 | 4-S(O)CF3 | 5-CF3 | | |
| 5-158 | 3-S(O)CF3 | 5-CF3 | | |
| 5-159 | 2-S(O)CF3 | 5-CF3 | | |
| 5-160 | 4-OSO2CF3 | 5-CF3 | | |
| 5-161 | 2-OSO2Me-4-CF3 | 5-CF3 | [159-161] | |

TABLE 5-continued

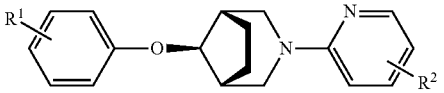

| Compound NO. | $R^1$ | $R^2$ | Physical constant [ ]: melting point ° C. | Note |
|---|---|---|---|---|
| 5-162 | 2-OSO2Et-4-CF3 | 5-CF3 | [123-126] | |
| 5-163 | 2-OSO2ⁿPr-4-CF3 | 5-CF3 | vis | |
| 5-164 | 2-OSO2ⁱPr-4-CF3 | 5-CF3 | [109-112] | |
| 5-165 | 3-OSO2CF3 | 5-CF3 | | |
| 5-166 | 2-OSO2CF3 | 5-CF3 | | |
| 5-167 | 4-OC(O)Ph | 5-CF3 | | |
| 5-168 | 3-OC(O)Ph | 5-CF3 | | |
| 5-169 | 2-OC(O)Ph | 5-CF3 | | |
| 5-170 | 4-OCH2Ph | 5-CF3 | | |
| 5-171 | 3-OCH2Ph | 5-CF3 | | |
| 5-172 | 2-OCH2Ph | 5-CF3 | | |
| 5-173 | 4-OCH2(Naph-1-yl) | 5-CF3 | | |
| 5-174 | 2-OCH2C(Me)═CH2-4-CF3 | 5-CF3 | [70-74] | |
| 5-175 | 2-OCH2CH═CHMe-4-CF3 | 5-CF3 | vis | mixture of cis and trans |
| 5-176 | 2-O(CH2)2CH═CH2-4-CF3 | 5-CF3 | vis | |
| 5-177 | 2-Oprapargyl-4-CF3 | 5-CF3 | vis | |
| 5-178 | 2-(OCH2CH═CCl2)-4-CF3 | 5-CF3 | | |
| 5-179 | 2,3,6-Cl3-4-OCH2CH═CCl2 | 3-Cl-5-CF3 | | |
| 5-180 | 2,3,6-Cl3-4-OCH2CH═CCl2 | 5-CF3 | | |
| 6-181 | 2-OAc-4-CF3 | 5-CF3 | [157-159] | |
| 5-182 | 2-OCH2C(═NOH)Me-4-CF3(anti) | 5-CF3 | [120-123] | (E) |
| 5-183 | 2-OCH2C(═NOH)Me-4-CF3(syn) | 5-CF3 | [55-59] | (Z) |
| 5-184 | 2-OCH2C(═NOMe)Me-4-CF3(anti) | 5-CF3 | nD23.6-1.5100 | (E) |
| 5-185 | 3-CF3-4-NH2 | 5-CF3 | | |
| 5-186 | 2-NH2-4-NH2 | 5-CF3 | [110-113] | |
| 5-187 | 2-NH2-4-CF3-6-Cl | 5-CF3 | | |
| 5-188 | 2-NHMe-4-CF3 | 5-CF3 | | |
| 5-189 | 2-NHEt-4-CF3 | 5-CF3 | | |
| 5-190 | 2-NHⁿPr-4-CF3 | 5-CF3 | [65-67] | |
| 5-191 | 2-N(Me)ⁿPr-4-CF3 | 5-CF3 | [64-67] | |
| 5-192 | 2-N(ⁿPr)2-4-CF3 | 5-CF3 | | |
| 5-193 | 2-NHAc-4-CF3 | 5-CF3 | [130-132] | |
| 5-194 | 2-N(Ac)ⁿPr-4-CF3 | 5-CF3 | | |
| 5-195 | 2-OC(O)OMe-4-CF3 | 5-CF3 | | |
| 5-196 | 2-OC(O)SMe-4-CF3 | 5-CF3 | | |
| 5-197 | 3-CF3-4-N(SO2Me)2 | 5-CF3 | | |
| 5-198 | 2-OC(O)Et-4-CF3 | 5-CF3 | [101-105] | |
| 5-199 | 2-OC(O)ⁿPr-4-CF3 | 5-CF3 | [104-106] | |
| 5-200 | 2-OC(O)ᵗBu-4-CF3 | 5-CF3 | [127-130] | |
| 5-201 | 2-NHSO2Me-4-CF3 | 5-CF3 | [179-182] | |
| 5-202 | 2(OᶜPr-2,2-Cl2)-4-CF3 | 5-CF2H | | |
| 5-203 | 2-(1,3-dioxolan-2-ylmethoxy)-4-CF3 | 5-CF3 | vis | |
| 5-204 | 2-(tetrahydrofuran-2-ylmethoxy)-4-CF3 | 5-CF3 | vis | |
| 5-205 | 2-(tetrahydrofuran-3-ylmethoxy)-4-CF3 | 5-CF3 | [53-55] | |
| 5-206 | 2-(furan-2-ylmethoxy)-4-CF3 | 5-CF3 | vis | |
| 5-207 | 2-(furan-3-ylmethoxy)-4-CF3 | 5-CF3 | vis | |
| 5-208 | 2-(thiophen-3-ylmethoxy)-4-CF3 | 5-CF3 | vis | |
| 5-209 | 2-(thiophen-2-ylmethoxy)-4-CF3 | 5-CF3 | vis | |
| 5-210 | 2(OcPr-2,2-Cl2)-4-CF3 | 5-Me | | |
| 5-211 | 2-(pyridin-3-ylmethoxy)-4-CF3 | 5-CF3 | nD22.3-1.5329 | |
| 5-212 | 2-(pyridin-2-ylmethoxy)-4-CF3 | 5-CF3 | nD22.3-1.5335 | |
| 5-213 | 2-(oxetan-2-ylmethoxy)-4-CF3 | 5-CF3 | nD23.2-1.5227 | |
| 5-214 | 2-(tetrahydrofuran-2-ylmethoxy)-4-CF3 | 5-CF3 | [78-80] | |
| 5-215 | 2-(1,3-dioxolan-2-yl)-4-CF3 | 5-CF3 | [123-126] | |
| 5-216 | 2-CHO-4-CF3 | 5-CF3 | [145-148] | |
| 5-217 | 2-CH2Oⁿ Pr-4-CF3 | 5-CF3 | nD22.2-1.5158 | |
| 5-218 | 2-(4-Me-1,3-dioxolan-2-yl)-4-CF3 | 5-CF3 | [134-138] | |
| 5-219 | 2-CH2OH-4-CF3 | 5-CF3 | [138-141] | |
| 5-220 | 2-CH2OEt-4-CF3 | 5-CF3 | [70-74] | |
| 5-221 | 2-CH2Cl-4-CF3 | 5-CF3 | [113-116] | |
| 5-222 | 2-CH2OCH(OMe)Et-4-CF3 | 5-CF3 | nD25.0-1.5087 | |
| 5-223 | 2-CH2OnBu-4-CF3 | 5-CF3 | Nd24.5-1.5123 | |
| 5-224 | 2-OnBu-4-CF3 | 5-CF3 | Nd24.9-1.5145 | |
| 5-225 | 2-CH2OiPr-4-CF3 | 5-CF3 | [88-91] | |
| 5-226 | 2-CH2OSO2Me-4-CF3 | 5-CF3 | Nd24.9-1.5265 | |
| 5-227 | 2-CH(OH)nPr-4-CF3 | 5-CF3 | Nd24.9-1.5188 | |
| 5-228 | 2-CH(OMe)nPr-4-CF3 | 5-CF3 | Nd24.8-1.5057 | |
| 5-229 | 2-CH2OCH(Me)OEt-4-CF3 | 5-CF3 | vis | |

TABLE 5-continued

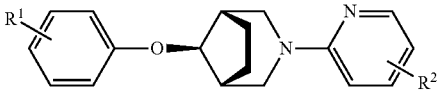

| Compound NO. | $R^1$ | $R^2$ | Physical constant [ ]: melting point ° C. | Note |
|---|---|---|---|---|
| 5-230 | 2-CH2OCH(Me)CN-4-CF3 | 5-CF3 | [105-109] | |
| 5-231 | 2-(CH2O-tetrahydrofuran-3-yl)-4-CF3 | 5-CF3 | [90-94] | |
| 5-232 | 2-OH2C═CMe-4-CF3 | 5-CF3 | Nd22.3-1.5241 | |
| 5-233 | 2-CO2Et-4-CF3 | 5-CF3 | [89-91] | |
| 5-234 | 2-OSO2CF3-4-CF3 | 5-CF3 | [96-98] | |
| 5-235 | 2-(2,3-dihydrofuran-2-yl)-4-CF3 | 5-CF3 | [109-111] | |
| 5-236 | 2-(2,5-dihydrofuran-2-yl)-4-CF3 | 5-CF3 | [110-112] | |
| 5-237 | 2-(tetrahydrofuran-2-yl)-4-CF3 | 5-CF3 | [124-126] | |
| 5-238 | 2-CH(OH)nBu-4-CF3 | 5-CF3 | [101-105] | |
| 5-239 | 2-CH(OH)iBu-4-CF3 | 5-CF3 | [50-53] | |
| 5-240 | 2-C(O)nPr-4-CF3 | 5-CF3 | [122-125] | |
| 5-241 | 2-(4,5-dihydrofuran-3-yl-4-yl)-4-CF3 | 5-CF3 | [126-128] | |
| 5-242 | 2-CH2OCH(Me)Et-4-CF3 | 5-CF3 | Nd23.2-1.5105 | |
| 5-243 | 2-CO2Me-4-CF3 | 5-CF3 | Nd22.3-1.5229 | |
| 5-244 | 2-CO2nPr-4-CF3 | 5-CF3 | [70-75] | |
| 5-245 | 2-CO2iPr-4-CF3 | 5-CF3 | [113-116] | |
| 5-246 | 2-CH2CH2OMe-4-CF3 | 5-CF3 | vis | |
| 5-247 | 2-CH═CHOMe-4-CF3 | 5-CF3 | vis | |
| 5-248 | 2-CO2H-4-CF3 | 5-CF3 | [151-155] | |
| 5-249 | 2-C(O)N(Me)Et-4-CF3 | 5-CF3 | 128-131] | |
| 5-250 | 2-CONH2-4-CF3 | 5-CF3 | [179-183] | |
| 5-251 | 2-C(O)NHEt-4-CF3 | 5-CF3 | [195-198] | |
| 5-252 | 2-(2-Me-1,3-dioxolan-2-yl)-4-CF3 | 5-CF3 | [162-164] | |
| 5-253 | 2-C(O)N(Me)-Pr-4-CF3 | 5-CF3 | [148-150] | |
| 5-254 | 2-C(O)NHiPr-4-CF3 | 5-CF3 | [196-199] | |
| 5-255 | 2-CH(OH)CH2tBu-4-CF3 | 5-CF3 | [143-145] | |
| 5-256 | 2-(3-Me-1,2,4-oxadizol-5-yl)-4-CF3 | 5-CF3 | [136-138] | |
| 5-257 | 2-CO2ᵗBu-4-CF3 | 5-CF3 | [159-162] | |
| 5-258 | 2-CH(OAc)CH2iPr-4-CF3 | 5-CF3 | Nd22.7-1.4952 | |
| 5-259 | 2-(4-Me-oxazolizin-2-yl)-4-CF3 | 5-CF3 | [122-126] | |
| 5-260 | 2-(5-Me-oxazolizin-2-yl)-4-CF3 | 5-CF3 | [97-99] | |
| 5-261 | 2-(4-Me-oxazol-2-yl)-4-CF3 | 5-CF3 | [126-129] | |
| 5-262 | 2-(4,4-Me2-oxazolizin-2-yl)-4-CF3 | 5-CF3 | [141-143] | |
| 5-263 | 2-(4-Et-oxazolizin-2-yl)-4-CF3 | 5-CF3 | [105-109] | |
| 5-264 | 4-CF3 | 5-CF3 | [112-115] | |
| 5-265 | 5-OCH2CN-4-CF3 | 5-CF3 | [80-83] | |

(Note 4)

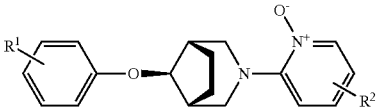

TABLE 6

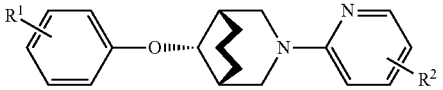

| Compound NO. | $R^1$ | $R^2$ | Physical constant [ ]: melting point ° C. |
|---|---|---|---|
| 6-1 | 4-OH | 5-CF3 | |
| 6-2 | 3-OH | 5-CF3 | |
| 6-3 | 2-OH | 5-CF3 | |
| 6-4 | 2-OH-4-CF3 | 5-CF3 | amor |
| 6-5 | 4-F | 5-CF3 | |
| 6-6 | 3-F | 5-CF3 | |
| 6-7 | 2-F | 5-CF3 | |
| 6-8 | 2-F-4-CF3 | 5-CF3 | |
| 6-9 | 3-CF3-4-F | 5-CF3 | |
| 6-10 | 4-Cl | 5-CF3 | |
| 6-11 | 3-Cl | 5-CF3 | |

TABLE 6-continued

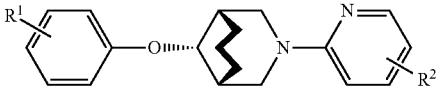

| Compound NO. | $R^1$ | $R^2$ | Physical constant [ ]: melting point ° C. |
|---|---|---|---|
| 6-12 | 2-Cl | 5-CF3 | |
| 6-13 | 2-Cl-4-CF3 | 5-CF3 | |
| 6-14 | 3-CF3-4-Cl | 5-CF3 | |
| 6-15 | 2,6-Cl2-4-CF3 | 5-CF3 | |
| 6-16 | 2-Br-4-CF3-6-Cl | 5-CF3 | |
| 6-17 | 2-Cl-6-O″Pr-4-CF3 | 5-CF3 | |
| 6-18 | 4-Br | 5-CF3 | |
| 6-19 | 3-Br | 5-CF3 | |
| 6-20 | 2-Br | 5-CF3 | |
| 6-21 | 2-Br-4-CF3 | 5-CF3 | |
| 6-22 | 3-CF3-4-Br | 5-CF3 | |

TABLE 6-continued

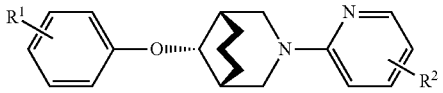

| Compound NO. | $R^1$ | $R^2$ | Physical constant [ ]: melting point ° C. |
|---|---|---|---|
| 6-23 | 4-I | 5-CF3 | |
| 6-24 | 3-I | 5-CF3 | |
| 6-25 | 2-I | 5-CF3 | |
| 6-26 | 2-I-4-CF3 | 5-CF3 | |
| 6-27 | 4-CN | 5-CF3 | |
| 6-28 | 3-CN | 5-CF3 | |
| 6-29 | 2-CN | 5-CF3 | |
| 6-30 | 2-CN-4-CF3 | 5-CF3 | |
| 6-31 | 4-NO2 | 5-CF3 | |
| 6-32 | 3-NO2 | 5-CF3 | |
| 6-33 | 2-NO2 | 5-CF3 | |
| 6-34 | 2-Cl-4-CF3-6-NO2 | 5-CF3 | |
| 6-35 | 2-NO2-4-CF3 | 5-CF3 | |
| 6-36 | 3-CF3-4-NO2 | 5-CF3 | |
| 6-37 | 2-CHO-4-CF3 | 5-CF3 | |
| 6-38 | 4-Me | 5-CF3 | |
| 6-39 | 3-Me | 5-CF3 | |
| 6-40 | 2-Me | 5-CF3 | |
| 6-41 | 2,4-Me2 | 5-CF3 | |
| 6-42 | 2-Me-3-CF3 | 5-CF3 | |
| 6-43 | 2-Me-4-CF3 | 5-CF3 | |
| 6-44 | 2-Me-4-OCF3 | 5-CF3 | |
| 6-45 | 2-Et-4-CF3 | 5-CF3 | |
| 6-46 | 2,4,6-Me3 | 5-CF3 | |
| 6-47 | 2-Me-4-F | 5-CF3 | |
| 6-48 | 2-Me-4-Cl | 5-CF3 | |
| 6-49 | 2-Et-4-Cl | 5-CF3 | |
| 6-50 | 2-″Pr-4-Cl | 5-CF3 | |
| 6-51 | 2-″Pr-4-CF3 | 5-CF3 | |
| 6-52 | 2-″Pr-4-CF3 | 5-CF3 | |
| 6-53 | 2-CH2OMe-4-CF3 | 5-CF3 | |
| 6-54 | 2-CH2OEt-4-CF3 | 5-CF3 | |
| 6-55 | 2-CH(OH)Et-4-CF3 | 5-CF3 | |
| 6-56 | 2-CH2OH-4-CF3 | 5-CF3 | |
| 6-57 | 2-CH2OCH2OMe-4-CF3 | 5-CF3 | |
| 6-58 | 2-CH2OCH2OEt-4-CF3 | 5-CF3 | |
| 6-59 | 2-CH2OCH(Me)OMe-4-CF3 | 5-CF3 | |
| 6-60 | 2-CH2OCH(Me)OMe-4-CF3 | 5-CF3 | |
| 6-61 | 2-CH—CHMe-4-CF3 | 5-CF3 | |
| 6-62 | 2-allyl-4-CF3 | 5-CF3 | |
| 6-63 | 4-CF3 | 5-CF3 | |
| 6-64 | 3-CF3 | 5-CF3 | |
| 6-65 | 2-CF3 | 5-CF3 | |
| 6-66 | 3,4-(CF3)2 | 5-CF3 | |
| 6-67 | 3,5-(CF3)2 | 5-CF3 | |
| 6-68 | 2,4-(CF3)2 | 5-CF3 | |
| 6-69 | 2-CH2Cl-4-CF3 | 5-CF3 | |
| 6-70 | 2-CH(Cl)Et-4-CF3 | 5-CF3 | |
| 6-71 | 4-CF3 | 3-Cl-5-CF3 | |
| 6-72 | 4-CF3 | 4-Me-6-CF3 | |
| 6-73 | 4-OMe | 5-CF3 | |
| 6-74 | 3-OMe | 5-CF3 | |
| 6-75 | 2-OMe | 5-CF3 | |
| 6-76 | 2-OMe-4-CN | 5-CF3 | |
| 6-77 | 2-OMe-4-CF3 | 5-CF3 | |
| 6-78 | 2-OEt-4-CF3 | 5-CF3 | |
| 6-79 | 2-OEt-4-CF3 | 5-Cl | |
| 6-80 | 2-OEt-4-CF3 | 5-Br | |
| 6-81 | 2-O″Pr-4-CN | 5-CF3 | |
| 6-82 | 2-O″Pr-4-CF3 | 5-CF3 | vis |
| 6-83 | 2-O″Pr-4-CF3 | 5-CF3 | |
| 6-84 | 2-O″Pr-4-CF3 | 5-CF3 | |
| 6-85 | 2-O″Pr-4-CF3 | 5-Cl | |
| 6-86 | 2-O″Pr-4-CF3 | 5-Br | |
| 6-87 | 2-O″Pr-4-CF3 | 5-NO2 | |
| 6-88 | 2-O″Pr-4-CF3 | 5-NH2 | |
| 6-89 | 2-O″Pr-4-CF3 | 5-Me | |
| 6-90 | 2-O″Pr-4-CF3 | 5-NHSO2Me | |
| 6-91 | 2-O″Pr-5-CF3 | 5-CF3 | |
| 6-92 | 2-O″Pr-4-CF3 | 6-CF3 | |
| 6-93 | 2-O″Pr-4-CF3 | 5-CN | |

TABLE 6-continued

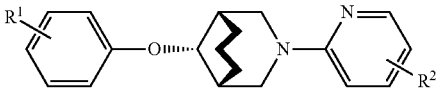

| Compound NO. | $R^1$ | $R^2$ | Physical constant [ ]: melting point ° C. |
|---|---|---|---|
| 6-94 | 2-O″Pr-4-CF3 | 5-CF3-6-CN | |
| 6-95 | 2-Cl-6-O″Pr-4-CF3 | 5-CF3 | |
| 6-96 | 2-O$^i$Pr-4-CF3 | 5-CF3 | |
| 6-97 | 2-O″Bu-4-CF3 | 5-CF3 | |
| 6-98 | 2-O$^i$Bu-4-CF3 | 5-CF3 | |
| 6-99 | 2-O″Hex-4-CF3 | 5-CF3 | |
| 6-100 | 2-O″Pen-4-CF3 | 5-CF3 | |
| 6-101 | 2-OCH2CN-4-CF3 | 5-CF3 | |
| 6-102 | 2-OCH2OMe-4-CF3 | 5-CF3 | [70-74] |
| 6-103 | 2-OCH2OEt-4-CF3 | 5-CF3 | |
| 6-104 | 2-OCH2O″Pr-4-CF3 | 5-CF3 | |
| 6-105 | 2-OCH2$^c$Pr-4-CF3 | 5-CF3 | |
| 6-106 | 2-OCH2$^c$Pr-4-CF3 | 5-CO2Me | |
| 6-107 | 2-OCH2$^c$Pr-4-CHF2 | 5-CF3 | |
| 6-108 | 2-OCH2$^c$Pr-4-CHO | 5-CF3 | |
| 6-109 | 2-OCH2$^c$Pr-4-CF3 | 5-CN | |
| 6-110 | 2-OCH2$^c$Pr-4-CN | 5-CF3 | |
| 6-111 | 2-OCH2cBu-4-CF3 | 5-CF3 | |
| 6-112 | 2-O(CH2)2OMe-4-CF3 | 5-CF3 | |
| 6-113 | 2-O(CH2)2OMe-4-CF3 | 5-CN | |
| 6-114 | 2-O(CH2)2OCH2OMe-4-CF3 | 5-CF3 | |
| 6-115 | 2-O(CH2)2OH-4-CF3 | 5-CF3 | |
| 6-116 | 2-OCH2Ac-4-CF3 | 5-CF3 | |
| 6-117 | 2-OCH2CH(OH)Me-4-CF3 | 5-CF3 | |
| 6-118 | 2-OCH2CH(OMe)Me-4-CF3 | 5-CF3 | |
| 6-119 | 2-OCH2C(OH)Me2-4-CF3 | 5-CF3 | |
| 6-120 | 2-OCH2C(OMe)Me2-4-CF3 | 5-CF3 | |
| 6-121 | 2-OCH2C(Me2)CO2Me-4-CF3 | 5-CF3 | |
| 6-122 | 2-OCH2C(O)OMe-4-CF3 | 5-CF3 | |
| 6-123 | 2-OCH2C(O)OEt-4-CF3 | 5-CF3 | |
| 6-124 | 2-O(CH2)2OAc-4-CF3 | 5-CF3 | |
| 6-125 | 2-O(CH2)2NH2-4-CF3 | 5-CF3 | |
| 6-126 | 2-O(CH2)2NHAc-4-CF3 | 5-CF3 | |
| 6-127 | 2-O(CH2)2NMe2-4-CF3 | 5-CF3 | |
| 6-128 | 2-OCH2CH(Cl)Me-4-CF3 | 5-CF3 | |
| 6-129 | 2-OCH2CH═CMe2-4-CF3 | 5-CF3 | |
| 6-130 | 2-OCH2CH(Me)OMe-4-CF3 | 5-CF3 | |
| 6-131 | 4-OCF3 | 5-CF3 | |
| 6-132 | 3-OCF3 | 5-CF3 | |
| 6-133 | 2-OCF3 | 5-CF3 | |
| 6-134 | 4-OCF2Br | 5-CF3 | |
| 6-135 | 3-OCF2Br | 5-CF3 | |
| 6-136 | 2-OCF2Br | 5-CF3 | |
| 6-137 | 2-O(CH2)2Br-4-CF3 | 5-CF3 | |
| 6-138 | 2-O(CH2)2Cl-4-CF3 | 5-CF3 | |
| 6-139 | 2-O(CH2)2F-4-CF3 | 5-CF3 | |
| 6-140 | 2-OCH2(Ph-4-Cl)-4-CF3 | 5-CF3 | |
| 6-141 | 2-Oallyl-4-CF3 | 5-CF3 | |
| 6-142 | 2-Oallenyl-4-CF3 | 5-CF3 | |
| 6-143 | 2-Opropargyl-4-CF3 | 5-CF3 | |
| 6-144 | 2-O(CH2)2CH═CH2-4-CF3 | 5-CF3 | |
| 6-145 | 2-OCH2CH═CHMe-4-CF3 | 5-CF3 | |
| 6-146 | 2-OCH2CH═CMe2-4-CF3 | 5-CF3 | |
| 6-147 | 2-OCH2C(Me)═CH2-4-CF3 | 5-CF3 | |
| 6-148 | 2-OCH2CH═CHCl-4-CF3 | 5-CF3 | |
| 6-149 | 2-OAc-4-CF3 | 5-CF3 | |
| 6-150 | 2-OC(O)$^t$Bu-4-CF3 | 5-CF3 | |
| 6-151 | 2-OSO2Me-4-CF3 | 5-CF3 | |
| 6-152 | 2-OSO2Et-4-CF3 | 5-CF3 | |
| 6-153 | 2-SO2″Pr-4-CF3 | 5-CF3 | |
| 6-154 | 2-OSO2″Bu-4-CF3 | 5-CF3 | |
| 6-155 | 2-OSO2NMe2-4-CF3 | 5-CF3 | |
| 6-156 | 2-OC(S)NMe2-4-CF3 | 5-CF3 | |
| 6-157 | 2-SC(O)NMe2-4-CF3 | 5-CF3 | |
| 6-158 | 2-NH2-4-CF3 | 5-CF3 | |
| 6-159 | 2-N(″Pr)2-4-CF3 | 5-CF3 | |
| 6-160 | 2-NH″Pr-4-CF3 | 5-CF3 | |
| 6-161 | 2-N(Me)″Pr-4-CF3 | 5-CF3 | |
| 6-162 | 2-NHSO2Me-4-CF3 | 5-CF3 | |
| 6-163 | 2-NHSO2Et-4-CF3 | 5-CF3 | |
| 6-164 | 2-N(SO2″Bu)2-4-CF3 | 5-CF3 | |

TABLE 6-continued

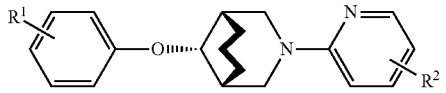

| Compound NO. | $R^1$ | $R^2$ | Physical constant [ ]: melting point ° C. |
|---|---|---|---|
| 6-165 | 2-S″Pr-4-CF3 | 5-CF3 | |
| 6-166 | 2-SCH2ᶜPr-4-CF3 | 5-CF3 | |
| 6-167 | 2-OP(O)(OEt)S″Pr-4-CF3 | 5-CF3 | |

TABLE 7

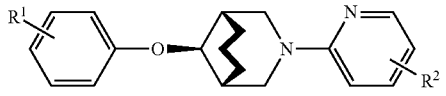

| Compound NO. | $R^1$ | $R^2$ | Physical constant [ ]: melting point ° C. |
|---|---|---|---|
| 7-1 | 4-OH | 5-CF3 | |
| 7-2 | 3-OH | 5-CF3 | |
| 7-3 | 2-OH | 5-CF3 | |
| 7-4 | 2-OH-4-CF3 | 5-CF3 | [108-110] |
| 7-5 | 4-F | 5-CF3 | |
| 7-6 | 3-F | 5-CF3 | |
| 7-7 | 2-F | 5-CF3 | |
| 7-8 | 2-F-4-CF3 | 5-CF3 | |
| 7-9 | 3-CF3-4-F | 5-CF3 | |
| 7-10 | 4-Cl | 5-CF3 | |
| 7-11 | 3-Cl | 5-CF3 | |
| 7-12 | 2-Cl | 5-CF3 | |
| 7-13 | 2-Cl-4-CF3 | 5-CF3 | |
| 7-14 | 3-CF3-4-Cl | 5-CF3 | |
| 7-15 | 2,6-Cl2-4-CF3 | 5-CF3 | |
| 7-16 | 2-Br-4-CF3-6-Cl | 5-CF3 | |
| 7-17 | 2-Cl-6-O″Pr-4-CF3 | 5-CF3 | |
| 7-18 | 4-Br | 5-CF3 | |
| 7-19 | 3-Br | 5-CF3 | |
| 7-20 | 2-Br | 5-CF3 | |
| 7-21 | 2-Br-4-CF3 | 5-CF3 | |
| 7-22 | 3-CF3-4-Br | 5-CF3 | |
| 7-23 | 4-I | 5-CF3 | |
| 7-24 | 3-I | 5-CF3 | |
| 7-25 | 2-I | 5-CF3 | |
| 7-26 | 2-I-4-CF3 | 5-CF3 | |
| 7-27 | 4-CN | 5-CF3 | |
| 7-28 | 3-CN | 5-CF3 | |
| 7-29 | 2-CN | 5-CF3 | |
| 7-30 | 2-CN-4-CF3 | 5-CF3 | |
| 7-31 | 4-NO2 | 5-CF3 | |
| 7-32 | 3-NO2 | 5-CF3 | |
| 7-33 | 2-NO2 | 5-CF3 | |
| 7-34 | 2-Cl-4-CF3-6-NO2 | 5-CF3 | |
| 7-35 | 2-NO2-4-CF3 | 5-CF3 | |
| 7-36 | 3-CF3-4-NO2 | 5-CF3 | |
| 7-37 | 2-CHO-4-CF3 | 5-CF3 | |
| 7-39 | 3-Me | 5-CF3 | |
| 7-40 | 2-Me | 5-CF3 | |
| 7-41 | 2,4-Me2 | 5-CF3 | |
| 7-42 | 2-Me-3-CF3 | 5-CF3 | |
| 7-43 | 2-Me-4-CF3 | 5-CF3 | |
| 7-44 | 2-Me-4-OCF3 | 5-CF3 | |
| 7-45 | 2-Et-4-CF3 | 5-CF3 | |
| 7-46 | 2,4,6-Me3 | 5-CF3 | |
| 7-47 | 2-Me-4-F | 5-CF3 | |
| 7-48 | 2-Me-4-Cl | 5-CF3 | |
| 7-49 | 2-Et-4-Cl | 5-CF3 | |
| 7-50 | 2-″Pr-4-Cl | 5-CF3 | |
| 7-51 | 2-″Pr-4-CF3 | 5-CF3 | |
| 7-52 | 2-″Pr-4-CF3 | 5-CF3 | |

TABLE 7-continued

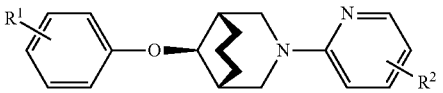

| Compound NO. | $R^1$ | $R^2$ | Physical constant [ ]: melting point ° C. |
|---|---|---|---|
| 7-53 | 2-CH2OMe-4-CF3 | 5-CF3 | |
| 7-54 | 2-CH2OEt-4-CF3 | 5-CF3 | |
| 7-55 | 2-CH(OH)Et-4-CF3 | 5-CF3 | |
| 7-56 | 2-CH2OH-4-CF3 | 5-CF3 | |
| 7-57 | 2-CH2OCH2OMe-4-CF3 | 5-CF3 | |
| 7-58 | 2-CH2OCH2OEt-4-CF3 | 5-CF3 | |
| 7-59 | 2-CH2OCH(Me)OMe-4-CF3 | 5-CF3 | |
| 7-60 | 2-CH2OCH(Me)OMe-4-CF3 | 5-CF3 | |
| 7-61 | 2-CH═CHMe-4-CF3 | 5-CF3 | |
| 7-62 | 2-allyl-4-CF3 | 5-CF3 | |
| 7-63 | 4-CF3 | 5-CF3 | |
| 7-64 | 3-CF3 | 5-CF3 | |
| 7-65 | 2-CF3 | 5-CF3 | |
| 7-66 | 3,4-(CF3)2 | 5-CF3 | |
| 7-67 | 3,5-(CF3)2 | 5-CF3 | |
| 7-68 | 2,4-(CF3)2 | 5-CF3 | |
| 7-69 | 2-CH2Cl-4-CF3 | 5-CF3 | |
| 7-70 | 2-CH(Cl)Et-4-CF3 | 5-CF3 | |
| 7-71 | 4-CF3 | 3-Cl-5-CF3 | |
| 7-72 | 4-CF3 | 4-Me-6-CF3 | |
| 7-73 | 4-OMe | 5-CF3 | |
| 7-74 | 3-OMe | 5-CF3 | |
| 7-75 | 2-OMe | 5-CF3 | |
| 7-76 | 2-OMe-4-CN | 5-CF3 | |
| 7-77 | 2-OMe-4-CF3 | 5-CF3 | |
| 7-78 | 2-OEt-4-CF3 | 5-CF3 | |
| 7-79 | 2-OEt-4-CF3 | 5-Cl | |
| 7-80 | 2-OEt-4-CF3 | 5-Br | |
| 7-81 | 2-O″Pr-4-CN | 5-CF3 | |
| 7-82 | 2-O″Pr-4-CF3 | 5-CF3 | vis |
| 7-83 | 2-O″Pr-4-CF3 | 5-Cl | |
| 7-84 | 2-O″Pr-4-CF3 | 5-Br | |
| 7-85 | 2-O″Pr-4-CF3 | 5-NO2 | |
| 7-86 | 2-O″Pr-4-CF3 | 5-NH2 | |
| 7-87 | 2-O″Pr-4-CF3 | 5-Me | |
| 7-88 | 2-O″Pr-4-CF3 | 5-NHSO2Me | |
| 7-89 | 2-O″Pr-5-CF3 | 5-CF3 | |
| 7-90 | 2-O″Pr-4-CF3 | 6-CF3 | |
| 7-91 | 2-O″Pr-4-CF3 | 5-CN | |
| 7-92 | 2-O″Pr-4-CF3 | 5-CF3-6-CN | |
| 7-93 | 2-Cl-6-O″Pr-4-CF3 | 5-CF3 | |
| 7-94 | 2-O$^{i}$Pr-4-CE3 | 5-CF3 | |
| 7-95 | 2-O″Bu-4-CF3 | 5-CF3 | |
| 7-96 | 2-O$^{i}$Bu-4-CF3 | 5-CF3 | |
| 7-97 | 2-O″Hex-4-CF3 | 5-CF3 | |
| 7-98 | 2-O″Pen-4-CF3 | 5-CF3 | |
| 7-99 | 2-OCH2CN-4-CF3 | 5-CF3 | |
| 7-100 | 2-OCH2OMe-4-CF3 | 5-CF3 | vis |
| 7-101 | 2-OCH2OEt-4-CF3 | 5-CF3 | |
| 7-102 | 2-OCH2O″Pr-4-CF3 | 5-CF3 | |
| 7-103 | 2-OCH2ᶜPr-4-CF3 | 5-CF3 | vis |
| 7-104 | 2-OCH2ᶜPr-4-CF3 | 5-CO2Me | |
| 7-105 | 2-OCH2ᶜPr-4-CHF2 | 5-CF3 | |
| 7-106 | 2-OCH2ᶜPr-4-CHO | 5-CF3 | |
| 7-107 | 2-OCH2ᶜPr-4-CF3 | 5-CN | |
| 7-108 | 2-OCH2ᶜPr-4-CN | 5-CF3 | |
| 7-109 | 2-OCH2′Bu-4-CF3 | 5-CF3 | |
| 7-110 | 2-O(CH2)2OMe-4-CF3 | 5-CF3 | |
| 7-111 | 2-O(CH2)2OMe-4-CF3 | 5-CN | |
| 7-112 | 2-O(CH2)2OCH2OMe-4-CF3 | 5-CF3 | |
| 7-113 | 2-O(CH2)2OH-4-CF3 | 5-CF3 | |
| 7-114 | 2-OCH2Ac-4-CF3 | 5-CF3 | |
| 7-115 | 2-OCH2CH(OH)Me-4-CF3 | 5-CF3 | |
| 7-116 | 2-OCH2CH(OMe)Me-4-CF3 | 5-CF3 | |
| 7-117 | 2-OCH2C(OH)Me2-4-CF3 | 5-CF3 | |
| 7-118 | 2-OCH2C(OMe)Me2-4-CF3 | 5-CF3 | |
| 7-119 | 2-OCH2C(Me2)CO2Me-4-CF3 | 5-CF3 | |
| 7-120 | 2-OCH2C(O)OMe-4-CF3 | 5-CF3 | |

TABLE 7-continued

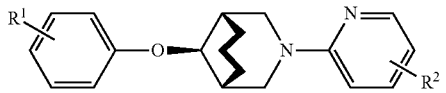

| Compound NO. | $R^1$ | $R^2$ | Physical constant [ ]: melting point ° C. |
|---|---|---|---|
| 7-121 | 2-OCH2C(O)OEt-4-CF3 | 5-CF3 | |
| 7-122 | 2-O(CH2)2OAc-4-CF3 | 5-CF3 | |
| 7-123 | 2-O(CH2)2NH2-4-CF3 | 5-CF3 | |
| 7-124 | 2-O(CH2)2NHAc-4-CF3 | 5-CF3 | |
| 7-125 | 2-O(CH2)2NMe2-4-CF3 | 5-CF3 | |
| 7-126 | 2-OCH2CH(Cl)Me-4-CF3 | 5-CF3 | |
| 7-127 | 2-OCH2CH═CMe2-4-CF3 | 5-CF3 | |
| 7-128 | 2-OCH2CH(Me)OMe-4-CF3 | 5-CF3 | |
| 7-129 | 4-OCF3 | 5-CF3 | |
| 7-130 | 3-OCF3 | 5-CF3 | |
| 7-131 | 2-OCF3 | 5-CF3 | |
| 7-132 | 4-OCF2Br | 5-CF3 | |
| 7-133 | 3-OCF2Br | 5-CF3 | |
| 7-134 | 2-OCF2Br | 5-CF3 | |
| 7-135 | 2-O(CH2)2Br-4-CF3 | 5-CF3 | |
| 7-136 | 2-O(CH2)2Cl-4-CF3 | 5-CF3 | |
| 7-137 | 2-O(CH2)2F-4-CF3 | 5-CF3 | |
| 7-138 | 2-OCH2(Ph-4-Cl)-4-CF3 | 5-CF3 | |
| 7-139 | 2-Oallyl-4-CF3 | 5-CF3 | |
| 7-140 | 2-Oallenyl-4-CF3 | 5-CF3 | |
| 7-141 | 2-Opropargyl-4-CF3 | 5-CF3 | |
| 7-142 | 2-O(CH2)2CH═CH2-4-CF3 | 5-CF3 | |
| 7-143 | 2-OCH2CH═CHMe-4-CF3 | 5-CF3 | |
| 7-144 | 2-OCH2CH═CMe2-4-CF3 | 5-CF3 | |
| 7-145 | 2-OCH2C(Me)═CH2-4-CF3 | 5-CF3 | |
| 7-146 | 2-OCH2CH═CHCl-4-CF3 | 5-CF3 | |
| 7-147 | 2-OAc-4-CF3 | 5-CF3 | |
| 7-148 | 2-OC(O)$^t$Bu-4-CF3 | 5-CF3 | |
| 7-149 | 2-OSO2Me-4-CF3 | 5-CF3 | |
| 7-150 | 2-OSO2Et-4-CF3 | 5-CF3 | |
| 7-151 | 2-SO2$^n$Pr-4-CF3 | 5-CF3 | |
| 7-152 | 2-OSO2$^n$Bu-4-CF3 | 5-CF3 | |
| 7-153 | 2-OSO2NMe2-4-CF3 | 5-CF3 | |
| 7-154 | 2-OC(S)NMe2-4-CF3 | 5-CF3 | |
| 7-155 | 2-SC(O)NMe2-4-CF3 | 5-CF3 | |
| 7-156 | 2-NH2-4-CF3 | 5-CF3 | |
| 7-157 | 2-N($^n$Pr)2-4-CF3 | 5-CF3 | |
| 7-158 | 2-NH$^n$Pr-4-CF3 | 5-CF3 | |
| 7-159 | 2-N(Me)$^n$Pr-4-CF3 | 5-CF3 | |
| 7-160 | 2-NHSO2Me-4-CF3 | 5-CF3 | |
| 7-161 | 2-NHSO2Et-4-CF3 | 5-CF3 | |
| 7-162 | 2-N(SO2$^n$Bu)2-4-CF3 | 5-CF3 | |
| 7-163 | 2-S$^n$Pr-4-CF3 | 5-CF3 | |
| 7-164 | 2-SCH2$^c$Pr-4-CF3 | 5-CF3 | |
| 7-165 | 2-OP(O)(OEt)S$^n$Pr-4-CF3 | 5-CF3 | |

TABLE 8

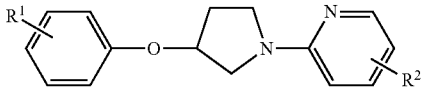

| Compound NO. | $R^1$ | $R^2$ | Physical constant [ ]: melting point ° C. | Note |
|---|---|---|---|---|
| 8-1 | 4-OH | 5-CF3 | | |
| 8-2 | 3-OH | 5-CF3 | | |
| 8-3 | 2-OH | 5-CF3 | | |
| 8-4 | 2-OH-4-CF3 | 5-CF3 | | |
| 8-5 | 4-F | 5-CF3 | | |
| 8-6 | 3-F | 5-CF3 | | |
| 8-7 | 2-F | 5-CF3 | | |

TABLE 8-continued

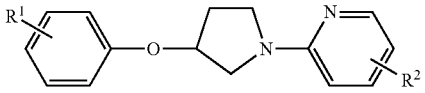

| Compound NO. | $R^1$ | $R^2$ | Physical constant [ ]: melting point ° C. | Note |
|---|---|---|---|---|
| 8-8 | 2-F-4-CF3 | 5-CF3 | | |
| 8-9 | 3-CF3-4-F | 5-CF3 | | |
| 8-10 | 4-Cl | 5-CF3 | | |
| 8-11 | 3-Cl | 5-CF3 | | |
| 8-12 | 2-Cl | 5-CF3 | | |
| 8-13 | 2-Cl-4-CF3 | 5-CF3 | | |
| 8-14 | 3-CF3-4-Cl | 5-CF3 | | |
| 8-15 | 2,6-Cl2-4-CF3 | 5-CF3 | | |
| 8-16 | 2-Br-4-CF3-6-Cl | 5-CF3 | | |
| 8-17 | 2-Cl-6-O$^n$Pr-4-CF3 | 5-CF3 | | |
| 8-18 | 4-Br | 5-CF3 | | |
| 8-19 | 3-Br | 5-CF3 | | |
| 8-20 | 2-Br | 5-CF3 | | |
| 8-21 | 2-Br-4-CF3 | 5-CF3 | | |
| 8-22 | 3-CF3-4-Br | 5-CF3 | | |
| 8-23 | 4-I | 5-CF3 | | |
| 8-24 | 3-I | 5-CF3 | | |
| 8-25 | 2-I | 5-CF3 | | |
| 8-26 | 2-I-4-CF3 | 5-CF3 | | |
| 8-27 | 4-CN | 5-CF3 | | |
| 8-28 | 3-CN | 5-CF3 | | |
| 8-29 | 2-CN | 5-CF3 | | |
| 8-30 | 2-CN-4-CF3 | 5-CF3 | | |
| 8-31 | 4-NO2 | 5-CF3 | | |
| 8-32 | 3-NO2 | 5-CF3 | | |
| 8-33 | 2-NO2 | 5-CF3 | | |
| 8-34 | 2-Cl-4-CF3-6-NO2 | 5-CF3 | | |
| 8-35 | 2-NO2-4-CF3 | 5-CF3 | | |
| 8-36 | 3-CF3-4-NO2 | 5-CF3 | | |
| 8-37 | 2-CHO-4-CF3 | 5-CF3 | | |
| 8-38 | 4-Me | 5-CF3 | | |
| 8-39 | 3-Me | 5-CF3 | | |
| 8-40 | 2-Me | 5-CF3 | | |
| 8-41 | 2,4-Me2 | 5-CF3 | | |
| 8-42 | 2-Me-3-CF3 | 5-CF3 | | |
| 8-43 | 2-Me-4-CF3 | 5-CF3 | | |
| 8-44 | 2-Me-4-OCF3 | S-CF3 | | |
| 8-45 | 2-Et-4-CF3 | 5-CF3 | | |
| 8-46 | 2,4,6-Me3 | 5-CF3 | | |
| 8-47 | 2-Me-4-F | 5-CF3 | | |
| 8-48 | 2-Me-4-Cl | 5-CF3 | | |
| 8-49 | 2-Et-4-Cl | 5-CF3 | | |
| 8-50 | 2-$^n$Pr-4-Cl | 5-CF3 | | |
| 8-51 | 2-$^n$Pr-4-CF3 | 5-CF3 | | |
| 8-52 | 2-$^i$Pr-4-CF3 | 5-CF3 | | |
| 8-53 | 2-CH2OMe-4-CF3 | 5-CF3 | | |
| 8-54 | 2-CH2OEt-4-CF3 | 5-CF3 | | |
| 8-55 | 2-CH(OH)Et-4-CF3 | 5-CF3 | | |
| 8-56 | 2-CH2OH-4-CF3 | 5-CF3 | | |
| 8-57 | 2-CH2OCH2OMe-4-CF3 | 5-CF3 | | |
| 8-58 | 2-CH2OCH2OEt-4-CF3 | 5-CF3 | | |
| 8-59 | 2-CH2OCH(Me)OMe-4-CF3 | 5-CF3 | | |
| 8-60 | 2-CH2OCH(Me)OMe-4-CF3 | 5-CF3 | | |
| 8-61 | 2-CH═CHMe-4-CF3 | 5-CF3 | | |
| 8-62 | 2-allyl-4-CF3 | 5-CF3 | | |
| 8-63 | 4-CF3 | 5-CF3 | [109-112] | |
| 8-64 | 3-CF3 | 5-CF3 | | |
| 8-65 | 2-CF3 | 5-CF3 | | |
| 8-66 | 3,4-(CF3)2 | 5-CF3 | | |
| 8-67 | 3,5-(CF3)2 | 5-CF3 | | |
| 8-68 | 2,4-(CF3)2 | 5-CF3 | | |
| 8-69 | 2-CH2Cl-4-CF3 | 5-CF3 | | |
| 8-70 | 2-CH(Cl)Et-4-CF3 | 5-CF3 | | |
| 8-71 | 4-CF3 | 3-Cl-5-CF3 | | |
| 8-72 | 4-CF3 | 4-Me-6-CF3 | | |
| 8-73 | 4-OMe | 5-CF3 | | |
| 8-74 | 3-OMe | 5-CF3 | | |
| 8-75 | 2-OMe | 5-CF3 | | |
| 8-76 | 2-OMe-4-CN | 5-CF3 | | |

TABLE 8-continued

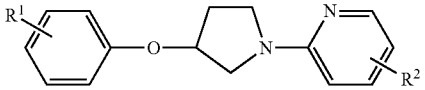

| Compound NO. | $R^1$ | $R^2$ | Physical constant [ ]: melting point ° C. | Note |
|---|---|---|---|---|
| 8-77 | 2-OMe-4-CF3 | 5-CF3 | | |
| 8-78 | 2-OEt-4-CF3 | 5-CF3 | | |
| 8-79 | 2-OEt-4-CF3 | 5-Cl | | |
| 8-80 | 2-OEt-4-CF3 | 5-Br | | |
| 8-81 | 2-O″Pr-4-CN | 5-CF3 | | |
| 8-82 | 2-O″Pr-4-CF3 | 5-CF3 | [47-50] | |
| 8-83 | 2-O″Pr-4-CF3 | 5-Cl | | |
| 8-84 | 2-O″Pr-4-CF3 | 5-Br | | |
| 8-85 | 2-O″Pr-4-CF3 | 5-NO2 | | |
| 8-86 | 2-O″Pr-4-CF3 | 5-NH2 | | |
| 8-87 | 2-O″Pr-4-CF3 | 5-Me | | |
| 8-88 | 2-O″Pr-4-CF3 | 5-NHSO2Me | | |
| 8-89 | 2-O″Pr-5-CF3 | 5-CF3 | | |
| 8-90 | 2-O″Pr-4-CF3 | 6-CF3 | | |
| 8-91 | 2-O″Pr-4-CF3 | 5-CN | | |
| 8-92 | 2-O″Pr-4-CF3 | 5-CF3-6-CN | | |
| 8-93 | 2-Cl-6-O″Pr-4-CF3 | 5-CF3 | | |
| 8-94 | 2-O$^i$Pr-4-CF3 | 5-CF3 | | |
| 8-95 | 2-O″Bu-4-CF3 | 5-CF3 | | |
| 8-96 | 2-O$^i$Bu-4-CF3 | 5-CF3 | | |
| 8-97 | 2-O″Hex-4-CF3 | 5-CF3 | | |
| 8-98 | 2-O″Pen-4-CF3 | 5-CF3 | | |
| 8-99 | 2-OCH2CN-4-CF3 | 5-CF3 | | |
| 8-100 | 2-OCH2OMe-4-CF3 | 5-CF3 | | |
| 8-101 | 2-OCH2OEt-4-CF3 | 5-CF3 | | |
| 8-102 | 2-OCH2O″Pr-4-CF3 | 5-CF3 | | |
| 8-103 | 2-OCH2$^c$Pr-4-CF3 | 5-CF3 | | |
| 8-104 | 2-OCH2$^c$Pr-4-CF3 | 5-CO2Me | | |
| 8-105 | 2-OCH2$^c$Pr-4-CHF2 | 5-CF3 | | |
| 8-106 | 2-OCH2$^c$Pr-4-CHO | 5-CF3 | | |
| 8-107 | 2-OCH$^c$Pr-4-CF3 | 5-CN | | |
| 8-108 | 2-OCH2$^c$Pr-4-CN | 5-CF3 | | |
| 8-109 | 2-OCH$^t$Bu-4-CF3 | 5-CF3 | | |
| 8-110 | 2-O(CH2)2OMe-4-CF3 | 5-CF3 | | |
| 8-111 | 2-O(CH2)2OMe-4-CF3 | 5-CN | | |
| 8-112 | 2-O(CH2)2OCH2OMe-4-CF3 | 5-CF3 | | |
| 8-113 | 2-O(CH2)2OH-4-CF3 | 5-CF3 | | |
| 8-114 | 2-OCH2Ac-4-CF3 | 5-CF3 | | |
| 8-115 | 2-OCH2CH(OH)Me-4-CF3 | 5-CF3 | | |
| 8-116 | 2-OCH2CH(OMe)Me-4-CF3 | 5-CF3 | | |
| 8-117 | 2-OCH2C(OH)Me2-4-CF3 | 5-CF3 | | |
| 8-118 | 2-OCH2C(OMe)Me2-4-CF3 | 5-CF3 | | |
| 8-119 | 2-OCH2C(Me2)CO2Me-4-CF3 | 5-CF3 | | |
| 8-120 | 2-OCH2C(O)OMe-4-CF3 | 5-CF3 | | |
| 8-121 | 2-OCH2C(O)OEt-4-CF3 | 5-CF3 | | |
| 8-122 | 2-O(CH2)2OAc-4-CF3 | 5-CF3 | | |
| 8-123 | 2-O(CH2)2NH2-4-CF3 | 5-CF3 | | |
| 8-124 | 2-O(CH2)2NHAc-4-CF3 | 5-CF3 | | |
| 8-125 | 2-O(CH2)2NMe2-4-CF3 | 5-CF3 | | |
| 8-126 | 2-OCH2CH(Cl)Me-4-CF3 | 5-CF3 | | |
| 8-127 | 2-OCH2CH═CMe2-4-CF3 | 5-CF3 | | |
| 8-128 | 2-OCH2CH(Me)OMe-4-CF3 | 5-CF3 | | |
| 8-129 | 4-OCF3 | 5-CF3 | [35-38] | |
| 8-130 | 3-OCF3 | 5-CF3 | | |
| 8-131 | 2-OCF3 | 5-CF3 | | |
| 8-132 | 4-OCF2Br | 5-CF3 | | |
| 8-133 | 3-OCF2Br | 5-CF3 | | |
| 8-134 | 2-OCF2Br | 5-CF3 | | |
| 8-135 | 2-O(CH2)2Br-4-CF3 | 5-CF3 | | |
| 8-136 | 2-O(CH2)2Cl-4-CF3 | 5-CF3 | | |
| 8-137 | 2-O(CH2)2F-4-CF3 | 5-CF3 | | |
| 8-138 | 2-OCH2(Ph-4-Cl)-4-CF3 | 5-CF3 | | |
| 8-139 | 2-Oallyl-4-CF3 | 5-CF3 | | |
| 8-140 | 2-Oallenyl-4-CF3 | 5-CF3 | | |
| 8-141 | 2-Opropargyl-4-CF3 | 5-CF3 | | |
| 8-142 | 2-O(CH2)2CH═CH2-4-CF3 | 5-CF3 | | |
| 8-143 | 2-OCH2CH═CHMe-4-CF3 | 5-CF3 | | |
| 8-144 | 2-OCH2CH═CMe2-4-CF3 | 5-CF3 | | |
| 8-145 | 2-OCH2C(Me)═CH2-4-CF3 | 5-CF3 | | |

TABLE 8-continued

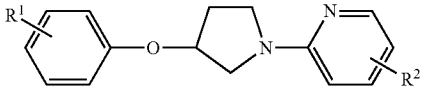

| Compound NO. | $R^1$ | $R^2$ | Physical constant [ ]: melting point ° C. | Note |
|---|---|---|---|---|
| 8-146 | 2-OCH2CH═CHCl-4-CF3 | 5-CF3 | | |
| 8-147 | 2-OAc-4-CF3 | 5-CF3 | | |
| 8-148 | 2-OC(O)Th-4-CF3 | 5-CF3 | | |
| 8-149 | 2-OSO2Me-4-CF3 | 5-CF3 | | |
| 8-150 | 2-OSO2Et-4-CF3 | 5-CF3 | | |
| 8-151 | 2-SO2″Pr-4-CF3 | 5-CF3 | | |
| 8-152 | 2-OSO2″Bu-4-CF3 | 5-CF3 | | |
| 8-153 | 2-OSO2NMe2-4-CF3 | 5-CF3 | | |
| 8-154 | 2-OC(S)NMe2-4-CF3 | 5-CF3 | | |
| 8-155 | 2-SC(O)NMe2-4-CF3 | 5-CF3 | | |
| 8-156 | 2-NH2-4-CF3 | 5-CF3 | | |
| 8-157 | 2-N(″Pr)2-4-CF3 | 5-CF3 | | |
| 8-158 | 2-NH″Pr-4-CF3 | 5-CF3 | | |
| 8-159 | 2-N(Me)″Pr-4-CF3 | 5-CF3 | | |
| 8-160 | 2-NHSO2Me-4-CF3 | 5-CF3 | | |
| 8-161 | 2-NHSO2Et-4-CF3 | 5-CF3 | | |
| 8-162 | 2-N(SO2″Bu)2-4-CF3 | 5-CF3 | | |
| 8-163 | 2-S″Pr-4-CF3 | 5-CF3 | | |
| 8-164 | 2-SCH2$^c$Pr-4-CF3 | 5-CF3 | | |
| 8-165 | 2-OP(O)(OEt)S″Pr-4-CF3 | 5-CF3 | | |

TABLE 9

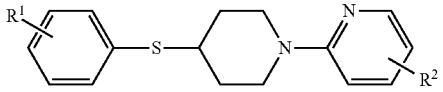

| Compound NO. | $R^1$ | $R^2$ | Physical constant [ ]: melting point ° C. | Note |
|---|---|---|---|---|
| 9-1 | 4-OH | 5-CF3 | | |
| 9-2 | 3-OH | 5-CF3 | | |
| 9-3 | 2-OH | 5-CF3 | | |
| 9-4 | 2-OH-4-CF3 | 5-CF3 | | |
| 9-5 | 4-F | 5-CF3 | | |
| 9-6 | 3-F | 5-CF3 | | |
| 9-7 | 2-F | 5-CF3 | | |
| 9-8 | 2-F-4-CF3 | 5-CF3 | | |
| 9-9 | 3-CF3-4-F | 5-CF3 | | |
| 9-10 | 4-Cl | 5-CF3 | | |
| 9-11 | 3-Cl | 5-CF3 | | |
| 9-12 | 2-Cl | 5-CF3 | | |
| 9-13 | 2-Cl-4-CF3 | 5-CF3 | | |
| 9-14 | 3-Cl-4-CF3 | 5-CF3 | | |
| 9-15 | 3-CF3-4-Cl | 5-CF3 | | |
| 9-16 | 2,6-Cl2-4-CF3 | 5-CF3 | | |
| 9-17 | 2-Br-4-CF3-6-Cl | 5-CF3 | | |
| 9-18 | 2-Cl-6-O″Pr-4-CF3 | 5-CF3 | | |
| 9-19 | 4-Br | 5-CF3 | | |
| 9-20 | 3-Br | 5-CF3 | | |
| 9-21 | 2-Br | 5-CF3 | | |
| 9-22 | 2-Br-4-CF3 | 5-CF3 | | |
| 9-23 | 3-CF3-4-Br | 5-CF3 | | |
| 9-24 | 4-I | 5-CF3 | | |
| 9-25 | 3-I | 5-CF3 | | |
| 9-26 | 2-I | 5-CF3 | | |
| 9-27 | 2-I-4-CF3 | 5-CF3 | | |
| 9-28 | 3-CF3-4-I | 5-CF3 | | |
| 9-29 | 4-CN | 5-CF3 | | |
| 9-30 | 3-CN | 5-CF3 | | |
| 9-31 | 2-CN | 5-CF3 | | |

TABLE 9-continued

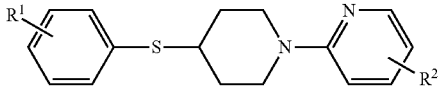

| Compound NO. | $R^1$ | $R^2$ | Physical constant [ ]: melting point ° C. | Note |
|---|---|---|---|---|
| 9-32 | 2-CN-4-CF3 | 5-CF3 | | |
| 9-33 | 2-CF3-4-CN | 5-CF3 | | |
| 9-34 | 4-NO2 | 5-CF3 | | |
| 9-35 | 3-NO2 | 5-CF3 | | |
| 9-36 | 2-NO2 | 5-CF3 | | |
| 9-37 | 2-Cl-4-CF3-6-NO2 | 5-CF3 | | |
| 9-38 | 2-NO2-4-CF3 | 5-CF3 | | |
| 9-39 | 3-CF3-4-NO2 | 5-CF3 | | |
| 9-40 | 2-CHO-4-CF3 | 5-CF3 | | |
| 9-41 | 4-Me | 5-CF3 | | |
| 9-42 | 3-Me | 5-CF3 | | |
| 9-43 | 2-Me | 5-CF3 | | |
| 9-44 | 2,4-Me2 | 5-CF3 | | |
| 9-45 | 2-Me-4-CF3 | 5-CF3 | | |
| 9-46 | 2-Me-4-OCF3 | 5-CF3 | | |
| 9-47 | 2,4,6-Me3 | 5-CF3 | | |
| 9-48 | 2-Me-4-F | 5-CF3 | | |
| 9-49 | 2-Me-4-Cl | 5-CF3 | | |
| 9-50 | 2-Me-4-Br | 5-CF3 | | |
| 9-51 | 2-Et-4-CF3 | 5-CF3 | | |
| 9-52 | 2-Me-4-Cl | 5-CF3 | | |
| 9-53 | 2-Me-4-Br | 5-CF3 | | |
| 9-54 | 2-Et-4-Cl | 5-CF3 | | |
| 9-55 | 2-Et-4-CF3 | 5-CF3 | | |
| 9-56 | 2-Et-4-OCF3 | 5-CF3 | | |
| 9-57 | 2-$^n$Pr-4-Cl | 5-CF3 | | |
| 9-58 | 2-$^n$nPr-4-Br | 5-CF3 | | |
| 9-59 | 2-$^n$Pr-4-CF3 | 5-CF3 | | |
| 9-60 | 2-$^i$Pr-4-CF3 | 5-CF3 | | |
| 9-61 | 2-$^i$Pr-4-Cl | 5-CF3 | | |
| 9-62 | 2-$^i$Pr-4-Br | 5-CF3 | | |
| 9-63 | 2-CH2OMe-4-CF3 | 5-CF3 | | |
| 9-64 | 2-CH2OMe-4-Cl | 5-CF3 | | |
| 9-65 | 2-CH2OMe-4-Br | 5-CF3 | | |
| 9-66 | 2-CH2OEt-4-CF3 | 5-CF3 | | |
| 9-67 | 2-CH(OH)Et-4-CF3 | 5-CF3 | | |
| 9-68 | 2-CH2OH-4-CF3 | 5-CF3 | | |
| 9-69 | 2-CH2OCH2OMe-4-CF3 | 5-CF3 | | |
| 9-70 | 3-CH2OCH2OMe-4-CF3 | 5-CF3 | | |
| 9-71 | 2-CH2OCH2OEt-4-CF3 | 5-CF3 | | |
| 9-72 | 2-CH2OCH(Me)OMe-4-CF3 | 5-CF3 | | |
| 9-73 | 2-CH═CHMe-4-CF3 | 5-CF3 | | |
| 9-74 | 2-allyl-4-CF3 | 5-CF3 | | |
| 9-75 | 4-CF3 | 5-CF3 | | |
| 9-76 | 3-CF3 | 5-CF3 | | |
| 9-77 | 2-CF3 | 5-CF3 | | |
| 9-78 | 3,4-(CF3)2 | 5-CF3 | | |
| 9-79 | 3,5-(CF3)2 | 5-CF3 | | |
| 9-80 | 2,4-(CF3)2 | 5-CF3 | | |
| 9-81 | 2-CH2Cl-4-CF3 | 5-CF3 | | |
| 9-82 | 2-CH(Cl)Et-4-CF3 | 5-CF3 | | |
| 9-83 | 4-CF3 | 3-Cl-5-CF3 | vis | |
| 9-84 | 4-CF3 | 3-Cl-5-CF3 | [131-133] | (Note 9-1) |
| 9-85 | 4-CF3 | 4-Me-6-CF3 | | |
| 9-86 | 4-OMe | 5-CF3 | | |
| 9-87 | 3-OMe | 5-CF3 | | |
| 9-88 | 2-OMe | 5-CF3 | | |
| 9-89 | 2-OMe-4-CF3 | 5-CF3 | | |
| 9-90 | 2-OEt-4-CF3 | 5-CF3 | | |
| 9-91 | 2-OEt-4-CF3 | 5-Cl | | |
| 9-92 | 2-OEt-4-CF3 | 5-Br | | |
| 9-93 | 2-O$^n$Pr-4-CF3 | 5-CF3 | | |
| 9-94 | 2-O$^n$Pr-4-CF3 | 5-CF3 | vis | |
| 9-95 | 2-O$^n$Pr-4-CF3 | 5-CF3 | [107-109] | (Note 9-2) |
| 9-96 | 2-O$^n$Pr-4-CF3 | 5-CF3 | [119-121] | (Note 9-3) |

TABLE 9-continued

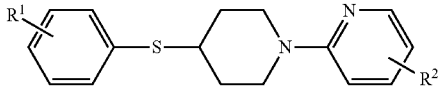

| Compound NO. | $R^1$ | $R^2$ | Physical constant [ ]: melting point ° C. | Note |
|---|---|---|---|---|
| 9-97 | 2-O$^n$Bu-4-CF3 | 5-CF3 | | |
| 9-98 | 2-O$^i$Bu-4-CF3 | 5-CF3 | | |
| 9-99 | 2-O$^n$Hex-4-CF3 | 5-CF3 | | |
| 9-100 | 2-O$^i$Pen-4-CF3 | 5-CF3 | | |
| 9-101 | 2-OCH2OMe-4-CF3 | 5-CF3 | | |
| 9-102 | 2-OCH2OEt-4-CF3 | 5-CF3 | | |
| 9-103 | 2-OCH2O$^n$Pr-4-CF3 | 5-CF3 | | |
| 9-104 | 2-OCH2$^c$Pr-4-CF3 | 5-CF3 | | |
| 9-105 | 2-OCH2$^c$Pr-4-CF3 | 5-CO2Me | | |
| 9-106 | 2-OCH2$^c$Pr-4-CHF2 | 5-CF3 | | |
| 9-107 | 2-OCH2$^c$Pr-4-CHO | 5-CF3 | | |
| 9-108 | 2-OCH2$^c$Pr-4-CF3 | 5-CN | | |
| 9-109 | 2-OCH2$^c$Pr-4-CN | 5-CF3 | | |
| 9-110 | 2-OCH2$^c$Bu-4-CF3 | 5-CF3 | | |
| 9-111 | 2-O(CH2)2OMe-4-CF3 | 5-CF3 | | |
| 9-112 | 2-O(CH2)2OMe-4-CF3 | 5-CN | | |
| 9-113 | 2-O(CH2)2OCH2OMe-4-CF3 | 5-CF3 | | |
| 9-114 | 2-O(CH2)2OH-4-CF3 | 5-CF3 | | |
| 9-115 | 2-OCH2Ac-4-CF3 | 5-CF3 | | |
| 9-116 | 2-OCH2CH(OH)Me-4-CF3 | 5-CF3 | | |
| 9-117 | 2-OCH2CH(OMe)Me-4-CF3 | 5-CF3 | | |
| 9-118 | 2-OCH2C(OH)Me2-4-CF3 | 5-CF3 | | |
| 9-119 | 2-OCH2C(OMe)Me2-4-CF3 | 5-CF3 | | |
| 9-120 | 2-OCH2C(Me2)CO2Me-4-CF3 | 5-CF3 | | |
| 9-121 | 2-OCH2C(O)OMe-4-CF3 | 5-CF3 | | |
| 9-122 | 2-OCH2C(O)OEt-4-CF3 | 5-CF3 | | |
| 9-123 | 2-O(CH2)2OAc-4-CF3 | 5-CF3 | | |
| 9-124 | 2-O(CH2)2NH2-4-CF3 | 5-CF3 | | |
| 9-125 | 2-O(CH2)2NHAc-4-CF3 | 5-CF3 | | |
| 9-126 | 2-O(CH2)2NMe2-4-CF3 | 5-CF3 | | |
| 9-127 | 2-OCH2CH(Cl)Me-4-CF3 | 5-CF3 | | |
| 9-128 | 2-OCH2CH═CMe2-4-CF3 | 5-CF3 | | |
| 9-129 | 4-OCF3 | 5-CF3 | | |
| 9-130 | 3-OCF3 | 5-CF3 | | |
| 9-131 | 2-OCF3 | 5-CF3 | | |
| 9-132 | 4-OCF2Br | 5-CF3 | | |
| 9-133 | 3-OCF2Br | 5-CF3 | | |
| 9-134 | 2-OCF2Br | 5-CF3 | | |
| 9-135 | 2-O(CH2)2Br-4-CF3 | 5-CF3 | | |
| 9-136 | 2-O(CH2)2Cl-4-CF3 | 5-CF3 | | |
| 9-137 | 2-O(CH2)2F-4-CF3 | 5-CF3 | | |
| 9-138 | 2-Oallyl-4-CF3 | 5-CF3 | | |
| 9-139 | 2-Oallenyl-4-CF3 | 5-CF3 | | |
| 9-140 | 4-CO2Me | 5-CF3 | | |
| 9-141 | 3-CO2Me | 5-CF3 | | |
| 9-142 | 2-CO2Me | 5-CF3 | | |
| 9-143 | 4-SCF3 | 5-CF3 | | |
| 9-144 | 3-SCF3 | 5-CF3 | | |
| 9-145 | 2-SCF3 | 5-CF3 | | |
| 9-146 | 4-S(O)CF3 | 5-CF3 | | |
| 9-147 | 3-S(O)CF3 | 5-CF3 | | |
| 9-148 | 2-S(O)CF3 | 5-CF3 | | |
| 9-149 | 4-OSO2CF3 | 5-CF3 | | |
| 9-150 | 3-OSO2CF3 | 5-CF3 | | |
| 9-151 | 2-OSO2CF3 | 5-CF3 | | |
| 9-152 | 4-OC(O)Ph | 5-CF3 | | |
| 9-153 | 3-OC(O)Ph | 5-CF3 | | |
| 9-154 | 2-OC(O)Ph | 5-CF3 | | |
| 9-155 | 4-OCH2Ph | 5-CF3 | | |
| 9-156 | 3-OCH2Ph | 5-CF3 | | |
| 9-157 | 2-OCH2Ph | 5-CF3 | | |
| 9-158 | 4-OCH2(Naph-1-yl) | 5-CF3 | | |
| 9-159 | 2-Opropargyl-4-CF3 | 5-CF3 | | |
| 9-160 | 2-(OCH2CH═CCl2)-4-CF3 | 5-CF3 | | |
| 9-161 | 2,3,6-Cl3-4-OCH2CH═CCl2 | 3-Cl-5-CF3 | | |
| 9-162 | 2,3,6-Cl3-4-OCH2CH═CCl2 | 5-CF3 | | |
| 9-163 | 2-OAc-4-CF3 | 5-CF3 | | |
| 9-164 | 3-CF3-4-NH2 | 5-CF3 | | |

TABLE 9-continued

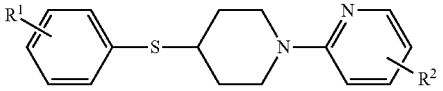

| Compound NO. | $R^1$ | $R^2$ | Physical constant [ ]: melting point ° C. | Note |
|---|---|---|---|---|
| 9-165 | 2-NH2-4-CF3 | 5-CF3 | | |
| 9-166 | 2-NH2-4-CF3-6-Cl | 5-CF3 | | |
| 9-167 | 2-NHMe-4-CF3 | 5-CF3 | | |
| 9-168 | 2-NHEt-4-CF3 | 5-CF3 | | |
| 9-169 | 2-NH"Pr-4-CF3 | 5-CF3 | | |
| 9-170 | 2-N("Pr)2-4-CF3 | 5-CF3 | | |
| 9-171 | 2-N(Ac)nPr-4-CF3 | 5-CF3 | | |
| 9-172 | 2-OC(O)OMe-4-CF3 | 5-CF3 | | |
| 9-173 | 2-OC(O)SMe-4-CF3 | 5-CF3 | | |
| 9-174 | 3-CF3-4-N(SO2Me)2 | 5-CF3 | | |
| 9-175 | 2-C(O)Et-4-CF3 | 5-CF3 | | |

(Note 9-1)

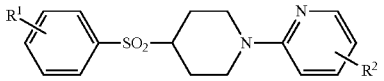

(Note 9-2)

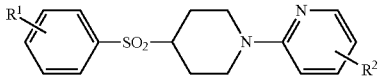

(Note 9-3)

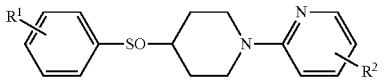

TABLE 10

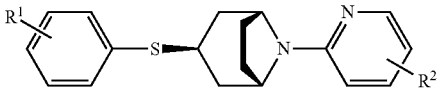

| Compound NO. | $R^1$ | $R^2$ | Physical constant [ ]: melting point ° C. | Note |
|---|---|---|---|---|
| 10-1 | 4-OH | 5-CF3 | | |
| 10-2 | 3-OH | 5-CF3 | | |
| 10-3 | 2-OH | 5-CF3 | | |
| 10-4 | 2-OH-4-CF3 | 5-CF3 | | |
| 10-5 | 4-F | 5-CF3 | | |
| 10-6 | 3-F | 5-CF3 | | |
| 10-7 | 2-F | 5-CF3 | | |
| 10-8 | 2-F-4-CF3 | 5-CF3 | | |
| 10-9 | 3-CF3-4-F | 5-CF3 | | |
| 10-10 | 4-Cl | 5-CF3 | | |
| 10-11 | 3-Cl | 5-CF3 | | |
| 10-12 | 2-Cl | 5-CF3 | | |
| 10-13 | 2-Cl-4-CF3 | 5-CF3 | | |
| 10-14 | 3-Cl-4-CF3 | 5-CF3 | | |
| 10-15 | 3-CF3-4-Cl | 5-CF3 | | |
| 10-16 | 2,6-Cl2-4-CF3 | 5-CF3 | | |
| 10-17 | 2-Br-4-CF3-6-Cl | 5-CF3 | | |
| 10-18 | 2-Cl-6-O"Pr-4-CF3 | 5-CF3 | | |
| 10-19 | 4-Br | 5-CF3 | | |
| 10-20 | 3-Br | 5-CF3 | | |
| 10-21 | 2-Br | 5-CF3 | | |
| 10-22 | 2-Br-4-CF3 | 5-CF3 | | |
| 10-23 | 3-CF3-4-Br | 5-CF3 | | |
| 10-24 | 4-I | 5-CF3 | | |

TABLE 10-continued

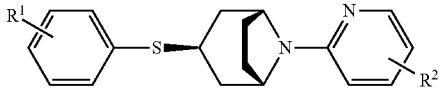

| Compound NO. | $R^1$ | $R^2$ | Physical constant [ ]: melting point ° C. | Note |
|---|---|---|---|---|
| 10-25 | 3-I | 5-CF3 | | |
| 10-26 | 2-I | 5-CF3 | | |
| 10-27 | 2-I-4-CF3 | 5-CF3 | | |
| 10-28 | 3-CF3-4-I | 5-CF3 | | |
| 10-29 | 4-CN | 5-CF3 | | |
| 10-30 | 3-CN | 5-CF3 | | |
| 10-31 | 2-CN | 5-CF3 | | |
| 10-32 | 2-CN-4-CF3 | 5-CF3 | | |
| 10-33 | 2-CF3-4-CN | 5-CF3 | | |
| 10-34 | 4-NO2 | 5-CF3 | | |
| 10-35 | 3-NO2 | 5-CF3 | | |
| 10-36 | 2-NO2 | 5-CF3 | | |
| 10-37 | 2-Cl-4-CF3-6-NO2 | 5-CF3 | | |
| 10-38 | 2-NO2-4-CF3 | 5-CF3 | | |
| 10-39 | 3-CF3-4-NO2 | 5-CF3 | | |
| 10-40 | 2-CHO-4-CF3 | 5-CF3 | | |
| 10-41 | 4-Me | 5-CF3 | | |
| 10-42 | 3-Me | 5-CF3 | | |
| 10-43 | 2-Me | 5-CF3 | | |
| 10-44 | 2,4-Me2 | 5-CF3 | | |
| 10-45 | 2-Me-4-CF3 | 5-CF3 | | |
| 10-46 | 2-Me-4-OCF3 | 5-CF3 | | |
| 10-47 | 2,4,6-Me3 | 5-CF3 | | |
| 10-48 | 2-Me-4-F | 5-CF3 | | |
| 10-49 | 2-Me-4-Cl | 5-CF3 | | |
| 10-50 | 2-Me-4-Br | 5-CF3 | | |
| 10-51 | 2-Et-4-CF3 | 5-CF3 | | |
| 10-52 | 2-Me-4-Cl | 5-CF3 | | |
| 10-53 | 2-Me-4-Br | 5-CF3 | | |
| 10-54 | 2-Et-4-Cl | 5-CF3 | | |
| 10-55 | 2-Et-4-CF3 | 5-CF3 | | |
| 10-56 | 2-Et-4-OCF3 | 5-CF3 | | |
| 10-57 | 2-"Pr-4-Cl | 5-CF3 | | |
| 10-58 | 2-"Pr-4-Br | 5-CF3 | | |
| 10-59 | 2-"Pr-4-CF3 | 5-CF3 | | |
| 10-60 | 2-$^i$Pr-4-CF3 | 5-CF3 | | |
| 10-61 | 2-$^i$Pr-4-Cl | 5-CF3 | | |
| 10-62 | 2-$^i$Pr-4-Br | 5-CF3 | | |
| 10-63 | 2-CH2OMe-4-CF3 | 5-CF3 | | |
| 10-64 | 2-CH2OMe-4-Cl | 5-CF3 | | |
| 10-65 | 2-CH2OMe-4-Br | 5-CF3 | | |
| 10-66 | 2-CH2OEt-4-CF3 | 5-CF3 | | |
| 10-67 | 2-CH(OH)Et-4-CF3 | 5-CF3 | | |
| 10-68 | 2-CH2OH-4-CF3 | 5-CF3 | | |
| 10-69 | 2-CH2OCH2OMe-4-CF3 | 5-CF3 | | |
| 10-70 | 3-CH2OCH2OMe-4-CF3 | 5-CF3 | | |
| 10-71 | 2-CH2OCH2OEt-4-CF3 | 5-CF3 | | |
| 10-72 | 2-CH2OCH(Me)OMe-4-CF3 | 5-CF3 | | |
| 10-73 | 2-CH═CHMe-4-CF3 | 5-CF3 | | |
| 10-74 | 2-allyl-4-CF3 | 5-CF3 | | |
| 10-75 | 4-CF3 | 5-CF3 | | |
| 10-76 | 3-CF3 | 5-CF3 | | |
| 10-77 | 2-CF3 | 5-CF3 | | |
| 10-78 | 3,4-(CF3)2 | 5-CF3 | | |
| 10-79 | 3,5-(CF3)2 | 5-CF3 | | |
| 10-80 | 2,4-(CF3)2 | 5-CF3 | | |
| 10-81 | 2-CH2Cl-4-CF3 | 5-CF3 | | |
| 10-82 | 2-CH(Cl)Et-4-CF3 | 5-CF3 | | |
| 10-83 | 4-CF3 | 3-Cl-5-CF3 | | |
| 10-84 | 4-CF3 | 4-Me-6-CF3 | | |
| 10-85 | 4-OMe | 5-CF3 | | |
| 10-86 | 3-OMe | 5-CF3 | | |
| 10-87 | 2-OMe | 5-CF3 | | |
| 10-88 | 2-OMe-4-CF3 | 5-CF3 | | |
| 10-89 | 2-OEt-4-CF3 | 5-CF3 | | |
| 10-90 | 2-OEt-4-CF3 | 5-Cl | | |
| 10-91 | 2-OEt-4-CF3 | 5-Br | | |

TABLE 10-continued

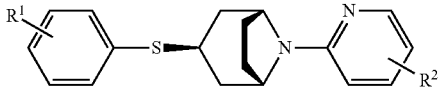

| Compound NO. | $R^1$ | $R^2$ | Physical constant [ ]: melting point ° C. | Note |
|---|---|---|---|---|
| 10-92 | 2-O″Pr-4-CF3 | 5-CF3 | | |
| 10-93 | 2-OnPr-4-CF3 | 5-CF3 | [74-74] | |
| 10-94 | 2-O″Bu-4-CF3 | 5-CF3 | | |
| 10-95 | 2-O$^i$Bu-4-CF3 | 5-CF3 | | |
| 10-96 | 2-O″Hex-4-CF3 | 5-CF3 | | |
| 10-97 | 2-O″Pen-4-CF3 | 5-CF3 | | |
| 10-98 | 2-OCH2OMe-4-CF3 | 5-CF3 | | |
| 10-99 | 2-OCH2OEt-4-CF3 | 5-CF3 | | |
| 10-100 | 2-OCH2O″Pr-4-CF3 | 5-CF3 | | |
| 10-101 | 2-OCH2$^c$Pr-4-CF3 | 5-CF3 | | |
| 10-102 | 2-OCH2$^c$Pr-4-CF3 | 5-CO2Me | | |
| 10-103 | 2-OCH2$^c$Pr-4-CHF2 | 5-CF3 | | |
| 10-104 | 2-OCH2$^c$Pr-4-CHO | 5-CF3 | | |
| 10-105 | 2-OCH2$^c$Pr-4-CF3 | 5-CN | | |
| 10-106 | 2-OCH2$^c$Pr-4-CN | 5-CF3 | | |
| 10-107 | 2-OCH2$^c$Bu-4-CF3 | 5-CF3 | | |
| 10-108 | 2-O(CH2)2OMe-4-CF3 | 5-CF3 | | |
| 10-109 | 2-O(CH2)2OMe-4-CF3 | 5-CN | | |
| 10-110 | 2-O(CH2)2OCH2OMe-4-CF3 | 5-CF3 | | |
| 10-111 | 2-O(CH2)2OH-4-CF3 | 5-CF3 | | |
| 10-112 | 2-OCH2Ac-4-CF3 | 5-CF3 | | |
| 10-113 | 2-OCH2CH(OH)Me-4-CF3 | 5-CF3 | | |
| 10-114 | 2-OCH2CH(OMe)Me-4-CF3 | 5-CF3 | | |
| 10-115 | 2-OCH2C(OH)Me2-4-CF3 | 5-CF3 | | |
| 10-116 | 2-OCH2C(OMe)Me2-4-CF3 | 5-CF3 | | |
| 10-117 | 2-OCH2C(Me2)CO2Me-4-CF3 | 5-CF3 | | |
| 10-118 | 2-OCH2C(O)OMe-4-CF3 | 5-CF3 | | |
| 10-119 | 2-OCH2C(O)OEt-4-CF3 | 5-CF3 | | |
| 10-120 | 2-O(CH2)2OAc-4-CF3 | 5-CF3 | | |
| 10-121 | 2-O(CH2)2NH2-4-CF3 | 5-CF3 | | |
| 10-122 | 2-O(CH2)2NHAc-4-CF3 | 5-CF3 | | |
| 10-123 | 2-O(CH2)2NMe2-4-CF3 | 5-CF3 | | |
| 10-124 | 2-OCH2CH(Cl)Me-4-CF3 | 5-CF3 | | |
| 10-125 | 2-OCH2CH═CMe2-4-CF3 | 5-CF3 | | |
| 10-128 | 4-OCF3 | 5-CF3 | | |
| 10-129 | 3-OCF3 | 5-CF3 | | |
| 10-130 | 2-OCF3 | 5-CF3 | | |
| 10-131 | 4-OCF2Br | 5-CF3 | | |
| 10-132 | 3-OCF2Br | 5-CF3 | | |
| 10-133 | 2-OCF2Br | 5-CF3 | | |
| 10-134 | 2-O(CH2)2Br-4-CF3 | 5-CF3 | | |
| 10-135 | 2-O(CH2)2Cl-4-CF3 | 5-CF3 | | |
| 10-136 | 2-O(CH2)2F-4-CF3 | 5-CF3 | | |
| 10-137 | 2-Oallyl-4-CF3 | 5-CF3 | | |
| 10-138 | 2-Oallenyl-4-CF3 | 5-CF3 | | |
| 10-139 | 4-CO2Me | 5-CF3 | | |
| 10-140 | 3-CO2Me | 5-CF3 | | |
| 10-141 | 2-CO2Me | 5-CF3 | | |
| 10-142 | 4-SCF3 | 5-CF3 | | |
| 10-143 | 3-SCF3 | 5-CF3 | | |
| 10-144 | 2-SCF3 | 5-CF3 | | |
| 10-145 | 4-S(O)CF3 | 5-CF3 | | |
| 10-146 | 3-S(O)CF3 | 5-CF3 | | |
| 10-147 | 2-S(O)CF3 | 5-CF3 | | |
| 10-148 | 4-OSO2CF3 | 5-CF3 | | |
| 10-149 | 3-OSO2CF3 | 5-CF3 | | |
| 10-150 | 2-OSO2CF3 | 5-CF3 | | |
| 10-151 | 4-OC(O)Ph | 5-CF3 | | |
| 10-152 | 3-OC(O)Ph | 5-CF3 | | |
| 10-153 | 2-OC(O)Ph | 5-CF3 | | |
| 10-154 | 4-OCH2Ph | 5-CF3 | | |
| 10-155 | 3-OCH2Ph | 5-CF3 | | |
| 10-156 | 2-OCH2Ph | 5-CF3 | | |
| 10-157 | 4-OCH2(Naph-1-yl) | 5-CF3 | | |
| 10-158 | 2-Opropargyl-4-CF3 | 5-CF3 | | |
| 10-159 | 2-(OCH2CH═CCl2)-4-CF3 | 5-CF3 | | |
| 10-160 | 2,3,6-Cl3-4-OCH2CH═CCl2 | 3-Cl-5-CF3 | | |

TABLE 10-continued

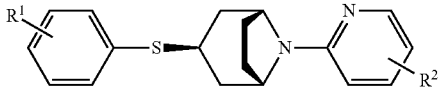

| Compound NO. | $R^1$ | $R^2$ | Physical constant [ ]: melting point ° C. | Note |
|---|---|---|---|---|
| 10-161 | 2,3,6-Cl3-4-OCH2CH═CCl2 | 5-CF3 | | |
| 10-162 | 2-OAc-4-CF3 | 5-CF3 | | |
| 10-163 | 3-CF3-4-NH2 | 5-CF3 | | |
| 10-164 | 2-NH2-4-CF3 | 5-CF3 | | |
| 10-165 | 2-NH2-4-CF3-6-Cl | 5-CF3 | | |
| 10-166 | 2-NHMe-4-CF3 | 5-CF3 | | |
| 10-167 | 2-NHEt-4-CF3 | 5-CF3 | | |
| 10-168 | 2-NH″Pr-4-CF3 | 5-CF3 | | |
| 10-169 | 2-N(″Pr)2-4-CF3 | 5-CF3 | | |
| 10-170 | 2-N(Ac)″Pr-4-CF3 | 5-CF3 | | |
| 10-171 | 2-OC(O)OMe-4-CF3 | 5-CF3 | | |
| 10-172 | 2-OC(O)SMe-4-CF3 | 5-CF3 | | |
| 10-173 | 3-CF3-4-N(SO2Me)2 | 5-CF3 | | |
| 10-174 | 2-C(O)Et-4-CF3 | 5-CF3 | | |

TABLE 11

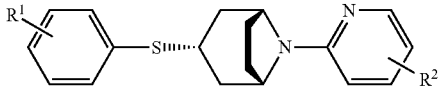

| Compound NO. | $R^1$ | $R^2$ | Physical constant [ ]: melting point ° C. | Note |
|---|---|---|---|---|
| 11-6 | 3-F | 5-CF3 | | |
| 11-7 | 2-F | 5-CF3 | | |
| 11-8 | 2-F-4-CF3 | 5-CF3 | | |
| 11-9 | 3-CF3-4-F | 5-CF3 | | |
| 11-10 | 4-Cl | 5-CF3 | | |
| 11-11 | 3-Cl | 5-CF3 | | |
| 11-12 | 2-Cl | 5-CF3 | | |
| 11-13 | 2-Cl-4-CF3 | 5-CF3 | | |
| 11-14 | 3-Cl-4-CF3 | 5-CF3 | | |
| 11-15 | 3-CF3-4-Cl | 5-CF3 | | |
| 11-16 | 2,6-Cl2-4-CF3 | 5-CF3 | | |
| 11-17 | 2-Br-4-CF3-6-Cl | 5-CF3 | | |
| 11-18 | 2-Cl-6-O″Pr-4-CF3 | 5-CF3 | | |
| 11-19 | 4-Br | 5-CF3 | | |
| 11-20 | 3-Br | 5-CF3 | | |
| 11-21 | 2-Br | 5-CF3 | | |
| 11-22 | 2-Br-4-CF3 | 5-CF3 | | |
| 11-23 | 3-CF3-4-Br | 5-CF3 | | |
| 11-24 | 4-I | 5-CF3 | | |
| 11-25 | 3-I | 5-CF3 | | |
| 11-26 | 2-I | 5-CF3 | | |
| 11-27 | 2-I-4-CF3 | 5-CF3 | | |
| 11-28 | 2-CF3-4-I | 5-CF3 | | |
| 11-29 | 4-CN | 5-CF3 | | |
| 11-30 | 3-CN | 5-CF3 | | |
| 11-31 | 2-CN | 5-CF3 | | |
| 11-32 | 2-CN-4-CF3 | 5-CF3 | | |
| 11-33 | 2-CF3-4-CN | 5-CF3 | | |
| 11-34 | 4-NO2 | 5-CF3 | | |
| 11-35 | 3-NO2 | 5-CF3 | | |
| 11-36 | 2-NO2 | 5-CF3 | | |
| 11-37 | 2-Cl-4-CF3-6-NO2 | 5-CF3 | | |
| 11-38 | 2-NO2-4-CF3 | 5-CF3 | | |
| 11-39 | 3-CF3-4-NO2 | 5-CF3 | | |
| 11-40 | 2-CHO-4-CF3 | 5-CF3 | | |
| 11-41 | 4-Me | 5-CF3 | | |

TABLE 11-continued

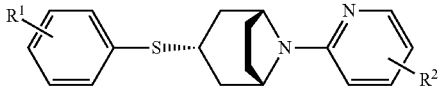

| Compound NO. | $R^1$ | $R^2$ | Physical constant [ ]: melting point ° C. | Note |
|---|---|---|---|---|
| 11-42 | 3-Me | 5-CF3 | | |
| 11-43 | 2-Me | 5-CF3 | | |
| 11-44 | 2,4-Me2 | 5-CF3 | | |
| 11-45 | 2-Me-4-CF3 | 5-CF3 | | |
| 11-46 | 2-Me-4-OCF3 | 5-CF3 | | |
| 11-47 | 2,4,6-Me3 | 5-CF3 | | |
| 11-48 | 2-Me-4-F | 5-CF3 | | |
| 11-49 | 2-Me-4-Cl | 5-CF3 | | |
| 11-50 | 2-Me-4-Br | 5-CF3 | | |
| 11-51 | 2-Et-4-CF3 | 5-CF3 | | |
| 11-52 | 2-Me-4-Cl | 5-CF3 | | |
| 11-53 | 2-Me-4-Br | 5-CF3 | | |
| 11-54 | 2-Et-4-Cl | 5-CF3 | | |
| 11-55 | 2-Et-4-CF3 | 5-CF3 | | |
| 11-56 | 2-Et-4-OCF3 | 5-CF3 | | |
| 11-57 | 2-$^n$Pr-4-Cl | 5-CF3 | | |
| 11-58 | 2-$^n$Pr-4-Br | 5-CF3 | | |
| 11-59 | 2-$^n$Pr-4-CF3 | 5-CF3 | | |
| 11-60 | 2-$^i$Pr-4-CF3 | 5-CF3 | | |
| 11-61 | 2-$^i$Pr-4-Cl | 5-CF3 | | |
| 11-62 | 2-$^i$Pr-4-Br | 5-CF3 | | |
| 11-63 | 2-CH2OMe-4-CF3 | 5-CF3 | | |
| 11-64 | 2-CH2OMe-4-Cl | 5-CF3 | | |
| 11-65 | 2-CH2OMe-4-Br | 5-CF3 | | |
| 11-66 | 2-CH2OEt-4-CF3 | 5-CF3 | | |
| 11-67 | 2-CH(OH)Et-4-CF3 | 5-CF3 | | |
| 11-68 | 2-CH2OH-4-CF3 | 5-CF3 | | |
| 11-69 | 2-CH2OCH2OMe-4-CF3 | 5-CF3 | | |
| 11-70 | 3-CH2OCH2OMe-4-CF3 | 5-CF3 | | |
| 11-71 | 2-CH2OCH2OEt-4-CF3 | 5-CF3 | | |
| 11-72 | 2-CH2OCH(Me)OMe-4-CF3 | 5-CF3 | | |
| 11-73 | 2-CH═CHMe-4-CF3 | 5-CF3 | | |
| 11-74 | 2-allyl-4-CF3 | 5-CF3 | | |
| 11-75 | 4-CF3 | 5-CF3 | | |
| 11-76 | 3-CF3 | 5-CF3 | | |
| 11-77 | 2-CF3 | 5-CF3 | | |
| 11-78 | 3,4-(CF3)2 | 5-CF3 | | |
| 11-79 | 3,5-(CF3)2 | 5-CF3 | | |
| 11-80 | 2,4-(CF3)2 | 5-CF3 | | |
| 11-81 | 2-CH2Cl-4-CF3 | 5-CF3 | | |
| 11-82 | 2-CH(Cl)Et-4-CF3 | 5-CF3 | | |
| 11-83 | 4-CF3 | 3-Cl-5-CF3 | | |
| 11-84 | 4-CF3 | 4-Me-6-CF3 | | |
| 11-85 | 4-OMe | 5-CF3 | | |
| 11-86 | 3-OMe | 5-CF3 | | |
| 11-87 | 2-OMe | 5-CF3 | | |
| 11-88 | 2-OMe-4-CF3 | 5-CF3 | | |
| 11-89 | 2-OEt-4-CF3 | 5-CF3 | | |
| 11-90 | 2-OEt-4-CF3 | 5-Cl | | |
| 11-91 | 2-OEt-4-CF3 | 5-Br | | |
| 11-92 | 2-O$^n$Pr-4-CF3 | 5-CF3 | | |
| 11-93 | 2-OnPr-4-CF3 | 5-CF3 | vis | |
| 11-94 | 2-O$^n$Bu-4-CF3 | 5-CF3 | | |
| 11-95 | 2-O$^i$Bu-4-CF3 | 5-CF3 | | |
| 11-96 | 2-O$^n$Hex-4-CF3 | 5-CF3 | | |
| 11-97 | 2-O$^n$Pen-4-CF3 | 5-CF3 | | |
| 11-98 | 2-OCH2OMe-4-CF3 | 5-CF3 | | |
| 11-99 | 2-OCH2OEt-4-CF3 | 5-CF3 | | |
| 11-100 | 2-OCH2O$^n$Pr-4-CF3 | 5-CF3 | | |
| 11-101 | 2-OCH2$^c$Pr-4-CF3 | 5-CF3 | | |
| 11-102 | 2-OCH2$^c$Pr-4-CF3 | 5-CO2Me | | |
| 11-103 | 2-OCH2$^{cP}$r-4-CHF2 | 5-CF3 | | |
| 11-104 | 2-OCH2$^c$Pr-4-CHO | 5-CF3 | | |
| 11-105 | 2-OCH2$^c$Pr-4-CF3 | 5-CN | | |
| 11-106 | 2-OCH2$^c$Pr-4-CN | 5-CF3 | | |
| 11-107 | 2-OCH2$^t$Bu-4-CF3 | 5-CF3 | | |
| 11-108 | 2-O(CH2)2OMe-4-CF3 | 5-CF3 | | |

TABLE 11-continued

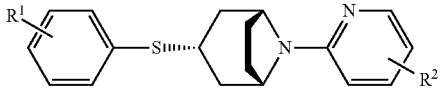

| Compound NO. | $R^1$ | $R^2$ | Physical constant [ ]: melting point ° C. | Note |
|---|---|---|---|---|
| 11-109 | 2-O(CH2)2OMe-4-CF3 | 5-CN | | |
| 11-110 | 2-O(CH2)2OCH2OMe-4-CF3 | 5-CF3 | | |
| 11-111 | 2-O(CH2)2OH-4-CF3 | 5-CF3 | | |
| 11-112 | 2-OCH2Ac-4-CF3 | 5-CF3 | | |
| 11-113 | 2-OCH2CH(OH)Me-4-CF3 | 5-CF3 | | |
| 11-114 | 2-OCH2CH(OMe)Me-4-CF3 | 5-CF3 | | |
| 11-115 | 2-OCH2C(OH)Me2-4-CF3 | 5-CF3 | | |
| 11-116 | 2-OCH2C(OMe)Me2-4-CF3 | 5-CF3 | | |
| 11-117 | 2-OCH2C(Me2)CO2Me-4-CF3 | 5-CF3 | | |
| 11-118 | 2-OCH2C(O)OMe-4-CF3 | 5-CF3 | | |
| 11-119 | 2-OCH2C(O)OEt-4-CF3 | 5-CF3 | | |
| 11-120 | 2-O(CH2)2OAc-4-CF3 | 5-CF3 | | |
| 11-121 | 2-O(CH2)2NH2-4-CF3 | 5-CF3 | | |
| 11-122 | 2-O(CH2)2NHAc-4-CF3 | 5-CF3 | | |
| 11-123 | 2-O(CH2)2NMe2-4-CF3 | 5-CF3 | | |
| 11-124 | 2-OCH2CH(Cl)Me-4-CF3 | 5-CF3 | | |
| 11-125 | 2-OCH2CH═OMe2-4-CF3 | 5-CF3 | | |
| 11-128 | 4-OCF3 | 5-CF3 | | |
| 11-129 | 3-OCF3 | 5-CF3 | | |
| 11-130 | 2-OCF3 | 5-CF3 | | |
| 11-131 | 4-OCF2Br | 5-CF3 | | |
| 11-132 | 3-OCF2Br | 5-CF3 | | |
| 11-133 | 2-OCF2Br | 5-CF3 | | |
| 11-134 | 2-O(CH2)2Br-4-CF3 | 5-CF3 | | |
| 11-135 | 2-O(CH2)2Cl-4-CF3 | 5-CF3 | | |
| 11-136 | 2-O(CH2)2F-4-CF3 | 5-CF3 | | |
| 11-137 | 2-Oallyl-4-CF3 | 5-CF3 | | |
| 11-138 | 2-Oallenyl-4-CF3 | 5-CF3 | | |
| 11-139 | 4-CO2Me | 5-CF3 | | |
| 11-140 | 3-CO2Me | 5-CF3 | | |
| 11-141 | 2-CO2Me | 5-CF3 | | |
| 11-142 | 4-SCF3 | 5-CF3 | | |
| 11-143 | 3-SCF3 | 5-CF3 | | |
| 11-144 | 2-SCF3 | 5-CF3 | | |
| 11-145 | 4-S(O)CF3 | 5-CF3 | | |
| 11-146 | 3-S(O)CF3 | 5-CF3 | | |
| 11-147 | 2-S(O)CF3 | 5-CF3 | | |
| 11-148 | 4-OSO2CF3 | 5-CF3 | | |
| 11-149 | 3-OSO2CF3 | 5-CF3 | | |
| 11-150 | 2-OSO2CF3 | 5-CF3 | | |
| 11-151 | 4-OC(O)Ph | 5-CF3 | | |
| 11-152 | 3-OC(O)Ph | 5-CF3 | | |
| 11-153 | 2-OC(O)Ph | 5-CF3 | | |
| 11-154 | 4-OCH2Ph | 5-CF3 | | |
| 11-155 | 3-OCH2Ph | 5-CF3 | | |
| 11-156 | 2-OCH2Ph | 5-CF3 | | |
| 11-157 | 4-OCH2(Naph-1-yl) | 5-CF3 | | |
| 11-158 | 2-Opropargyl-4-CF3 | 5-CF3 | | |
| 11-159 | 2-(OCH2CH═CCl2)-4-CF3 | 5-CF3 | | |
| 11-160 | 2,3,6-Cl3-4-OCH2CH═CCl2 | 3-Cl-5-CF3 | | |
| 11-161 | 2,3,6-Cl3-4-OCH2CH═CCl2 | 5-CF3 | | |
| 11-162 | 2-OAc-4-CF3 | 5-CF3 | | |
| 11-163 | 3-CF3-4-NH2 | 5-CF3 | | |
| 11-164 | 2-NH2-4-CF3 | 5-CF3 | | |
| 11-165 | 2-NH2-4-CF3-6-Cl | 5-CF3 | | |
| 11-166 | 2-NHMe-4-CF3 | 5-CF3 | | |
| 11-167 | 2-NHEt-4-CF3 | 5-CF3 | | |
| 11-168 | 2-NH$^n$Pr-4-CF3 | 5-CF3 | | |
| 11-169 | 2-N($^n$Pr)2-4-CF3 | 5-CF3 | | |
| 11-170 | 2-N(Ac)$^n$Pr-4-CF3 | 5-CF3 | | |
| 11-171 | 2-OC(O)OMe-4-CF3 | 5-CF3 | | |
| 11-172 | 2-OC(O)SMe-4-CF3 | 5-CF3 | | |
| 11-173 | 3-CF3-4-N(SO2Me)2 | 5-CF3 | | |
| 11-174 | 2-C(O)Et-4-CF3 | 5-CF3 | | |

TABLE 12

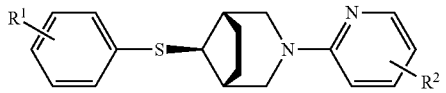

| Compound NO. | $R^1$ | $R^2$ | Physical constant [ ]: melting point ° C. | Note |
|---|---|---|---|---|
| 12-1 | 4-OH | 5-CF3 | | |
| 12-2 | 3-OH | 5-CF3 | | |
| 12-3 | 2-OH | 5-CF3 | | |
| 12-4 | 2-OH-4-CF3 | 5-CF3 | | |
| 12-5 | 4-F | 5-CF3 | | |
| 12-6 | 3-F | 5-CF3 | | |
| 12-7 | 2-F | 5-CF3 | | |
| 12-8 | 2-F-4-CF3 | 5-CF3 | | |
| 12-9 | 3-CF3-4-F | 5-CF3 | | |
| 12-10 | 4-Cl | 5-CF3 | | |
| 12-11 | 3-Cl | 5-CF3 | | |
| 12-12 | 2-Cl | 5-CF3 | | |
| 12-13 | 2-Cl-4-CF3 | 5-CF3 | | |
| 12-14 | 2-Cl-4-CF3 | 5-CF3 | | |
| 12-15 | 3-CF3-4-Cl | 5-CF3 | | |
| 12-16 | 2,6-Cl2-4-CF3 | 5-CF3 | | |
| 12-17 | 2-Br-4-CF3-6-Cl | 5-CF3 | | |
| 12-18 | 2-Cl-6-O″Pr-4-CF3 | 5-CF3 | | |
| 12-19 | 4-Br | 5-CF3 | | |
| 12-20 | 3-Br | 5-CF3 | | |
| 12-21 | 2-Br | 5-CF3 | | |
| 12-22 | 2-Br-4-CF3 | 5-CF3 | | |
| 12-23 | 3-CF3-5-Br | 5-CF3 | | |
| 12-24 | 4-I | 5-CF3 | | |
| 12-25 | 3-I | 5-CF3 | | |
| 12-26 | 2-I | 5-CF3 | | |
| 12-27 | 2-I-4-CF3 | 5-CF3 | | |
| 12-28 | 2-CF3-4-I | 5-CF3 | | |
| 12-29 | 4-CN | 5-CF3 | | |
| 12-30 | 3-CN | 5-CF3 | | |
| 12-31 | 2-CN | 5-CF3 | | |
| 12-32 | 2-CN-4-CF3 | 5-CF3 | | |
| 12-33 | 2-CF3-4-CN | 5-CF3 | | |
| 12-34 | 4-NO2 | 5-CF3 | | |
| 12-35 | 3-NO2 | 5-CF3 | | |
| 12-36 | 2-NO2 | 5-CF3 | | |
| 12-37 | 2-Cl-4-CF3-6-NO2 | 5-CF3 | | |
| 12-38 | 2-NO2-4-CF3 | 5-CF3 | | |
| 12-39 | 3-CF3-4-NO2 | 5-CF3 | | |
| 12-40 | 2-CHO-4-CF3 | 5-CF3 | | |
| 12-41 | 4-Me | 5-CF3 | | |
| 12-42 | 3-Me | 5-CF3 | | |
| 12-43 | 2-Me | 5-CF3 | | |
| 12-44 | 2,4-Me2 | 5-CF3 | | |
| 12-45 | 2-Me-4-CF3 | 5-CF3 | | |
| 12-46 | 2-Me-4-OCF3 | 5-CF3 | | |
| 12-47 | 2,4,6-Me3 | 5-CF3 | | |
| 12-48 | 2-Me-4-F | 5-CF3 | | |
| 12-49 | 2-Me-4-Cl | 5-CF3 | | |
| 12-50 | 2-Me-4-Br | 5-CF3 | | |
| 12-51 | 2-Et-4-CF3 | 5-CF3 | | |
| 12-52 | 2-Me-4-Cl | 5-CF3 | | |
| 12-53 | 2-Me-4-Br | 5-CF3 | | |
| 12-54 | 2-Et-4-Cl | 5-CF3 | | |
| 12-55 | 2-Et-4-CF3 | 5-CF3 | | |
| 12-56 | 2-Et-4-OCF3 | 5-CF3 | | |
| 12-57 | 2-$^n$Pr-4-Cl | 5-CF3 | | |
| 12-58 | 2-$^n$Pr-4-Br | 5-CF3 | | |
| 12-59 | 2-$^n$Pr-4-CF3 | 5-CF3 | | |
| 12-60 | 2-$^i$Pr-4-CF3 | 5-CF3 | | |
| 12-61 | 2-$^i$Pr-4-Cl | 5-CF3 | | |
| 12-62 | 2-$^i$Pr-4-Br | 5-CF3 | | |
| 12-63 | 2-CH2OMe-4-CF3 | 5-CF3 | | |
| 12-64 | 2-CH2OMe-4-Cl | 5-CF3 | | |
| 12-65 | 2-CH2OMe-4-Br | 5-CF3 | | |
| 12-66 | 2-CH2OEt-4-CF3 | 5-CF3 | | |
| 12-67 | 2-CH(OH)Et-4-CF3 | 5-CF3 | | |

TABLE 12-continued

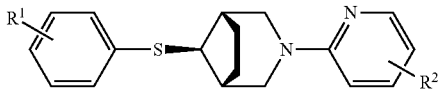

| Compound NO. | $R^1$ | $R^2$ | Physical constant [ ]: melting point ° C. | Note |
|---|---|---|---|---|
| 12-68 | 2-CH2OH-4-CF3 | 5-CF3 | | |
| 12-69 | 2-CH2OCH2OMe-4-CF3 | 5-CF3 | | |
| 12-70 | 3-CH2OCH2OMe-4-CF3 | 5-CF3 | | |
| 12-71 | 2-CH2OCH2OEt-4-CF3 | 5-CF3 | | |
| 12-72 | 2-CH2OCH(Me)OMe-4-CF3 | 5-CF3 | | |
| 12-73 | 2-CH(Me)OCH2OMe-4-CF3 | 5-CF3 | | |
| 12-74 | 2-CH═CHMe-4-CF3 | 5-CF3 | | |
| 12-75 | 2-allyl-4-CF3 | 5-CF3 | | |
| 12-76 | 4-CF3 | 5-CF3 | | |
| 12-77 | 3-CF3 | 5-CF3 | | |
| 12-78 | 2-CF3 | 5-CF3 | | |
| 12-79 | 3,4-(CF3)2 | 5-CF3 | | |
| 12-80 | 3,5-(CF3)2 | 5-CF3 | | |
| 12-81 | 2,4-(CF3)2 | 5-CF3 | | |
| 12-82 | 2-CH2Cl-4-CF3 | 5-CF3 | | |
| 12-83 | 2-CH(Cl)Et-4-CF3 | 5-CF3 | | |
| 12-84 | 4-CF3 | 3-Cl-5-CF3 | | |
| 12-85 | 4-CF3 | 4-Me-6-CF3 | | |
| 12-86 | 4-OMe | 5-CF3 | | |
| 12-87 | 3-OMe | 5-CF3 | | |
| 12-88 | 2-OMe | 5-CF3 | | |
| 12-89 | 2-OMe-4-CF3 | 5-CF3 | | |
| 12-90 | 2-OEt-4-CF3 | 5-CF3 | | |
| 12-91 | 2-OEt-4-CF3 | 5-Cl | | |
| 12-92 | 2-OEt-4-CF3 | 5-Br | | |
| 12-93 | 2-O″Pr-4-CF3 | 5-CH2F | | |
| 12-94 | 2-OnPr-4-CF3 | 5-Me | | |
| 12-95 | 2-O″Pr-4-CF3 | 5-CF3 | [94-96] | |
| 12-96 | 2-O″Pr-4-CF3 | 5-CN | | |
| 12-97 | 2-O″Pr-4-CF3 | 5-CF3 | | |
| 12-98 | 2-O″Pr-4-CF3 | 5-CHF2 | | |
| 12-99 | 2-O″Pr-4-CF3 | 5-CHO | | |
| 12-100 | 2-O″Pr-4-CF3 | 5-CH2OH | | |
| 12-101 | 2-O″Pr-4-CN | 5-CF3 | | |
| 12-102 | 3-O″Pr-5-CF3 | 5-CF3 | | |
| 12-103 | 2-(O$^c$Pr-2,2-Cl2)-4-CF3 | 5-CF3 | | |
| 12-104 | 2-O$^i$Bu-4-CF3 | 5-CF3 | | |
| 12-105 | 2-OBn-4-CF3 | 5-CF3 | | |
| 12-106 | 2-O$^i$Bu-4-CF3 | 5-CF3 | | |
| 12-107 | 2-O″Hex-4-CF3 | 5-CF3 | | |
| 12-108 | 2-O″Pen-4-CF3 | 5-CF3 | | |
| 12-109 | 2-OCH2OMe-4-CF3 | 5-CF3 | | |
| 12-110 | 2-OCH2OMe-4-CF3 | 5-CN | | |
| 12-111 | 2-OCH2OEt-4-CF3 | 5-CF3 | | |
| 12-112 | 2-OCH2O″Pr-4-CF3 | 5-CF3 | | |
| 12-113 | 2-OCH2CH(Me)OAc-4-CF3 | 5-CF3 | | |
| 12-114 | 2-OCH2C(Me2)OAc-4-CF3 | 5-CF3 | | |
| 12-115 | 2-OCH2$^c$Pr-4-CF3 | 5-CF3 | | |
| 12-116 | 2-OCH2$^c$Pr-4-CF3 | 5-CO2Me | | |
| 12-117 | 2-OCH2$^c$Pr-4-CHF2 | 5-CF3 | | |
| 12-118 | 2-OCH2$^c$Pr-4-CHO | 5-CF3 | | |
| 12-119 | 2-OCH2$^c$Pr-4-CF3 | 5-CN | | |
| 12-120 | 2-OCH2$^c$Pr-4-CN | 5-CF3 | | |
| 12-121 | 2-OCH2$^t$Bu-4-CF3 | 5-CF3 | | |
| 12-122 | 2-O(CH2)2OH-4-CF3 | 5-CF3 | | |
| 12-123 | 2-O(CH2)2OMe-4-CF3 | 5-CF3 | | |
| 12-124 | 2-O(CH2)2OMe-4-CF3 | 5-CN | | |
| 12-125 | 2-OCH2Ac-4-CF3 | 5-CF3 | | |
| 12-126 | 2-OCH2CH(OH)Me-4-CF3 | 5-CF3 | | |
| 12-127 | 2-OCH2CH(OMe)Me-4-CF3 | 5-CF3 | | |
| 12-128 | 2-OCH2C(OH)Me2-4-CF3 | 5-CF3 | | |
| 12-129 | 2-OCH2C(OMe)Me2-4-CF3 | 5-CF3 | | |
| 12-130 | 2-OCH2C(Me2)CO2Me-4-CF3 | 5-CF3 | | |
| 12-131 | 2-OCH2C(O)OMe-4-CF3 | 5-CF3 | | |
| 12-132 | 2-OCH2C(O)OEt-4-CF3 | 5-CF3 | | |
| 12-133 | 2-O(CH2)2OAc-4-CF3 | 5-CF3 | | |
| 12-134 | 2-O(CH2)2NH2-4-CF3 | 5-CF3 | | |

TABLE 12-continued

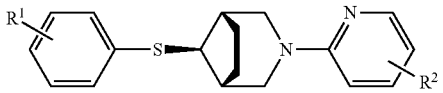

| Compound NO. | $R^1$ | $R^2$ | Physical constant [ ]: melting point ° C. | Note |
|---|---|---|---|---|
| 12-135 | 2-O(CH2)2NHAc-4-CF3 | 5-CF3 | | |
| 12-136 | 2-O(CH2)2NMe2-4-CF3 | 5-CF3 | | |
| 12-137 | 2-OCH2CH(Cl)Me-4-CF3 | 5-CF3 | | |
| 12-138 | 2-OCH2CH═CMe2-4-CF3 | 5-CF3 | | |
| 12-139 | 4-OCF3 | 5-CF3 | | |
| 12-140 | 3-OCF3 | 5-CF3 | | |
| 12-141 | 2-OCF3 | 5-CF3 | | |
| 12-142 | 4-OCF2Br | 5-CF3 | | |
| 12-143 | 3-OCF2Br | 5-CF3 | | |
| 12-144 | 2-OCF2Br | 5-CF3 | | |
| 12-145 | 2-O(CH2)2Br-4-CF3 | 5-CF3 | | |
| 12-146 | 2-O(CH2)2Cl-4-CF3 | 5-CF3 | | |
| 12-147 | 2-O(CH2)2F-4-CF3 | 5-CF3 | | |
| 12-148 | 2-Oallyl-4-CF3 | 5-CF3 | | |
| 12-149 | 2-Oallenyl-4-CF3 | 5-CF3 | | |
| 12-150 | 4-CO2Me | 5-CF3 | | |
| 12-151 | 3-CO2Me | 5-CF3 | | |
| 12-152 | 2-CO2Me | 5-CF3 | | |
| 12-153 | 4-SCF3 | 5-CF3 | | |
| 12-154 | 3-SCF3 | 5-CF3 | | |
| 12-155 | 2-SCF3 | 5-CF3 | | |
| 12-156 | 4-S(O)CF3 | 5-CF3 | | |
| 12-157 | 3-S(O)CF3 | 5-CF3 | | |
| 12-158 | 2-S(O)CF3 | 5-CF3 | | |
| 12-159 | 4-OSO2CF3 | 5-CF3 | | |
| 12-160 | 2-OSO2Me-4-CF3 | 5-CF3 | | |
| 12-161 | 2-OSO2Et-4-CF3 | 5-CF3 | | |
| 12-162 | 2-OSO2$^n$Pr-4-CF3 | 5-CF3 | | |
| 12-163 | 2-OSO2$^i$Pr-4-CF3 | 5-CF3 | | |
| 12-164 | 3-OSO2CF3 | 5-CF3 | | |
| 12-165 | 2-OSO2CF3 | 5-CF3 | | |
| 12-166 | 4-OC(O)Ph | 5-CF3 | | |
| 12-167 | 3-OC(O)Ph | 5-CF3 | | |
| 12-168 | 2-OC(O)Ph | 5-CF3 | | |
| 12-169 | 4-OCH2Ph | 5-CF3 | | |
| 12-170 | 3-OCH2Ph | 5-CF3 | | |
| 12-171 | 2-OCH2Ph | 5-CF3 | | |
| 12-172 | 4-OCH2(Naph-1-yl) | 5-CF3 | | |
| 12-173 | 2-OCH2C(Me)═CH2-4-CF3 | 5-CF3 | | |
| 12-174 | 2-OCH2CH═CHMe-4-CF3 | 5-CF3 | | |
| 12-175 | 2-O(CH2)2CH═CH2-4-CF3 | 5-CF3 | | |
| 12-176 | 2-Opropargyl-4-CF3 | 5-CF3 | | |
| 12-177 | 2-(OCH2CH═CCl2)-4-CF3 | 5-CF3 | | |
| 12-178 | 2,3,6-Cl3-4-OCH2CH═CCl2 | 3-Cl-5-CF3 | | |
| 12-179 | 2,3,6-Cl3-4-OCH2CH═CCl2 | 5-CF3 | | |
| 12-180 | 2-OAc-4-CF3 | 5-CF3 | | |
| 12-181 | 2-OCH2C(═NOH)Me-4-CHO(anti) | 5-CF3 | | |
| 12-182 | 2-OCH2C(═NOH)Me-4-CHO(syn) | 5-CF3 | | |
| 12-183 | 2-OCH2C(═NOMe)Me-4-CHO(anti) | 5-CF3 | | |
| 12-184 | 3-CF3-4-NH2 | 5-CF3 | | |
| 12-185 | 2-NH2-4-CF3 | 5-CF3 | | |
| 12-186 | 2-NH2-4-CF3-6-Cl | 5-CF3 | | |
| 12-187 | 2-NHMe-4-CF3 | 5-CF3 | | |
| 12-188 | 2-NHEt-4-CF3 | 5-CF3 | | |
| 12-189 | 2-NH$^n$Pr-4-CF3 | 5-CF3 | | |
| 12-190 | 2-N(Me)$^n$Pr-4-CF3 | 5-CF3 | | |
| 12-191 | 2-N($^n$Pr)2-4-CF3 | 5-CF3 | | |
| 12-192 | 2-NHAc-4-CF3 | 5-CF3 | | |
| 12-193 | 2-N(Ac)$^n$Pr-4-CF3 | 5-CF3 | | |
| 12-194 | 2-OC(O)OMe-4-CF3 | 5-CF3 | | |
| 12-195 | 2-OC(O)SMe-4-CF3 | 5-CF3 | | |
| 12-196 | 3-CF3-4-N(SO2Me)2 | 5-CF3 | | |
| 12-197 | 2-OC(O)Et-4-CF3 | 5-CF3 | | |
| 12-198 | 2-0C(O)$^n$Pr-4-CF3 | 5-CF3 | | |

TABLE 12-continued

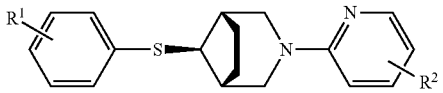

| Compound NO. | $R^1$ | $R^2$ | Physical constant [ ]: melting point ° C. | Note |
|---|---|---|---|---|
| 12-199 | 2-0C(O)$^t$Bu-4-CF3 | 5-CF3 | | |
| 12-200 | 2-NHSO2Me-4-CF3 | 5-CF3 | | |
| 12-201 | 2-(O$^c$Pr-2,2-Cl2)-4-CF3 | 5-CF3 | | |

TABLE 13

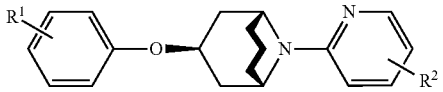

| Compound NO. | $R^1$ | $R^2$ | Physical constant [ ]: melting point ° C. |
|---|---|---|---|
| 13-1 | 4-OH | 5-CF3 | |
| 13-2 | 3-OH | 5-CF3 | |
| 13-3 | 2-OH | 5-CF3 | |
| 13-4 | 2-OH-4-CF3 | 5-CF3 | |
| 13-5 | 4-F | 5-CF3 | |
| 13-6 | 3-F | 5-CF3 | |
| 13-7 | 2-F | 5-CF3 | |
| 13-8 | 2-F-4-CF3 | 5-CF3 | |
| 13-9 | 3-CF3-4-F | 5-CF3 | |
| 13-10 | 4-Cl | 5-CF3 | |
| 13-11 | 3-Cl | 5-CF3 | |
| 13-12 | 2-Cl | 5-CF3 | |
| 13-13 | 2-Cl-4-CF3 | 5-CF3 | |
| 13-14 | 3-CF3-4-CF3 | 5-CF3 | |
| 13-15 | 2,6-Cl2-4-CF3 | 5-CF3 | |
| 13-16 | 2-Br-4-CF3-6-Cl | 5-CF3 | |
| 13-17 | 2-Cl-6-O$^n$Pr-4-CF3 | 5-CF3 | |
| 13-18 | 4-Br | 5-CF3 | |
| 13-19 | 3-Br | 5-CF3 | |
| 13-20 | 2-Br | 5-CF3 | |
| 13-21 | 2-Br-4-CF3 | 5-CF3 | |
| 13-22 | 3-CF3-4-Br | 5-CF3 | |
| 13-23 | 4-I | 5-CF3 | |
| 13-24 | 3-I | 5-CF3 | |
| 13-25 | 2-I | 5-CF3 | |
| 13-26 | 2-I-4-CF3 | 5-CF3 | |
| 13-27 | 4-CN | 5-CF3 | |
| 13-28 | 3-CN | 5-CF3 | |
| 13-29 | 2-CN | 5-CF3 | |
| 13-30 | 2-CN-4-CF3 | 5-CF3 | |
| 13-31 | 4-NO2 | 5-CF3 | |
| 13-32 | 3-NO2 | 5-CF3 | |
| 13-33 | 2-NO2 | 5-CF3 | |
| 13-34 | 2-Cl-4-CF3-6-NO2 | 5-CF3 | |
| 13-35 | 2-NO2-4-CF3 | 5-CF3 | |
| 13-36 | 3-CF3-4-NO2 | 5-CF3 | |
| 13-37 | 2-CHO-4-CF3 | 5-CF3 | |
| 13-38 | 3-Me | 5-CF3 | |
| 13-39 | 2-Me | 5-CF3 | |
| 13-40 | 2,4-Me2 | 5-CF3 | |
| 13-41 | 2-Me-3-CF3 | 5-CF3 | |
| 13-42 | 2-Me-4-CF3 | 5-CF3 | |
| 13-43 | 2-Me-4-OCF3 | 5-CF3 | |
| 13-44 | 2-Et-4-CF3 | 5-CF3 | |
| 13-45 | 2,4,6-Me3 | 5-CF3 | |
| 13-46 | 2-Me-4-F | 5-CF3 | |
| 13-47 | 2-Me-4-Cl | 5-CF3 | |
| 13-48 | 2-Et-4-Cl | 5-CF3 | |

TABLE 13-continued

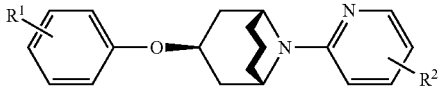

| Compound NO. | $R^1$ | $R^2$ | Physical constant [ ]: melting point ° C. |
|---|---|---|---|
| 13-49 | 2-ⁿPr-4-Cl | 5-CF3 | |
| 13-50 | 2-ⁿPr-4-CF3 | 5-CF3 | |
| 13-51 | 2-ⁱPr-4-CF3 | 5-CF3 | |
| 13-52 | 2-CH2OMe-4-CF3 | 5-CF3 | |
| 13-53 | 2-CH2OEt-4-CF3 | 5-CF3 | |
| 13-54 | 2-CH(OH)Et-4-CF3 | 5-CF3 | |
| 13-55 | 2-CH2OH-4-CF3 | 5-CF3 | |
| 13-56 | 2-CH2OCH2OMe-4-CF3 | 5-CF3 | |
| 13-57 | 2-CH2OCH2OEt-4-CF3 | 5-CF3 | |
| 13-58 | 2-CH2OCH(Me)OMe-4-CF3 | 5-CF3 | |
| 13-59 | 2-CH2OCH(Me)OMe-4-CF3 | 5-CF3 | |
| 13-60 | 2-CH═CHMe-4-CF3 | 5-CF3 | |
| 13-61 | 2-allyl-4-CF3 | 5-CF3 | |
| 13-62 | 4-CF3 | 5-CF3 | |
| 13-63 | 3-CF3 | 5-CF3 | |
| 13-64 | 2-CF3 | 5-CF3 | |
| 13-65 | 3,4-(CF3)2 | 5-CF3 | |
| 13-66 | 3,5-(CF3)2 | 5-CF3 | |
| 13-67 | 2,4-(CF3)2 | 5-CF3 | |
| 13-68 | 2-CH2Cl-4-CF3 | 5-CF3 | |
| 13-69 | 2-CH(Cl)Et-4-CF3 | 5-CF3 | |
| 13-70 | 4-CF3 | 3-Cl-5-CF3 | |
| 13-71 | 4-CF3 | 4-Me-6-CF3 | |
| 13-72 | 4-OMe | 5-CF3 | |
| 13-73 | 3-OMe | 5-CF3 | |
| 13-74 | 2-OMe | 5-CF3 | |
| 13-75 | 2-OMe-4-CN | 5-CF3 | |
| 13-76 | 2-OMe-4-CF3 | 5-CF3 | |
| 13-77 | 2-OEt-4-CF3 | 5-CF3 | |
| 13-78 | 2-OEt-4-CF3 | 5-Cl | |
| 13-79 | 2-OEt-4-CF3 | 5-Br | |
| 13-80 | 2-Oⁿ Pr-4-CN | 5-CF3 | |
| 13-81 | 2-Oⁿ Pr-4-CF3 | 5-CF3 | Nd22.2-1.5140 |
| 13-82 | 2-Oⁿ Pr-4-CF3 | 5-Cl | |
| 13-83 | 2-Oⁿ Pr-4-CF3 | 5-Br | |
| 13-84 | 2-Oⁿ Pr-4-CF3 | 5-NO2 | |
| 13-85 | 2-Oⁿ Pr-4-CF3 | 5-NH2 | |
| 13-86 | 2-Oⁿ Pr-4-CF3 | 5-Me | |
| 13-87 | 2-Oⁿ Pr-4-CF3 | 5-NHSO2Me | |
| 13-88 | 2-Oⁿ Pr-5-CF3 | 5-CF3 | |
| 13-89 | 2-Oⁿ Pr-4-CF3 | 6-CF3 | |
| 13-90 | 2-Oⁿ Pr-4-CF3 | 5-CN | |
| 13-91 | 2-Oⁿ Pr-4-CF3 | 5-CF3-6-CN | |
| 13-92 | 2-Cl-6-Oⁿ Pr-4-CF3 | 5-CF3 | |
| 13-93 | 2-Oⁱ Pr-4-CF3 | 5-CF3 | |
| 13-94 | 2-Oⁿ Bu-4-CF3 | 5-CF3 | |
| 13-95 | 2-Oⁱ Bu-4-CF3 | 5-CF3 | |
| 13-96 | 2-Oⁿ Hex-4-CF3 | 5-CF3 | |
| 13-97 | 2-Oⁿ Pen-4-CF3 | 5-CF3 | |
| 13-98 | 2-OCH2CN-4-CF3 | 5-CF3 | |
| 13-99 | 2-OCH2OMe-4-CF3 | 5-CF3 | |
| 13-100 | 2-OCH2OEt-4-CF3 | 5-CF3 | |
| 13-101 | 2-OCH2Oⁿ Pr-4-CF3 | 5-CF3 | |
| 13-102 | 2-OCH2ᶜ Pr-4-CF3 | 5-CF3 | |
| 13-103 | 2-OCH2ᶜ Pr-4-CF3 | 5-CO2Me | |
| 13-104 | 2-OCH2ᶜ Pr-4-CHF2 | 5-CF3 | |
| 13-105 | 2-OCH2ᶜ Pr-4-CHO | 5-CF3 | |
| 13-106 | 2-OCH2ᶜ Pr-4-CF3 | 5-CN | |
| 13-107 | 2-OCH2ᶜ Pr-4-CN | 5-CF3 | |
| 13-108 | 2-OCH2ᵗ Bu-4-CF3 | 5-CF3 | |
| 13-109 | 2-O(CH2)2OMe-4-CF3 | 5-CF3 | |
| 13-110 | 2-O(CH2)2OMe-4-CF3 | 5-CN | |
| 13-111 | 2-O(CH2)2OCH2OMe-4-CF3 | 5-CF3 | |
| 13-112 | 2-O(CH2)2OH-4-CF3 | 5-CF3 | |
| 13-113 | 2-OCH2Ac-4-CF3 | 5-CF3 | |
| 13-114 | 2-OCH2CH(OH)Me-4-CF3 | 5-CF3 | |
| 13-115 | 2-OCH2CH(OMe)Me-4-CF3 | 5-CF3 | |
| 13-116 | 2-OCH2C(OH)Me-4-CF3 | 5-CF3 | |

TABLE 13-continued

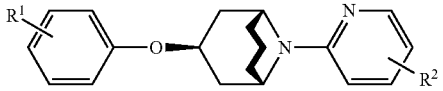

| Compound NO. | $R^1$ | $R^2$ | Physical constant [ ]: melting point ° C. |
|---|---|---|---|
| 13-117 | 2-OCH2C(OMe)Me-4-CF3 | 5-CF3 | |
| 13-118 | 2-OCH2C(Me2)CO2Me-4-CF3 | 5-CF3 | |
| 13-119 | 2-OCH2C(O)OMe-4-CF3 | 5-CF3 | |
| 13-120 | 2-OCH2C(O)OEt-4-CF3 | 5-CF3 | |
| 13-121 | 2-O(CH2)2OAc-4-CF3 | 5-CF3 | |
| 13-122 | 2-O(CH2)2NH2-4-CF3 | 5-CF3 | |
| 13-123 | 2-O(CH2)2NHAc-4-CF3 | 5-CF3 | |
| 13-124 | 2-O(CH2)2NMe2-4-CF3 | 5-CF3 | |
| 13-125 | 2-OCH2CH(Cl)Me-4-CF3 | 5-CF3 | |
| 13-126 | 2-OCH2CH═CMe2-4-CF3 | 5-CF3 | |
| 13-127 | 2-OCH2CH(Me)OMe-4-CF3 | 5-CF3 | |
| 13-128 | 4-OCF3 | 5-CF3 | |
| 13-129 | 3-OCF3 | 5-CF3 | |
| 13-130 | 2-OCF3 | 5-CF3 | |
| 13-131 | 4-OCF2Br | 5-CF3 | |
| 13-132 | 3-OCF2Br | 5-CF3 | |
| 13-133 | 2-OCF2Br | 5-CF3 | |
| 13-134 | 2-O(CH2)2Br-4-CF3 | 5-CF3 | |
| 13-135 | 2-O(CH2)2Cl-4-CF3 | 5-CF3 | |
| 13-136 | 2-O(CH2)2F-4-CF3 | 5-CF3 | |
| 13-137 | 2-OCH2(Ph-4-Cl)-4-CF3 | 5-CF3 | |
| 13-138 | 2-Oallyl-4-CF3 | 5-CF3 | |
| 13-139 | 2-Oallenyl-4-CF3 | 5-CF3 | |
| 13-140 | 2-Opropargyl-4-CF3 | 5-CF3 | |
| 13-141 | 2-O(CH2)2CH═CH2-4-CF3 | 5-CF3 | |
| 13-142 | 2-OCH2CH═CHMe-4-CF3 | 5-CF3 | |
| 13-143 | 2-OCH2CH═CMe2-4-CF3 | 5-CF3 | |
| 13-144 | 2-OCH2C(Me)═CH2-4-CF3 | 5-CF3 | |
| 13-145 | 2-OCH2CH═CHCl-4-CF3 | 5-CF3 | |
| 13-146 | 2-OAc-4-CF3 | 5-CF3 | |
| 13-147 | 2-OC(O)ᵗ Bu-4-CF3 | 5-CF3 | |
| 13-148 | 2-OSO2Me-4-CF3 | 5-CF3 | |
| 13-149 | 2-OSO2Et-4-CF3 | 5-CF3 | |
| 13-150 | 2-SO2ⁿ Pr-4-CF3 | 5-CF3 | |
| 13-151 | 2-OSO2ⁿ Bu-4-CF3 | 5-CF3 | |
| 13-152 | 2-OSO2NMe2-4-CF3 | 5-CF3 | |
| 13-153 | 2-OC(S)NMe2-4-CF3 | 5-CF3 | |
| 13-154 | 2-SC(O)NMe2-4-CF3 | 5-CF3 | |
| 13-155 | 2-NH2-4-CF3 | 5-CF3 | |
| 13-156 | 2-N(ⁿ Pr)2-4-CF3 | 5-CF3 | |
| 13-157 | 2-NHⁿ Pr-4-CF3 | 5-CF3 | |
| 13-158 | 2-N(Me)ⁿ Pr-4-CF3 | 5-CF3 | |
| 13-159 | 2-NHSO2Me-4-CF3 | 5-CF3 | |
| 13-160 | 2-NHSO2Et-4-CF3 | 5-CF3 | |
| 13-161 | 2-N(SO2ⁿ Bu)2-4-CF3 | 5-CF3 | |
| 13-162 | 2-Sⁿ Pr-4-CF3 | 5-CF3 | |
| 13-163 | 2-SCH2ᶜ Pr-4-CF3 | 5-CF3 | |
| 13-164 | 2-OP(O)(OEt)Sⁿ Pr-4-CF3 | 5-CF3 | |

TABLE 14

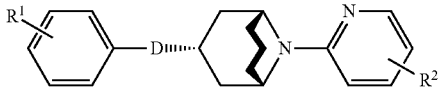

| Compound NO. | $R^1$ | $R^2$ | Physical constant [ ]: melting point ° C. |
|---|---|---|---|
| 14-1 | 4-OH | 5-CF3 | |
| 14-2 | 3-OH | 5-CF3 | |
| 14-3 | 2-OH | 5-CF3 | |
| 14-4 | 2-OH-4-CF3 | 5-CF3 | |

TABLE 14-continued

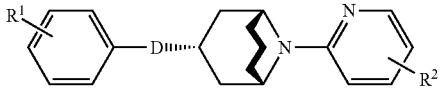

| Compound NO. | $R^1$ | $R^2$ | Physical constant [ ]: melting point ° C. |
|---|---|---|---|
| 14-5 | 4-F | 5-CF3 | |
| 14-6 | 3-F | 5-CF3 | |
| 14-7 | 2-F | 5-CF3 | |
| 14-8 | 2-F-4-CF3 | 5-CF3 | |
| 14-9 | 3-CF3-4-F | 5-CF3 | |
| 14-10 | 4-Cl | 5-CF3 | |
| 14-11 | 3-Cl | 5-CF3 | |
| 14-12 | 2-Cl | 5-CF3 | |
| 14-13 | 2-Cl-4-CF3 | 5-CF3 | |
| 14-14 | 3-CF3-4-CF3 | 5-CF3 | |
| 14-15 | 2,6-Cl2-4-CF3 | 5-CF3 | |
| 14-16 | 2-Br-4-CF3-6-Cl | 5-CF3 | |
| 14-17 | 2-Cl-6-O$^n$Pr-4-CF3 | 5-CF3 | |
| 14-18 | 4-Br | 5-CF3 | |
| 14-19 | 3-Br | 5-CF3 | |
| 14-20 | 2-Br | 5-CF3 | |
| 14-21 | 2-Br-4-CF3 | 5-CF3 | |
| 14-22 | 3-CF3-4-Br | 5-CF3 | |
| 14-23 | 4-I | 5-CF3 | |
| 14-24 | 3-I | 5-CF3 | |
| 14-25 | 2-I | 5-CF3 | |
| 14-26 | 2-I-4-CF3 | 5-CF3 | |
| 14-27 | 4-CN | 5-CF3 | |
| 14-28 | 3-CN | 5-CF3 | |
| 14-29 | 2-CN | 5-CF3 | |
| 14-30 | 2-CN-4-CF3 | 5-CF3 | |
| 14-31 | 4-NO2 | 5-CF3 | |
| 14-32 | 3-NO2 | 5-CF3 | |
| 14-33 | 2-NO2 | 5-CF3 | |
| 14-34 | 2-Cl-4-CF3-6-NO2 | 5-CF3 | |
| 14-35 | 2-NO2-4-CF3 | 5-CF3 | |
| 14-36 | 3-CF3-4-NO2 | 5-CF3 | |
| 14-37 | 2-CHO-4-CF3 | 5-CF3 | |
| 14-38 | 4-Me | 5-CF3 | |
| 14-39 | 3-Me | 5-CF3 | |
| 14-40 | 2-Me | 5-CF3 | |
| 14-41 | 2,4-Me2 | 5-CF3 | |
| 14-42 | 2-Me-3-CF3 | 5-CF3 | |
| 14-43 | 2-Me-4-CF3 | 5-CF3 | |
| 14-44 | 2-Me-4-OCF3 | 5-CF3 | |
| 14-45 | 2-Et-4-CF3 | 5-CF3 | |
| 14-46 | 2,4,6-Me3 | 5-CF3 | |
| 14-47 | 2-Me-4-F | 5-CF3 | |
| 14-48 | 2-Me-4-Cl | 5-CF3 | |
| 14-49 | 2-Et-4-Cl | 5-CF3 | |
| 14-50 | 2-$^n$Pr-4-Cl | 5-CF3 | |
| 14-51 | 2-$^n$Pr-4-CF3 | 5-CF3 | |
| 14-52 | 2-$^i$Pr-4-CF3 | 5-CF3 | |
| 14-53 | 2-CH2OMe-4-CF3 | 5-CF3 | |
| 14-54 | 2-CH2OEt-4-CF3 | 5-CF3 | |
| 14-55 | 2-CH(OH)Et-4-CF3 | 5-CF3 | |
| 14-56 | 2-CH2OH-4-CF3 | 5-CF3 | |
| 14-57 | 2-CH2OCH2OMe-4-CF3 | 5-CF3 | |
| 14-58 | 2-CH2OCH2OEt-4-CF3 | 5-CF3 | |
| 14-59 | 2-CH2OCH(Me)OMe-4-CF3 | 5-CF3 | |
| 14-60 | 2-CH2OCH(Me)OMe-4-CF3 | 5-CF3 | |
| 14-61 | 2-CH═CHMe-4-CF3 | 5-CF3 | |
| 14-62 | 2-allyl-4-CF3 | 5-CF3 | |
| 14-63 | 4-CF3 | 5-CF3 | |
| 14-64 | 3-CF3 | 5-CF3 | |
| 14-65 | 2-CF3 | 5-CF3 | |
| 14-66 | 3,4-(CF3)2 | 5-CF3 | |
| 14-67 | 3,5-(CF3)2 | 5-CF3 | |
| 14-68 | 2,4-(CF3)2 | 5-CF3 | |
| 14-69 | 2-CH2Cl-4-CF3 | 5-CF3 | |
| 14-70 | 2-CH(Cl)Et-4-CF3 | 5-CF3 | |
| 14-71 | 4-CF3 | 3-Cl-5-CF3 | |
| 14-72 | 4-CF3 | 4-Me-6-CF3 | |

TABLE 14-continued

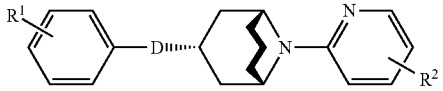

| Compound NO. | $R^1$ | $R^2$ | Physical constant [ ]: melting point ° C. |
|---|---|---|---|
| 14-73 | 4-OMe | 5-CF3 | |
| 14-74 | 3-OMe | 5-CF3 | |
| 14-75 | 2-OMe | 5-CF3 | |
| 14-76 | 2-OMe-4-CN | 5-CF3 | |
| 14-77 | 2-OMe-4-CF3 | 5-CF3 | |
| 14-78 | 2-OEt-4-CF3 | 5-CF3 | |
| 14-79 | 2-OEt-4-CF3 | 5-Cl | |
| 14-80 | 2-OEt-4-CF3 | 5-Br | |
| 14-81 | 2-O$^n$Pr-4-CN | 5-CF3 | |
| 14-82 | 2-O$^n$Pr-4-CF3 | 5-CF3 | vis |
| 14-83 | 2-O$^n$Pr-4-CF3 | 5-CF3 | |
| 14-84 | 2-O$^n$Pr-4-CF3 | 5-CF3 | |
| 14-85 | 2-O$^n$Pr-4-CF3 | 5-Cl | |
| 14-86 | 2-O$^n$Pr-4-CF3 | 5-Br | |
| 14-87 | 2-O$^n$Pr-4-CF3 | 5-NO2 | |
| 14-88 | 2-O$^n$Pr-4-CF3 | 5-NH2 | |
| 14-89 | 2-O$^n$Pr-4-CF3 | 5-Me | |
| 14-90 | 2-O$^n$Pr-4-CF3 | 5-NHSO2Me | |
| 14-91 | 2-O$^n$Pr-5-CF3 | 5-CF3 | |
| 14-92 | 2-O$^n$Pr-4-CF3 | 6-CF3 | |
| 14-93 | 2-O$^n$Pr-4-CF3 | 5-CN | |
| 14-94 | 2-O$^n$Pr-4-CF3 | 5-CF3-6-CN | |
| 14-95 | 2-Cl-6-O$^n$Pr-4-CF3 | 5-CF3 | |
| 14-96 | 2-O$^i$Pr-4-CF3 | 5-CF3 | |
| 14-97 | 2-O$^n$Bu-4-CF3 | 5-CF3 | |
| 14-98 | 2-O$^i$Bu-4-CF3 | 5-CF3 | |
| 14-99 | 2-O$^n$Hex-4-CF3 | 5-CF3 | |
| 14-100 | 2-O$^n$Pen-4-CF3 | 5-CF3 | |
| 14-101 | 2-OCH2CN-4-CF3 | 5-CF3 | |
| 14-102 | 2-OCH2OMe-4-CF3 | 5-CF3 | |
| 14-103 | 2-OCH2OEt-4-CF3 | 5-CF3 | |
| 14-104 | 2-OCH2O$^n$Pr-4-CF3 | 5-CF3 | |
| 14-105 | 2-OCH2$^c$Pr-4-CF3 | 5-CF3 | |
| 14-106 | 2-OCH2$^c$Pr-4-CF3 | 5-CO2Me | |
| 14-107 | 2-OCH2$^c$Pr-4-CHF2 | 5-CF3 | |
| 14-108 | 2-OCH2$^c$Pr-4-CHO | 5-CF3 | |
| 14-109 | 2-OCH2$^c$Pr-4-CF3 | 5-CN | |
| 14-110 | 2-OCH2$^c$Pr-4-CN | 5-CF3 | |
| 14-111 | 2-OCH2$^t$Bu-4-CF3 | 5-CF3 | |
| 14-112 | 2-O(CH2)2OMe-4-CF3 | 5-CF3 | |
| 14-113 | 2-O(CH2)2OMe-4-CF3 | 5-CN | |
| 14-114 | 2-O(CH2)2OCH2OMe-4-CF3 | 5-CF3 | |
| 14-115 | 2-O(CH2)2OH-4-CF3 | 5-CF3 | |
| 14-116 | 2-OCH2Ac-4-CF3 | 5-CF3 | |
| 14-117 | 2-OCH2CH(OH)Me-4-CF3 | 5-CF3 | |
| 14-118 | 2-OCH2CH(OMe)Me-4-CF3 | 5-CF3 | |
| 14-119 | 2-OCH2C(OH)Me2-4-CF3 | 5-CF3 | |
| 14-120 | 2-OCH2C(OMe)Me2-4-CF3 | 5-CF3 | |
| 14-121 | 2-OCH2C(Me2)CO2Me-4-CF3 | 5-CF3 | |
| 14-122 | 2-OCH2C(O)OMe-4-CF3 | 5-CF3 | |
| 14-123 | 2-OCH2C(O)OEt-4-CF3 | 5-CF3 | |
| 14-124 | 2-O(CH2)2OAc-4-CF3 | 5-CF3 | |
| 14-125 | 2-O(CH2)2NH2-4-CF3 | 5-CF3 | |
| 14-126 | 2-O(CH2)2NHAc-4-CF3 | 5-CF3 | |
| 14-127 | 2-O(CH2)2NMe2-4-CF3 | 5-CF3 | |
| 14-128 | 2-OCH2CH(Cl)Me-4-CF3 | 5-CF3 | |
| 14-129 | 2-OCH2CH═CMe2-4-CF3 | 5-CF3 | |
| 14-130 | 2-OCH2CH(Me)OMe-4-CF3 | 5-CF3 | |
| 14-131 | 4-OCF3 | 5-CF3 | |
| 14-132 | 3-OCF3 | 5-CF3 | |
| 14-133 | 2-OCF3 | 5-CF3 | |
| 14-134 | 4-OCF2Br | 5-CF3 | |
| 14-135 | 3-OCF2Br | 5-CF3 | |
| 14-136 | 2-OCF2Br | 5-CF3 | |
| 14-137 | 2-O(CH2)2Br-4-CF3 | 5-CF3 | |
| 14-138 | 2-O(CH2)2Cl-4-CF3 | 5-CF3 | |
| 14-139 | 2-O(CH2)2F-4-CF3 | 5-CF3 | |
| 14-140 | 2-OCH2(Ph-4-Cl)-4-CF3 | 5-CF3 | |

TABLE 14-continued

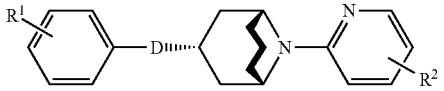

| Compound NO. | $R^1$ | $R^2$ | Physical constant [ ]: melting point ° C. |
|---|---|---|---|
| 14-141 | 2-Oallyl-4-CF3 | 5-CF3 | |
| 14-142 | 2-Oallenyl-4-CF3 | 5-CF3 | |
| 14-143 | 2-Opropargyl-4-CF3 | 5-CF3 | |
| 14-144 | 2-O(CH2)2CH═CH2-4-CF3 | 5-CF3 | |
| 14-145 | 2-OCH2CH═CHMe-4-CF3 | 5-CF3 | |
| 14-146 | 2-OCH2CH═CMe2-4-CF3 | 5-CF3 | |
| 14-147 | 2-OCH2C(Me)═CH2-4-CF3 | 5-CF3 | |
| 14-148 | 2-OCH2CH═CHCl-4-CF3 | 5-CF3 | |
| 14-149 | 2-OAc-4-CF3 | 5-CF3 | |
| 14-150 | 2-OC(O)ᵗBu-4-CF3 | 5-CF3 | |
| 14-151 | 2-OSO2Me-4-CF3 | 5-CF3 | |
| 14-152 | 2-OSO2Et-4-CF3 | 5-CF3 | |
| 14-153 | 2-SO2ⁿPr-4-CF3 | 5-CF3 | |
| 14-154 | 2-OSO2ⁿBu-4-CF3 | 5-CF3 | |
| 14-155 | 2-OSO2NMe2-4-CF3 | 5-CF3 | |
| 14-156 | 2-OC(S)NMe2-4-CF3 | 5-CF3 | |
| 14-157 | 2-SC(O)NMe2-4-CF3 | 5-CF3 | |
| 14-158 | 2-NH2-4-CF3 | 5-CF3 | |
| 14-159 | 2-N(ⁿPr)2-4-CF3 | 5-CF3 | |
| 14-160 | 2-NHⁿPr-4-CF3 | 5-CF3 | |
| 14-161 | 2-N(Me)ⁿPr-4-CF3 | 5-CF3 | |
| 14-162 | 2-NHSO2Me-4-CF3 | 5-CF3 | |
| 14-163 | 2-NHSO2Et-4-CF3 | 5-CF3 | |
| 14-164 | 2-N(SO2ⁿBu)2-4-CF3 | 5-CF3 | |
| 14-165 | 2-SiPr-4-CF3 | 5-CF3 | |
| 14-166 | 2-SCH2ᶜPr-4-CF3 | 5-CF3 | |
| 14-167 | 2-OP(O)(OEt)Sⁿ Pr-4-CF3 | 5-CF3 | |

NMR data $^1$H-NMR ($CDCl_3$)

Chemical Compound No. 1-169

δ 1.85-1.95 (m, 2H), 2.05-2.24 (m, 2H), 3.57-3.65 (m, 2H), 3.93-4.01 (m, 4H), 4.62-4.69 (m, 1H), 6.68 (d, 1H), 6.86 (d, 1H), 6.96 (a set of s and d, 2H), 7.63 (d, 1H), 8.40 (s, 1H)

Chemical Compound No. 1-80

δ 1.98-2.05 (m, 4H), 3.69-3.78 (m, 2H), 3.86-3.94 (m, 2H), 4.82-4.86 (m, 1H), 6.68 (d, 1H), 7.10 (d, 1H), 7.63 (d, 1H), 7.77 (d, 1H), 7.86 (s, 1H), 8.40 (s, 1H)

Chemical Compound No. 1-143

δ 1.89-2.06 (m, 4H), 3.61-3.70 (m, 2H), 3.91-4.00 (m, 2H), 4.63-4.67 (m, 1H), 5.42 (d, 2H), 6.68 (d, 1H), 6.85 (t, 1H), 7.03 (d, 1H), 7.30 (d, 1H), 7.36 (s, 1H), 7.62 (d, 1H), 8.39 (s, 1H)

Chemical Compound No. 1-163

δ 1.86-2.09 (m, 4H), 2.53 (t, 1H), 3.57-3.66 (m, 2H), 3.94-4.03 (m, 2H), 4.60-4.67 (m, 1H), 4.77 (d, 1H), 6.68 (d, 1H), 7.02 (d, 1H), 7.24-7.29 (m, 2H), 7.62 (d, 1H), 8.39 (s, 1H)

Chemical Compound No. 1-172

δ 1.29 (t, 3H), 1.83-1.94 (m, 2H), 2.04-2.14 (m, 2H), 3.15-3.24 (m, 2H), 3.53-3.62 (m, 2H), 3.95-4.01 (m, 2H), 4.23 (brs, 1H), 4.61-4.67 (m, 1H), 6.68 (d, 1H), 6.77-6.89 (m, 3H), 7.63 (d, 1H), 8.40 (s, 1H)

Chemical Compound No. 1-69

δ 1.88-2.09 (m, 4H), 3.41 (s, 3H), 3.66-3.74 (m, 2H), 3.84-3.93 (m, 2H), 4.66 (2, 2H), 4.68-4.75 (m, 3H), 6.68 (d, 1H), 6.95 (d, 1H), 7.52 (d, 1H), 7.63 (d, 1H), 7.71 (s, 1H), 8.40 (s, 1H)

Chemical Compound No. 1-173

δ 1.00 (t, 3H), 1.67 (q, 2H), 1.86-1.93 (m, 2H), 2.06-2.12 (m, 2H), 3.07-3.15 (m, 2H), 3.55-3.63 (m, 2H), 3.93-4.01 (m, 2H), 4.32 (brs, 1H), 4.64-4.66 (m, 1H), 6.68 (d, 1H), 6.77-6.90 (m, 3H), 7.63 (d, 1H), 8.40 (s, 1H)

Chemical Compound No. 1-140

δ 1.87-2.06 (m, 4H), 3.60-3.68 (m, 2H), 3.84 (t, 2H), 3.86-3.99 (m, 2H), 4.30 (t, 2H), 4.63-4.68 (m, 1H), 6.68 (d, 1H), 7.03 (d, 1H), 7.14 (s, 1H), 7.22 (d, 1H), 7.62 (d, 1H), 8.40 (s, 1H)

Chemical Compound No. 1-74

δ 1.91-2.08 (m, 4H), 3.42 (d, 2H), 3.74-3.86 (m, 4H), 4.69-4.71 (m, 1H), 5.04-5.10 (m, 2H), 5.91-6.00 (m, 1H), 6.68 (d, 1H), 6.92 (d, 1H), 7.42-7.47 (m, 2H), 7.64 (d, 1H), 8.41 (s, 1H)

Chemical Compound No. 1-67

δ 0.97 (t, 3H), 1.74-1.95 (m, 4H), 2.04-2.14 (m, 3H), 3.66-3.73 (m, 2H), 3.85-3.94 (m, 2H), 4.71-4.74 (m, 1H), 4.93-4.96 (m, 1H), 6.69 (d, 1H), 6.94 (d, 1H), 7.49 (d, 1H), 7.64 (d, 1H), 7.69 (s, 1H), 8.40 (s, 1H)

Chemical Compound No. 2-57

δ 2.00-2.31 (m, 8H), 3.44 (s, 3H), 4.58-4.64 (m, 3H), 4.70 (s, 2H), 4.79 (s, 2H), 6.57 (d, 1H), 6.72 (d, 1H), 7.50 (d, 1H), 7.63 (d, 1H), 7.72 (s, 1H), 8.41 (s, 1H)

Chemical Compound No. 2-58

δ 1.25 (t, 3H), 2.00-2.29 (m, 8H), 3.68 (q, 2H), 4.58-4.64 (m, 3H), 4.71 (s, 2H), 4.84 (s, 2H), 6.57 (d, 1H), 6.72 (d, 1H), 7.49 (d, 1H), 7.63 (d, 1H), 7.72 (s, 1H), 8.41 (s, 1H)

Chemical Compound No. 2-78

δ 1.46 (t, 3H), 2.00-2.21 (m, 6H), 2.44-2.46 (m, 2H), 4.10 (q, 2H), 4.55 (brs, 2H), 4.61 (brs, 1H), 6.56 (d, 1H), 6.78 (d, 1H), 7.08 (d, 1H), 7.15 (d, 1H), 7.60 (d, 1H), 8.40 (s, 1H)

Chemical Compound No. 2-141

δ 2.01-2.31 (m, 6H), 2.40-2.47 (m, 2H), 4.56-4.63 (m, 5H), 5.32 (d, 1H), 5.46 (d, 1H), 6.01-6.14 (m, 1H), 6.55 (d, 1H), 6.78 (d, 1H), 7.11 (s, 1H), 7.17 (d, 1H), 7.61 (d, 1H), 8.40 (s, 1H)

Chemical Compound No. 3-62

δ 1.78-1.93 (m, 4H), 2.14-2.19 (m, 4H), 3.28 (d, 2H), 4.69 (brs, 2H), 4.83-4.90 (m, 1H), 4.95-5.02 (m, 2H), 5.77-5.91 (m, 1H), 6.59 (d, 1H), 6.92 (d, 1H), 7.35 (s, 1H), 7.41 (d, 1H), 7.65 (d, 1H), 8.43 (s, 1H)

Chemical Compound No. 2-148

δ 2.00-2.23 (m, 6H), 2.35-2.44 (m, 2H), 4.56-4.61 (m, 4H), 4.82 (q, 1H), 6.06-6.64 (m, 2H), 6.56 (d, 1H), 6.78 (d, 1H), 7.12 (d, 1H), 7.20 (d, 1H), 7.61 (d, 1H), 8.40 (s, 1H)

Chemical Compound No. 2-144

δ 1.99-2.20 (m, 6H), 2.40-2.47 (m, 2H), 2.57-2.64 (m, 2H), 4.07 (t, 2H), 4.55-4.60 (m, 3H), 5.14 (dd, 2H), 5.86-5.99 (m, 1H), 6.56 (d, 1H), 6.77 (d, 1H), 7.08 (s, 1H), 7.12 (d, 1H), 7.60 (dd, 1H), 8.40 (s, 1H)

Chemical Compound No. 2-115

δ 2.00-2.30 (m, 7H), 2.35-2.44 (m, 2H), 3.97-4.03 (m, 2H), 4.16 (t, 2H), 4.52-4.65 (brs, plus t, 3H), 6.56 (d, 1H), 6.78 (d, 1H), 7.14 (s, 1H), 7.19 (d, 1H), 7.62 (dd, 1H), 8.40 (s, 1H)

Chemical Compound No. 2-153

δ 1.05 (t, 3H), 1.76-1.84 (m, 2H), 2.03 (d, 2H), 2.17-2.20 (m, 2H), 2.36-2.40 (m, 4H), 3.36 (t, 2H), 4.61 (brs, 2H), 4.72 (t, 1H), 6.58 (d, 1H), 6.92 (d, 1H), 7.64 (d, 1H), 7.80 (d, 1H), 8.28 (s, 1H), 8.42 (s, 1H)

Chemical Compound No. 2-112

δ 2.00-2.21 (m, 6H), 2.39-2.47 (m, 2H), 3.44 (s, 3H), 3.79 (t, 2H), 4.16 (t, 2H), 4.56 (brs, 2H), 4.62 (brs, 1H), 6.55 (d, 1H), 6.78 (d, 1H), 7.12 (s, 1H), 7.18 (d, 1H), 7.61 (d, 1H), 8.40 (s, 1H)

Chemical Compound No. 2-161

δ 0.89 (t, 3H), 1.47-1.63 (m, 2H), 2.07-2.11 (m, 4H), 2.19-2.27 (m, 2H), 2.38-2.45 (m, 2H), 2.80 (s, 3H), 3.08 (t, 2H), 4.56 (brs, 2H), 4.60 (t, 1H), 6.56 (d, 1H), 6.72 (d, 1H), 7.15 (s, 1H), 7.17 (d, 1H), 7.60 (dd, 1H), 8.40 (s, 1H)

Chemical Compound No. 2-143

δ 2.00-2.24 (m, 6H), 2.38-2.45 (m, 2H), 2.54-2.56 (m, 1H), 4.56-4.63 (brs, plus t, 3H), 4.77 (d, 2H), 6.56 (d, 1H), 6.79 (d, 1H), 7.22 (s, 1H), 7.25 (d, 1H), 7.61 (dd, 1H), 8.40 (s, 1H)

Chemical Compound No. 2-138

δ 2.05-2.26 (m, 6H), 2.41-2.48 (m, 2H), 3.87 (t, 2H), 4.31 (t, 2H), 4.61-4.64 (brs, plus t, 3H), 6.56 (d, 1H), 6.80 (d, 1H), 7.09 (s, 1H), 7.20 (d, 1H), 7.60 (dd, 1H), 8.40 (s, 1H)

Chemical Compound No. 2-101

δ 2.11-2.40 (m, 8H), 4.58 (brs, 2H), 4.65 (t, 1H), 4.86 (s, 2H), 6.57 (d, 1H), 6.73 (d, 1H), 7.27 (s, 1H), 7.37 (d, 1H), 7.62 (dd, 1H), 8.41 (s, 1H)

Chemical Compound No. 5-175

δ 1.57-1.64 (m, 2H), 1.75 (d, 3H), 2.03-2.06 (m, 2H), 2.58 (brs, 2H), 3.08 (d, 2H), 4.18 (dd, 2H), 4.51 (d, 2H), 4.62-4.67 (m, 1H), 5.66-5.90 (m, 2H), 6.61 (d, 1H), 7.01 (d, 1H), 7.13 (s, 1H), 7.20 (d, 1H), 7.62 (dd, 1H), 8.39 (s, 1H)

Chemical Compound No. 5-89

δ 1.57-1.69 (m, 2H), 2.03-2.07 (m, 2H), 2.59 (brs, 2H), 3.10 (d, 2H), 3.89 (s, 3H), 4.18 (d, 2H), 4.62 (s, 1H), 6.61 (d, 1H), 7.01 (d, 1H), 7.11 (s, 1H), 7.18 (d, 1H), 7.62 (dd, 1H), 8.39 (s, 1H)

Chemical Compound No. 5-90

δ 1.45 (t, 3H), 1.57-1.68 (m, 2H), 2.03-2.07 (m, 2H), 2.58 (brs, 2H), 3.08 (d, 2H), 4.06-4.20 (m, 4H), 4.62 (s, 1H), 6.60 (d, 1H), 7.01 (d, 1H), 7.11 (s, 1H), 7.20 (d, 1H), 7.62 (dd, 1H), 8.39 (s, 1H)

Chemical Compound No. 5-176

δ 1.55-1.63 (m, 2H), 2.02-2.04 (m, 2H), 2.55-2.62 (m, 4H), 3.08 (d, 2H), 4.07 (t, 2H), 4.15 (dd, 2H), 4.63 (s, 1H), 5.16 (dd, 2H), 5.84-5.97 (m, 1H), 6.60 (d, 1H), 7.01 (d, 1H), 7.12 (s, 1H), 7.18 (d, 1H), 7.62 (dd, 1H), 8.39 (s, 1H)

Chemical Compound No. 5-139

δ 1.53-1.63 (m, 2H), 1.76 (d, 6H), 2.02-2.07 (m, 2H), 2.58 (brs, 2H), 3.08 (d, 2H), 4.16 (dd, 2H), 4.57 (d, 2H), 4.62 (s, 1H), 5.46 (t, 1H), 6.60 (d, 1H), 7.01 (d, 1H), 7.13 (s, 1H), 7.18 (d, 1H), 7.62 (dd, 1H), 8.39 (s, 1H)

Chemical Compound No. 5-123

δ 1.60-1.67 (m, 2H), 2.00-2.09 (m, 2H), 2.29 (brs, 1H), 2.60 (brs, 2H), 3.11 (d, 2H), 3.94 (brs, 2H), 4.08-4.22 (m, 4H), 4.62 (s, 1H), 6.61 (d, 1H), 7.04 (d, 1H), 7.19 (s, 1H), 7.20-7.30 (m, 1H), 7.62 (dd, 1H), 8.39 (s, 1H)

Chemical Compound No. 5-147

δ 1.58-1.65 (m, 2H), 2.04-2.06 (m, 2H), 2.58 (brs, 2H), 3.10 (d, 2H), 3.84 (t, 2H), 4.16-4.30 (m, 4H), 4.67 (s, 1H), 6.61 (d, 1H), 7.05 (d, 1H), 7.16 (s, 1H), 7.24-7.26 (m, 1H), 7.62 (dd, 1H), 8.40 (s, 1H)

Chemical Compound No. 5-124

δ 1.57-1.69 (m, 2H), 2.02-2.05 (m, 2H), 2.57 (brs, 2H), 3.09 (d, 2H), 3.43 (s, 3H), 3.77 (t, 2H), 4.13-4.20 (m, 4H), 4.65 (s, 1H), 6.60 (d, 1H), 7.02 (d, 1H), 7.16 (s, 1H), 7.17-7.25 (m, 1H), 7.62 (dd, 1H), 8.39 (s, 1H)

Chemical Compound No. 5-132

δ 1.57-1.66 (m, 2H), 2.00-2.06 (m, 2H), 2.59 (brs, 2H), 3.11 (d, 2H), 3.79 (s, 3H), 4.12-4.22 (m, 2H), 4.65-4.69 (m, 3H), 6.60 (d, 1H), 7.05 (d, 1H), 7.13 (s, 1H), 7.21-7.28 (m, 1H), 7.62 (dd, 1H), 8.39 (s, 1H)

Chemical Compound 5-134

δ 1.58-1.64 (m, 2H), 1.95-2.13 (m, 2H), 2.06 (s, 3H), 2.58 (brs, 2H), 3.09 (d, 2H), 4.16-4.25 (m, 4H), 4.44 (t, 2H), 4.63 (s, 1H), 6.61 (d, 1H), 7.04 (d, 1H), 7.16 (s, 1H), 7.22-7.29 (m, 1H), 7.62 (dd, 1H), 8.39 (s, 1H)

Chemical Compound No. 5-133

δ 1.31 (t, 3H), 1.59-1.65 (m, 2H), 2.04-2.07 (m, 2H), 2.60 (brs, 2H), 3.10 (d, 2H), 4.14-4.30 (m, 4H), 4.68 (s, 3H), 6.61 (d, 1H), 7.05 (d, 1H), 7.13 (s, 1H), 7.25-7.28 (m, 1H), 7.62 (dd, 1H), 8.39 (s, 1H)

Chemical Compound No. 5-163

δ 1.15 (t, 3H), 1.62-1.69 (m, 2H), 1.99-2.12 (m, 4H), 2.64 (brs, 2H), 3.14 (d, 2H), 3.32 (t, 2H), 4.23 (dd, 2H), 4.64 (s, 1H), 6.62 (d, 1H), 7.14 (d, 1H), 7.53 (d, 1H), 7.54 (s, 1H), 7.64 (dd, 1H), 8.41 (s, 1H)

Chemical Compound 5-126

δ 1.63-1.68 (m, 2H), 1.93-2.04 (m, 2H), 2.35 (s, 3H), 2.61 (brs, 2H), 3.12 (d, 2H), 4.21 (dd, 2H), 4.58 (s, 2H), 4.66 (s, 1H), 6.62 (d, 1H), 7.05 (s-like, 2H), 7.26 (s-like, 1H), 7.63 (dd, 8.40 (s, 1H)

Chemical Compound 5-127

δ 1.27 (d, 3H), 1.59-1.67 (m, 2H), 2.00-2.04 (m, 2H), 2.61 (brs, 3H), 3.12 (d, 2H), 3.81 (t, 1H), 4.04 (dd, 1H), 4.08-4.22 (m, 3H), 4.62 (s, 1H), 6.61 (d, 1H), 7.03 (d, 1H), 7.12 (s, 1H), 7.20 (s-like, 1H), 7.63 (dd, 1H), 8.40 (s, 1H)

Chemical Compound 5-128

δ 1.28 (d, 3H), 1.57-1.64 (m, 2H), 2.01-2.04 (m, 2H), 2.58 (brs, 2H), 3.09 (d, 2H), 3.46 (s, 3H), 3.69-3.80 (m, 1H), 3.91-4.04 (m, 1H), 4.18 (brd, 2H), 4.64 (s, 1H), 6.61 (d, 1H), 7.01 (d, 1H), 7.12 (s, 1H), 7.16 (d, 1H), 7.62 (dd, 1H), 8.39 (s, 1H)

Chemical Compound 5-129

δ 1.28 (s, 6H), 1.56-1.67 (m, 2H), 1.99-2.04 (m, 2H), 2.46 (s, 1H), 2.60 (brs, 2H), 3.11 (d, 2H), 3.85 (s, 2H), 4.20 (dd, 2H), 4.62 (s, 1H), 6.62 (d, 1H), 7.02 (d, 1H), 7.14 (s, 1H), 7.18 (s-like, 1H), 7.63 (dd, 1H), 8.40 (s, 1H)

Chemical Compound 5-130

δ 1.33 (s, 6H), 1.58-1.64 (m, 2H), 2.02-2.05 (m, 2H), 2.58 (brs, 2H), 3.10 (d, 2H), 3.31 (s, 3H), 3.87 (s, 2H), 4.18 (dd, 2H), 4.65 (s, 1H), 6.61 (d, 1H), 7.01 (d, 1H), 7.13 (s, 1H), 7.18 (d, 1H), 7.62 (dd, 1H), 8.40 (s, 1H)

Chemical Compound 5-114

δ 1.37 (d, 3H), 1.57-1.64 (m, 2H), 1.77-1.90 (m, 1H), 2.03-2.05 (m, 2H), 2.04 (s, 3H), 2.57 (brs, 2H), 3.09 (d, 2H), 3.57 (t, 1H), 4.03-4.20 (m, 2H), 4.62 (s, 1H), 5.25-5.35 (m, 1H), 6.61 (d, 1H), 7.02 (d, 1H), 7.13 (s, 1H), 7.22 (d, 1H), 7.62 (dd, 1H), 8.39 (s, 1H)

Chemical Compound 5-138

δ 1.58-1.70 (m plus d, 5H), 2.02-2.05 (m, 2H), 2.58 (brs, 2H), 3.10 (d, 2H), 4.03-4.21 (m, 4H), 4.28-4.38 (m, 1H), 4.66 (s, 1H), 6.61 (d, 1H), 7.04 (d, 1H), 7.13 (s, 1H), 7.17 (d, 1H), 7.62 (dd, 1H), 8.40 (s, 1H)

Chemical Compound 5-98

δ 1.06 (t, 3H), 1.80-1.92 (m, 2H), 2.01-2.04 (m, 4H), 2.57 (brs, 2H), 2.93 (d, 2H), 3.97 (t, 2H), 4.18 (dd, 2H), 4.57 (s, 1H), 6.85 (d, 1H), 7.01 (d, 1H), 7.11 (s, 1H), 7.17 (d, 1H), 7.35 (dd, 1H), 8.40 (s, 1H)

Chemical Compound 5-202

δ 1.41 (t, 1H), 1.59-1.66 (m, 2H), 1.77 (t, 1H), 2.05-2.22 (m, 3H), 2.60 (brs, 2H), 3.11 (dd, 2H), 4.05 (t, 1H), 4.19 (dd, 2H), 4.29 (dd, 1H), 4.66 (s, 1H), 6.61 (d, 1H), 7.05 (d, 1H), 7.14 (s, 1H), 7.23 (d-like, 1H), 7.62 (dd, 1H), 8.39 (s, 1H)

Chemical Compound 6-82

δ 0.92 (t, 3H), 1.42-1.47 (m, 1H), 1.57-1.80 (m, 5H), 1.98-2.04 (m, 2H), 2.35 (brs, 2H), 3.55 (dd, 2H), 3.93 (t, 2H), 4.08 (d, 2H), 4.48 (t, 1H), 6.62 (d, 1H), 6.99 (d, 1H), 7.09 (s, 1H), 7.12 (d, 1H), 7.62 (dd, 1H), 8.42 (s, 1H)

Chemical Compound 7-103

δ 0.35-0.40 (m, 2H), 0.61-0.67 (m, 2H), 1.24-1.36 (m, 1H), 1.45-1.51 (m, 1H), 1.57-1.63 (m, 2H), 1.67-1.88 (m, 1H), 2.18-2.31 (m, 4H), 3.25 (d, 2H), 3.91 (d, 2H), 4.46 (d, 2H), 4.62 (s, 1H), 6.66 (d, 1H), 7.02 (d, 1H), 7.12 (s, 1H), 7.18 (d, 1H), 7.63 (dd, 1H), 8.42 (s, 1H)

Chemical Compound 2-130

δ 1.31 (d, 3H), 2.00-2.22 (m, 6H), 2.40-2.50 (m, 2H), 3.45 (s, 3H), 3.72-3.81 (m, 1H), 3.88-3.93 (m, 1H), 4.01-4.06 (m,

1H), 4.56-4.61 (m+brs, 3H), 6.56 (d, 1H), 6.77 (d, 1H), 7.10 (s, 1H), 7.17 (d, 1H), 7.61 (dd, 1H), 8.40 (s, 1H)

Chemical Compound 1-98

δ 1.05 (t, 3H), 1.13 (d, 3H), 1.71-1.91 (m, 4H), 2.05-2.15 (m, 2H), 3.00 (dd, 1H), 3.22-3.30 (m, 1H), 3.98 (t, 2H), 4.10-4.24 (m, 2H), 6.67 (d, 1H), 6.98 (d, 1H), 7.10 (d, 1H), 7.16 (d, 1H), 7.61 (dd, 1H), 8.39 (s, 1H)

Chemical Compound 5-118

δ 0.36 (q, 2H), 0.63 (q, 2H), 1.19-1.31 (m, 1H), 1.55-1.63 (m, 2H), 2.07 (brt, 2H), 2.57 (brs, 2H), 3.07 (d, 2H), 3.87 (d, 2H), 4.17 (dd, 2H), 4.63 (s, 1H), 6.59 (d+q, 2H), 6.99-7.03 (m, 3H), 7.61 (dd, 1H), 8.39 (s, 1H)

Chemical Compound 6-4

δ 1.40-1.56 (m, 1H), 1.75-1.86 (m, 3H), 1.91-2.05 (m, 2H), 2.61 (brs, 2H), 3.40 (dd, 2H), 4.16 (d, 2H), 4.56 (t, 1H), 5.81 (s, 1H), 6.62 (d, 1H), 6.91 (d, 1H), 7.13 (d, 1H), 7.19 (s, 1H), 7.63 (dd, 1H), 8.42 (s, 1H)

Chemical Compound 2-90

δ 1.08 (t, 3H), 1.81-1.93 (m, 2H), 1.97-2.09 (m, 4H), 2.16-2.24 (m, 2H), 2.40-2.46 (m, 2H), 2.98 (s, 3H), 3.97 (t, 2H), 4.48 (brs, 2H), 4.59 (t, 1H), 6.57 (d, 1H), 6.77 (d, 1H), 7.07 (s, 1H), 7.14 (d, 1H), 7.51 (dd, 1H), 8.07 (s, 1H)

Chemical Compound 2-167

δ 0.98 (t, 3H), 1.42 (t, 3H), 1.67-1.75 (m, 2H), 2.01-2.23 (m, 6H), 2.42 (d, 2H), 2.87-2.97 (m, 2H), 4.28-4.35 (m, 2H), 4.57 (brs, 2H), 4.62 (t, 1H), 6.56 (d, 1H), 6.84 (d, 1H), 7.39 (d, 1H), 7.62 (dd, 1H), 7.70 (s, 1H), 8.41 (s, 1H)

Chemical Compound 1-95

δ 1.02-1.16 (m, 8H), 1.26 (s, 3H), 1.79-1.94 (m, 4H), 3.30 (m, 1H), 3.80 (d, 1H), 3.90-3.99 (m, 2H), 4.08 (q, 2H), 4.13-4.38 (m, 2H), 4.77 (brs, 1H), 6.71 (d, 1H), 7.06 (s, 1H), 7.09 (d, 1H), 7.16 (d, 1H), 7.60 (dd, 1H), 8.37 (s, 1H)

Chemical Compound 5-93

δ 1.06 (t, 3H), 1.63-1.69 (m, 2H), 1.74-1.88 (m, 2H), 2.00-2.02 (m, 2H), 2.55 (brs, 2H), 3.01 (d, 2H), 4.00 (t, 2H), 4.07-4.16 (m, 2H), 4.38 (s, 2H), 4.59 (s, 1H), 6.59 (d, 1H), 7.01 (d, 1H), 7.10 (s, 1H), 7.13 (d, 1H), 7.50 (dd, 1H), 8.12 (s, 1H)

Chemical Compound 2-81

δ 1.09 (t, 3H), 1.84-2.21 (m, 8H), 2.40-2.43 (m, 2H), 3.97 (t, 2H), 4.56-4.62 (brm, 3H), 6.56 (d, 1H), 6.73 (d, 1H), 7.08 (s, 1H), 7.23 (m, 1H), 7.62 (dd, 1H), 8.41 (s, 1H)

Chemical Compound 2-67

δ 2.00-2.21 (m, 4H), 2.28-2.35 (m, 4H), 4.59 (brs, 2H), 4.66 (t, 1H), 6.58 (d, 1H), 6.88 (d, 1H), 7.63 (dd, 1H), 7.74 (d, 1H), 7.86 (s, 1H), 8.41 (s, 1H)

Chemical Compound 5-99

δ 1.06 (t, 3H), 1.58-1.63 (m, 2H), 1.65-1.89 (m, 2H), 2.02-2.04 (m, 2H), 2.57 (brs, 2H), 3.06 (d, 2H), 4.00 (t, 2H), 4.16 (d, 2H), 4.62 (s, 1H), 6.57 (t, 1H), 6.63 (d, 1H), 7.01 (d, 1H), 7.11 (s, 1H), 7.17 (d, 1H), 7.60 (dd, 1H), 8.24 (s, 1H)

Chemical Compound 5-103

δ 1.04 (t, 3H), 1.57-1.64 (m, 2H), 1.77-1.88 (m, 2H), 1.96-2.04 (m, 2H), 2.58 (brs, 2H), 3.13 (d, 2H), 3.91 (t, 2H), 4.17 (d, 2H), 4.52 (s, 1H), 6.61 (d, 1H), 6.63 (d, 1H), 6.75 (s-like, 2H), 7.63 (dd, 1H), 8.40 (s, 1H)

Chemical Compound 5-101

δ 1.06 (t, 3H), 1.47-1.67 (m, 3H), 1.79-1.91 (m, 2H), 2.01-2.04 (m, 2H), 2.56 (brs, 2H), 3.03 (d, 2H), 3.97 (t, 2H), 4.09 (dd, 2H), 4.57 (brs, 2H), 4.60 (s, 1H), 6.61 (d, 1H), 7.01 (d, 1H), 7.11 (s, 1H), 7.17 (d, 1H), 7.52 (dd, 1H), 8.14 (s, 1H)

Chemical Compound 5-4

δ 1.69 (m, 2H), 1.97 (m, 2H), 2.65 (bs, 2H), 3.14 (d, 2H), 4.24 (dd, 2H), 4.65 (s, 1H), 5.65 (s, 1H), 6.63 (d, 1H), 6.99 (d, 1H), 7.14 (d, 1H), 7.20 (s, 1H), 7.65 (d, 1H), 8.40 (s, 1H)

Chemical Compound 5-177

δ 1.62 (m, 2H), 2.04 (m, 2H), 2.53 (s, 1H), 2.60 (bs, 2H), 3.10 (d, 2H), 4.19 (dd, 2H), 4.63 (s, 1H), 4.77 (s, 2H), 6.61 (d, 1H), 7.04 (d, 1H), 7.27 (m, 2H), 7.62 (d, 1H), 8.40 (s, 1H)

Chemical Compound 5-75

δ 1.63 (m, 2H), 1.98 (m, 2H), 2.61 (bs, 2H), 3.15 (d, 2H), 3.37 (d, 1H), 3.68 (d, 1H), 4.20 (dd, 2H), 4.61 (s, 1H), 5.07 (d, 2H), 5.93 (m, 1H), 6.63 (d, 1H), 6.97 (d, 1H), 7.41 (s, 1H), 7.45 (d, 1H), 7.63 (d, 1H), 8.41 (s, 1H)

Chemical Compound 5-69

δ 1.65 (m, 2H), 1.94 (m, 2H), 2.61 (bs, 2H), 3.15 (d, 2H), 3.43 (s, 3H), 4.21 (dd, 2H), 4.63 (m, 3H), 4.77 (s, 2H), 6.62 (d, 1H), 7.00 (d, 1H), 7.53 (d, 1H), 7.65 (d, 1H), 7.70 (d, 1H), 8.40 (s, 1H)

Chemical Compound 5-131

δ 1.35 (s, 6H), 1.58 (m, 2H), 2.02 (m, 2H), 2.55 (bs, 2H), 3.07 (d, 2H), 3.68 (s, 3H), 4.02 (s, 2H), 4.15 (dd, 2H), 4.58 (s, 1H), 6.61 (d, 1H), 6.99 (d, 1H), 7.10 (s, 1H), 7.19 (d, 1H), 7.62 (d, 1H), 8.39 (s, 1H)

Chemical Compound 5-137

δ 1.62 (m, 2H), 2.03 (m, 2H), 2.36 (s, 6H), 2.58 (bs, 2H), 2.77 (t, 2H), 3.09 (d, 2H), 4.14 (m, 4H), 4.63 (s, 1H), 6.60 (d, 1H), 7.00 (d, 1H), 7.14 (s, 1H), 7.20 (d, 1H), 7.63 (d, 1H), 8.40 (s, 1H)

Chemical Compound 5-136

δ 1.65 (m, 2H), 2.00 (m, 5H), 2.60 (bs, 2H), 3.11 (d, 2H), 3.67 (q, 2H), 4.10 (t, 2H), 4.21 (dd, 2H), 4.62 (s, 1H), 5.94 (bs, 1H), 6.62 (d, 1H), 7.05 (d, 1H), 7.15 (s, 1H), 7.23 (d, 1H), 7.63 (d, 1H), 8.40 (s, 1H)

Chemical Compound 5-73

δ 1.41 (d, 3H), 1.65 (d, 2H), 1.97 (m, 2H), 2.62 (bs, 1H), 3.15 (d, 2H), 3.37 (s, 3H), 4.20 (m, 2H), 4.62 (m, 3H), 5.08 (q, 1H), 6.63 (d, 1H), 6.97 (d, 1H), 7.49 (d, 1H), 7.63 (d, 1H), 7.73 (s, 1H), 8.40 (s, 1H)

Chemical Compound 5-229

$^1$H NMR ($CDCl_3$) δ 1.22 (t, 3H), 1.40 (d, 3H), 1.60-1.66 (m, 2H), 1.95-1.99 (m, 2H), 2.61 (brs, 2H), 3.14 (d, 2H), 3.49-3.59 (m, 1H), 3.63-3.73 (m, 1H), 4.22 (dd, 2H), 4.50-4.66 (m, 3H), 4.86 (q, 1H), 6.62 (d, 1H), 6.98 (d, 1H), 7.51 (dd, 1H), 7.63 (dd, 1H), 7.71 (s, 1H), 8.40

Chemical compound 9-94

$^1$H NMR ($CDCl_3$) δ 1.09 (t, 3H), 1.63-1.75 (m, 2H), 1.84-195 (m, 2H), 2.04-2.10 (m, 2H), 3.19-3.28 (m, 2H), 3.54-3.62 (m, 1H), 4.03 (t, 2H), 4.21-4.28 (m, 2H), 6.64 (d, 1H), 7.04 (s, 1H), 7.16 (d, 1H), 7.40 (d, 1H), 7.61 (dd, 1H), 8.38 (s, 1H)

Chemical Compound 11-93

$^1$H NMR ($CDCl_3$) δ 1.08 (t, 3H), 1.79-1.95 (m, 8H), 2.10-2.17 (m, 2H), 3.85-3.96 (m, 1H), 4.01 (t, 2H), 4.61 (brs, 2H), 6.52 (d, 1H), 7.01 (s, 1H), 7.12 (dd, 1H), 7.35 (d, 1H), 7.60 (dd, 1H), 8.39 (s, 1H)

Chemical Compound 5-246

$^1$HNMR ($CDCl_3$) δ 1.63-1.68 (m, 2H), 1.96-2.03 (m, 2H), 2.62 (brs, 2H), 2.90 (t, 2H), 3.15 (d, 2H), 3.35 (s, 3H), 3.57 (t, 2H), 4.22 (dd, 2H), 4.60 (s, 1H), 6.63 (d, 1H), 6.96 (d, 1H), 7.44 (s, 1H), 7.45 (d, 1H), 7.63 (dd, 1H), 8.40 (s, 1H)

Chemical Compound 5-247 (trans/cis=59/41)

Tans Form $^1$HNMR ($CDCl_3$) δ 1.56-1.68 (m, 2H), 1.98-2.06 (m, 2H), 2.62 (brs, 2H), 3.13 (d, 2H), 3.70 (s, 3H), 4.20 (d, 2H), 4.63 (s, 1H), 5.95 (d, 1H), 6.61 (d, 1H), 6.98 (d, 1H), 7.16 (d, 1H), 7.36 (d, 1H), 7.49 (s, 1H), 7.64 (dd, 1H), 8.40 (s, 1H)

C is form $^1$H NMR ($CDCl_3$) δ 1.56-1.68 (m, 2H), 1.98-2.06 (m, 2H), 2.62 (brs, 2H), 3.13 (d, 2H), 3.81 (s, 3H), 4.20 (d, 2H), 4.60 (s, 1H), 5.56 (d, 1H), 6.23 (d, 1H), 6.61 (d, 1H), 6.95 (d, 1H), 7.36 (d, 1H), 7.64 (dd, 1H), 8.31 (s, 1H), 8.40 (s, 1H)

Chemical Compound 2-203

$^1$H NMR ($CDCl_3$) δ 1.36 (t, 3H), 1.99-2.35 (m, 8H), 4.27 (q, 2H), 4.59 (brs, 2H), 4.65 (t, 1H), 6.57 (d, 1H), 6.76 (d, 1H), 7.54 (dd, 1H), 7.63 (dd, 1H), 8.11 (s, 1H), 8.41 (s, 1H), 8.43 (s, 1H)

Chemical Compound 2-224

$^1$H NMR ($CDCl_3$) δ 1.36 (t, 3H), 1.83 (s, 3H), 1.92-2.07 (m, 4H), 2.15-2.29 (m, 4H), 4.26 (q, 2H), 4.53 (brs, 2H), 4.60 (t, 1H), 6.54 (d, 1H), 6.76 (d, 1H), 7.04 (s, 1H), 7.24 (d, 1H), 7.61 (dd, 1H), 8.40 (s, 1H)

Chemical Compound 2-148

δ 2.00-2.23 (m, 6H), 2.35-2.44 (m, 2H), 4.56-4.61 (m, 4H). 4.82 (q, 1H), 6.06-6.64 (m, 2H), 6.56 (d, 1H), 6.78 (d, 1H), 7.12 (d, 1H), 7.20 (d, 1H), 7.61 (d, 1H), 8.40 (s, 1H)

Chemical Compound 2-144

δ 1.99-2.20 (m, 6H), 2.40-2.47 (m, 2H), 2.57-2.64 (m, 2H), 4.07 (t, 2H), 4.55-4.60 (m, 3H), 5.14 (dd, 2H), 5.86-5.99 (m, 1H), 6.56 (d, 1H), 6.77 (d, 1H), 7.08 (s, 1H), 7.12 (d, 1H), 7.60 (dd, 1H), 8.40 (s, 1H)

Chemical Compound 2-115

δ 2.00-2.30 (m, 7H), 2.35-2.44 (m, 2H), 3.97-4.03 (m, 2H), 4.16 (t, 2H), 4.52-4.65 (brs, plus t, 3H), 6.56 (d, 1H), 6.78 (d, 1H), 7.14 (s, 1H), 7.19 (d, 1H), 7.62 (dd, 1H), 8.40 (s, 1H)

Chemical Compound 2-153

δ 1.05 (t, 3H), 1.76-1.84 (m, 2H), 2.03 (d, 2H), 2.17-2.20 (m, 2H), 2.36-2.40 (m, 4H), 3.36 (t, 2H), 4.61 (brs, 2H), 4.72 (t, 1H), 6.58 (d, 1H), 6.92 (d, 1H), 7.64 (d, 1H), 7.80 (d, 1H), 8.28 (s, 1H), 8.42 (s, 1H)

Chemical Compound 2-112

δ 2.00-2.21 (m, 6H), 2.39-2.47 (m, 2H), 3.44 (s, 3H), 3.79 (t, 2H), 4.16 (t, 2H), 4.56 (brs, 2H), 4.62 (brs, 1H), 6.55 (d, 1H), 6.78 (d, 1H), 7.12 (s, 1H), 7.18 (d, 1H), 7.61 (d, 1H), 8.40 (s, 1H)

Chemical Compound 2-161

δ 0.89 (t, 3H), 1.47-1.63 (m, 2H), 2.07-2.11 (m, 4H), 2.19-2.27 (m, 2H), 2.38-2.45 (m, 2H), 2.80 (s, 3H), 3.08 (t, 2H), 4.56 (brs, 2H), 4.60 (t, 1H), 6.56 (d, 1H), 6.72 (d, 1H), 7.15 (s, 1H), 7.17 (d, 1H), 7.60 (dd, 1H), 8.40 (s, 1H)

Chemical Compound 2-143

δ 2.00-2.24 (m, 6H), 2.38-2.45 (m, 2H), 2.54-2.56 (m, 1H), 4.56-4.63 (brs, plus t, 3H), 4.77 (d, 2H), 6.56 (d, 1H), 6.79 (d, 1H), 7.22 (s, 1H), 7.25 (d, 1H), 7.61 (dd, 1H), 8.40 (s, 1H)

Chemical Compound 2-138

δ 2.05-2.26 (m, 6H), 2.41-2.48 (m, 2H), 3.87 (t, 2H), 4.31 (t, 2H), 4.61-4.64 (brs, plus t, 3H), 6.56 (d, 1H), 6.80 (d, 1H), 7.09 (s, 1H), 7.20 (d, 1H), 7.60 (dd, 1H), 8.40 (s, 1H)

Chemical Compound 2-101

δ 2.11-2.40 (m, 8H), 4.58 (brs, 2H), 4.65 (t, 1H), 4.86 (s, 2H), 6.57 (d, 1H), 6.73 (d, 1H), 7.27 (s, 1H), 7.37 (d, 1H), 7.62 (dd, 1H), 8.41 (s, 1H)

Chemical Compound 5-175

δ 1.57-1.64 (m, 2H), 1.75 (d, 3H), 2.03-2.06 (m, 2H), 2.58 (brs, 2H), 3.08 (d, 2H), 4.18 (dd, 2H), 4.51 (d, 2H), 4.62-4.67 (m, 1H), 5.66-5.90 (m, 2H), 6.61 (d, 1H), 7.01 (d, 1H), 7.13 (s, 1H), 7.20 (d, 1H), 7.62 (dd, 1H), 8.39 (s, 1H)

Chemical Compound 5-89

δ 1.57-1.69 (m, 2H), 2.03-2.07 (m, 2H), 2.59 (brs, 2H), 3.10 (d, 2H), 3.89 (s, 3H), 4.18 (d, 2H), 4.62 (s, 1H), 6.61 (d, 1H), 7.01 (d, 1H), 7.11 (s, 1H), 7.18 (d, 1H), 7.62 (dd, 1H), 8.39 (s, 1H)

Chemical Compound 5-90

δ 1.45 (t, 3H), 1.57-1.68 (m, 2H), 2.03-2.07 (m, 2H), 2.58 (brs, 2H), 3.08 (d, 2H), 4.06-4.20 (m, 4H), 4.62 (s, 1H), 6.60 (d, 1H), 7.01 (d, 1H), 7.11 (s, 1H), 7.20 (d, 1H), 7.62 (dd, 1H), 8.39 (s, 1H)

Chemical Compound 5-176

δ 1.55-1.63 (m, 2H), 2.02-2.04 (m, 2H), 2.55-2.62 (m, 4H), 3.08 (d, 2H), 4.07 (t, 2H), 4.15 (dd, 2H), 4.63 (s, 1H), 5.16 (dd, 2H), 5.84-5.97 (m, 1H), 6.60 (d, 1H), 7.01 (d, 1H), 7.12 (s, 1H), 7.18 (d, 1H), 7.62 (dd, 1H), 8.39 (s, 1H)

Chemical Compound 5-139

δ 1.53-1.63 (m, 2H), 1.76 (d, 6H), 2.02-2.07 (m, 2H), 2.58 (brs, 2H), 3.08 (d, 2H), 4.16 (dd, 2H), 4.57 (d, 2H), 4.62 (s, 1H), 5.46 (t, 1H), 6.60 (d, 1H), 7.01 (d, 1H), 7.13 (s, 1H), 7.18 (d, 1H), 7.62 (dd, 1H), 8.39 (s, 1H)

Chemical Compound 5-123

δ 1.60-1.67 (m, 2H), 2.00-2.09 (m, 2H), 2.29 (brs, 1H), 2.60 (brs, 2H), 3.11 (d, 2H), 3.94 (brs, 2H), 4.08-4.22 (m, 4H), 4.62 (s, 1H), 6.61 (d, 1H), 7.04 (d, 1H), 7.19 (s, 1H), 7.20-7.30 (m, 1H), 7.62 (dd, 1H), 8.39 (s, 1H)

Chemical Compound 5-147

δ 1.58-1.65 (m, 2H), 2.04-2.06 (m, 2H), 2.58 (brs, 2H), 3.10 (d, 2H), 3.84 (t, 2H), 4.16-4.30 (m, 4H), 4.67 (s, 1H), 6.61 (d, 1H), 7.05 (d, 1H), 7.16 (s, 1H), 7.24-7.26 (m, 1H), 7.62 (dd, 1H), 8.40 (s, 1H)

Chemical Compound 5-124

δ 1.57-1.69 (m, 2H), 2.02-2.05 (m, 2H), 2.57 (brs, 2H), 3.09 (d, 2H), 3.43 (s, 3H), 3.77 (t, 2H), 4.13-4.20 (m, 4H), 4.65 (s, 1H), 6.60 (d, 1H), 7.02 (d, 1H), 7.16 (s, 1H), 7.17-7.25 (m, 1H), 7.62 (dd, 1H), 8.39 (s, 1H)

Chemical Compound 5-132

δ 1.57-1.66 (m, 2H), 2.00-2.06 (m, 2H), 2.59 (brs, 2H), 3.11 (d, 2H), 3.79 (s, 3H), 4.12-4.22 (m, 2H), 4.65-4.69 (m, 3H), 6.60 (d, 1H), 7.05 (d, 1H), 7.13 (s, 1H), 7.21-7.28 (m, 1H), 7.62 (dd, 1H), 8.39 (s, 1H)

Chemical Compound 5-134

δ 1.58-1.64 (m, 2H), 1.95-2.13 (m, 2H), 2.06 (s, 3H), 2.58 (brs, 2H), 3.09 (d, 2H), 4.16-4.25 (m, 4H), 4.44 (t, 2H), 4.63 (s, 1H), 6.61 (d, 1H), 7.04 (d, 1H), 7.16 (s, 1H), 7.22-7.29 (m, 1H), 7.62 (dd, 1H), 8.39 (s, 1H)

Chemical Compound 5-133

δ 1.31 (t, 3H), 1.59-1.65 (m, 2H), 2.04-2.07 (m, 2H), 2.60 (brs, 2H), 3.10 (d, 2H), 4.14-4.30 (m, 4H), 4.68 (s, 3H), 6.61 (d, 1H), 7.05 (d, 1H), 7.13 (s, 1H), 7.25-7.28 (m, 1H), 7.62 (dd, 1H), 8.39 (s, 1H)

Chemical Compound 5-203

δ 1.57-1.64 (m, 2H), 2.01-2.09 (m, 2H), 2.57 (brs, 2H), 3.10 (d, 2H), 3.93-4.21 (m, 8H), 4.64 (s, 1H), 5.32 (t, 1H), 6.61 (d, 1H), 7.01 (d, 1H), 7.17 (s, 1H), 7.21-7.26 (m, 1H), 7.62 (dd, 1H), 8.39 (s, 1H)

Chemical Compound 5-163

δ 1.15 (t, 3H), 1.62-1.69 (m, 2H), 1.99-2.12 (m, 4H), 2.64 (brs, 2H), 3.14 (d, 2H), 3.32 (t, 2H), 4.23 (dd, 2H), 4.64 (s, 1H), 6.62 (d, 1H), 7.14 (d, 1H), 7.53 (d, 1H), 7.54 (s, 1H), 7.64 (dd, 1H), 8.41 (s, 1H)

Chemical Compound 5-204

δ 1.59-1.70 (m, 2H), 1.85-2.09 (m, 6H), 2.57, 2.64 (two s, total 2H), 3.12 (t-like, 2H), 3.82 (q, 1H), 3.93 (q, 1H), 4.02 (d, 2H), 4.11-4.30 (m, 3H), 4.64 (s, 1H), 6.60 (d, 1H), 7.01 (d, 1H), 7.14 (s, 1H), 7.17 (d, 1H), 7.62 (dd, 1H), 8.40 (s, 1H)

Chemical Compound 5-126

δ 1.63-1.68 (m, 2H), 1.93-2.04 (m, 2H), 2.35 (s, 3H), 2.61 (brs, 2H), 3.12 (d, 2H), 4.21 (dd, 2H), 4.58 (s, 2H), 4.66 (s, 1H), 6.62 (d, 1H), 7.05 (s-like, 2H), 7.26 (s-like, 1H), 7.63 (dd, 1H), 8.40 (s, 1H)

Chemical Compound 5-127

δ 1.27 (d, 3H), 1.59-1.67 (m, 2H), 2.00-2.04 (m, 2H), 2.61 (brs, 3H), 3.12 (d, 2H), 3.81 (t, 1H), 4.04 (dd, 1H), 4.08-4.22 (m, 3H), 4.62 (s, 1H), 6.61 (d, 1H), 7.03 (d, 1H), 7.12 (s, 1H), 7.20 (s-like, 1H), 7.63 (dd, 1H), 8.40 (s, 1H)

Chemical Compound 5-128

δ 1.28 (d, 3H), 1.57-1.64 (m, 2H), 2.01-2.04 (m, 2H), 2.58 (brs, 2H), 3.09 (d, 2H), 3.46 (s, 3H), 3.69-3.80 (m, 1H), 3.91-4.04 (m, 1H), 4.18 (brd, 2H), 4.64 (s, 1H), 6.61 (d, 1H), 7.01 (d, 1H), 7.12 (s, 1H), 7.16 (d, 1H), 7.62 (dd, 1H), 8.39 (s, 1H)

Chemical Compound 5-129

δ 1.28 (s, 6H), 1.56-1.67 (m, 2H), 1.99-2.04 (m, 2H), 2.46 (s, 1H), 2.60 (brs, 2H), 3.11 (d, 2H), 3.85 (s, 2H), 4.20 (dd, 2H), 4.62 (s, 1H), 6.62 (d, 1H), 7.02 (d, 1H), 7.14 (s, 1H), 7.18 (s-like, 1H), 7.63 (dd, 1H), 8.40 (s, 1H)

Chemical Compound 5-130

δ 1.33 (s, 6H), 1.58-1.64 (m, 2H), 2.02-2.05 (m, 2H), 2.58 (brs, 2H), 3.10 (d, 2H), 3.31 (s, 3H), 3.87 (s, 2H), 4.18 (dd, 2H), 4.65 (s, 1H), 6.61 (d, 1H), 7.01 (d, 1H), 7.13 (s, 1H), 7.18 (d, 1H), 7.62 (dd, 1H), 8.40 (s, 1H)

Chemical Compound 5-114

δ 1.37 (d, 3H), 1.57-1.64 (m, 2H), 1.77-1.90 (m, 1H), 2.03-2.05 (m, 2H), 2.04 (s, 3H), 2.57 (brs, 2H), 3.09 (d, 2H), 3.57 (t, 1H), 4.03-4.20 (m, 2H), 4.62 (s, 1H), 5.25-5.35 (m, 1H), 6.61 (d, 1H), 7.02 (d, 1H), 7.13 (s, 1H), 7.22 (d, 1H), 7.62 (dd, 1H), 8.39 (s, 1H)

Chemical Compound 5-138

δ 1.58-1.70 (m plus d, 5H), 2.02-2.05 (m, 2H), 2.58 (brs, 2H), 3.10 (d, 2H), 4.03-4.21 (m, 4H), 4.28-4.38 (m, 1H), 4.66 (s, 1H), 6.61 (d, 1H), 7.04 (d, 1H), 7.13 (s, 1H), 7.17 (d, 1H), 7.62 (dd, 1H), 8.40 (s, 1H)

Chemical Compound 5-206

δ 1.58-1.63 (m, 2H), 2.00-2.04 (m, 2H), 2.56 (brs, 2H), 3.06 (d, 2H), 4.17 (dd, 2H), 4.62 (s, 1H), 5.05 (s, 2H), 6.34-6.41 (m, 2H), 6.60 (d, 1H), 7.02 (d, 1H), 7.22 (s-like, 2H), 7.43 (s, 1H), 7.62 (dd, 1H), 8.39 (s, 1H)

Chemical Compound 5-208

δ 1.57-1.64 (m, 2H), 2.00-2.04 (m, 2H), 2.58 (brs, 2H), 3.06 (d, 2H), 4.17 (dd, 2H), 4.62 (s, 1H), 5.12 (s, 2H), 6.61 (d, 1H), 7.03 (d, 1H), 7.14 (d, 1H), 7.20-7.21 (m, 2H), 7.31-7.35 (m, 2H), 7.62 (dd, 1H), 8.39 (s, 1H)

Chemical Compound 5-207

δ 1.57-1.64 (m, 2H), 2.00-2.03 (m, 2H), 2.57 (brs, 2H), 3.07 (d, 2H), 4.18 (dd, 2H), 4.62 (s, 1H), 5.00 (s, 2H), 6.47 (s, 1H), 6.60 (d, 1H), 7.03 (d, 1H), 7.21 (d-like, 2H), 7.43 (s, 1H), 7.49 (s, 1H), 7.62 (dd, 1H), 8.40 (s, 1H)

Chemical Compound 5-98

δ 1.06 (t, 3H), 1.80-1.92 (m, 2H), 2.01-2.04 (m, 4H), 2.57 (brs, 2H), 2.93 (d, 2H), 3.97 (t, 2H), 4.18 (dd, 2H), 4.57 (s, 1H), 6.85 (d, 1H), 7.01 (d, 1H), 7.11 (s, 1H), 7.17 (d, 1H), 7.35 (dd, 1H), 8.40 (s, 1H)

Chemical Compound 5-209

δ 1.57-1.63 (m, 2H), 2.04-2.06 (m, 2H), 2.58 (brs, 2H), 3.07 (d, 2H), 4.17 (dd, 2H), 4.64 (s, 1H), 5.27 (s, 2H), 6.60 (d, 1H), 6.98-7.09 (m, 3H), 7.24 (d-like, 2H), 7.32 (d, 1H), 7.62 (dd, 1H), 8.39 (s, 1H)

Chemical Compound 5-104

δ 1.41 (t, 1H), 1.59-1.66 (m, 2H), 1.77 (t, 1H), 2.05-2.22 (m, 3H), 2.60 (brs, 2H), 3.11 (dd, 2H), 4.05 (t, 1H), 4.19 (dd, 2H), 4.29 (dd, 1H), 4.66 (s, 1H), 6.61 (d, 1H), 7.05 (d, 1H), 7.14 (s, 1H), 7.23 (d-like, 1H), 7.62 (dd, 1H), 8.39 (s, 1H)

Chemical Compound 5-206

δ 0.92 (t, 3H), 1.42-1.47 (m, 1H), 1.57-1.80 (m, 5H), 1.98-2.04 (m, 2H), 2.35 (brs, 2H), 3.55 (dd, 2H), 3.93 (t, 2H), 4.08 (d, 2H), 4.48 (t, 1H), 6.62 (d, 1H), 6.99 (d, 1H), 7.09 (s, 1H), 7.12 (d, 1H), 7.62 (dd, 1H), 8.42 (s, 1H)

Chemical Compound 7-103

δ 0.35-0.40 (m, 2H), 0.61-0.67 (m, 2H), 1.24-1.36 (m, 1H), 1.45-1.51 (m, 1H), 1.57-1.63 (m, 2H), 1.67-1.88 (m, 1H), 2.18-2.31 (m, 4H), 3.25 (d, 2H), 3.91 (d, 2H), 4.46 (d, 2H), 4.62 (s, 1H), 6.66 (d, 1H), 7.02 (d, 1H), 7.12 (s, 1H), 7.18 (d, 1H), 7.63 (dd, 1H), 8.42 (s, 1H)

Chemical Compound 2-130

δ 1.31 (d, 3H), 2.00-2.22 (m, 6H), 2.40-2.50 (m, 2H), 3.45 (s, 3H), 3.72-3.81 (m, 1H), 3.88-3.93 (m, 1H), 4.01-4.06 (m, 1H), 4.56-4.61 (m+brs, 3H), 6.56 (d, 1H), 6.77 (d, 1H), 7.10 (s, 1H), 7.17 (d, 1H), 7.61 (dd, 1H), 8.40 (s, 1H)

Chemical Compound 1-98

δ 1.05 (t, 3H), 1.13 (d, 3H), 1.71-1.91 (m, 4H), 2.05-2.15 (m, 2H), 3.00 (dd, 1H), 3.22-3.30 (m, 1H), 3.98 (t, 2H), 4.10-4.24 (m, 2H), 6.67 (d, 1H), 6.98 (d, 1H), 7.10 (d, 7.16 (d, 1H), 7.61 (dd, 1H), 8.39 (s, 1H)

Chemical Compound 5-118

δ 0.36 (q, 2H), 0.63 (q, 2H), 1.19-1.31 (m, 1H), 1.55-1.63 (m, 2H), 2.07 (brt, 2H), 2.57 (brs, 2H), 3.07 (d, 2H), 3.87 (d, 2H), 4.17 (dd, 2H), 4.63 (s, 1H), 6.59 (d+q, 2H), 6.99-7.03 (m, 3H), 7.61 (dd, 1H), 8.39 (s, 1H)

Chemical Compound 8-4

δ 1.40-1.56 (m, 1H), 1.75-1.86 (m, 3H), 1.91-2.05 (m, 2H), 2.61 (brs, 2H), 3.40 (dd, 2H), 4.16 (d, 2H), 4.56 (t, 1H), 5.81 (s, 1H), 6.62 (d, 1H), 6.91 (d, 1H), 7.13 (d, 1H), 7.19 (s, 1H), 7.63 (dd, 1H), 8.42 (s, 1H)

Chemical Compound 2-90

δ 1.08 (t, 3H), 1.81-1.93 (m, 2H), 1.97-2.09 (m, 4H), 2.16-2.24 (m, 2H), 2.40-2.46 (m, 2H), 2.98 (s, 3H), 3.97 (t, 2H), 4.48 (brs, 2H), 4.59 (t, 1H), 6.57 (d, 1H), 6.77 (d, 1H), 7.07 (s, 1H), 7.14 (d, 1H), 7.51 (dd, 1H), 8.07 (s, 1H)

Chemical Compound 2-167

δ 0.98 (t, 3H), 1.42 (t, 3H), 1.67-1.75 (m, 2H), 2.01-2.23 (m, 6H), 2.42 (d, 2H), 2.87-2.97 (m, 2H), 4.28-4.35 (m, 2H), 4.57 (brs, 2H), 4.62 (t, 1H), 6.56 (d, 1H), 6.84 (d, 1H), 7.39 (d, 1H), 7.62 (dd, 1H), 7.70 (s, 1H), 8.41 (s, 1H)

Chemical Compound 1-95

δ 1.02-1.16 (m, 8H), 1.26 (s, 3H), 1.79-1.94 (m, 4H), 3.30 (m, 1H), 3.80 (d, 1H), 3.90-3.99 (m, 2H), 4.08 (q, 2H), 4.13-4.38 (m, 2H), 4.77 (brs, 1H), 6.71 (d, 1H), 7.06 (s, 1H), 7.09 (d, 1H), 7.16 (d, 1H), 7.60 (dd, 1H), 8.37 (s, 1H)

Chemical Compound 5-93

δ 1.06 (t, 3H), 1.63-1.69 (m, 2H), 1.74-1.88 (m, 2H), 2.00-2.02 (m, 2H), 2.55 (brs, 2H), 3.01 (d, 2H), 4.00 (t, 2H), 4.07-4.16 (m, 2H), 4.38 (s, 2H), 4.59 (s, 1H), 6.59 (d, 1H), 7.01 (d, 1H), 7.10 (s, 1H), 7.13 (d, 1H), 7.50 (dd, 1H), 8.12 (s, 1H)

Chemical Compound 2-81

δ 1.09 (t, 3H), 1.84-2.21 (m, 8H), 2.40-2.43 (m, 2H), 3.97 (t, 2H), 4.56-4.62 (brm, 3H), 6.56 (d, 1H), 6.73 (d, 1H), 7.08 (s, 1H), 7.23 (m, 1H), 7.62 (dd, 1H), 8.41 (s, 1H)

Chemical Compound 2-67

δ 2.00-2.21 (m, 4H), 2.28-2.35 (m, 4H), 4.59 (brs, 2H), 4.66 (t, 1H), 6.58 (d, 1H), 6.88 (d, 1H), 7.63 (dd, 1H), 7.74 (d, 1H), 7.86 (s, 1H), 8.41 (s, 1H)

Chemical Compound 5-99

δ 1.06 (t, 3H), 1.58-1.63 (m, 2H), 1.65-1.89 (m, 2H), 2.02-2.04 (m, 2H), 2.57 (brs, 2H), 3.06 (d, 2H), 4.00 (t, 2H), 4.16 (d, 2H), 4.62 (s, 1H), 6.57 (t, 1H), 6.63 (d, 1H), 7.01 (d, 1H), 7.11 (s, 1H), 7.17 (d, 1H), 7.60 (dd, 1H), 8.24 (s, 1H)

Chemical Compound 5-103

δ 1.04 (t, 3H), 1.57-1.64 (m, 2H), 1.77-1.88 (m, 2H), 1.96-2.04 (m, 2H), 2.58 (brs, 2H), 3.13 (d, 2H), 3.91 (t, 2H), 4.17 (d, 2H), 4.52 (s, 1H), 6.61 (d, 1H), 6.63 (d, 1H), 6.75 (s-like, 2H), 7.63 (dd, 1H), 8.40 (s, 1H)

Chemical Compound 5-101

δ 1.06 (t, 3H), 1.47-1.67 (m, 3H), 1.79-1.91 (m, 2H), 2.01-2.04 (m, 2H), 2.56 (brs, 2H), 3.03 (d, 2H), 3.97 (t, 2H), 4.09

(dd, 2H), 4.57 (brs, 2H), 4.60 (s, 1H), 6.61 (d, 1H), 7.01 (d, 1H), 7.11 (s, 1H), 7.17 (d, 1H), 7.52 (dd, 1H), 8.14 (s, 1H)

FORMULATION EXAMPLES

Insecticide, Acaricide

Although certain examples of compositions of the present invention are shown in the following, additives and the additive ratio should not be limited to these examples, and can be broadly changed. Parts shown in the Formulation Examples mean parts by weight.

| Formulation Example 1 Wettable powder | |
|---|---|
| The chemical compound of the present invention | 40 parts |
| Diatomaceous earth | 53 parts |
| Higher alcohol sulfate ester | 4 parts |
| Alkylnaphthalene sulfonate | 3 parts |

The above were mixed homogeneously together and finely ground to produce a water dispersible powder containing its active constituent at a ratio of 40%.

| Formulation Example 2 Emulsifiable concentrate | |
|---|---|
| The chemical compound of the present invention | 30 parts |
| Xylene | 33 parts |
| Dimethylformamide | 30 parts |
| Polyoxyethylene alkylaryl ether | 7 parts |

The above were mixed and dissolved together to produce an emulsion containing its active constituent at a ratio of 30%.

| Formulation Example 3 Dusting powder | |
|---|---|
| The chemical compound of the present invention | 10 parts |
| Talc | 89 parts |
| Polyoxyethylenealkylaryl ether | 1 part |

The above were homogeneously mixed and finely ground to produce a dusting powder containing its active constituent at a ratio of 10%.

| Formulation Example 4 Granule | |
|---|---|
| The chemical compound of the present invention | 5 parts |
| Clay | 73 parts |
| Bentonite | 20 parts |
| Sodium dioctylsulfosuccinate | 1 part |
| Sodium phosphate | 1 part |

The above were ground and mixed well, into which water was then added, followed by kneading well together. It was granulated and then dried to produce a granule containing its active constituent at a ratio of 5%.

| Formulation Example 5 Suspension | |
|---|---|
| The chemical compound of the present invention | 10 parts |
| Sodium lignin sulfonate | 4 parts |
| Sodium dodecylbenzenesulfonate | 1 part |
| Xanthan gum | 0.2 parts |
| Water | 84.8 parts |

The above were mixed together and wet-ground until its particle size became 1 micron or less to produce a suspension containing its active constituent at a ratio of 10%.

In the following, test examples show that the chemical compounds of the present invention are useful as active ingredients of various acaricides.

Test Example 1

Effect on Two-spotted Spider Mite 17 female adults of organophosphorous agent resistant two-spotted spider mites were inoculated onto the first leaves of kidney beans seeded onto 3.5 inch pots and germinated 7 to 10 days before, onto which each of liquid agents, diluted with water so as to adjust the respective concentration of the chemical compounds to 125 ppm according to the formulation of the water dispersible powder shown in the aforementioned Formulation Example 1, was sprayed. After they were left in a thermostatic chamber at 25° C. in 65% humidity for 3 days, the rate of killed adults was investigated. The examination was repeated twice. As the results, the following chemical compounds killed 100% of the adults.

1-8, 1-9, 1-10, 1-13, 1-15, 1-16, 1-17, 1-18, 1-19, 1-22, 1-23, 1-27, 1-29, 1-44, 1-45, 1-46, 1-47, 1-48, 1-49, 1-54, 1-57, 1-59, 1-63, 1-66, 1-67, 1-69, 1-71, 1-72, 1-73, 1-74, 1-75, 1-76, 1-79, 1-80, 1-81, 1-82, 1-88, 1-89, 1-90, 1-91, 1-92, 1-93, 1-94, 1-97, 1-98, 1-100, 1-101, 1-102, 1-105, 1-108, 1-114, 1-115, 1-117, 1-118, 1-133, 1-136, 1-139, 1-140, 1-142, 1-143, 1-147, 1-150, 1-153, 1-163, 1-172, 1-173, 1-174, 1-179, 1-180, 1-181, 1-182, 1-183, 1-184, 1-186, 1-187, 1-188, 1-189, 1-190, 1-191, 1-192,
2-51, 2-54, 2-57, 2-58, 2-59, 2-60, 2-62,
2-77, 2-78, 2-81, 2-82, 2-83, 2-84, 2-85, 2-86, 2-89, 2-93, 2-95, 2-96, 2-97, 2-98, 2-100, 2-102, 2-105, 2-111, 2-112, 2-115, 2-130, 2-138, 2-141, 2-143, 2-144, 2-145, 2-147, 2-148, 2-150, 2-151, 2-152, 2-155, 2-157, 2-159, 2-160, 2-161, 2-165, 2-166, 2-168, 2-169, 2-171, 2-173, 2-174, 2-175, 2-177, 2-178, 2-179, 2-181, 2-182, 2-183, 2-184, 2-186, 2-187, 2-190, 2-192, 2-193, 2-194, 2-195, 2-196, 2-198, 2-199, 2-200, 2-201, 2-203, 2-205, 2-208, 2-209, 2-210, 2-211, 2-212, 2-213, 2-220, 2-221, 2-223, 2-225, 2-226, 2-227, 2-230, 2-232, 2-233, 2-234, 2-235, 2-236, 2-237, 2-239, 2-240, 2-245, 2-246, 2-247, 2-248, 2-249, 2-250,
5-22, 5-32, 5-38, 5-69, 5-70, 5-72, 5-73, 5-75, 5-89, 5-90, 5-96, 5-97, 5-98, 5-99, 5-100, 5-102, 5-104, 5-105, 5-106, 5-110, 5-111, 5-114, 5-116, 5-118, 5-120, 5-121, 5-124, 5-125, 5-126, 5-127, 5-128, 5-129, 5-130, 5-134, 5-138, 5-139, 5-147, 5-149, 5-161, 5-162, 5-163, 5-164, 5-174, 5-175, 5-176, 5-177, 5-182, 5-183, 5-184, 5-190, 5-191, 5-198, 5-199, 5-200, 5-203, 5-204, 5-205, 5-206, 5-207, 5-208, 5-209, 5-210, 5-211, 5-212, 5-213, 5-214, 5-215, 5-217, 5-218, 5-220, 5-222, 5-223, 5-224, 5-225, 5-227, 5-229, 5-230, 5-231, 5-232, 5-233, 5-234, 5-235, 5-236, 5-237, 5-238, 5-239, 5-240, 5-242, 5-243, 5-244, 5-245, 5-246, 5-247, 5-249, 5-255, 5-256, 5-257, 5-258, 5-259, 5-260, 5-261, 5-262, 5-263, 5-264,
7-82, 7-100, 7-103,
8-63.

Test Example 2

Effect on Citrus Red Mite 10 female adults of acaricide resistant citrus red mites were inoculated onto leaves of a mandarin orange placed on dishes, onto which each of liquid agents, diluted with water so as to adjust the respective concentration of the chemical compounds to 31 ppm according to the formulation of the emulsifiable concentrate shown in the aforementioned Formulation Example 2, was sprayed by using a rotating sparge tower. After they were left in a thermostatic chamber at 25° C. in 65% humidity for 3 days, and were then removed from the dishes, eggs laid for 3 days were investigated whether they could grow to adults or not on the eleventh day. As the results, the following chemical compounds killed 100% of the adults. 1-13, 1-15, 1-22, 1-27, 1-45, 1-54, 1-59, 1-63, 1-66, 1-69, 1-71, 1-72, 1-75, 1-80, 1-88, 1-89, 1-92, 1-93, 1-94, 1-97, 1-98, 1-100, 1-102, 1-105, 1-108, 1-133, 1-136, 1-142, 1-153, 1-181, 1-183, 1-186, 1-187, 1-188, 1-189, 1-190, 1-191,
2-54, 2-57, 2-58, 2-59, 2-60, 2-78, 2-81, 2-82, 2-84, 2-97, 2-98, 2-105, 2-130, 2-141, 2-147, 2-177, 2-181, 2-183, 2-193, 2-196, 2-208, 2-209, 2-210, 2-212, 2-247, 2-249,
5-22, 5-69, 5-72, 5-73, 5-90, 5-97, 5-105, 5-110, 5-111, 5-116, 5-118, 5-120, 5-121, 5-124, 5-149, 5-162, 5-174, 5-175, 5-177, 5-190, 5-203, 5-215, 5-217, 5-218, 5-220, 5-222, 5-224, 5-225, 5-227, 5-229, 5-230, 5-233, 5-234, 5-236, 5-237, 5-239, 5-243, 5-245, 5-256, 5-257, 5-259, 5-260, 5-261, 5-262,
7-82, 7-100, 7-103.

Test Example 3

Effect on Army Worm

Test feeds were prepared by filling plastic test tubes (capacity of 1.4 ml) with 0.2 ml of a commercial artificial feed (Insecta LFS, manufactured by Nosan Corporation). Each of 1% chemical compound solutions was prepared by using DMSO (containing 0.5% tween 20), which was then dropped into the surface of the feed in amount of 10 μg of the respective chemical compounds. 2 army worms, each of which was in the second instar, were inoculated into each of the test tubes, which were then sealed by their plastic caps. After they were left at 25° C. for 5 days, the rate of killed army worms and their feed consumptions were investigated. The test was repeated twice. As the results, the following chemical compounds killed 100% of the army worms, or inhibited their feed consumptions, in comparison with the feed consumption of a solvent control area, to 10% or less, which show that the following chemical compounds were effective. 1-8, 1-9, 1-13, 1-15, 1-17, 1-22, 1-23, 1-27, 1-39, 1-45, 1-46, 1-59, 1-69, 1-72, 1-74, 1-75, 1-79, 1-80, 1-83, 1-95, 1-97, 1-981-100, 1-105, 1-108, 1-114, 1-133, 1-140, 1-147, 1-153, 1-165, 1-166, 1-181, 1-182, 1-183, 1-184, 1-187, 1-189, 1-190,
2-21, 2-30, 2-51, 2-54, 2-57, 2-67, 2-82, 2-83, 2-94, 2-130, 2-138, 2-141, 2-143, 2-144, 2-148, 2-160, 2-161, 2-162, 2-166, 2-167, 2-169, 2-170, 2-171, 2-176, 2-177, 2-181, 2-182, 2-185, 2-193, 2-203, 2-204, 2-208, 2-211, 2-213, 2-226, 2-233, 2-235, 2-236, 2-237, 2-238, 2-239, 2-240, 2-246,
3-62, 3-131,
5-22, 5-73, 5-75, 5-89, 5-90, 5-96, 5-97, 5-105, 5-110, 5-116, 5-120, 5-138, 5-147, 5-149, 5-147, 5-149, 5-174, 5-175, 5-176, 5-190, 5-210, 5-212, 5-224, 5-225, 5-228, 5-237, 5-241, 5-242, 5-243, 5-244, 5-245, 5-246, 5-256, 5-259, 5-262, 5-265,
6-82,
7-82, 7-103,
9-83, 9-94.

The cyclic amine compounds represented by the formula [I], and, the salts or the oxides thereof can exert excellent effects as active ingredients of insecticides or acaricides.

The invention claimed is:

1. A chemical compound represented by the formula [I]:

[I]

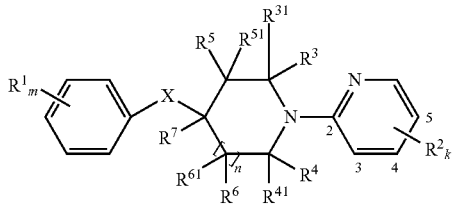

wherein:

$R^1$ represents a hydroxyl group, a halogen atom, a cyano group, a nitro group, a formyl group, a $C_{1-6}$ alkyl group which may be substituted by $G^1$, a $C_{2-6}$ alkenyl group, a $C_{2-6}$ alkynyl group, a $C_{1-6}$ haloalkyl group, a $C_{1-6}$ haloalkenyl group, a $C_{1-6}$ alkylcarbonyl group, a $C_{1-6}$ alkoxy group which may be substituted by $G^2$, a $C_{1-6}$ haloalkoxy group, a $C_{2-6}$ alkenyloxy group, a $C_{2-6}$ haloalkenyloxy group, a $C_{2-6}$ alkynyloxy group, a $C_{1-6}$ alkylcarbonyloxy group, a $C_{1-6}$ alkoxycarbonyloxy group, a $C_{1-6}$ alkylthiocarbonyloxy group, a $C_{1-6}$ alkylthio group, a $C_{1-6}$ haloalkylthio group, $C_{1-6}$ alkylsulfinyl group, a $C_{1-6}$ haloalkylsulfinyl group, a $C_{1-6}$ alkylsulfonyl group, a $C_{1-6}$ haloalkylsulfonyl group, a $C_{1-6}$ alkylsulfonyloxy group, a $C_{1-6}$ haloalkylsulfonyloxy group, a tetrahydrofuranyl group which may be substituted by $G^4$, a dioxolanyl group which may be substituted by $G^4$, or a substituent represented by a formula selected from:

$$—Y^1C(=Y^2)—Y^3R^8$$

$$—CO_2—R^{10}$$

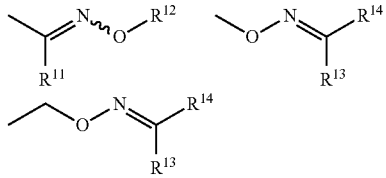

wherein $R^8$ represents a $C_{1-6}$ alkyl group, $Y^1$, $Y^2$, and $Y^3$ each independently represents an oxygen atom or a sulfur atom, $R^{10}$ represents a $C_{1-6}$ alkyl group, a $C_{2-6}$ alkenyl group, a $C_{2-6}$ alkynyl group, a $C_{1-6}$ alkyl $C_{1-6}$ alkoxy group, or a $C_{1-6}$ haloalkyl group, $R^{11}$ and $R^{12}$ each independently represents a hydrogen atom, a $C_{1-6}$ alkyl group, a $C_{2-6}$ alkenyl group, or a $C_{2-6}$ alkynyl group, and $R^{13}$ and $R^{14}$ each independently represents a $C_{1-6}$ alkyl group, and $R^{13}$ and $R^{14}$ may be bound together to form a ring, m represents 0 or an integer of 1 to 5, $R^2$ represents a halogen atom, a nitro group, a $C_{1-6}$ alkyl group, a $C_{1-6}$ alkoxy group, a $C_{1-6}$ haloalkyl group, or a $C_{1-6}$ haloalkoxy group, k represents an integer of 1 to 4, $R^3$, $R^{31}$, $R^4$, $R^{41}$, $R^5$, $R^{51}$, $R^6$, $R^{61}$, and $R^7$ each independently represents a hydrogen atom, a $C_{1-6}$ alkyl group, a $C_{1-6}$ alkoxycarbonyl group, or a $C_{1-6}$ alkoxy group, X represents an oxygen atom, a sulfur atom, a sulfinyl group, or a sulfonyl group, $G^1$ represents a hydroxyl group, a $C_{1-6}$ alkoxycarbonyl group, a $C_{1-6}$ alkoxy group, a $C_{1-6}$ alkoxy $C_{1-6}$ alkoxy group, or a $C_{3-6}$ cycloalkyl group, $G^2$ represents a hydroxyl group, a cyano group, an amino group which may be substituted by $G^4$, a $C_{1-6}$ alkoxycarbonyl group, a $C_{1-6}$ alkylthio group, a $C_{1-6}$ alkylsulfonyl group, a $C_{1-6}$ alkoxy group, a $C_{1-6}$ alkoxy $C_{1-6}$ alkoxy group, $C_{3-6}$ cycloalkyl group, or a $C_{6-10}$ aryl group which may be substituted by a halogen atom or a $C_{1-6}$ alkyl group, $G^4$ represents a $C_{1-6}$ alkyl group, or a $C_{1-6}$ alkoxy group, and n is equal to 1;

or a salt or an N-oxide of the chemical compound represented by formula (I).

2. A chemical compound according to claim 1, wherein k is at least 1, and an $R^2$ substituent is at the five position on the pyridine ring.

3. A chemical compound according to claim 1, wherein m is at least 1, and an $R^1$ substituent is at the two position on the benzene ring.

4. A pest control agent comprising, as its active constituent, the chemical compound of claim 1.

5. An insecticide comprising, as its active constituent, the chemical compound of claim 1.

6. An acaricide comprising, as its active constituent, the chemical compound of claim 1.

7. A chemical compound according to claim 2, wherein m is at least 1, and an $R^1$ substituent is at the two position on the benzene ring.

8. A pest control agent comprising, as its active constituent, the chemical compound of claim 2.

9. An insecticide comprising, as its active constituent, the chemical compound of claim 2.

10. An acaricide comprising, as its active constituent, the chemical compound of claim 2.

11. A pest control agent comprising, as its active constituent, the chemical compound of claim 3.

12. An insecticide comprising, as its active constituent, the chemical compound of claim 3.

13. An acaricide comprising, as its active constituent, the chemical compound of claim 3.

*14. A chemical compound represented by formula (II):*

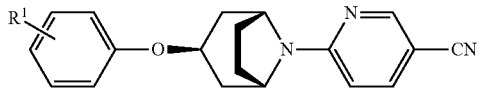

(II)

*wherein $R^1$ is selected from the group consisting of 2-O$^n$Pr-4-CF$_3$, 2-OCH$_2$$^c$Pr-4-CF$_3$, and 2-O(CH$_2$)$_2$OMe-4-CF$_3$.*

*15. A chemical compound represented by formula (III):*

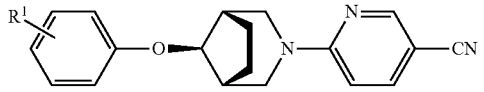

(III)

*wherein $R^1$ is selected from the group consisting of 2-O$^n$Pr-4-CF$_3$, 2-OCH$_2$OMe-4-CF$_3$, 2-OCH$_2$$^c$Pr-4-CF$_3$, and 2-O(CH$_2$)$_2$OMe-4-CF$_3$.*

* * * * *